US008957062B2

(12) United States Patent
Edmondson et al.

(10) Patent No.: US 8,957,062 B2
(45) Date of Patent: Feb. 17, 2015

(54) SUBSTITUTED CYCLOPROPYL COMPOUNDS, COMPOSITIONS CONTAINING SUCH COMPOUNDS AND METHODS OF TREATMENT

(75) Inventors: Scott Edmondson, Clark, NJ (US); Zhiqiang Guo, Morganville, NJ (US); Harold B. Wood, Westfield, NJ (US); Andrew W. Stamford, Rahway, NJ (US); Michael W. Miller, Scotch Plains, NJ (US); Duane E. DeMong, Somerset, NJ (US); Gregori J. Morriello, Randolph, NJ (US); Rajan Anand, Fanwood, NJ (US); Vincent J. Colandrea, North Brunswick, NJ (US); Megan Macala, Westfield, NJ (US); Milana Maletic, Summit, NJ (US); Cheng Zhu, Edison, NJ (US); Yuping Zhu, Basking Ridge, NJ (US); Wanying Sun, Edison, NJ (US); Kake Zhao, Westfield, NJ (US); Yong Huang, West Windsor, NJ (US); Joel M. Harris, Minnetonka, MN (US); Lehua Chang, Ramsey, NJ (US); Nam Fung Kar, Brooklyn, NY (US); Zhiyong Hu, Livingston, NJ (US); Liping Wang, Cranbury, NJ (US); Bowei Wang, Westfield, NJ (US); Ping Liu, Westfield, NJ (US); Jason W. Szewczyk, Collegeville, PA (US); William B. Geiss, Athens, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/110,332

(22) PCT Filed: Apr. 5, 2012

(86) PCT No.: PCT/US2012/032303

§ 371 (c)(1), (2), (4) Date: Oct. 7, 2013

(87) PCT Pub. No.: WO2012/138845

PCT Pub. Date: Oct. 11, 2012

(65) Prior Publication Data

US 2014/0057893 A1 Feb. 27, 2014

Related U.S. Application Data

(60) Provisional application No. 61/578,411, filed on Dec. 21, 2011, provisional application No. 61/473,397, filed on Apr. 8, 2011.

(51) Int. Cl.

| | |
|---|---|
| ***C07D 513/04*** | (2006.01) |
| ***C07D 401/12*** | (2006.01) |
| ***C07D 413/14*** | (2006.01) |
| ***C07D 413/04*** | (2006.01) |
| ***C07D 211/22*** | (2006.01) |

(Continued)

(52) U.S. Cl.

CPC ............ *C07D 513/04* (2013.01); *C07D 413/14* (2013.01); *A61K 9/4858* (2013.01); *C07D 401/12* (2013.01); *C07D 413/04* (2013.01); *C07D 417/14* (2013.01); *C07D 471/04* (2013.01); *C07D 487/04* (2013.01); *C07D 495/04* (2013.01); *C07D 498/04* (2013.01); *C07D 211/22* (2013.01); *C07D 405/04* (2013.01)

USPC .................. 514/210.18; 514/235.5; 514/249; 514/264.1; 514/269; 514/300; 514/301; 514/302; 514/328; 514/326; 544/130; 544/279; 544/319; 544/350; 546/144; 546/115; 546/122; 546/194; 546/209; 546/210

(58) Field of Classification Search

None

See application file for complete search history.

(56) References Cited

U.S. PATENT DOCUMENTS

| | | | |
|---|---|---|---|
| 6,054,587 | A | 4/2000 | Reddy et al. |
| 6,110,903 | A | 8/2000 | Kasibhatla et al. |

(Continued)

FOREIGN PATENT DOCUMENTS

| | | | |
|---|---|---|---|
| WO | 98/04528 | A2 | 2/1998 |
| WO | 99/01423 | A1 | 1/1999 |

(Continued)

OTHER PUBLICATIONS

A. Charette, et al., Enantioselective Cyclpropanation of Allylic Alcohols with Dioxaborolane Ligands: Scope and Synthetic Applications, Jun. 12, 1998, pp. 11943-11952, vol. 120.

(Continued)

*Primary Examiner* — Timothy R Rozof

(74) *Attorney, Agent, or Firm* — Anna L. Cocuzzo; Catherine D. Fitch

(57) ABSTRACT

Substituted cyclopropyl compounds of the formula I: and pharmaceutically acceptable salts thereof are disclosed as useful for treating or preventing type 2 diabetes and similar conditions. The compounds are useful as agonists of the G-protein coupled receptor GPR-119. Pharmaceutical compositions and methods of treatment are also included.

formula I

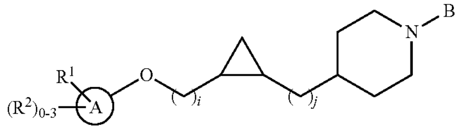

18 Claims, No Drawings

(51) Int. Cl.

| | |
|---|---|
| ***C07D 405/04*** | (2006.01) |
| ***C07D 471/04*** | (2006.01) |
| ***C07D 487/04*** | (2006.01) |
| ***C07D 498/04*** | (2006.01) |
| ***A61K 9/48*** | (2006.01) |
| ***C07D 417/14*** | (2006.01) |
| ***C07D 495/04*** | (2006.01) |

(56) References Cited

U.S. PATENT DOCUMENTS

| | | | |
|---|---|---|---|
| 6,284,748 | B1 | 9/2001 | Dang et al. |
| 6,399,782 | B1 | 6/2002 | Kasibhatla et al. |
| 6,489,476 | B1 | 12/2002 | Dang et al. |
| 6,699,871 | B2 | 3/2004 | Edmondson et al. |
| 6,730,690 | B2 | 5/2004 | Olson et al. |
| 2009/0270409 | A1 | 10/2009 | Alper et al. |
| 2010/0022591 | A1 | 1/2010 | Bertram et al. |
| 2010/0286112 | A1 | 11/2010 | Barba et al. |
| 2011/0028501 | A1 | 2/2011 | Wood et al. |
| 2011/0212939 | A1 | 9/2011 | Bertram et al. |
| 2012/0053180 | A1 | 3/2012 | Kang et al. |
| 2012/0142706 | A1 | 6/2012 | Wood et al. |

FOREIGN PATENT DOCUMENTS

| | | | |
|---|---|---|---|
| WO | 00/39088 | A1 | 7/2000 |
| WO | 00/69810 | A1 | 11/2000 |
| WO | 02/08188 | A1 | 1/2002 |
| WO | 02/060388 | A2 | 8/2002 |
| WO | 03/104207 | A2 | 12/2003 |
| WO | 2004/019869 | A2 | 3/2004 |
| WO | 2004/020408 | A1 | 3/2004 |
| WO | 2004/020409 | A1 | 3/2004 |
| WO | 2004/058741 | A1 | 7/2004 |
| WO | 2004/066963 | A2 | 8/2004 |
| WO | 2006/067531 | A1 | 6/2006 |
| WO | 2006/067532 | A1 | 6/2006 |
| WO | 2007/003962 | A2 | 1/2007 |
| WO | 2007/003964 | A1 | 1/2007 |
| WO | 2009/011836 | A1 | 1/2009 |
| WO | WO2009034388 | A1 | 3/2009 |
| WO | 2009/042053 | A2 | 4/2009 |
| WO | WO2009129036 | A1 | 10/2009 |
| WO | 2009/000087 | A1 | 12/2009 |
| WO | WO2010004343 | A1 | 1/2010 |
| WO | WO2010004344 | A1 | 1/2010 |
| WO | WO2010004346 | A1 | 1/2010 |
| WO | WO2010004347 | A1 | 1/2010 |
| WO | WO2010004348 | A1 | 1/2010 |
| WO | 2010/146605 | A1 | 12/2010 |
| WO | 2011/008663 | A2 | 1/2011 |
| WO | 2011/019538 | A1 | 2/2011 |
| WO | 2011/113947 | A1 | 9/2011 |
| WO | 2012/138845 | A1 | 10/2012 |
| WO | 2012/173917 | A1 | 12/2012 |
| WO | 2013/048916 | A1 | 4/2013 |
| WO | 2013/062838 | A1 | 5/2013 |
| WO | 2013/074388 | A1 | 5/2013 |
| WO | 2013/122821 | A1 | 8/2013 |
| WO | 2014/025379 | A1 | 4/2014 |

OTHER PUBLICATIONS

A. Charette, et al., Stability, Reactivity, Solution, and Solid-State Structure of Halomethylzinc Alkoxides, Mar. 30, 2001, pp. 12160-12167, vol. 123.

F. Eymery, et at., The Usefulness of Phosphorus Compounds in Alkyne Synthesis, 2000, 185-213, No. 2.

Costanzi, et al., “On the applicability of GPCR Homology Models . . . ”, J. Med. Chem., vol. 51, pp. 2907-2914 (2008).

Lima, et al., “Bioisosterism: A Useful Strategy for Molecular Modification and Drug Design”, Current Medicinal Chemistry, vol. 12, pp. 23-49 (2005).

Chaki, et al., “Recent Advances in feeding suppressing agents: potential therapeutic strategy for the treatment of obesity”, Expert Opinion Ther. Patents, vol. 11, No. 11, pp. 1677-1692 (2001).

Spanswick, et al., “Emerging antiobesity drugs”, Expert Opinion Emerging Drugs, vol. 8, No. 1, pp. 217-237 (2003).

Fernandez-Lopez, et al., “Pharmacological Approaches for the Treatment of Obesity”, Drugs, vol. 62, No. 6, pp. 915-944 (2002).

Gadde, et al., “Combination pharmaceutical therapies for obesity”, Expert Opin. Pharmacother., vol. 10, No. 6, pp. 921-925 (2009).

Szewczyk, et al., “Design of potent and selective GPR119 agonists for type II diabetes,” Bioorganic & Medicinal Chemistry Letters, vol. 21, pp. 2665-2668 (2011).

International Search Report for PCT/US12/32303, mailed Jul. 9, 2012.

European Search Report of PCT/US2012/032303, dated Sep. 11, 2014.

SUBSTITUTED CYCLOPROPYL COMPOUNDS, COMPOSITIONS CONTAINING SUCH COMPOUNDS AND METHODS OF TREATMENT

CROSS-REFERENCE TO RELATED APPLICATIONS

This application is a U.S. National Phase application under 35 U.S.C. §371 of PCT/US12/032303, filed Apr. 5, 2012, which claims priority from U.S. provisional applications 61/578,411, filed Dec. 21, 2011 and 61/473,397, filed Apr. 8, 2011.

BACKGROUND OF THE INVENTION

The present invention relates to G-protein coupled receptor agonists. In particular, the present invention is directed to agonists of GPR 119 that are useful for the treatment of diabetes, especially type 2 diabetes, as well as related diseases and conditions such as obesity and metabolic syndrome.

Diabetes is a disease derived from multiple causative factors. It is characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (T2DM), insulin is still produced in the body, and patients demonstrate resistance to the effects of insulin in stimulating glucose and lipid metabolism in the main insulin-sensitive tissues, namely, muscle, liver and adipose tissue. These patients often have normal levels of insulin, and may have hyperinsulinemia (elevated plasma insulin levels), as they compensate for the reduced effectiveness of insulin by secreting increased amounts of insulin.

There has been renewed focus on pancreatic islet-based insulin secretion that is controlled by glucose-dependent insulin secretion (GDIS). In this regard, several orphan G-protein coupled receptors (GPCR's) have recently been identified that are preferentially expressed in the β-cell and are implicated in GDIS. GPR119 is a cell-surface GPCR that is highly expressed in human (and rodent) islets as well as in insulin-secreting cell lines. Synthetic GPR119 agonists augment the release of insulin from isolated static mouse islets only under conditions of elevated glucose, and improve glucose tolerance in diabetic mice and diet-induced obese (DIO) C57/B6 mice without causing hypoglycemia. Novel GPR119 agonists therefore have the potential to function as anti-hyperglycemic agents that produce weight loss.

SUMMARY OF THE INVENTION

The present invention relates to compounds represented by the formula:

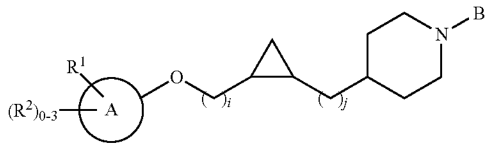

as well as pharmaceutically acceptable salts thereof.

The present invention further relates to methods of treating diabetes and related diseases and conditions.

DETAILED DESCRIPTION OF THE INVENTION

The present invention relates to compounds represented by the formula:

I

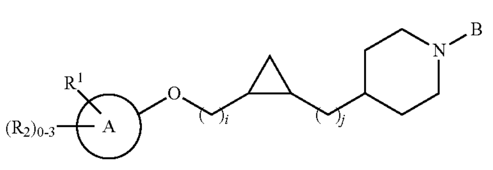

or a pharmaceutically acceptable salt thereof, wherein:

ring A is phenyl or a 6-membered heteroaryl, containing 1-2 N atoms;

B is a member selected from the group consisting of (1) $C(O)R^3$, (2) $C(O)OR^3$, (3) $C(O)NHR^3$, and (4) 5-membered heteroaryl containing 1-4 heteroatoms selected from O, S and N, wherein the 5-membered heteroaryl ring can be optionally fused with a 5- or 6-membered ring system; which can be optionally substituted with 1-3 $R^4$;

$R^1$ represents a member selected from the group consisting of (1) 3- to 6-membered heterocyclyl, containing 1-3 O, S, or N, (2) 5-membered heteroaryl, containing 1-4 O, S, or N, (3) aryl, (4) $C(O)C_{1-6}$alkyl, (5) $C(O)C_{3-8}$cycloalkyl, (6) $S(O)C_{1-6}$alkyl, (7) $SO_2C_{1-6}$alkyl, (8) $SO_2NH_2$, (9) $SO_2C_{3-8}$cycloalkyl,

(10) $SO_2NHC_{1-6}$alkyl,

(11) $SO_2N(C_{1-6}alkyl)_2$,

(12) CN,

(13) $C(O)NR^8R^9$, and

(14) $CH_2C(O)NR^5R^6$, wherein the heterocyclyl and heteroaryl moieties are optionally substituted by oxo, hydroxy, $C_{1-3}$alkyl, $C_{1-3}$alkoxy, or halo$C_{1-3}$alkyl, and the heterocyclyl moiety is further optionally substituted by oxo;

each $R^2$ is independently selected from the group consisting of (1) halogen, (2) $C_{1-6}$alkyl, (3) —$OC_{1-6}$alkyl, (4) CN, and (5) halo$C_{1-6}$alkyl;

$R^3$ represents a member selected from the group consisting of:

(1) $C_{1-6}$ alkyl, (2) halo$C_{1-6}$alkyl, (3) $C_{3-8}$cycloalkyl and (4) aryl, wherein alkyl moiety is optionally substituted with 1-2 of $C_{3-8}$cycloalkyl, phenyl, or 5-membered heteroaryl containing 1-3 O, S, or N; and wherein the cycloalkyl moiety is optionally fused with a $C_{3-6}$cycloalkyl or $C_{3-6}$cycloalkenyl;

$R^4$ is selected from the group consisting of:

(1) hydroxy, (2) $C_{1-6}$alkyl, (3) $C_{1-6}$alkoxy, (4) $C_{1-6}$alkyl-O—$C_{1-3}$alkyl, (5) $C_{1-6}$alkyl-O-halo$C_{1-3}$alkyl, (6) $C_{3-6}$cycloalkyl, optionally substituted by $C_{1-3}$alkyl or halo$C_{1-3}$alkyl, (7) $C_{3-6}$cycloalkoxy, and (8) aryl, wherein the alkyl moiety is optionally substituted by 1-3 halo, or hydroxy;

$R^5$ and $R^6$ are independently selected from the group consisting of (1) hydrogen, (2) $C_{1-6}$alkyl, (3) $C_{3-6}$cycloalkyl, optionally substituted by halo, haloalkyl, or alkyl (4) $C_{1-6}$alkyl-OH, (5) $C_{1-3}$alkyl-$C_{3-6}$cycloalkyl, (6) $C_{1-3}$alkyl-$C_{3-5}$heterocyclyl containing 1-3 N, O, or S, (7) $C_{3-5}$heterocyclyl containing 1-3 N, O or S, optionally substituted by 1-2 oxo, or alkyl, (8) $C_{1-3}$alkyl-5-membered heteroaryl containing 1-3 N, O or S, optionally substituted by $C_{1-3}$alkyl, (9) halo$C_{1-6}$alkyl, or $R^5$ and $R^6$ are linked together with the nitrogen to which they are both attached to form a 4-9 membered monocyclic or bicyclic heterocyclic ring, comprising C, O, N, and S ring atoms, wherein the heterocyclic ring is optionally substituted with 1-3 $R^7$;

each $R^7$ is selected from the group consisting of:

(1) halo, (2) hydroxy, (3) $C_{1-3}$alkoxy, (4) $C_{1-3}$alkyl, (5) halo$C_{1-3}$alkyl, (6) $C_{1-3}$alkyl-OH, (7) $C_{3-6}$cycloalkyl, (8) 5- or 6-membered heteroaryl, containing 1-3 N, O, or S, and (9) oxo;

$R^8$ and $R^9$ are independently selected from the group consisting of (1) hydrogen, (2) $C_{1-6}$alkyl, (3) $C_{1-6}$alkyl-OH, and (4) $C_{3-8}$cycloalkyl; and i and j independently represent integers selected from 0, 1 and 2, such that i plus j is 0, 1 or 2.

In one embodiment, the present invention relates to compounds of formula I, or a pharmaceutically acceptable salt thereof, wherein ring A is phenyl or a 6-membered heteroaryl, containing 1-2 N atoms.

In another class of this embodiment, ring A is a 6-membered heteroaryl, containing 1-2 N atoms.

In one subclass of this class, ring A is phenyl, pyridinyl, pyrimidinyl, pyridazinyl, or pyrazinyl.

In another subclass of this class, ring A is phenyl, pyridinyl, or pyrimidinyl.

In a subclass of this class, ring A is phenyl or pyrimidinyl.

In a subclass of this class, ring A is phenyl.

In a subclass of this class, ring A is pyridinyl.

In a subclass of this class, ring A is pyrimidinyl.

In one embodiment, the present invention relates to compounds of formula I, or a pharmaceutically acceptable salt thereof, wherein B is a member selected from the group consisting of $C(O)R^3$, $C(O)OR^3$, $C(O)NHR^3$, and 5-membered heteroaryl containing 1-4 heteroatoms selected from O, S and N, wherein the 5-membered heteroaryl ring can be optionally fused with a 5- or 6-membered ring system; which can be optionally substituted with 1-3 $R^4$.

In one embodiment, $R^4$ is selected from the group consisting of hydroxy, $C_{1-6}$alkyl, $C_{1-6}$alkoxy, $C_{1-6}$alkyl-O—$C_{1-3}$ alkyl, $C_{1-6}$alkyl-O-halo$C_{1-3}$alkyl, $C_{3-6}$cycloalkyl, optionally substituted by $C_{1-3}$alkyl or halo$C_{1-3}$alkyl, $C_{3-6}$cycloalkoxy, and aryl; wherein the alkyl moiety is optionally substituted by 1-3 halo, or hydroxy.

In one class of this embodiment, $R^4$ is selected from the group consisting of

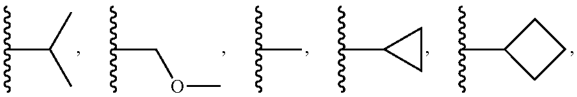,

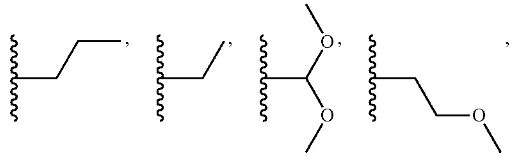,

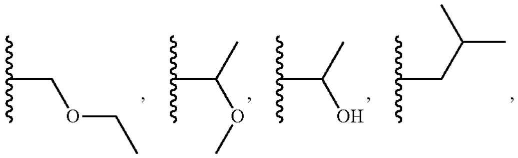,

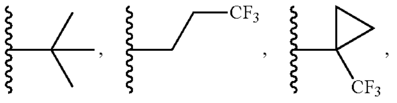,

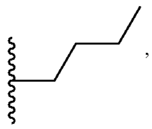, and 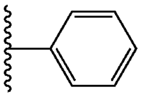.

In one embodiment, the present invention relates to compounds of formula I, or a pharmaceutically acceptable salt thereof, wherein B is a 5,5- or 5,6-fused heteroaryl moiety with the C ring being any 5-membered heteroaryl moiety:

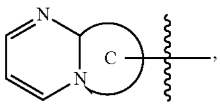, 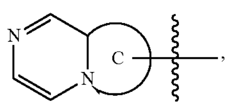,

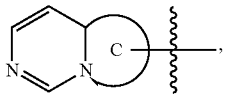, 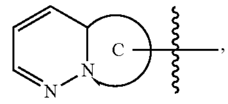,

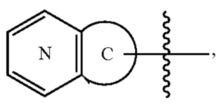, 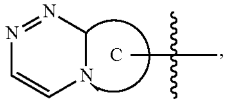,

-continued

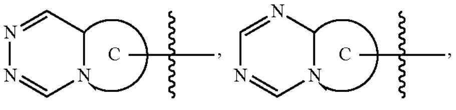

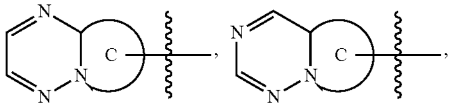

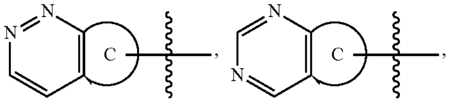

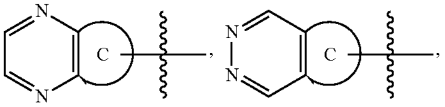

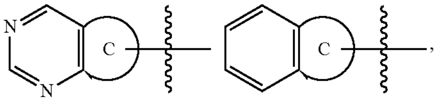

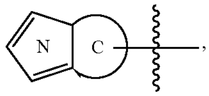, 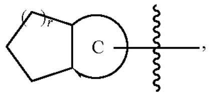, and

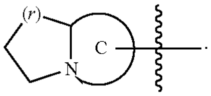.

In one embodiment, the present invention relates to compounds of formula I, or a pharmaceutically acceptable salt thereof, wherein B is selected from the group consisting of

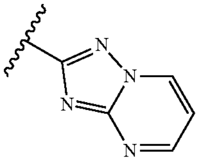, 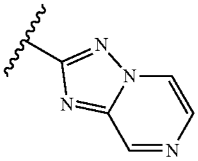, and

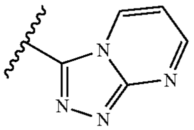.

In one embodiment, the present invention relates to compounds of formula I, or a pharmaceutically acceptable salt thereof, wherein B is selected from the group consisting of

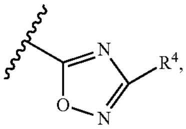 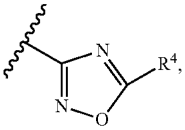 and

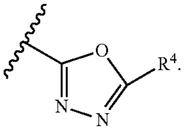

In one class of this embodiment, $R^4$ is selected from the group consisting of

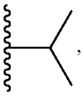, 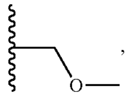, 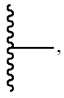, 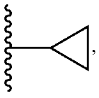, 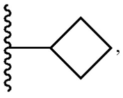,

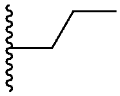, 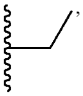, 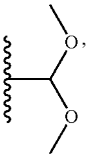, 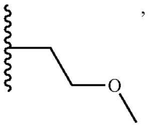,

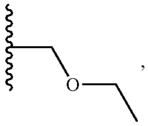, 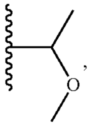, 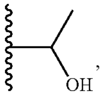, 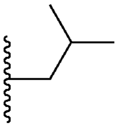,

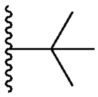, 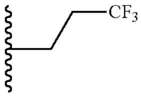, 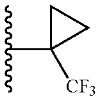,

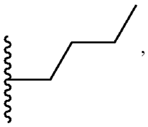, and 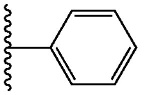.

In one class of this embodiment, B is selected from the group consisting of

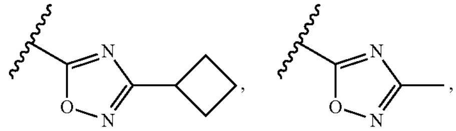

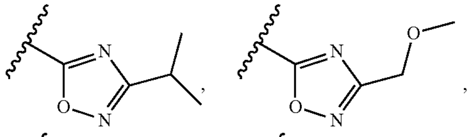

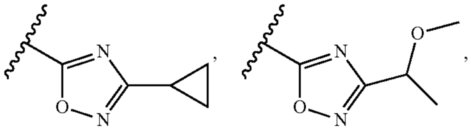

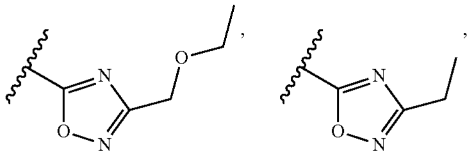

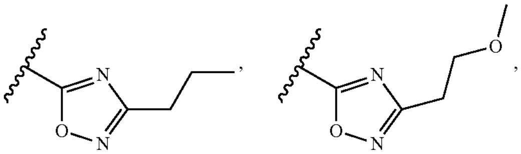

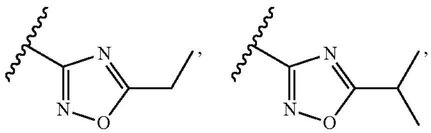

-continued

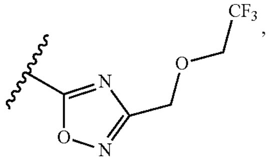

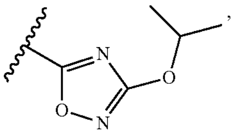

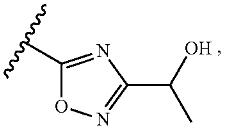

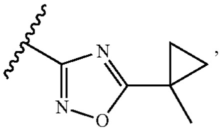

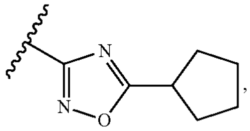

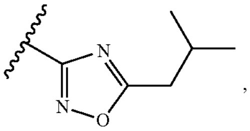

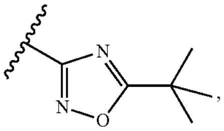

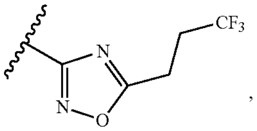

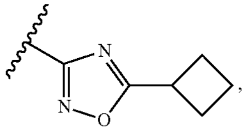

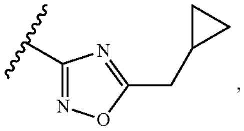

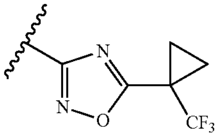

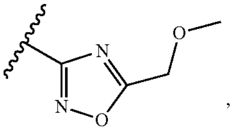

,

,

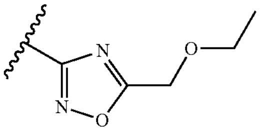

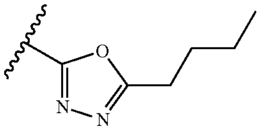

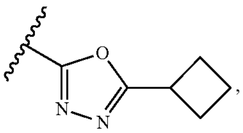

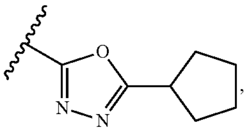

and

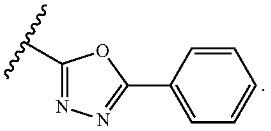

In one embodiment, the present invention relates to compounds of formula I, or a pharmaceutically acceptable salt thereof, wherein B is $C(O)R^3$, and $R^3$ is $C_{1-6}$ alkyl, or halo$C_{1-6}$ alkyl;

wherein alkyl is optionally substituted with $C_{3-8}$cycloalkyl, or 5-membered heteroaryl containing 1-3 O, S, or N; and wherein the cycloalkyl is optionally fused with a $C_{3-6}$cycloalkyl or $C_{3-6}$cycloalkenyl.

In one class of this embodiment, B is selected from the group consisting of

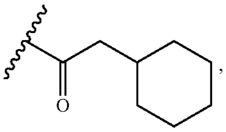

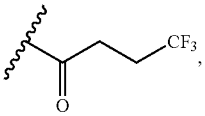

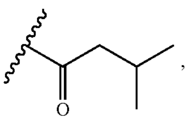

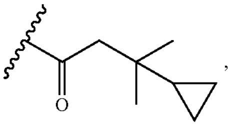

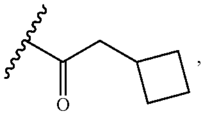

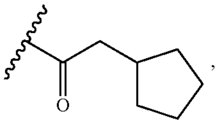

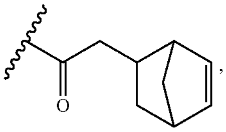

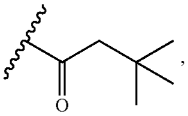

and

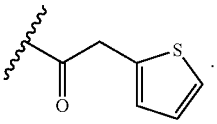

In one embodiment, the present invention relates to compounds of formula I, or a pharmaceutically acceptable salt thereof, wherein B is $C(O)OR^3$, and $R^3$ is $C_{1-6}$ alkyl, halo$C_{1-6}$ alkyl, or $C_{3-8}$cycloalkyl, wherein alkyl is optionally substituted with $C_{3-8}$cycloalkyl, or phenyl.

In one embodiment, B is selected from the group consisting of

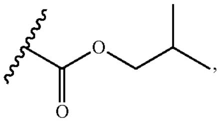

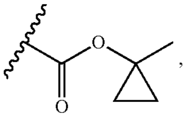

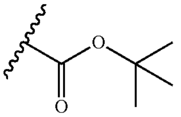

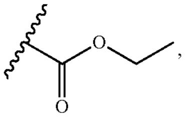

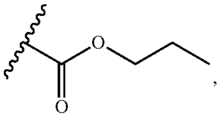

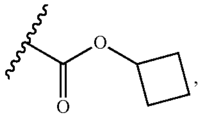

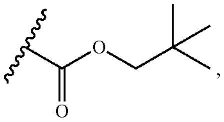

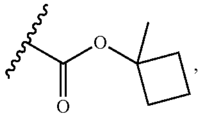

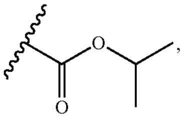

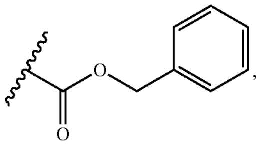

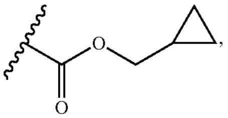

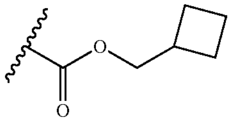

-continued
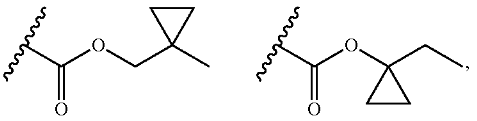
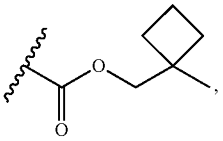
and
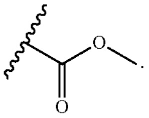
In one embodiment, the present invention relates to compounds of formula I, or a pharmaceutically acceptable salt thereof, wherein B is selected from the group consisting of
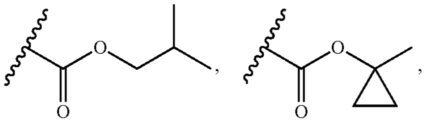
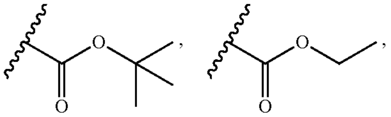
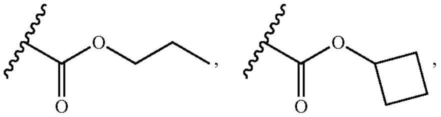
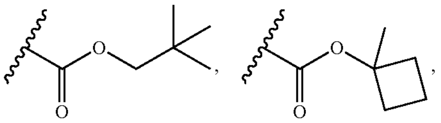
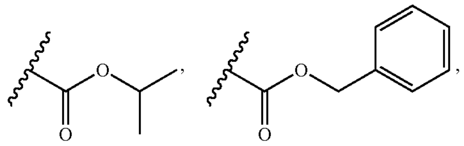
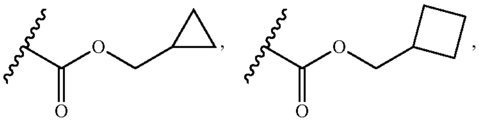
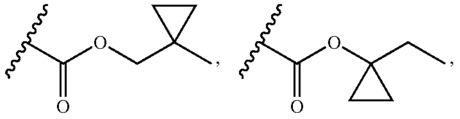
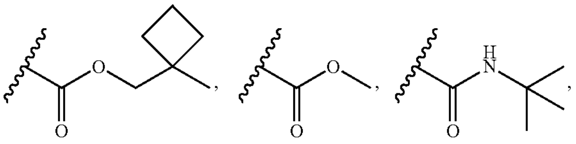
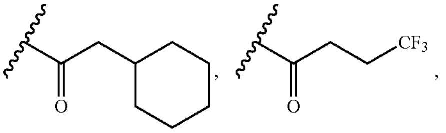
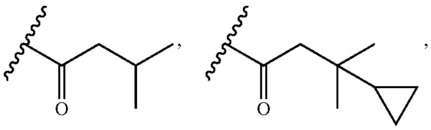
-continued
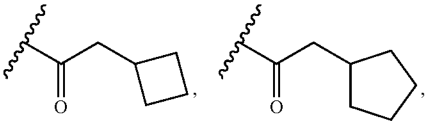
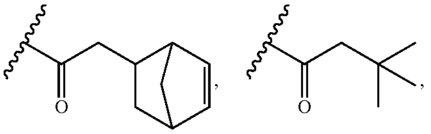
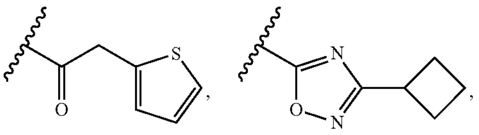
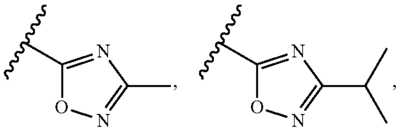
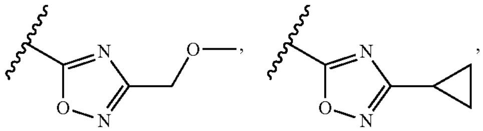
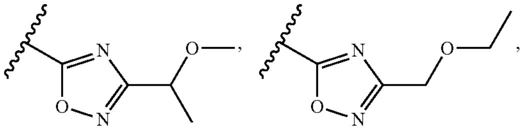
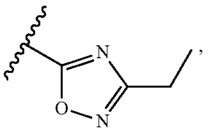
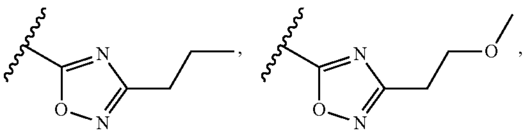
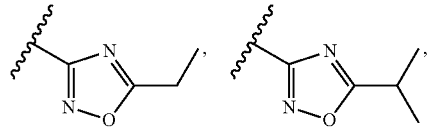
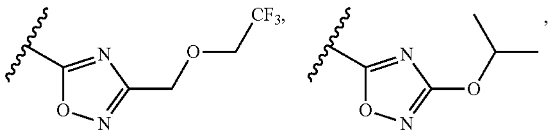
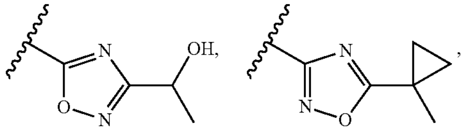
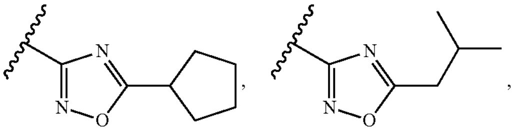
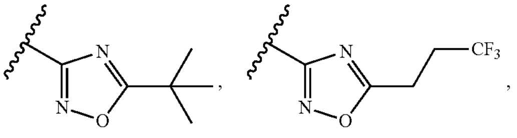

-continued

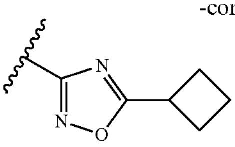, 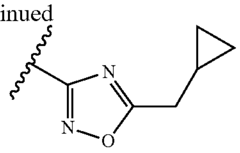,

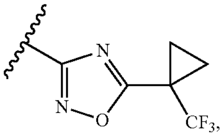 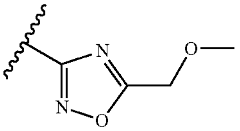,

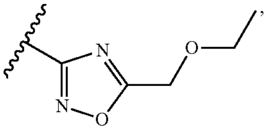 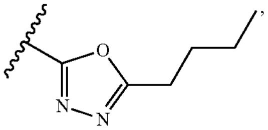

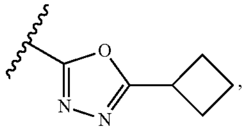, 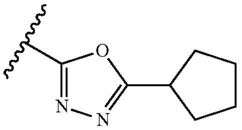,

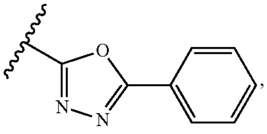, 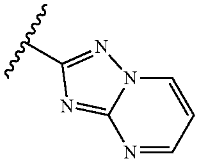,

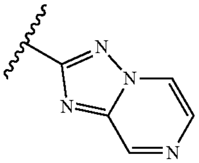, and 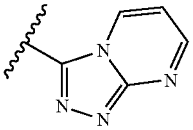.

In one embodiment, the present invention relates to compounds of formula I, or a pharmaceutically acceptable salt thereof, wherein $R^1$ represents a member selected from the group consisting of 3- to 6-membered heterocyclyl, containing 1-3 O, S, or N; 5-membered heteroaryl, containing 1-4 O, S, or N, optionally substituted by $C_{1-3}$alkyl; aryl; $C(O)C_{1-6}$alkyl; $C(O)C_{3-8}$cycloalkyl; $S(O)C_{1-6}$alkyl; $SO_2C_{1-6}$alkyl; $SO_2NH_2$; $SO_2C_{3-8}$cycloalkyl; $SO_2NHC_{1-6}$alkyl; $SO_2N(C_{1-6}alkyl)_2$; CN; $C(O)NR^8R^9$; and $CH_2C(O)NR^5R^6$; wherein the heterocyclyl and heteroaryl moieties are optionally substituted by oxo, hydroxy, $C_{1-3}$alkyl, $C_{1-3}$alkoxy, or halo$C_{1-3}$alkyl, and the heterocyclyl moiety is further optionally substituted by oxo.

In one class of this embodiment, $R^1$ represents a member selected from the group consisting of 3- to 6-membered heterocyclyl, containing 1-3 O, S, or N, optionally substituted by oxo; 5-membered heteroaryl, containing 1-4 O, S, or N, optionally substituted by $C_{1-3}$alkyl; aryl; $C(O)C_{1-6}$alkyl; $C(O)C_{3-8}$cycloalkyl; $SO_2C_{1-6}$alkyl; $SO_2C_{3-8}$cycloalkyl; CN; $C(O)NR^8R^9$; and $CH_2C(O)NR^5R^6$.

In one class of this embodiment, $R^1$ is CN.

In a subclass of this class, ring A is pyrimidinyl.

In one class of this embodiment, $R^1$ is 3- to 6-membered heterocyclyl, containing 1-3 O, S, or N, optionally substituted by oxo.

In a subclass of this class, $R^1$ is

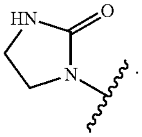.

In one sub-subclass of this subclass, ring A is phenyl.

In one sub-subclass of this subclass, ring A is pyridinyl.

In one class of this embodiment, $R^1$ is 5-membered heteroaryl, containing 1-4 O, S, or N, optionally substituted by $C_{1-3}$alkyl.

In a subclass of this class, $R^1$ is

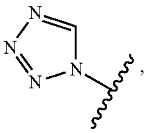, 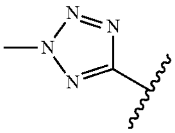, 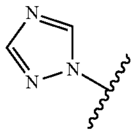, and

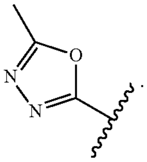.

In one sub-subclass of this subclass, ring A is phenyl.

In one sub-subclass of this subclass, ring A is pyridinyl.

In one class of this embodiment, $R^1$ is $C(O)C_{1-6}$alkyl or $C(O)C_{3-8}$cycloalkyl.

In a subclass of this class, $R^1$ is

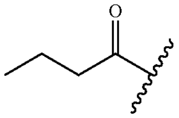 or 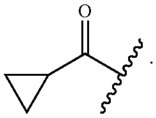.

In one sub-subclass of this subclass, ring A is phenyl.

In one sub-subclass of this subclass, ring A is pyridinyl.

In one class of this embodiment, $R^1$ is $S(O)C_{1-6}$alkyl, or $SO_2C_{3-8}$cycloalkyl.

In a subclass of this class, $R^1$ is

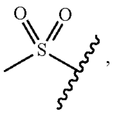, 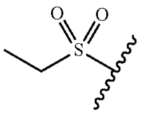, 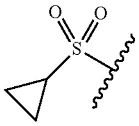,

In one sub-subclass of this subclass, ring A is phenyl.

In one sub-subclass of this subclass, ring A is pyridinyl.

In one class of this embodiment, $R^1$ is $C(O)NR^8R^9$.
In a subclass of this class, $R^1$ is
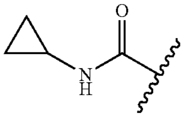, or 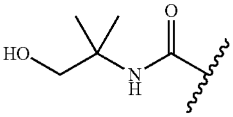.
In one sub-subclass of this subclass, ring A is phenyl.
In one sub-subclass of this subclass, ring A is pyridinyl.
In one class of this embodiment, $R^1$ is $CH_2C(O)NR^5R^6$.
In a subclass of this class, $R^1$ is selected from the group consisting of
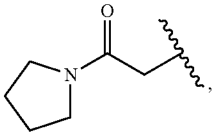, 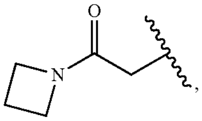,
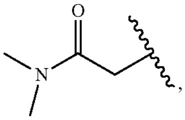, 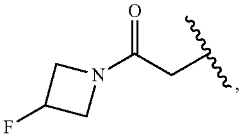,
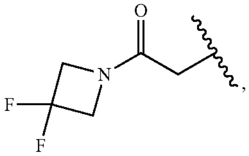, 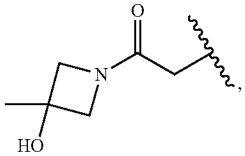,
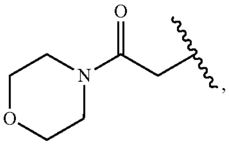, 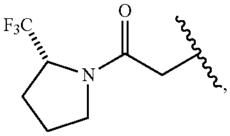,
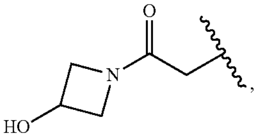, 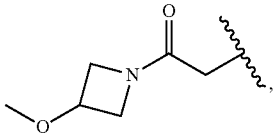,
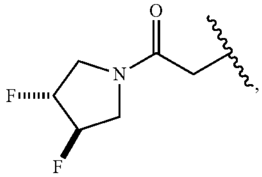, 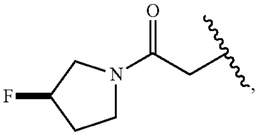,
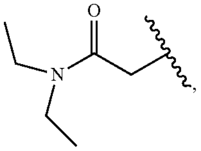, 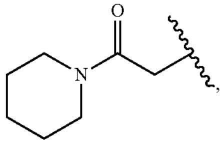,
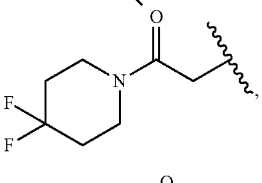, 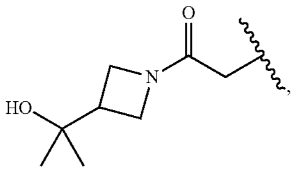,
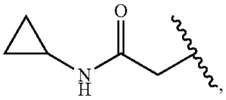, 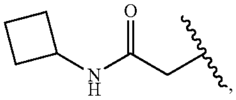,
-continued
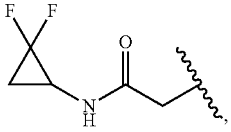, 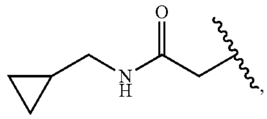,
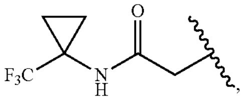, 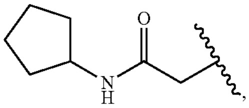,
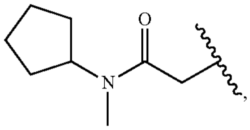, 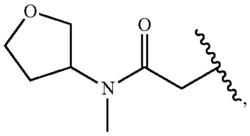,
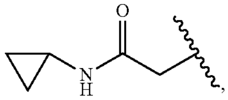, 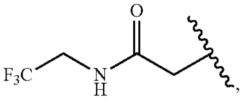,
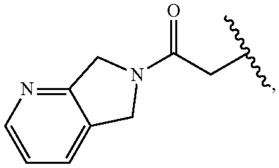, 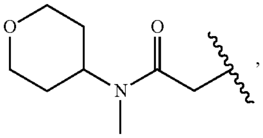,
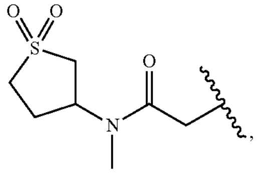, 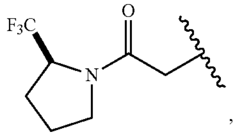,
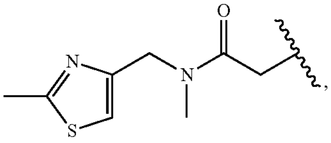,
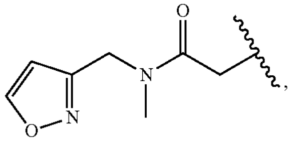, 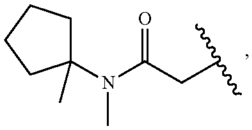,
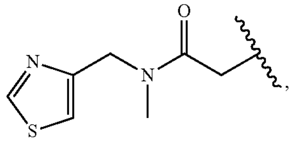, 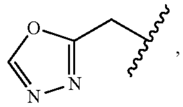,
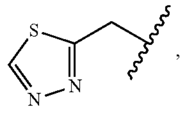, 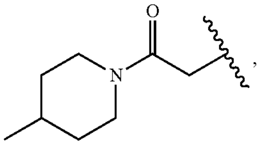,
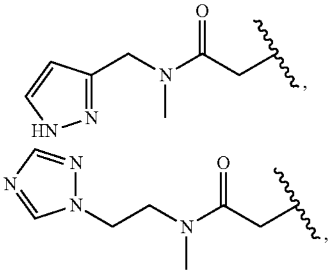, -continued
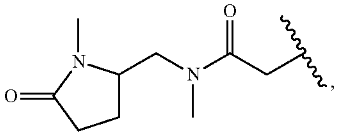,
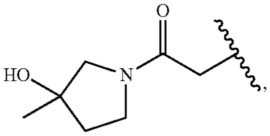, 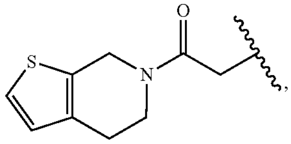,
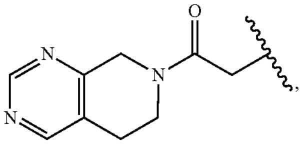,
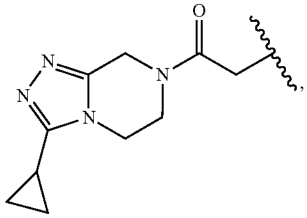,
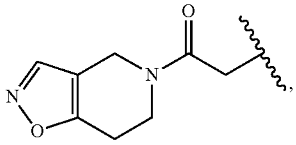,
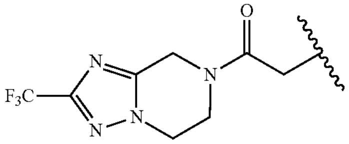,
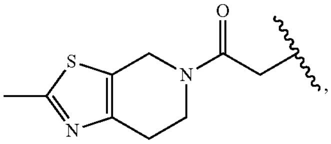,
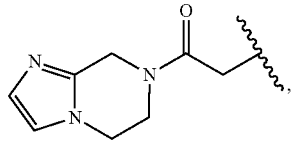,
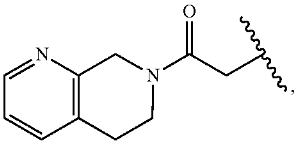,
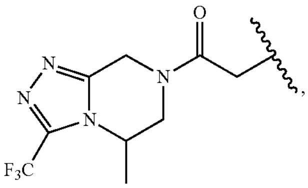,
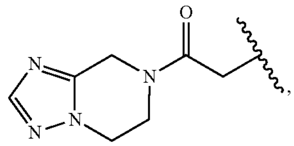,
-continued
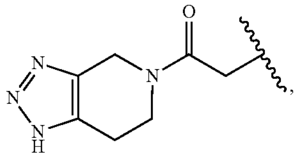, 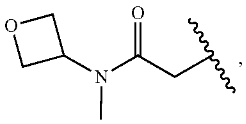,
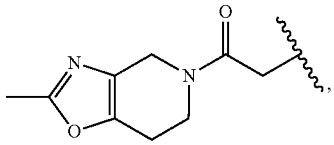,
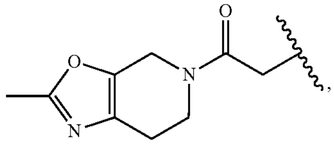,
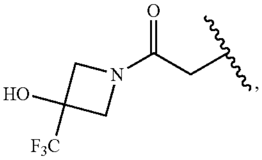, 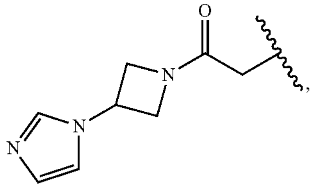,
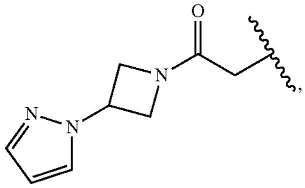,
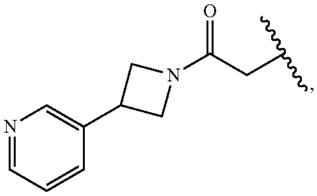,
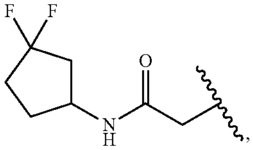, 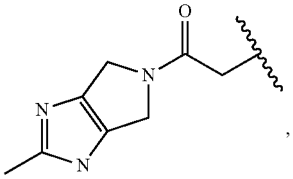,
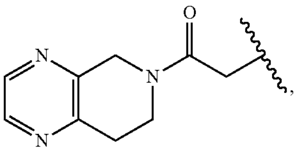,
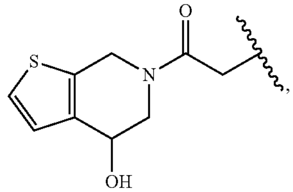,
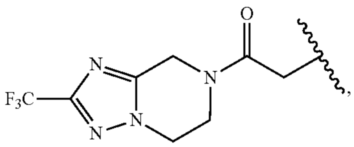, -continued
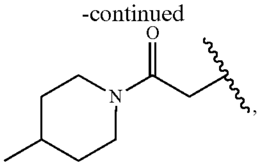,
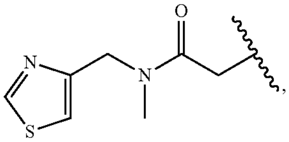, 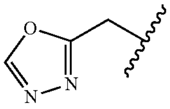,
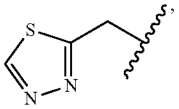, 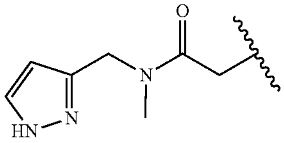,
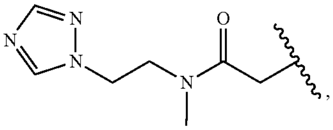, and
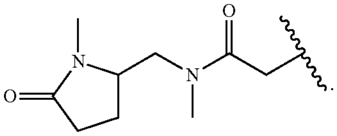.
In one sub-subclass of this subclass, ring A is phenyl.
In one sub-subclass of this subclass, ring A is pyridinyl.
In one class of this embodiment, $R^1$ is selected from the group consisting of
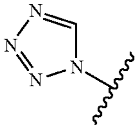, 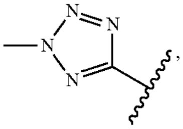, 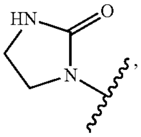 [SMILES: *N1CCNC1=O],
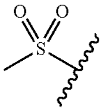, 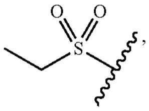, 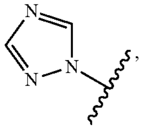,
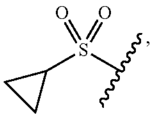, 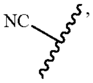, 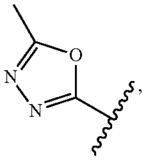,
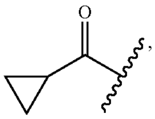, 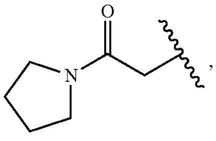,
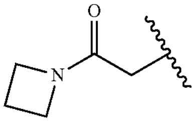, 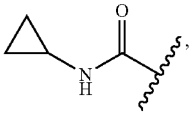,
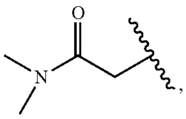, 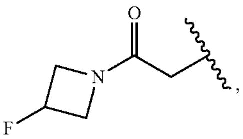,
-continued
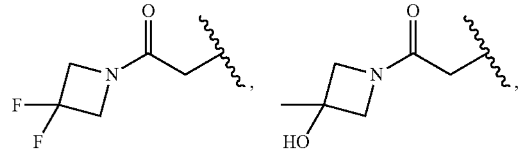
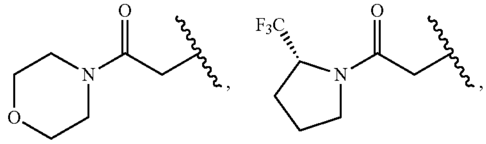
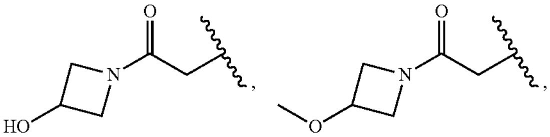
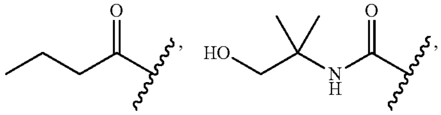
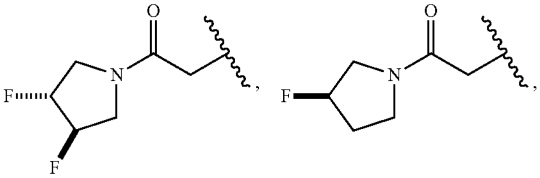
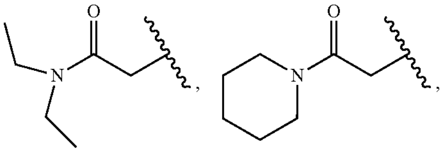
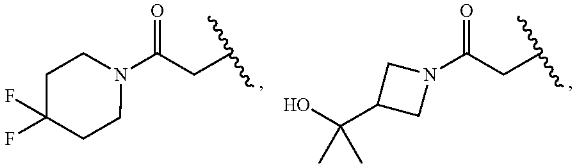
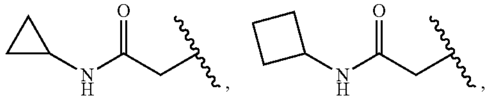
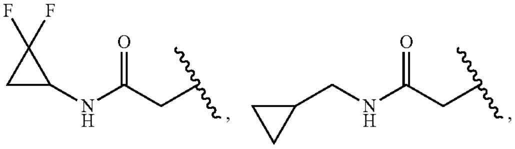
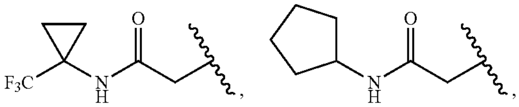
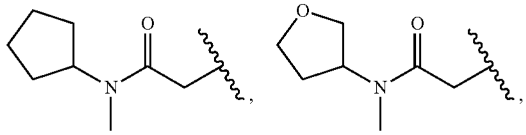
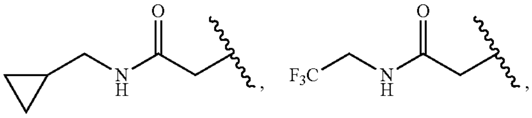

-continued
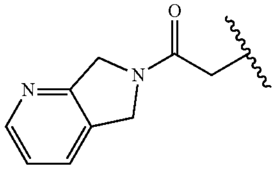,
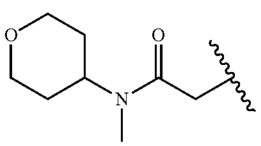,
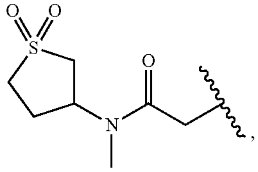,
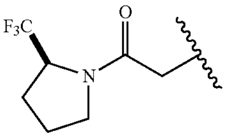,
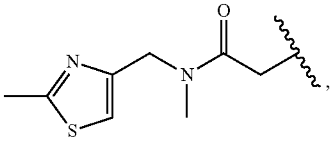,
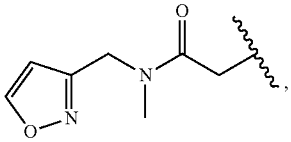,
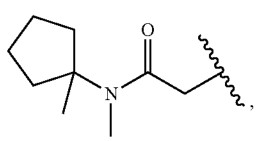,
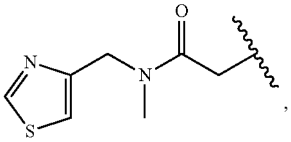,
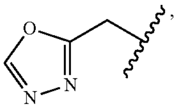,
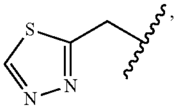,
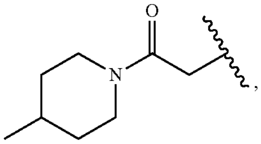,
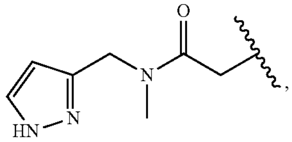,
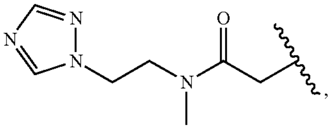,
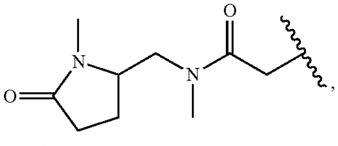,
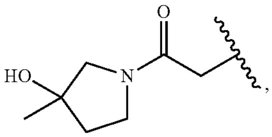,
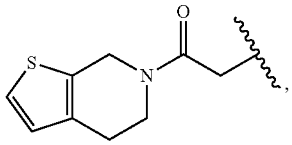,
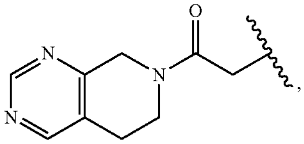,
-continued
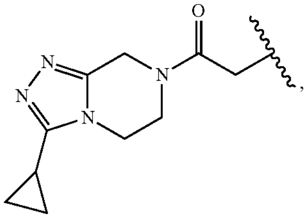,
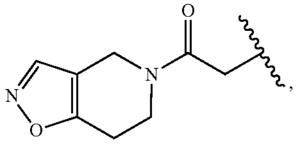,
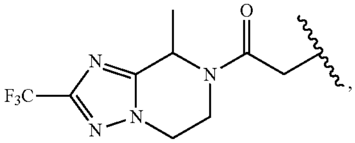,
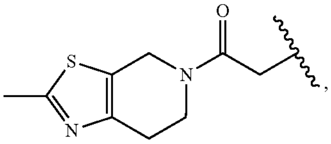,
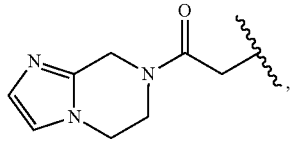,
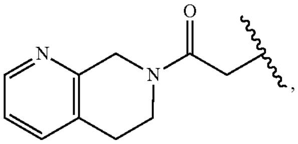,
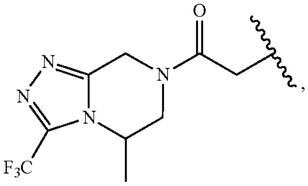,
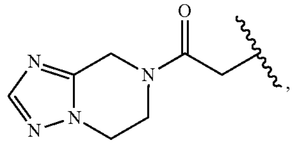,
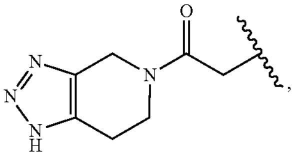,
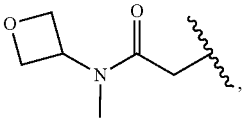,
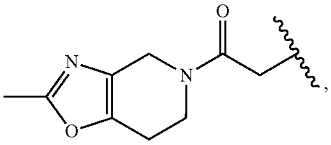,
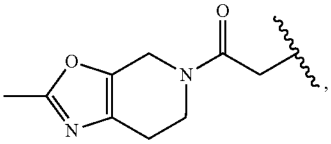, -continued

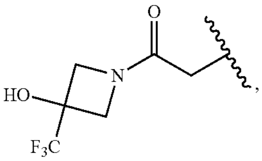,

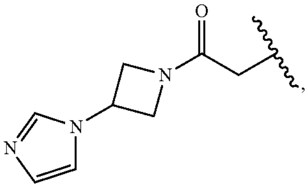,

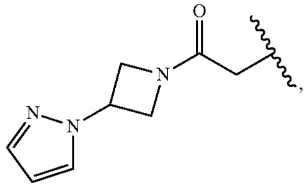,

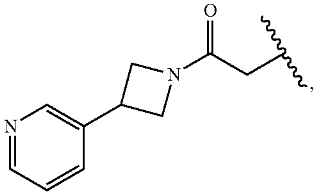,

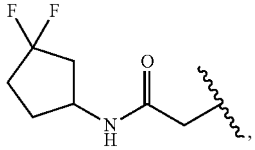,

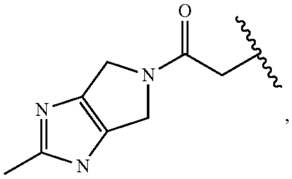,

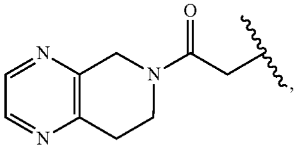,

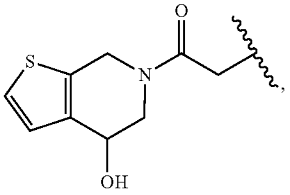,

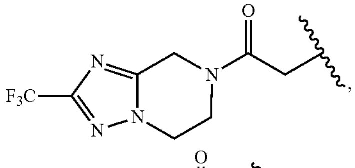,

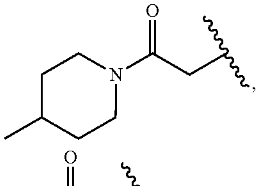,

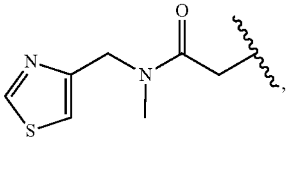,

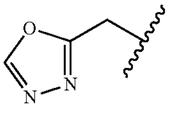,

-continued

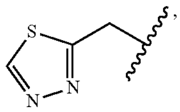,

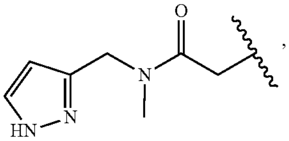,

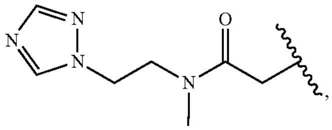, and

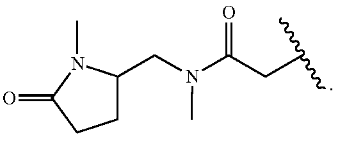.

In one embodiment, the present invention relates to compounds of formula I, or a pharmaceutically acceptable salt thereof, wherein each $R^2$ is independently selected from the group consisting of from halogen, $C_{1-6}$alkyl, —$OC_{1-6}$ alkyl, CN, and halo$C_{1-6}$alkyl.

In one class of this embodiment, each $R^2$ is methyl, chloro, fluoro, CN, or methoxy.

In one embodiment, the present invention relates to compounds of formula I, or a pharmaceutically acceptable salt thereof, wherein i and j represent 0, 1 or 2, such that the sum of i and j is 2.

In one class of this embodiment, i is 2; and j is 0. In another class of this embodiment, i is 1; and j is 1. In yet another embodiment, i is 0; and j is 2.

In one embodiment, the invention relates to compounds of formula I, or a pharmaceutically acceptable salt, thereof, wherein the cyclopropyl ring is the cis cyclopropyl isomer.

In one class of this embodiment, the cyclopropyl ring of formula I has the 1S and 2S stereocenters.

In one class of this embodiment, the cyclopropyl ring of formula I has the 1R and 2R stereocenters.

In one class of this embodiment, the cyclopropyl ring of formula I has the 1S and 2R stereocenters.

In one subclass of this class, the compound is present in at least 90% diastereomeric excess.

In one subclass of this class, the compound is present in at least 95% diastereomeric excess.

In one subclass of this class, the compound is present in at least 99% diastereomeric excess.

In one embodiment, ring A is phenyl; and B is $C(O)R^3$.

In one class of this embodiment, $R^3$ is $C_{1-6}$ alkyl, or halo$C_{1-6}$ alkyl;

wherein alkyl is optionally substituted with $C_{3-8}$cycloalkyl, or 5-membered heteroaryl containing 1-3 O, S, or N; and wherein the cycloalkyl is optionally fused with a $C_{3-6}$cycloalkyl or $C_{3-6}$cycloalkenyl.

In one embodiment, ring A is phenyl; and B is $C(O)OR^3$.

In one class of this embodiment, $R^3$ is $C_{1-6}$ alkyl, halo$C_{1-6}$ alkyl, or $C_{3-8}$cycloalkyl, wherein alkyl is optionally substituted with $C_{3-8}$cycloalkyl, or phenyl.

In one embodiment, ring A is pyridinyl; and B is C(O) $NHR^3$.

In one class of this embodiment, B is

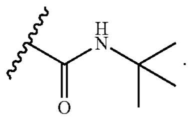 [SMILES: *C(=O)NC(C)(C)C]

In a subclass of this class, ring A is phenyl.

In a subclass of this class, ring A is pyridinyl.

In one embodiment, ring A is phenyl; and B is a 5-membered heteroaryl containing 1-4 heteroatoms selected from O, S and N, wherein the 5-membered heteroaryl ring can be optionally fused with a 5- or 6-membered ring system; which can be optionally substituted with 1-3 $R^4$.

In one class of this embodiment, B is selected from the group consisting of

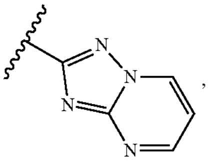
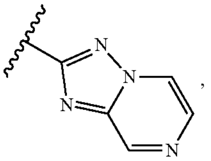
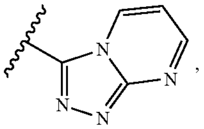
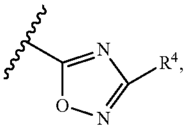
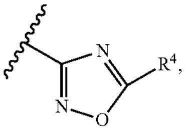 and 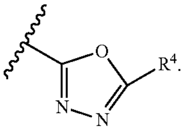

In a subclass of this class, $R^4$ is $C_{1-6}$alkyl-O—$C_{1-3}$alkyl.

In one embodiment, ring A is pyridinyl; and B is $C(O)R^3$.

In one class of this embodiment, $R^3$ is $C_{1-6}$ alkyl, or halo$C_{1-6}$ alkyl;

wherein alkyl is optionally substituted with $C_{3-8}$cycloalkyl, or 5-membered heteroaryl containing 1-3 O, S, or N; and wherein the cycloalkyl is optionally fused with a $C_{3-6}$cycloalkyl or $C_{3-6}$cycloalkenyl.

In one embodiment, ring A is pyridinyl; and B is $C(O)OR^3$.

In one class of this embodiment, $R^3$ is $C_{1-6}$ alkyl, halo$C_{1-6}$ alkyl, or $C_{3-8}$cycloalkyl, wherein alkyl is optionally substituted with $C_{3-8}$cycloalkyl, or phenyl.

In one embodiment, ring A is pyridinyl; and B is C(O) $NHR^3$.

In one class of this embodiment, B is

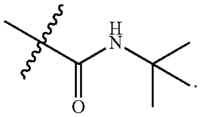 [SMILES: *C(=O)NC(C)(C)C]

In one embodiment, ring A is pyridinyl; and B is a 5-membered heteroaryl containing 1-4 heteroatoms selected from O, S and N, wherein the 5-membered heteroaryl ring can be optionally fused with a 5- or 6-membered ring system; which can be optionally substituted with 1-3 $R^4$.

In one class of this embodiment, B is selected from the group consisting of

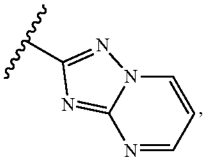
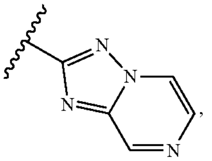
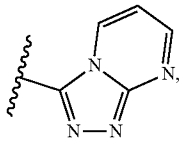
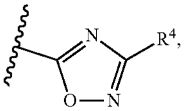
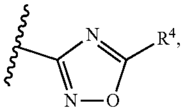 and 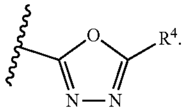

In a subclass of this class, $R^4$ is $C_{1-6}$alkyl-O—$C_{1-3}$alkyl.

In one embodiment, the present invention relates to compounds of formula I-A:

I-A

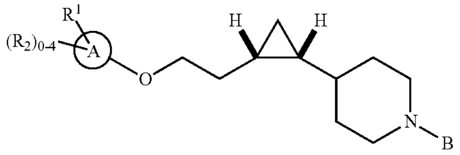

or a pharmaceutically acceptable salt thereof, wherein ring A, B, $R^1$, and $R^2$ are previously defined.

In one embodiment, the present invention relates to compounds of formula I-B:

I-B

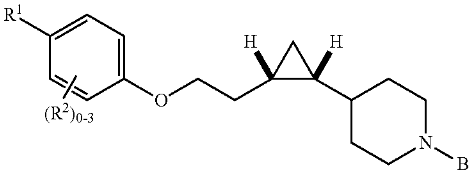

or a pharmaceutically acceptable salt thereof, wherein B, $R^1$, and $R^2$ are previously defined.

In one embodiment, the present invention relates to compounds of formula I-C:

I-C

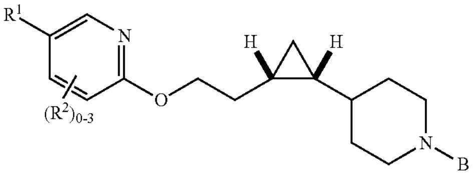

or a pharmaceutically acceptable salt thereof, wherein B, $R^1$, and $R^2$ are previously defined.

In one class of this embodiment, B is $C(O)R^3$.

In one class of this embodiment, B is $C(O)OR^3$.

In one class of this embodiment. B is selected from the group consisting of

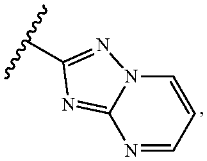,
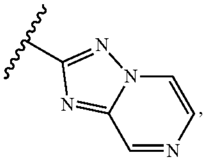,
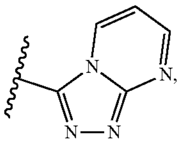,
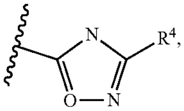,
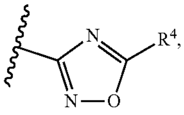, and
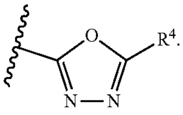.

The present invention further relates to compounds of formula I-D:

I-D

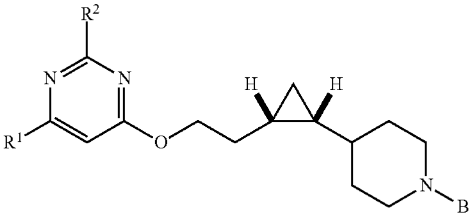

or a pharmaceutically acceptable salt thereof, wherein B, $R^1$, and $R^2$ are previously defined.

In one class of this embodiment, B is $C(O)R^3$.

In one class of this embodiment, B is $C(O)OR^3$.

In one class of this embodiment, B is selected from the group consisting of

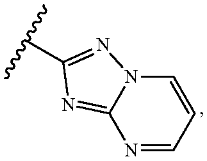,
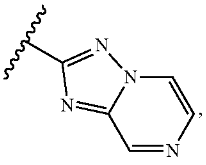,
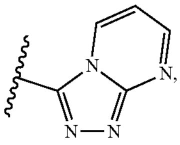,
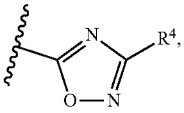,
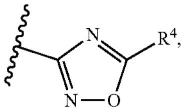, and
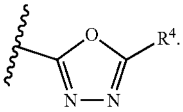.

The present invention further relates to compounds of formula I-E:

I-E

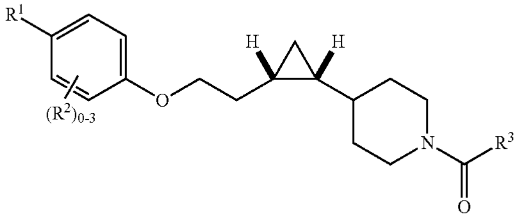

or a pharmaceutically acceptable salt thereof, wherein $R^1$, $R^2$ and $R^3$ are previously defined.

The present invention further relates to compounds of formula I-F:

I-F

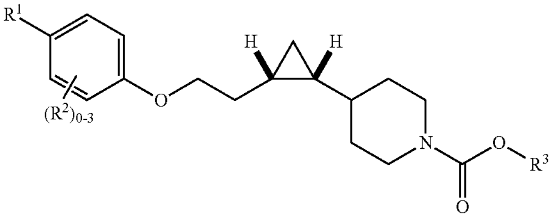

or a pharmaceutically acceptable salt thereof, wherein $R^1$, $R^2$ and $R^3$ are previously defined.

The present invention further relates to compounds of formula I-G:

I-G

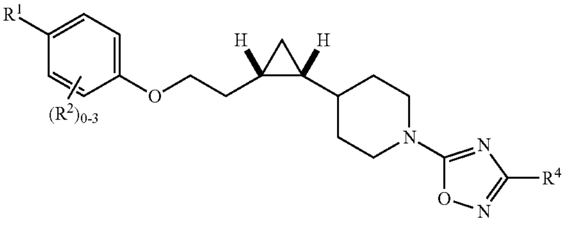

or a pharmaceutically acceptable salt thereof, wherein $R^1$, $R^2$, and $R^4$ are previously defined.

The present invention further relates to compounds of formula I-H:

I-H

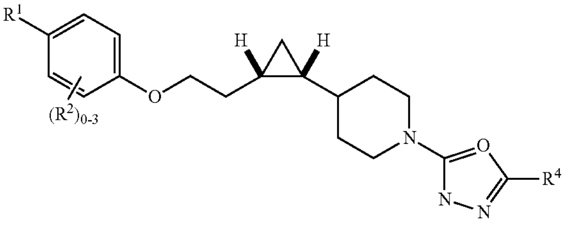

or a pharmaceutically acceptable salt thereof, wherein $R^1$, $R^2$, and $R^4$ are previously defined.

The present invention further relates to compounds of formula I-I:

I-I

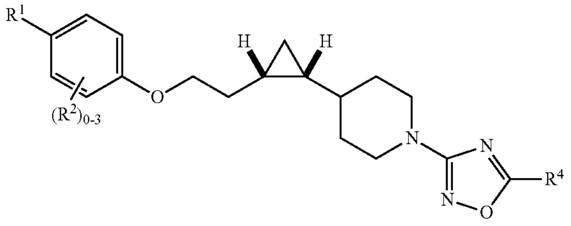

or a pharmaceutically acceptable salt thereof, wherein $R^1$, $R^2$, and $R^4$ are previously defined.

The invention is described herein in detail using the terms defined below unless otherwise specified.

"Alkyl", as well as other groups having the prefix "alk", such as alkoxy, and the like, means carbon chains which may be linear or branched, or combinations thereof, containing the indicated number of carbon atoms. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, heptyl, octyl, nonyl and the like.

As used herein, "cycloalkyl" means a saturated cyclic hydrocarbon radical having the number of carbon atoms designated if no number of atoms is specified, 3-7 carbon atoms are intended, forming 1-3 carbocyclic rings that are fused. "Cycloalkyl" also includes monocyclic rings fused to an aryl group in which the point of attachment is on the non-aromatic portion. Examples of cycloalkyl include cyclopropyl, cyclobutyl, cyclopentyl, cyclohexyl, cycloheptyl, tetrahydronaphthyl, decahydronaphthyl, indanyl and the like.

"Alkyl-OH" or "hydroxyalkyl" means an alkyl group linked to a hydroxy group.

"Alkoxy" refers to an alkyl group linked to oxygen.

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

"Haloalkoxy" and "haloalkylO" are used interchangeably and refer to halo substituted alkyl groups linked through the oxygen atom. Haloalkoxy include mono-substituted as well as multiple halo substituted alkoxy groups, up to perhalo substituted alkoxy. For example, trifluoromethoxy is included.

"Haloalkyl" include mono-substituted as well as multiple halo substituted alkyl groups, up to perhalo substituted alkyl. For example, trifluoromethyl is included.

As used herein, "heterocyclyl" "heterocycle" or "heterocyclic" refers to nonaromatic cyclic ring structures in which one or more atoms in the ring, the heteroatom(s), is an element other than carbon. Heteroatoms are typically O, S or N atoms. Examples of heterocyclyl groups include: piperidine, piperazine, morpholine, pyrrolidine, tetrahydrofuran, azetidine, oxirane, or aziridine, and the like.

"Heteroaryl" (HAR) unless otherwise specified, means an aromatic or partially aromatic heterocycle that contains at least one ring heteroatom selected from O, S and N. Heteroaryls thus includes heteroaryls fused to other kinds of rings, such as aryls, cycloalkyls and heterocycles that are not aromatic. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like. For heterocyclic and heteroaryl groups, rings and ring systems containing from 3-15 atoms are included, forming 1-3 rings.

"Halogen" (Halo) includes fluorine, chlorine, bromine and iodine.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within the formulas described herein can be prepared without undue experimentation by conventional techniques well known to those skilled in the art or by processes analogous to those described in the Schemes and Examples herein using appropriate isotopically-enriched reagents and/or intermediates.

The individual tautomers of the compounds of the formulas described herein, as well as mixture thereof, are encompassed with compounds of the formulas described herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds of the formulas described herein may be separated into diastereoisomeric pairs of enantiomers by, for example, fractional crystallization from a suitable solvent. The pair of enantiomers thus obtained may be separated into individual stereoisomers by conventional means, for example by the use of an optically active amine or acid as a resolving agent or on a chiral HPLC column.

Alternatively, any enantiomer of a compound of the formulas described herein may be obtained by stereospecific synthesis using optically pure starting materials or reagents of known configuration.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced within the formulas. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of Formula I and pharmaceutically acceptable salts thereof.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I or Ia may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of the structural formulas described herein are also included in the present invention.

Compounds of the present invention are potent agonists of the GPR 119 receptor. These compounds and pharmaceutically acceptable salts thereof are modulators of the receptor known as GPR 119, and are therefore useful in the treatment of diseases that are modulated by GPR119 ligands and agonists. Many of these diseases are summarized below. Said compounds may be used for the manufacture of a medicament for treating one or more of diseases or conditions, including, without limitation:

(1) noninsulin dependent diabetes mellitus (type 2 diabetes);

(2) hyperglycemia;

(3) metabolic syndrome/syndrome X;

(4) obesity;

(5) ischemia and myocardial infarction;

(6) neurological disorders such as Alzheimer's disease, schizophrenia, and impaired cognition;

(5) hypercholesterolemia;

(6) hypertriglyceridemia (elevated levels of triglyceride-rich-lipoproteins);

(7) mixed or diabetic dyslipidemia;

(8) low HDL cholesterol;

(9) high LDL cholesterol;

(10) Hyperapobetalipoproteinemia; and

(11) atherosclerosis.

Because the compounds are agonists of the GPR119 receptor, the compounds will be useful for lowering glucose, lipids, and insulin resistance in diabetic patients and in non-diabetic patients who have impaired glucose tolerance and/or are in a pre-diabetic condition. The compounds are useful to ameliorate hyperinsulinemia, which often occurs in diabetic or prediabetic patients, by modulating the swings in the level of serum glucose that often occurs in these patients. The compounds are useful for treating or reducing insulin resistance. The compounds are useful for treating or preventing gestational diabetes.

Additionally, by keeping hyperglycemia under control, the compounds are useful to delay or for preventing vascular restenosis and diabetic retinopathy.

The compounds of this invention are useful in improving or restoring β-cell function, so that they may be useful in treating type 1 diabetes or in delaying or preventing a patient with type 2 diabetes from needing insulin therapy.

The compounds, compositions, and medicaments as described herein are further useful for reducing the risks of adverse sequelae associated with metabolic syndrome, or Syndrome X, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

The compounds may be useful for reducing appetite and body weight in obese subjects and may therefore be useful in reducing the risk of co-morbidities associated with obesity such as hypertension, atherosclerosis, diabetes, and dyslipidemia.

By elevating levels of active GLP-1 in vivo, the compounds are useful in treating neurological disorders such as Alzheimer's disease, multiple sclerosis, and schizophrenia.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of the formulas described herein or a pharmaceutically acceptable salt thereof. The compound may be used alone or advantageously may be administered with a cholesterol biosynthesis inhibitor, particularly an HMG-CoA reductase inhibitor (e.g., simvastatin, atorvastatin, and the like). The compound may also be used advantageously in combination with other lipid lowering drugs such as cholesterol absorption inhibitors (e.g., stanol esters, sterol glycosides or azetidinones such as ezetimibe), ACAT inhibitors (e.g., avasimibe), CETP inhibitors (e.g. anacetrapib), niacin, bile acid sequestrants, microsomal triglyceride transport inhibitors, and bile acid reuptake inhibitors. Such combination treatments are useful for the treatment or control of conditions such hypercholesterolemia, atherosclerosis, hyperlipidemia, hypertriglyceridemia, dyslipidemia, high LDL, and low HDL.

Another aspect of the invention provides a method for the treatment and control of obesity or metabolic syndrome, which comprises administering to a patient in need of such treatment a therapeutically effective amount of a compound having the formulas described herein or a pharmaceutically acceptable salt thereof. The compound may be used alone or advantageously may be administered with an anti-obesity agent, such as a lipase inhibitor (e.g., orlistat,) or a monoamine neurotransmitter uptake inhibitor (e.g., sibutramine or phentermine). The compound may also be used advantageously in combination with CB-I inverse agonists or antagonists (e.g., rimonabant or taranabant).

The present invention further relates to a method of treating hyperglycemia, diabetes or insulin resistance in a mammalian patient in need of such treatment which comprises administering to said patient a compound in accordance with the formulas described herein or a pharmaceutically acceptable salt thereof in an amount that is effective to treat hyperglycemia, diabetes or insulin resistance.

Yet another aspect of the invention that is of interest relates to a method of treating atherosclerosis in a mammalian patient in need of such treatment, comprising administering to said patient a compound in accordance with a compound in accordance with the formulas described herein or a pharmaceutically acceptable salt thereof in an amount that is effective to treat atherosclerosis.

Yet another aspect of the invention that is of interest relates to a method of delaying the onset of one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to delay the onset of said condition.

Yet another aspect of the invention that is of interest relates to a method of reducing the risk of developing one of the aforementioned conditions and disorders where insulin resistance is a component in a mammalian patient in need thereof, comprising administering to the patient a compound in accordance with the formulas described herein or a pharmaceutically acceptable salt thereof in an amount that is effective to reduce the risk of developing said condition.

Yet another aspect of the invention that is of interest relates to a method of treating a condition or reducing the risk of developing a condition or delaying the onset of a condition selected from the group consisting of (1) hyperglycemia, (2) impaired glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, (21) hypertension and other conditions and disorders where insulin resistance is a component, in a mammalian patient in need of such treatment, comprising administering to the patient a compound in accordance with the formulas described herein or a pharmaceutically acceptable salt thereof in an amount that is effective to treat said condition, and a compound selected from the group consisting of:

(a) DPP-IV inhibitors;

(b) insulin sensitizers selected from the group consisting of (i) PPAR agonists and (ii) biguanides;

(c) insulin and insulin mimetics;

(d) sulfonylureas and other insulin secretagogues;

(e) α-glucosidase inhibitors;

(f) glucagon receptor antagonists;

(g) GLP-1, GLP-1 mimetics, and GLP-1 receptor agonists (e.g., exenatide, liraglutide, lixisenatide);

(h) GIP, GIP mimetics, and GIP receptor agonists;

(i) PACAP, PACAP mimetics, and PACAP receptor 3 agonists;

(j) cholesterol lowering agents selected from the group consisting of (i) HMG-CoA reductase inhibitors, (ii) sequestrants, (iii) nicotinyl alcohol, nicotinic acid and salts thereof, (iv) PPARα agonists, (v) PPAR α/γ dual agonists, (vi) inhibitors of cholesterol absorption, (vii) acyl CoA:cholesterol acyltransferase inhibitors, and (viii) anti-oxidants;

(k) PPARδ agonists;

(l) SGLT inhibitors (e.g., dapagliflozin, canagliflozin, BI-10773, PF-729, tofogliflozin, ipragliflozin, LX-4211);

(m) antiobesity compounds;

(n) ileal bile acid transporter inhibitors;

(o) anti-inflammatory agents excluding glucocorticoids;

(p) protein tyrosine phosphatase-1B (PTP-1B) inhibitors; and (q) antihypertensives including those acting on the angiotensin or renin systems, such as angiotensin converting enzyme inhibitors, angiotensin II receptor antagonists or renin inhibitors, (e.g., lisinopril, losartan); said compounds being administered to the patient in an amount that is effective to treat said condition.

For dosing purposes, any suitable route of administration may be employed for providing a mammal, especially a human, with an effective amount of a compound of the present invention. Dosage forms may include tablets, troches, dispersions, suspensions, solutions, capsules, creams, ointments, aerosols, and the like. Most preferably, compounds of the formulas described herein or a pharmaceutically acceptable salt thereof are administered orally. The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus or other diseases for which compounds of the formulas described herein are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 350 milligrams. For a particularly potent compound, the dosage for an adult human may be as low as 0.1 mg. The dosage regimen may be adjusted within this range or even outside of this range to provide the optimal therapeutic response. Oral administration will usually be carried out using tablets or capsules. Examples of doses in tablets and capsules are 0.1 mg, 0.25 mg, 0.5 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 12 mg, 15 mg, 20 mg, 25 mg, 50 mg, 100 mg, 200 mg, 350 mg, 500 mg, 700 mg, 750 mg, 800 mg and 1000 mg. Other oral forms may also have the same or similar dosages.

Another aspect of the invention that is of interest is a pharmaceutical composition comprised of a compound of the formulas described herein or a pharmaceutically acceptable salt thereof in combination with a pharmaceutically acceptable carrier. The pharmaceutical compositions of the present invention comprise a compound of the formulas described herein or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

A pharmaceutical composition may also comprise a prodrug, or a pharmaceutically acceptable salt thereof, if a prodrug is administered.

The compositions are typically suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the condition being treated and on the particular active ingredient selected. They may be conveniently presented in unit dosage form and prepared by any of the methods well-known in the art.

In practical use, compounds of the formulas described herein, or the pharmaceutically acceptable salts thereof can be combined as the active ingredient in intimate admixture with the pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage form. Solid pharmaceutical carriers are therefore typically employed. If desired, tablets may be coated by standard aqueous or nonaqueous techniques. Such compositions and preparations typically comprise at least about 0.1 percent of active compound, the remainder of the composition being the carrier. The percentage of active compound in these compositions may, of course, be varied and is conveniently between about 2 percent to about 60 percent of the weight of the dosage form. The amount of active compound in such therapeutically useful compositions is such that an effective dosage will be delivered.

Alternatively, the active compound can be administered intranasally as, for example, in the form of liquid drops or a spray.

The tablets, capsules and the like also typically contain a binder. Examples of suitable binders include gum tragacanth, acacia, gelatin and a synthetic or semisynthetic starch derivative, such as hydroxypropylmethylcellulose (HPMC); excipients such as dicalcium phosphate; a disintegrating agent such as corn starch, potato starch, alginic acid; a lubricant such as magnesium stearate; and in some instances, a sweetening agent such as sucrose, lactose or saccharin. When the dosage form employed is a capsule, it may contain, in addition to the components described above, a liquid carrier such as fatty oil.

Various other materials may be present as coatings or to modify the physical form of the dosage unit. For instance, tablets may be coated with shellac, sugar or both. Syrups and elixirs typically contain, in addition to the active ingredient, sucrose as a sweetening agent, methyl or propylparabens as a preservative, a dye and a flavoring such as cherry or orange flavor.

The compound of the formulas described herein or a pharmaceutically acceptable salt thereof may also be administered parenterally. Solutions or suspensions of these active compounds can be prepared in water, saline or another biocompatible vehicle, suitably mixed with a surfactant, buffer, and the like. Dispersions can also be prepared in glycerol, liquid polyethylene glycols and mixtures thereof in an oil. Under ordinary conditions of storage and use, these preparations can also contain a preservative to prevent the growth of microorganisms.

The pharmaceutical forms suitable for injectable use include sterile aqueous solutions and dispersions, and sterile powders for the extemporaneous preparation of sterile injectable solutions and dispersions. The preparation should be prepared under sterile conditions and be fluid to the extent that easy syringability exists. It should be sufficiently stable under the conditions of manufacture and storage and preserved against the growth of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and suitable oils.

As discussed supra, compounds of the present invention may be used in combination with other drugs that may also be useful in the treatment or amelioration of the diseases and conditions described herein. Such other drugs may be administered by a route and in an amount commonly used therefore, contemporaneously or sequentially with a compound of the formulas described herein or a pharmaceutically acceptable salt thereof. In the treatment of patients who have type 2 diabetes, insulin resistance, obesity, metabolic syndrome, neurological disorders, and co-morbidities that accompany these diseases, more than one drug is commonly administered. The compounds of this invention may generally be administered to a patient who is already taking one or more other drugs for these conditions.

When a compound of the formulas described herein is used contemporaneously with one or more other drugs, a pharmaceutical composition in unit dosage form containing such other drugs and the compound of the formulas described herein is preferred. However, the combination therapy also includes therapies in which a compound of the formulas described herein and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the formulas described herein.

Examples of other active ingredients that may be administered separately or in the same pharmaceutical composition in combination with a compound of the formulas described herein include, but are not limited to:

(1) dipeptidyl peptidase-IV (DPP-4) inhibitors;

(2) insulin sensitizers, including (i) PPARγ agonists, such as the glitazones (e.g. pioglitazone), and other PPAR ligands, including (1) PPARα/γ dual agonists (e.g., muraglitazar,); (2) PPARα agonists, such as fenofibric acid derivatives (e.g., gemfibrozil), (3) selective PPARγ modulators (SPPARγM's); and (4) PPARγ partial agonists;

(ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors;

(3) insulin or insulin analogs;

(4) leptin and leptin derivatives and agonists;

(5) amylin and amylin analogs, such as pramlintide;

(6) sulfonylurea and non-sulfonylurea insulin secretagogues;

(7) α-glucosidase inhibitors (e.g., acarbose);

(8) glucagon receptor antagonists;

(9) incretin mimetics, such as GLP-1, GLP-1 analogs, derivatives, and mimetics; and GLP-1 receptor agonists (e.g., exenatide, liraglutide, lixisenatide);

(10) LDL cholesterol lowering agents such as (i) HMG-CoA reductase inhibitors (e.g., simvastatin), (ii) bile acid sequestering agents (e.g., cholestyramine), (iii) inhibitors of cholesterol absorption, (e.g., ezetimibe), and (iv) acyl CoA: cholesterol acyltransferase inhibitors, (e.g., avasimibe);

(11) HDL-raising drugs, (e.g., niacin and nicotinic acid receptor agonists);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril), A-II receptor blockers (e.g., losartan), renin inhibitors (e.g., aliskiren), beta blockers, and calcium channel blockers;

(15) glucokinase activators (GKAs);

(16) inhibitors of 11β-hydroxysteroid dehydrogenase type 1, (e.g., those disclosed in U.S. Pat. No. 6,730,690);

(17) CETP inhibitors (e.g., anacetrapib);

(18) inhibitors of fructose 1,6-bisphosphatase, (e.g., those disclosed in U.S. Pat. No. 6,054,587);

(19) inhibitors of acetyl CoA carboxylase-1 or 2;

(20) AMP-activated Protein Kinase (AMPK) activators;

(21) other agonists of the G-protein-coupled receptors: GPR-109, GPR-119, and GPR-40;

(22) SSTR3 antagonists;

(23) neuromedin U receptor agonists;

(24) SCD inhibitors;

(25) GPR-105 antagonists;

(26) SGLT inhibitors (e.g., dapagliflozin, canagliflozin, BI-10773, PF-729, tofogliflozin, ipragliflozin, LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acetyl-CoA carboxylase-1 and 2 (ACC-1 and ACC-2);

(30) inhibitors of acyl coenzyme A:monoacylglycerol acyltransferase 1 and 2 (MGAT-1 and MGAT-2);

(31) agonists of the TGR5 receptor (also known as GPBAR1, BG37, GPCR19, GPR131, and M-BAR);

(32) ileal bile acid transporter inhibitors;

(33) PACAP, PACAP mimetics, and PACAP receptor 3 agonists;

(34) PPAR agonists;

(35) protein tyrosine phosphatase-1B (PTP-1B) inhibitors; and

(36) bromocriptine mesylate and rapid-release formulations thereof.

Of particular interest are dipeptidyl peptidase-IV (DPP-4) inhibitors that can be used in combination with compounds of the present invention. Such inhibitors include, without limitation, sitagliptin (disclosed in U.S. Pat. No. 6,699,871), MK-3102, SYR-472, teneligliptin, KRP104, TS021, AMG222, SK0403, LC15-0444, vildagliptin, saxagliptin, alogliptin, denagliptin, carmegliptin, dutogliptin, melogliptin, linagliptin, and pharmaceutically acceptable salts thereof, and fixed-dose combinations of these compounds with metformin hydrochloride, pioglitazone, rosiglitazone, simvastatin, atorvastatin, or a sulfonylurea.

Other dipeptidyl peptidase-IV (DPP-4) inhibitors that can be used in combination with compounds of the formulas described herein include, but are not limited to:

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-5-(1-methyl-4,6-dihydropyrrolo[3,4-c]pyrazol-5(1H)-yl)-2-(2,4,5-trifluorophenyl)tetrahydro-2H-pyran-3-amine;

(2R,3S,5R)-2-(2,5-difluorophenyl)tetrahydro)-5-(4,6-dihydropyrrolo[3,4-c]pyrazol-5(1H)-yl)tetrahydro-2H-pyran-3-amine;

(3R)-4-[(3R)-3-amino-4-(2,4,5-trifluorophenyl)butanoyl]-hexahydro-3-methyl-2H-1,4-diazepin-2-one;

4-[(3R)-3-amino-4-(2,5-difluorophenyl)butanoyl]hexahydro-1-methyl-2H-1,4-diazepin-2-one hydrochloride; and (3R)-4-[(3R)-3-amino-4-(2,4,5-trifluorophenyl)butanoyl] hexahydro-3-(2,2,2-trifluoroethyl)-2H-1,4-diazepin-2-one; and pharmaceutically acceptable salts thereof.

Another aspect of the invention that is of interest relates to the use of a compound in accordance with the formulas described herein or a pharmaceutically acceptable salt thereof in the manufacture of a medicament for use in treating a disease or condition described herein.

Assays

Compounds of the present invention were shown to be biologically active in one or more of the following assays:

Measurement of GPR119 Signaling (Cyclic AMP (cAMP) Assay)

Human embryonic kidney (HEK) 293 cell lines stably transfected with human GPR119 were maintained in Dulbecco's Modified Eagle Medium (DMEM) containing fetal bovine serum (FBS), penicillin-streptomycin, HEPES buffer (4-(2-hydroxyethyl)-1-piperazineethane sulfonic acid), and hygromycin. For the cAMP assay, the transfected cells were harvested using a non-enzymatic cell dissociation solution (GIBCO 2672), pelleted and resuspended in stimulation buffer (DMEM, 25 mM HEPES, 0.1% bovine serum albumin (BSA), pH 7.4 in the presence of 100 μM phosphodiesterase inhibitors). The adenylate cyclase assay was constructed following the LANCE™ cAMP Kit (Perkin Elmer, AD0264) instructions.

Briefly, cells with Alexa Fluor® 647-anti cAMP antibody were incubated with 10 point series diluted test article in stimulation buffer with a final concentration of 2.5% DMSO for 45 minutes. The reaction was stopped by incubating with the supplied detection buffer containing the europium chelate of the Eu-SA/Biotin-cAMP tracer for 3 hours. The assay was performed in duplicate in a 384 well plate for duplicate plates and fluorescence was measured at 665 nm. Basal activity was determined using a DMSO control and maximum response was defined as cAMP stimulation produced by an internal agonist control. Standard cAMP concentrations were assayed concurrently for conversion of fluorescence signal to cAMP level. The data was analyzed using 4-parameter curve fit in Microsoft Excel.

Measurement of GPR119 Signaling (cAMP Homogenous Time Resolved Fluorescence (HTRF) Assay)

Chinese hamster ovary (CHO) cell lines stably transfected with the permissive guanine nucleotide binding protein alpha 15 (Gα15) and murine GPR119 were maintained in DMEM media containing FBS, penicillin-streptomycin, puromycin, and G418 (geneticin). Alternatively, human embryonic kidney (HEK)293 Flp-In cells (Invitrogen, Carlsbad, Calif.) were stably transfected with a human SNP variant (S309L) of GPR119 and maintained in DMEM media containing FBS, penicillin-streptomycin, and hygromycin. Agonist activation of the GPR119 receptor was measured in receptor transfected cells described above, treated with compounds of this invention, using a commercial homogenous time resolved fluorescence (HTRF) kit for measurement of cAMP (CisBio, Bedford, Mass.). The assay was performed in 96-well half-volume plates (murine) or 384-well plates (human) following the manufacturers instructions. Briefly, suspended cells were incubated with a dose titration of test compound at RT for 60 min, lysed, and incubated with HTRF reagents for an additional 60 min. The plate was read using an Envision multilabel reader (Perkin Elmer) adjusted to read time resolved fluorescence and the cAMP concentrations were extrapolated from a cAMP calibration curve. GPR119 agonists exhibit a concentration-dependent increase in intracellular cAMP. The concentration of test compound required to stimulate a half-maximal response (EC50), and efficacy as compared to an internal agonist control, was determined from a sigmoidal 4-parameter curve fit of the resulting plot of normalized activity versus compound concentration.

Evaluation of GDIS in Static Isolated Mouse Islets.

Pancreatic islets of Langerhans were isolated from the pancreata of 10-12 wk-old C57BL/6 mice by collagenase digestion and discontinuous Ficoll gradient separation, a modification of the original method of Lacy and Kostianovsky (Lacy & Kostianovsky, Diabetes (16) 35-39 (1967)). The islets were cultured overnight in RPMI 1640 medium (11 mM glucose, 10% FCS) before experimental treatment. The acute effects of compounds of this invention on GDIS were determined by 60-min static incubation with islets in Krebs-Ringers' bicarbonate (KRB) medium. The KRB medium contained, in mM, 143.5 $Na^+$, 5.8 $K^+$, 2.5 $Ca^{2+}$, 1.2 $Mg^{2+}$, 124.1 $Cl^+$, 1.2 $PO_4^{3-}$, 1.2 $SO_4^{2+}$, 25 $CO_3^{2-}$, and 10 HEPES, pH 7.4, in addition to 2 mg/ml bovine serum albumin, and either 2 (G2) or 16 (G16) mM glucose (pH 7.4). The static incubation was performed with round-bottomed 96-well plates (one islet/well with 200 μl KRB medium). The compounds were added to KRB medium just before the initiation of the 60-mM incubation. Insulin concentration in aliquots of the incubation buffer was measured by the ultra-sensitive rat insulin EIA kit from ALPCO Diagnostics (Windham, N.H.).

General Schemes

The compounds of the invention can be prepared using the synthetic schemes described herein as well as any of several alternate methods which will be apparent to a chemist skilled in the art.

The following abbreviations may be used in the synthetic schemes or Examples: BOP is benzotriazol-1-yloxy-tris-(dimethylamino)-phosphonium hexafluorophosphate; BuTMDOB is trans 2-butyl-N,N,N,N-tetramethyl-1,3,2-dioxaborolane-4,5-dicarboxamide, as specified R,R or S,S; DCM is dichloromethane; DEAD is diethyl azodicarboxylate; DIAD is diisopropylazodicarboxylate; DIPEA is N,N-Diisopropylethylamine, or Hünig's base; DMAP is dimethylaminopyridine; DMF is N,N-dimethylformamide; DMSO is dimethyl sulfoxide; EDC is 1-ethyl-3-[3-(dimethylamino) propyl]-carbodiimide HCl; EtOAc is ethyl acetate; EtOH is ethanol; HCl is hydrochloric acid; HOBt is 1-hydroxybenzotriazole; HPLC is high performance liquid chromatography; iPrOAc is isopropyl acetate; LRMS is low resolution mass spectrometry; M is molar; mmol is millimole; n-BuLi is n-butyllithium; room temperature is RT; TEA is triethylamine; TFA is trifluoroacetic acid; THF is tetrahydrofuran; TLC is thin layer chromatography; TPAP is tetrapropylammonium perruthenate.

Reaction Schemes below illustrate the methods employed in the synthesis of the compounds of the present invention of Formula I. All substituents are as defined above unless indicated otherwise. The synthesis of the novel compounds of the present invention may be accomplished by one or more of synthetic scheme.

Substituted aryl and heteroaryl coupling intermediates shown in the schemes are commercially available or may be prepared from readily accessible aryl, heterocyclic, or other congeners via a host of routes. Many intermediates are accessible through either modification of a pre-formed heteroaryl scaffold or through de novo ring synthesis.

The cyclopropyl residue in the connecting chain of the present examples may be introduced by any of several methods. A particularly convenient method is outlined in Scheme 1 below. Conversion of the readily available hydroxymethyl piperidine to the acetylene by a multistep protocol allows ready access to the indicated cis olefins after Lindlar reduction. (see, e.g., Eymery, et al, *Synth* 2000, 185-213 at page 196 for a convenient protocol). Charette's $Et_2Zn/CH_2I_2$ cyclopropanation affords racemic, diasteromerically enriched or enantiomerically enriched cyclopropyl analogs. (Charette et al, *JACS* 1998, 120, 11943-11952; further details in Charette, et al, *JACS,* 2001, 123, 12160-12167.) In the absence of an auxiliary chiral Lewis acid the cis allylic olefin affords good yields of the desired racemic analog. Also in the absence of an auxiliary chiral Lewis acid, the chiral alcohol derived from the opening of R or S glycidyl epoxide affords reasonable ratios the chiral diasteromeric cyclopropanation products.

With the addition of the auxiliary chiral Lewis acid RR or SS BuTMDOB, the same cyclopropanation protocol leads to very good ratios of the desired enantiomer in either the allylic or homoallylic cyclopropanation. The depicted chiral homoallylic alcohol requires the "matched" dioxaborolane in the double diasteroselection protocol.

SCHEME 1:
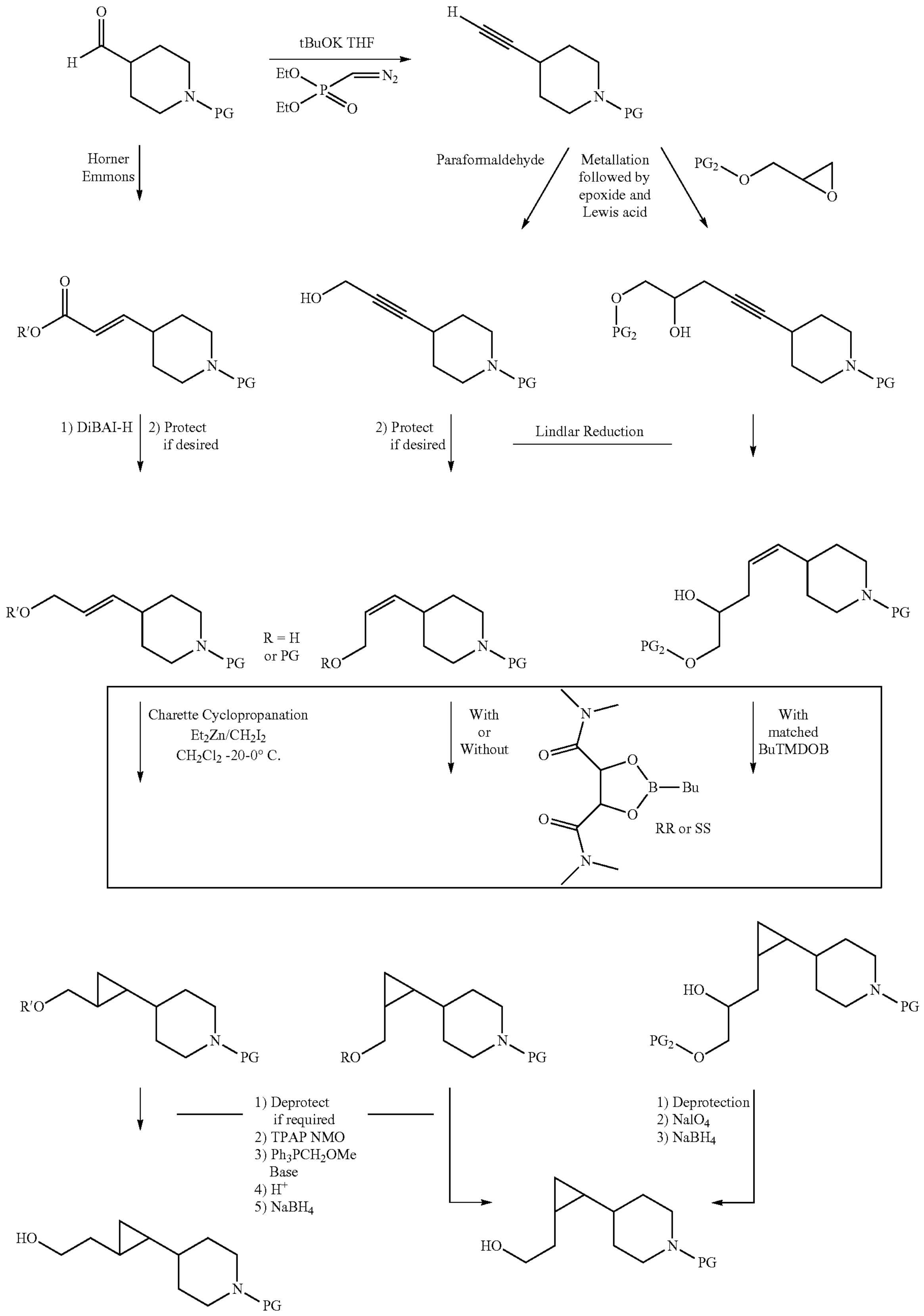
R′ represents lower alkyl, $PG_2$ represents a protecting group, preferably benzyl With the starting alcohol available from the above described procedures, many analogs can be made via several different routes. Scheme 2 outlines a particularly convenient method for conversion of the cyclopropyl alcohol to substituted aryl/heteroaryl ethers via treatment with aryl/heteroaryl halides in the presence of a base, such as sodium hydride, heated to between 40-100° C., for a period of 2 to 24 hours. Depending on the amino protecting group, several methods can be used for removal which will be apparent to the skilled artisan. For example, t-butylcarbonyl can be removed via treatment with an acid, such as HCl or TFA. Another commonly used protecting group is carboxybenzyl, which can be removed via hydrogenation.

SCHEME 2:

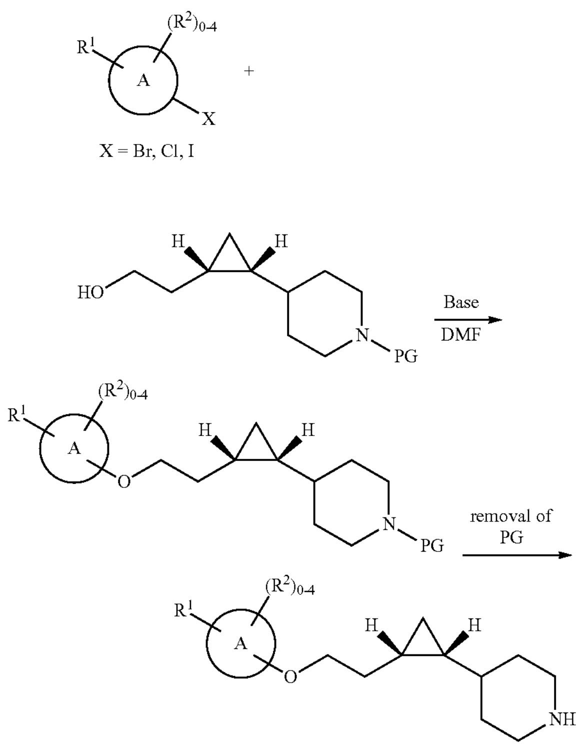

Scheme 3 outlines another preparation for aryl ethers via Mitsunobu reaction with phenols. A mixture of the cyclopropyl alcohol and phenol can be treated with DIAD or DEAD in the presence of triphenylphosphine and a suitable solvent to afford substituted aryl ethers.

SCHEME 3

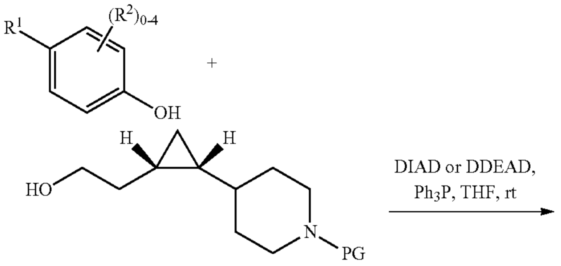

-continued

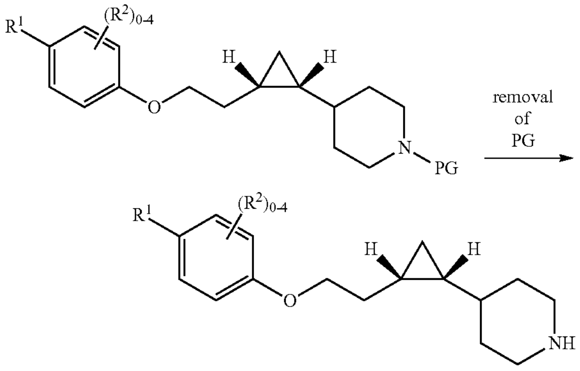

Phenols can also be used in a nucleophilic displacement via the activated cyclopropyl alcohol intermediate. (Scheme 3A) The cyclopropyl alcohol can be converted to a tosylate or mesylate via treatment with tosyl or mesyl chloride in the presence of an organic base, such as TEA, and an activating agent, such as DMAP, in the appropriate solvent. This tosyl/mesylate can then be treated with the choice of substituted phenols in the presence of base, such as sodium hydride to form the desired phenoxy-ethers

SCHEME 3A:

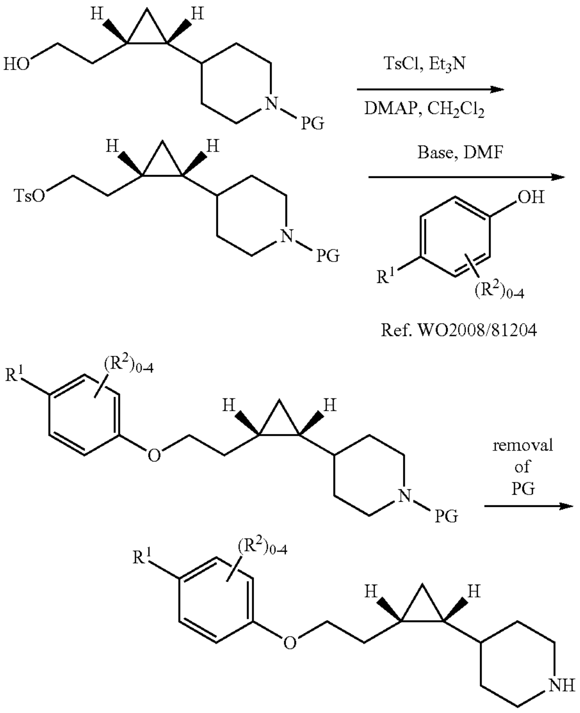

The intermediates formed from the previous schemes can then be used in the final synthesis of GPR119 agonists. The formation of carbamate analogs are outlined in Scheme 4. Commercially available alkyl or aryl chloroformates or preformed succinamides can be used in the acylation of the nitrogen of the cyclopropyl intermediate via treatment with base, such as DIEA or TEA, to yield the carbamate GPR119 agonist analogs.

Scheme 4:

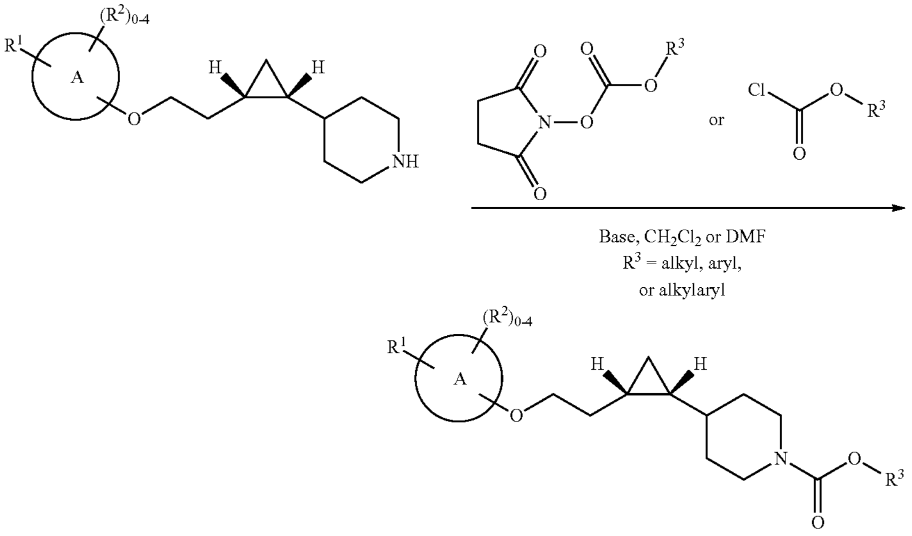

Similar analogs can be made via a reverse route in which the carbamate intermediates are synthesized first with treatment of the cyclopropyl alcohol piperidine amine with similar reagents as described previously. Formation of the ether can be chosen from the several methods described in Schemes 2, 3 and 3A. Particularly interesting carbamates can be chosen for a high throughput variation of the aryl/heteroaryl ether moiety via this route.

Scheme 5:

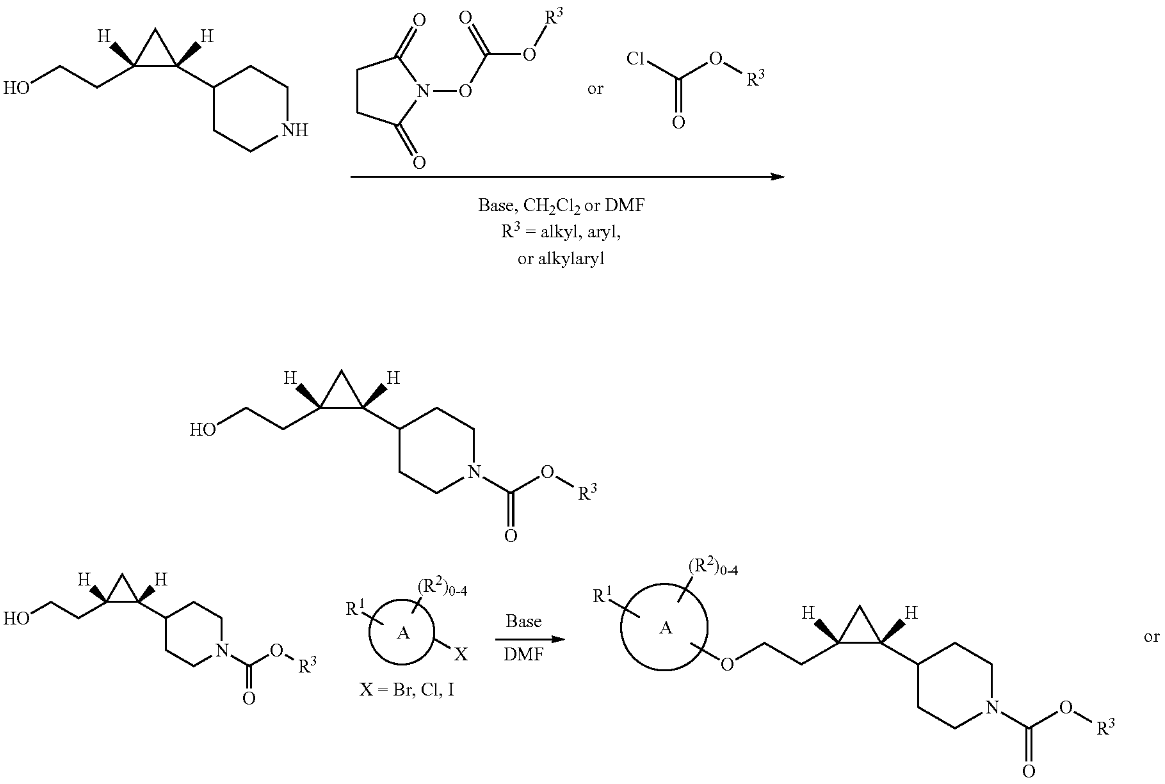

-continued

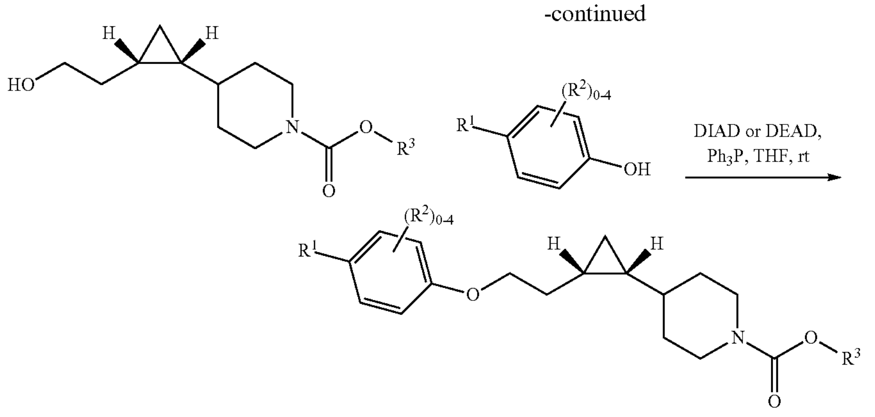

Introduction of the piperidine nitrogen 5-membered heterocyclic substituents can be accomplished by a particularly wide variety of routes. Some of the most versatile routes for the examples reported here are represented in schemes 6-8. Scheme 6 outlines the synthesis of 3-substituted 1,2,4-oxadiazoles starting particularly with selected aryl or heteroaryl substituted ethers. The amine of the piperidine is converted to a cyano substituted piperidine via treatment with cyanogen bromide in the presence of base refluxed in a suitable chlorinated solvent. The cyano intermediate can then be converted to a 3-substituted 1,2,4-oxadiazole via reaction with an N-hydroxyalkylimidamide or N-hydroxyarylimidamide.

Scheme 6:

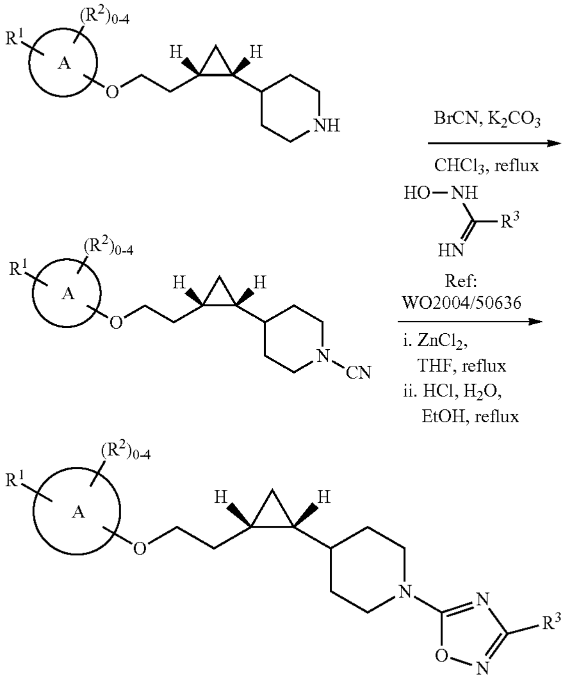

The order of introduction of aryl ether and piperidine N-substituents is easily inverted by using the cyclopropyl alcohol piperidine amine and introducing the oxadiazole first. Similar chemistry is used in Scheme 7 as already represented in the prior schemes, which will be apparent to the skilled artisan.

SCHEME 7:

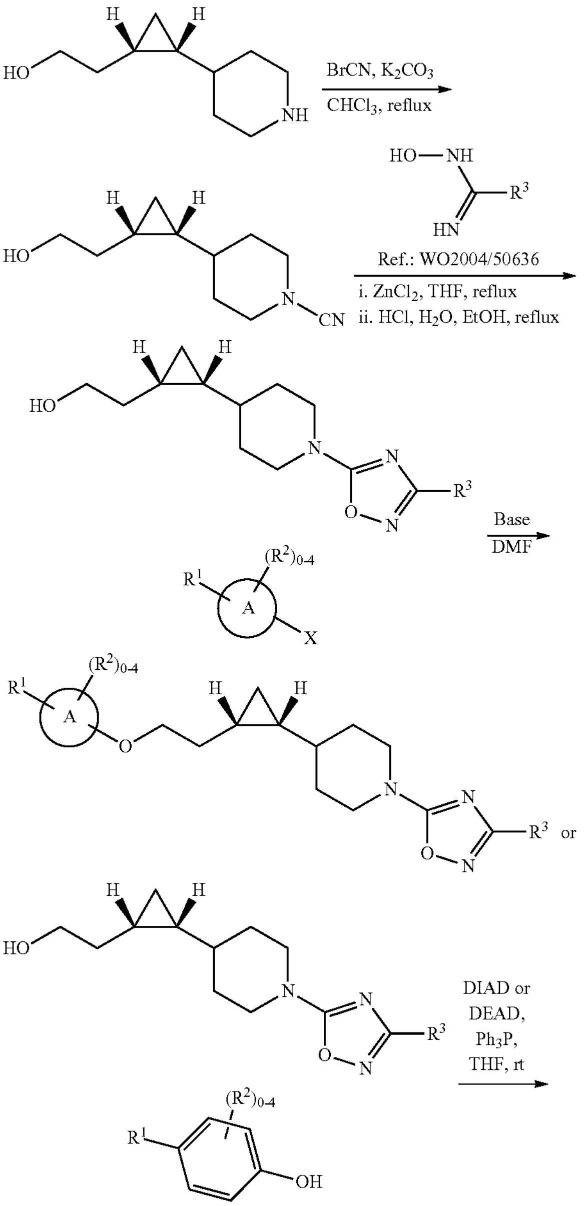

-continued

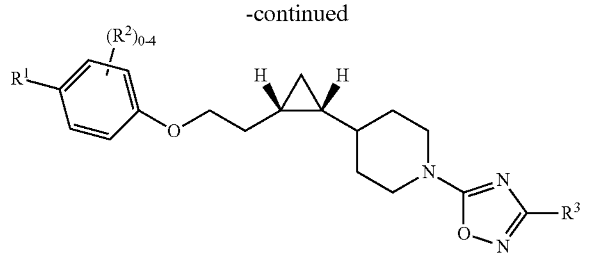

X = Br, Cl, I

The isosteric oxadiazole can be synthesized similarly to the previously described 3-substituted 1,2,4-oxidazole, however the N-hydroxylimidamide is synthesized using the cyclopropyl piperidine intermediate via treatment with cyanogen bromide in the presence of N-hydroxylamine and a suitable base. The hydroxylimidamide intermediate is then reacted with any selected substituted carboxylic acids in the presences of BOP heated in a microwave reactor at 100-140° C. for a period of 1-16 hours.

SCHEME 8:

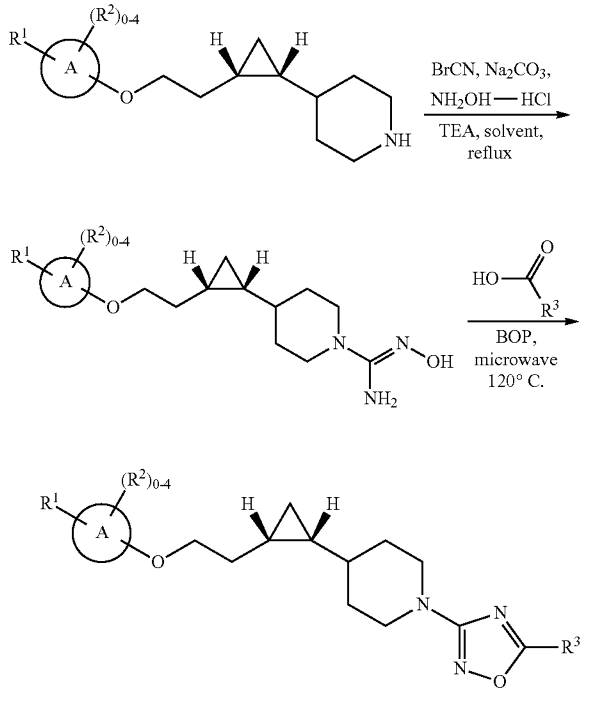

Direct displacement of labile heteroaryl halides or similar leaving groups can often be used to introduce the nitrogen substituent directly. Direct displacement on heteroaryl systems are all well known to the skilled artisan. Scheme 9 demonstrates the direct incorporation of both substituted-5-member heteroaryl and 5,5- and 5,6-fused heteroaryl moieties via direct displacement. The base used can be selected from organic bases, such as TEA, and inorganic bases, such as potassium carbonate. Moderate to high boiling point solvents, such as t-amyl alcohol or DMF, can be used as deemed appropriate by the skilled artisan. Microwave and hot silica oil baths can be used as heat sources that can easily be monitored for accuracy of heating temperature.

SCHEME 9:

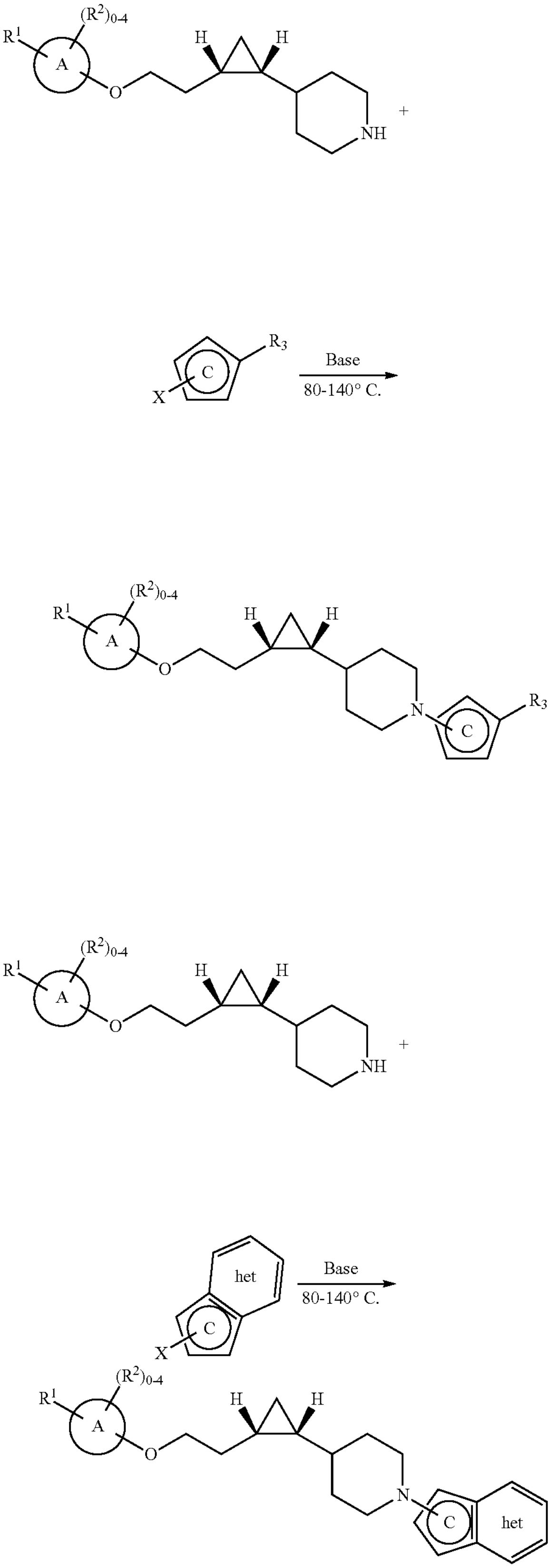

X = halide, OTs, OMs

INTERMEDIATES

Intermediate 1

Preparation of cyclopropylmethyl 2,5-dioxopyrrolidin-1-yl carbonate

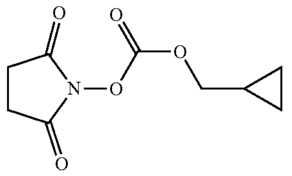 [SMILES: O=C(OCC1CC1)ON1C(=O)CCC1=O]

Step A: cyclopropylmethyl 2,5-dioxopyrrolidin-1-yl carbonate

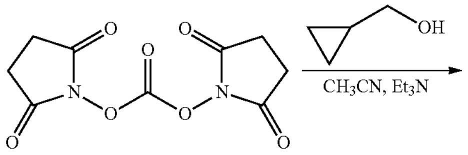

-continued

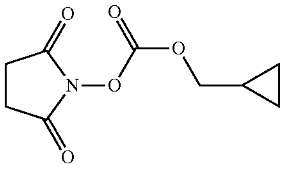

To a stirred solution of cyclopropylmethanol (1.0 g, 13.8 mmol) in acetonitrile (15 mL) was added bis(2,5-dioxopyrrolidin-1-yl) carbonate (7.1 g, 27.7 mmol) and triethylamine (5.8 mL, 41.6 mmol). The reaction was stirred overnight then quenched with saturated $NaHCO_3$ (aq.) and extracted with ethyl acetate (3×50 mL), dried over sodium sulfate, filtered and concentrated under reduced pressure to provide the title compound as an amber oil: $^1H$ NMR (300 MHz, $CDCl_3$) δ 4.16 (d, J=7.5 Hz, 2H), 2.84 (s, 4H), 1.26 (m, 1H), 0.70-0.64 (m, 2H), 0.40-0.35 (m, 2H).

The remaining intermediates in Table 1 were synthesized according to the method described above.

TABLE 1

| Number | Name | Chemical Structure |
|---|---|---|
| 2 | 1-({[(1 methylcyclopropyl)oxy] carbonyl}oxy)pyrrolidine-2,5-dione | 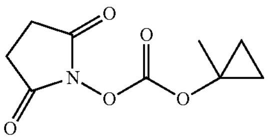 |
| 3 | cyclobutylmethyl 2,5-dioxopyrrolidin-1-yl carbonate | 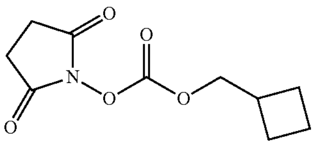 [SMILES: O=C(OCC1CCC1)ON1C(=O)CCC1=O] |
| 4 | 2,5-dioxopyrrolidin-1-yl (1-methylcyclopropyl)methyl carbonate | 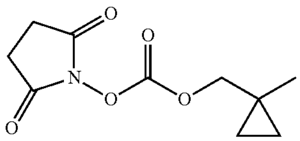 [SMILES: CC1(COC(=O)ON2C(=O)CCC2=O)CC1] |
| 5 | 2,5-dioxopyrrolidin-1-yl 1-ethylcyclopropyl carbonate | 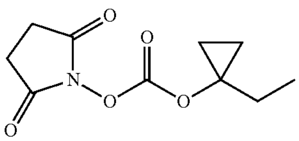 [SMILES: CCC1(OC(=O)ON2C(=O)CCC2=O)CC1] |
| 6 | 2,5 -dioxopyrrolidin-1-yl (1-methylcyclobutyl)methyl carbonate | 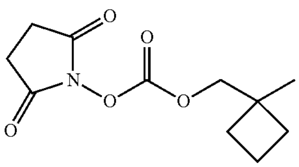 [SMILES: CC1(COC(=O)ON2C(=O)CCC2=O)CCC1] |

TABLE 1-continued

| Number | Name | Chemical Structure |
|---|---|---|
| 7 | cyclobutyl 2,5-dioxopyrrolidin-1-yl carbonate | 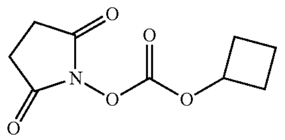 [SMILES: O=C(OC1CCC1)ON1C(=O)CCC1=O] |
| 8 | 2,5-dioxopyrrolidin-1-yl 1-methylcyclobutyl carbonate | 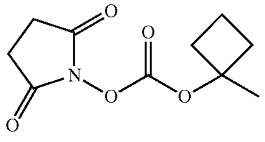 [SMILES: CC1(OC(=O)ON2C(=O)CCC2=O)CCC1] |

Intermediate 2

Preparation of rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl] piperidine-1-carboxylate and tert-butyl 4-[(1R,2S)-2-(2-hydroxyethyl)cyclopronyl]piperidine-1-carboxylate)

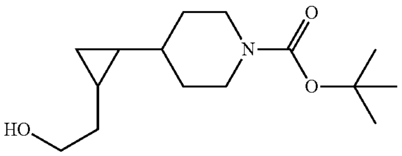 [SMILES: CC(C)(C)OC(=O)N1CCC(C2CC2CCO)CC1]

Step A. Preparation of racemic tert-Butyl 4-[(1Z)-4-(benzyloxy)but-1-en-1-yl]piperidine-1-carboxylate

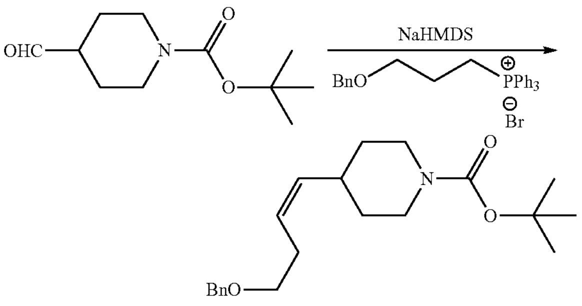

(3-Benzyloxypropyl)triphenylphosphonium bromide (2.88 g, 5.86 mmol) was suspended in 15 mL THF and cooled to 0° C. Sodium bis(trimethylsily)amide (1M in THF, 5.63 mL, 5.63 mmol) was added dropwise. The mixture turned deep orange. tert-Butyl 4-formylpiperidine-1-carboxylate (1 g, 4.69 mmol) in 3 mL THF was added after 5 minutes. Color faded to slight yellow. The reaction was stirred at RT for 1.5 hours, before quenching with saturated aqueous ammonium chloride solution. The aqueous layer was extracted twice with ethyl acetate. The organic layers were combined, washed with water and brine, dried over sodium sulfate, filtered, concentrated and purified by passing through a 40 gram Biotage silica gel cartridge using 20% EtOAc/hexanes to afford the product as colorless oil. NMR integration indicated >20:1 Z/E selectivity. LRMS calc: 345.2; obs: 346.5 (M+1).

Step B. rac-tert-butyl 4-{2-[2-(benzyloxy)ethyl] cyclopropyl}piperidine-1-carboxylate, i.e., (tert-butyl 4-{(1S,2R)-2-[2-(benzyloxy)ethyl] cyclopropyl}piperidine-1-carboxylate and tert-butyl 4-{(1R,2S)-2-[2-(benzyloxy)ethyl] cyclopropyl}piperidine-1-carboxylate)

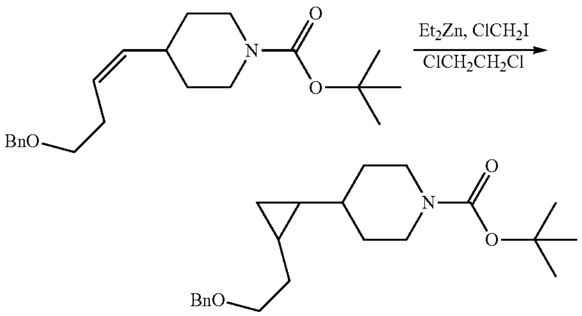

Dichloroethane (5 mL) was degassed and purged with argon three times before diethylzinc solution (1M in hexanes, 1.74 mL, 1.74 mmol) was added. The solution was cooled to −20° C. Chloroiodomethane (613 mg, 3.47 mmol) was added dropwise while maintaining internal temperature below −15° C. After stirring for 10 minutes at −20° C., tert-butyl 4-[(1Z)-4-(benzyloxy)but-1-en-1-yl]piperidine-1-carboxylate (from step 1, this Example 200 mg, 0.579 mmol) in degassed dichloroethane (1 mL) was added dropwise. The reaction was stirred at −20° for 10 minutes before slowly warming to RT. The reaction mixture was cooled to −10° C. after 1 hour. A 1:4 mixture of saturated aqueous ammonium chloride and aqueous ammonium hydroxide (28% w/w) was slowly introduced to quench excess reagents. The mixture was stirred at RT for 3 hours. The aqueous layer was separated and extracted twice with dichloromethane. The combined organic layers were washed with brine, dried over sodium sulfate, concentrated and purified by column chromatography eluting with 25%

EtOAc/hexanes to give the product as colorless oil. LRMS calc: 359.25; obs: 360.5 (M+1).

Step C. rac cis tert-Butyl 4-[2-(2-hydroxyethyl)cyclopropyl]piperidine-1-carboxylate, i.e. (tert-butyl 4-[(1S,2R)-2-(2-hydroxyethyl)cyclopropyl]piperidine-1-carboxylate and tert-butyl 4-[(1R,2S)-2-(2-hydroxyethyl)cyclopropyl]piperidine-1-carboxylate)

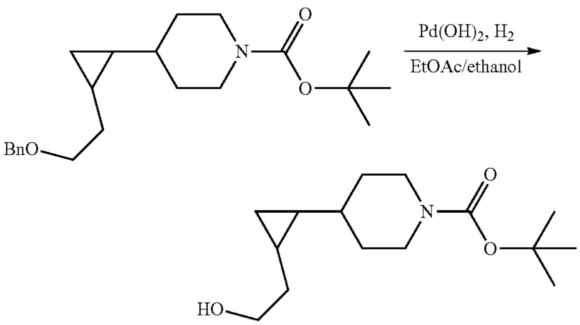

Racemic-cis tert-butyl 4-{2-[2-(benzyloxy)ethyl]cyclopropyl}piperidine-1-carboxylate from step 2 (140 mg, 0.39 mmol) was dissolved in 5 mL ethyl acetate and ethanol (1:1). The solution was degassed and purged with nitrogen 3 times, before palladium hydroxide (20% on carbon, 54.6 mg, 0.08 mmol) was added. The mixture was degassed and purged with hydrogen three times. The reaction was stirred under a hydrogen balloon at RT for 1 hour and filtered through a small plug of silica gel to remove catalyst. The silica gel plug was thoroughly washed with acetone. The eluent was concentrated to give the crude product, which was used without further purification. LRMS calc: 269.2; obs: 270.2 (M+1).

Intermediate 3

Preparation of benzyl 4-[(1R,2S)-2-(2-hydroxyethyl)cyclopropyl]piperidine-1-carboxylate

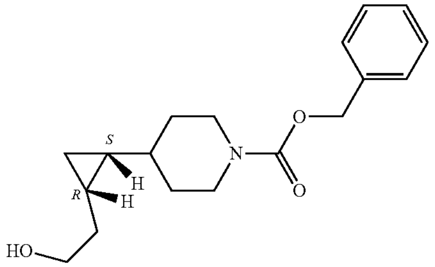

Step A Preparation of tert-butyl 4-[(4R)-5-(benzyloxy)-4-hydroxypent-1-yn-1-yl]piperidine-1-carboxylate

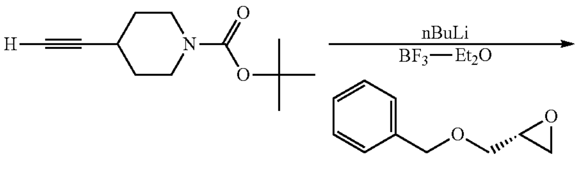

-continued

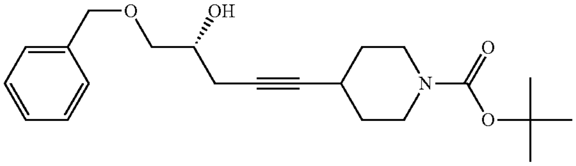

Commercially available tert-butyl 4-ethynylpiperidine-1-carboxylate was dissolved in 40 ml of THF and cooled to −78° C. forming a white slurry. Titrated n-BuLi (2.2 M in hexanes, 23.9 ml, 52.6 mmol) was added dropwise with stirring. The clear colorless solution was stirred at −78° C. for 5 minutes. A solution of the R-(+) benzyl glycidyl epoxide (8.63 g, 52.6 mmol) in THF (20 ml) was added dropwise. $BF_3$ etherate (8.43 g, 59.7 mmol) was then added dropwise with a syringe and the solution stirred at −78° C. for 1 hour. Sat'd aq. $NH_4Cl$ was added (100 ml), the mixture warmed to RT, diluted with water to dissolve any remaining solids, and extracted with iPrOAc (3×100 ml). The organic fractions were combined, washed with brine, dried over $MgSO_4$, filtered and stripped. Crude product was purified by chromatography on $SiO_2$ eluting with 30% EtOAc:Hexanes. The alcohol was repurified by chromatography on a C18 reversed phase column (12-100% water:acetonitrile 0.1% TFA as two runs.). Product containing fractions were combined, reduced in volume by approximately 50%, —made basic by addition of sat'd aq. $NaHCO_3$, water was added to dissolve some white solids, and the mixture extracted with iPrOAc (3×100). The organic fractions were combined, washed with brine, dried over $MgSO_4$, filtered, and stripped.

Step B Preparation of tert-butyl 4-[(1Z,4R)-5-(benzyloxy)-4-hydroxypent-1-en-1-yl]piperidine-1-carboxylate

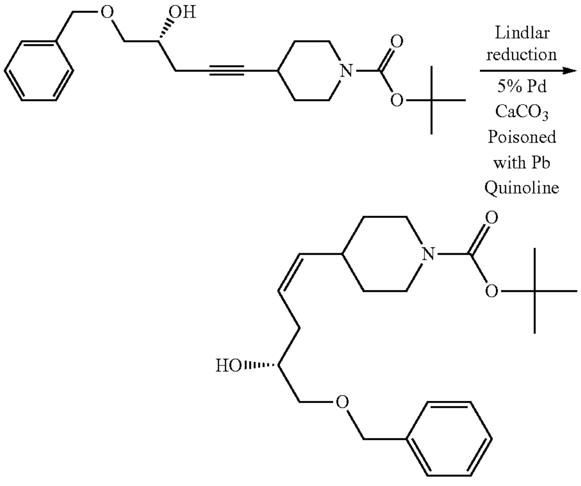

The alcohol from step 1 of this example (9.1 g, 24.4 mmol) was dissolved in EtOAc (100 ml) and quinoline (0.48 ml, 4.03 mmol) was added. Lindlar's catalyst (1.04 g) was added and the vessel evacuated and refilled three times with $H_2$. The slurry was stirred under a $H_2$ atmosphere for 40 min. The starting material was completely consumed. The mixture was filtered through celite and rinsed with EtOAc (4×50 ml). The volume of EtOAc was reduced ~80% in vac. The remaining solution was diluted with ether (100 ml) and washed with 2N HCl (100 ml). The aqueous fraction was re-extracted with ether (2×50 ml), organics combined and washed with 15 ml 2 N HCl. The organic fraction was washed with sat'd aq. $NaHCO_3$, brine, dried over $MgSO_4$, filtered, and stripped. The resulting oil was purified by chromatography on $SiO_2$ 30% eluting with EtOAc:Hexanes.

Step C Preparation of cis tert-butyl 4-{2-[(2R)-3-(benzyloxy)-2-hydroxypropyl]cyclopropyl}piperidine-1-carboxylate

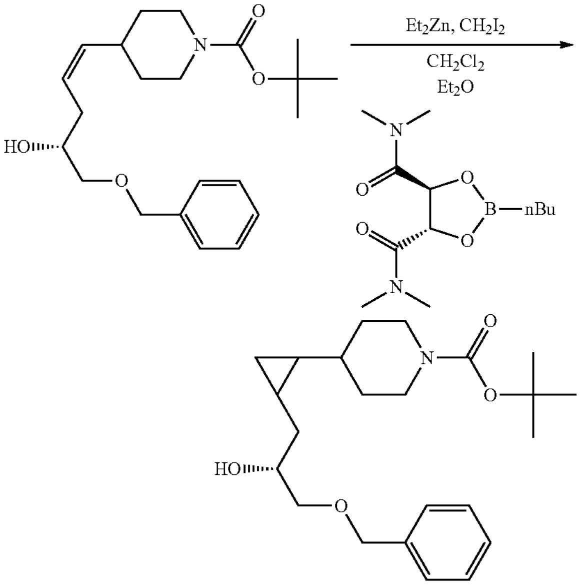

Dichloromethane stabilized with EtOH was distilled from $CaH_2$ under $N_2$ and sparged with $N_2$ to maintain oxygen free solvents. A 500 ml three neck round bottom flask was equipped with an addition funnel topped with a 3 way stopcock and internal thermal couple. The apparatus was evacuated and backfilled with $N_2$ 4 times. 20 mL DCM, Diethyl Ether (5.06 g, transferred by weight) and a solution of $Et_2Zn$ (8.43 g, 68.2 mmol, in 30 ml DCM) was added to this degassed vessel under a $N_2$ atmosphere. The solution was cooled to −20° C. and a solution of $CH_2I_2$ (36.5 g, 136 mmol, in 20 ml DCM) was added dropwise. The temperature was monitored with an internal temperature probe. The rate of addition was altered to maintain a constant −20° C. internal temperature. A fine precipitate formed after the addition was ~80% complete. The mixture was stirred for 10 minutes.

A solution of the commercially available (S, S) dioxaborolane ligand (7.37 g, 27.3 mmol) in DCM (20 mL) was added. The mixture was stirred for 10 minutes. The precipitate dissolves yielding a clear solution. A solution of the alkene from step 2 of this example (8.53 g, 22.7 mmol) in DCM (20 mL) was added. The solution was warmed to 0° C. and stirred for 24 hours. The solution remains clear after stirring for 24 hours. The reaction was quenched after 24 hr by addition of 50 ml of sat'd aq. $NH_4Cl$. The mixture was placed in a separatory funnel, 250 ml DCM and 200 ml 10% HCl (aq) added, shaken, and the layers separated. The aqueous layer was re-extracted with DCM (2×150 ml), the organic layers combined, transferred to a Morton flask. 2N NaOH (300 ml) and 50 ml of 30% $H_2O_2$ were added. The biphasic solution was stirred vigorously for 12 hours. The layers were separated and the aqueous phase was re-extracted with DCM (2×150 ml), the organic phases were combined, washed with 10% HCl (aq, 250 ml), 1N $Na_2S_2O_3$ (250 ml), sat'd $NaHCO_3$ (250 ml), brine (250 ml), dried over $MgSO_4$, filtered and stripped. The material was purified by chromatography on $SiO_2$ eluting with 30% EtOAc:Hexanes. The desired product is obtained as a mixture with the minor diastereomer and the residual SM. The desired diastereomer was isolated by Chiralpak IA stationary phase chromatography.

Step D Preparation of cis tert-butyl 4-[2-(2-hydroxyethyl)cyclopropyl]piperidine-1-carboxylate

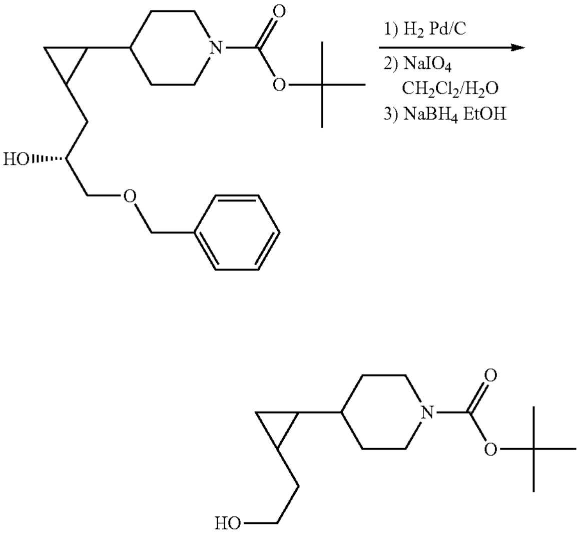

The tert-butyl 4-{2-[(2R)-3-(benzyloxy)-2-hydroxypropyl]cyclopropyl}piperidine-1-carboxylate from step 3 of this example (4.3 g, 11 mmol) was transferred to a Parr shaker pressure tube in 55 ml 1:1 EtOAc/Ethanol with 0.88 mgs Aldrich palladium hydroxide (20% wt on carbon-Degussa type E101). The mixture was shaken at 50 psig hydrogen on a Parr shaker. HPLC check at 30 min. indicated complete conversion. The product was filtered through Celite, washed with ethanol, and reduced to an oil in vacuo.

The crude debenzylation product was dissolved in $CH_2Cl_2$ (56 ml) and cooled in ice. Sodium periodate (4.77 g, 22.3 mmol) was dissolved in water (56 ml) and added slowly dropwise. The milky mixture was stirred vigorously at 0° C. HPLC indicated complete cleavage at 30 min. at 0° C. The reaction mixture was diluted with brine and $CH_2Cl_2$. The mixture was extracted three times with $CH_2Cl_2$, dried over $MgSO_4$ and reduced in vacuo.

The crude aldehyde was redissolved in EtOH (56 ml), sodium borohydride (0.422 g, 11.2 mmol) was added as a solid and the mixture stirred at RT. The reduction is complete in 30 min. Saturated aq $NH_4Cl$ aq (70 ml) was added to quench, and the mixture reduced to a paste i. vac. The result was diluted with water (350 ml), and iPrOAc. The mixture was extracted with iPrOAc (3×), washed with brine, dried over $MgSO_4$, filtered and reduced in vacuo. The crude product was purified by chromatography on $SiO_2$ eluting with 40% EtOAc:Hexanes.

Step E: benzyl 4-[-2-(2-hydroxyethyl)cyclopropyl] piperidine-1-carboxylate

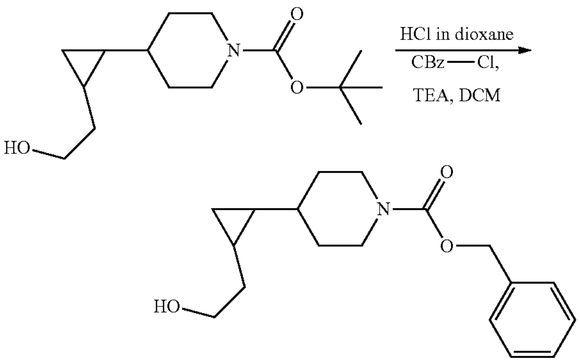

Cis tert-butyl 4-[2-(2-hydroxyethyl)cyclopropyl]piperidine-1-carboxylate (2.0 g, 7.44 mmol) was treated with 4M HCl in dioxane (200 mL) at room temperature for 2 hours. The mixture was concentrated under reduced pressure and the residue taken up in 200 mL DCM. To this solution was added TEA (10.0 mL, 7.64 mmol) followed by benzylchloroformate (1.30 g, 7.64 mmol) and the resulting mixture stirred at room temperature overnight. The mixture was washed with 1N aqueous HCl (75 mL), followed by saturated aqueous sodium bicarbonate (75 mL) and brine (75 mL). The organics were dried over sodium sulfate, filtered, and concentrated under reduced pressure. The residue was purified via Biotage (40M+ silica gel) eluting with a gradient of 0-80% ethyl acetate to afford the title compound as a viscous oil.

Step F: Separation of benzyl 4-[(1R,2S)-2-(2-hydroxyethyl)cyclopropyl]piperidine-1-carboxylate and benzyl 4-[(1S,2R)-2-(2-hydroxyethyl)cyclopropyl] piperidine-1-carboxylate

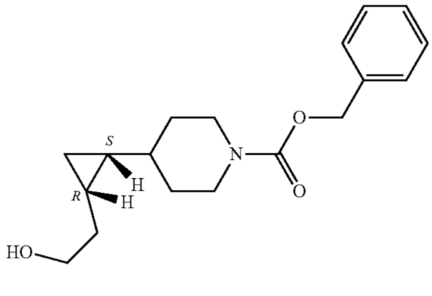

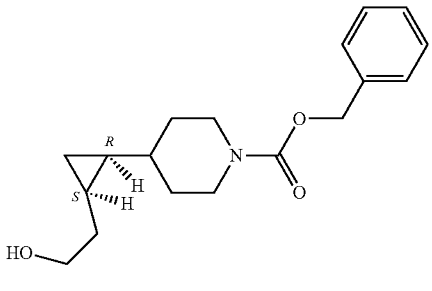

Separation of the cis isomers to afford the pure diastereomers were done via an enzymatic enantiomeric excess (ee) enrichment.

Step F-1: Preparation of 4-[2-(2-{1-[(benzylox)carbonyl]piperidin-4-yl}cyclopropyl)ethyoxy]-4-oxobutanoic acid

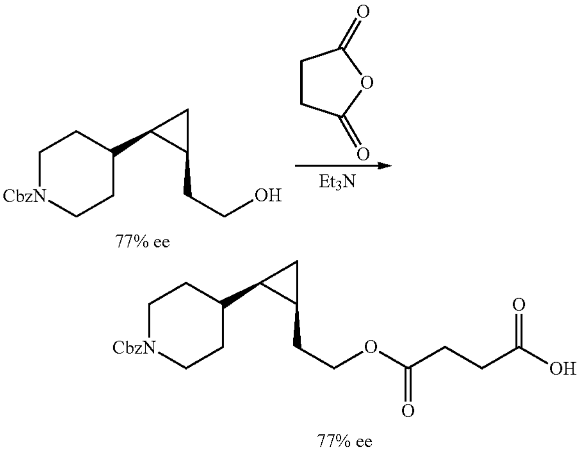

To a solution of benzyl 4-[2-(2-hydroxyethyl)cyclopropyl] piperidine-1-carboxylate (2 g, 6.70 mmol) and TEA (10.0 mL, 7.60 mmol) in ethyl acetate (40 mL) was added succinamide (760 mg, 7.60 mmol) and the resulting mixture was heated to reflux via oil bath for 4 hours. The mixture was allowed to cool to room temperature over 1 hour and then the mixture was quenched with 1N HCl. The organics were separated and washed with water followed by brine. The organics were dried over sodium sulfate, filtered, and the filtrate was concentrate to dryness under reduced pressure to afford the product.

Step F-2: Preparation of benzyl 4-[(1R,2S)-2-(2-hydroxyethyl)cyclopropyl]piperidine-1-carboxylate

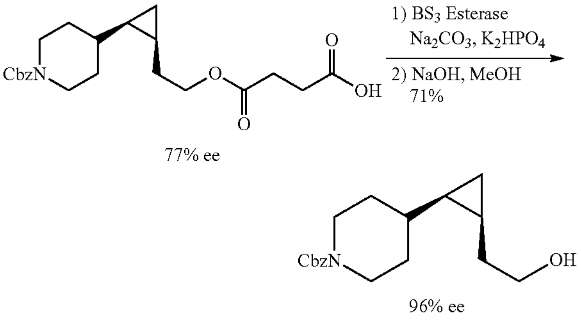

A solution of potassium phosphate (dibasic; 1.05 g, 6.00 mmol) and sodium carbonate (610 mg, 5.76 mmol) in water (60 mL) was premixed and aged until all solids were dissolved. The solution was cooled to 0° C. via ice/water bath and a solution of 4-[2-(2-{1-[(benzylox)carbonyl]piperidin-4-yl}cyclopropyl)ethyoxy]-4-oxobutanoic acid (2.60 g, 6.47 mmol) in DMSO/methanol (1:3, 20 mL) was added via syringe. The pH of the solution was checked to make sure it was between 7 and 8 to ensure the proper condition for the enzyme. Codexis BS3 (110 mg, ~5% by wt of the starting material) was added and the reaction temperature was monitored to make sure it did not exceed 25° C. The reaction mixture was then aged at 21° C. for 7 hours and then the pH was adjusted to 11 by addition of a solution of potassium carbonate in water. The solution was diluted with ethyl acetate and the aqueous was separated. The organics were washed with aqueous potassium carbonate solution (25 mL) and all the aqueous cuts were combined. The combined aqueous was then cooled to 5° C. and treated with 47% sodium hydroxide solution (5 mL) keeping the temperature at less than 40° C. The pH of the mixture was ~14 and >99% hydrolysis had occurred after 30 minutes of treatment based on HPLC. The mixture was then cooled to room temperature and diluted with ethyl acetate (75 mL). The biphasic mixture was filtered through a pad of Solka Floc and the clarified phases separated. The organics were separate, dried over sodium sulfate, filtered, and the filtrate concentrated to dryness under reduced pressure to afford the title compound with an ee of 96%. $^1$H NMR (500 MHz, $CDCl_3$) δ 7.46-7.30 (m, 5H), 5.16 (s, 2H), 4.20 (br s, 2H), 3.82-3.70 (m, 2H), 2.77 (br s, 2H), 1.95-1.87 (m, 1H), 1.76-1.72 (m, 2H), 1.46-1.23 (m, 4H), 1.02-0.87 (m, 1H), 0.86-0.76 (m, 1H), 0.67-0.61 (m, 1H), 0.60-0.52 (m, 1H), −0.18 (q, J=4.5 Hz, 1H).

Intermediate 4

Preparation of 2-((1S,2R)-2-(piperidin-4-yl)cyclopropyl)ethanol

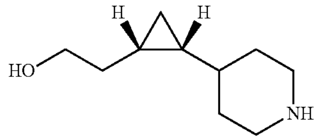 [SMILES: OCC[C@@H]1C[C@@H]1C1CCNCC1]

Step A: 2-((1S,2R)-2-(piperidin-4-yl)cyclopropyl) ethanol

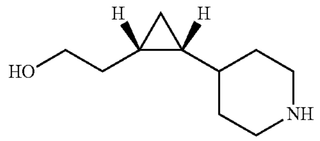 [SMILES: OCC[C@@H]1C[C@@H]1C1CCNCC1]

Benzyl 4-((1R,2S)-2-(2-hydroxyethyl)cyclopropyl)piperidine-1-carboxylate (7.50 g, 24.7 mmol) and palladium on activated carbon (10%, wet, 1.00 g) in methanol (130 mL) were stirred under an atmosphere of hydrogen (1 atm) at RT for 48 h. The mixture was filtered through Celite® and the filter cake washed with methanol. The filtrate was concentrated to dryness under reduced pressure to afford the compound as a white solid. $^1$H NMR (500 MHz, $CDCl_3$) δ 3.74 (m, 2H), 3.15-3.05 (m, 2H), 2.56 (m, 2H), 1.91-1.87 (m, 2H), 1.76-1.72 (m, 3H), 1.36-1.28 (m, 3H), 0.92-0.87 (m, 1H), 0.84-0.76 (m, 1H), 0.67-0.61 (m, 1H), 0.60-0.56 (m, 1H), −0.18 (q, J=4.5 Hz, 1H).

Intermediate 5

Preparation of benzyl 4-((1R,2S)-2-(2-(5-(methylsulfonyl)pyridin-2-yloxy)ethyl)cyclopropyl)piperidine-1-carboxylate

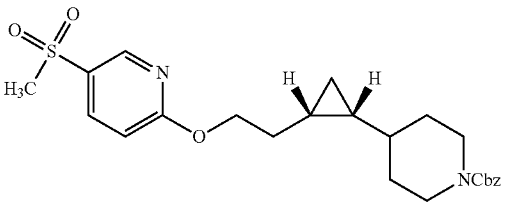 [SMILES: CS(=O)(=O)c1ccc(OCC[C@@H]2C[C@@H]2C2CCN(C(=O)OCc3ccccc3)CC2)nc1]

Step A: benzyl 4-((1R,2S)-2-(2-(5-(methylsulfonyl) pyridin-2-yloxy)ethyl)cyclopropyl)piperidine-1-carboxylate Sodium hydride (424 mg, 60% dispersion in mineral oil, 10.6 mmol) was added to a solution of benzyl 4-((1R,2S)-2-(2-hydroxyethyl)cyclopropyl)piperidine-1-carboxylate (1.07 g, 3.53 mmol) in N,N-dimethylformamide (10 mL) under nitrogen at RT. The mixture was stirred for 30 min at RT and 2-bromo-5-(methylsulfonyl)pyridine (1.25 g, 5.30 mmol) was added. The mixture was stirred overnight, diluted with ethyl acetate (100 mL) and water (50 mL), and the layers were separated. The organic layer was washed with brine (2×25 mL), dried ($Na_2SO_4$), filtered, and concentrated under reduced pressure. The residue was purified by silica gel chromatography (40 g RediSep, eluted with a gradient of hexanes to ethyl acetate, 9:1, 200 mL; 4:1, 500 mL; 1:1, 1 L) to provide the title compound as a light yellow oil. $^1$H NMR (300 MHz, $CDCl_3$) δ 8.71 (dd, J=0.5, 2.5 Hz, 1H), 8.03 (dd, J=2.5, 8.7 Hz, 1H), 7.40-7.28 (m, 5H), 6.84 (dd, J=0.6, 8.7 Hz, 1H), 5.13 (s, 2H), 4.48 (t, J=7.2 Hz, 2H), 4.30-4.10 (m, 2H), 3.07 (s, 3H), 2.90-2.60 (m, 2H), 2.20-2.00 (m, 1H), 1.85-1.65 (m, 2H), 1.60-1.45 (m, 1H), 1.45-1.20 (m, 2H), 1.10-0.85 (m, 2H), 0.75-0.50 (m, 2H), −0.12 (q, J=5.1 Hz, 1H). MS (Multimode) m/z 459 $[M+H]^+$.

Intermediate 6

Step A: benzyl 4-((1R,2S)-2-(2-(4-(1H-tetrazol-1-yl) phenoxy)ethyl)cyclopropyl)piperidine-1-carboxylate

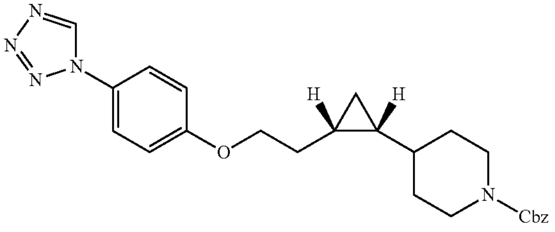 [SMILES: O=C(OCc1ccccc1)N1CCC([C@H]2C[C@H]2CCOc2ccc(-n3cnnn3)cc2)CC1]

4-(1H-Tetrazol-1-yl)phenol (1.10 g, 6.80 mmol), benzyl 441R,2S)-2-(2-hydroxyethyl)cyclopropyl)piperidine-1-carboxylate (2.06 g, 6.80 mmol), and triphenylphosphine (5.34 g, 20.4 mmol) were dissolved in tetrahydrofuran (100 mL) under an atmosphere of nitrogen and cooled at 0° C. Diisopropyl azodicarboxylate (2.47 g, 12.2 mmol) was added. The mixture was warmed to RT and stirred overnight. The mixture was diluted with ethyl acetate (400 mL) and water (200 mL), and the layers were separated. The organic layer was washed with brine (2×200 mL), dried ($Na_2SO_4$), filtered, and concentrated under reduced pressure. The residue was purified by silica gel chromatography (500 g of silica gel, eluted with a gradient of hexanes/ethyl acetate, 9:1, 1 L; 4:1, 1 L; 7:3, 1 L; 1:1, 2 L) provide the title compound as a colorless oil. $^1H$ NMR (300 MHz, $CDCl_3$) δ 8.92 (s, 1H), 7.60 (d, J=9.0 Hz, 2H), 7.40-7.28 (m, 5H), 7.06 (d, J=9.0 Hz, 2H), 5.13 (s, 2H), 4.30-4.10 (m, 2H), 4.12 (t, J=6.5 Hz, 2H), 2.90-2.60 (m, 2H), 2.25-2.10 (m, 1H), 1.90-1.65 (m, 2H), 1.62-1.45 (m, 1H), 1.45-1.20 (m, 2H), 1.10-0.85 (m, 2H), 0.78-0.55 (m, 2H), −0.10 (q, J=5.1 Hz, 1H). MS (Multimode) m/z 448 $[M+H]^+$.

Intermediate 7

Preparation of methyl (2-fluoro-4-hydroxyphenyl) acetate

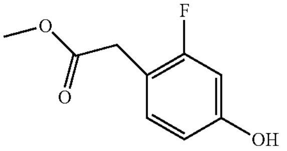

To a solution of (2-fluoro-4-hydroxylphenyl) acetic acid (10 g, 58.8 mmol) in 400 ml methanol was added sulfuric acid (15.7 ml, 294 mmol). The reaction was refluxed overnight. The mixture was concentrated, and diluted with water, adjusted pH~7 with 1N NaOH, and extracted with EtOAC (3×250 ml), washed with brine and the organics were combined, dried over magnesium sulfate, filtered, and the filtrate concentrated under reduced pressure. The residue was purified on Biotage column (100 g silica gel) using a gradient eluent of 10-100% ethyl acetate in hexanes (2500 ml) to afford the title compound. LC/MS (m/z) 185.2 $(M+H)^+$.

Intermediate 8

Preparation of 1-(azetidin-1-yl)-2-(3-fluoro-4-hydroxyphenyl)ethanone

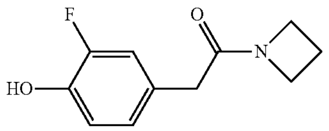 [SMILES: O=C(Cc1ccc(O)c(F)c1)N1CCC1]

To a solution of (3-fluoro-4-methoxyphenyl)acetic acid (0.94 g, 5.52 mmol) in 8 ml anhydrous DMF at RT was added azetidine (0.379 g, 6.63 mmol) and N,N-diisopropylethylamine (2.89 ml, 16.6 mmol), and EDC (1.59 g, 8.29 mmol) was added into the solution and stirred at RT for 4 hrs. The residue was purified by reverse-phase HPLC (SunFire Prep C18 OBD 5 um 19×100 mm column; 10-100% acetonitrile in 0.1% formic acid in water gradient), to give the title compound. LC/MS (m/z) 210.2 $(M+15)^+$.

Intermediate 9

Preparation of 1-(azetidin-1-yl)-2-(4-hydroxy-2-methylphenyl)ethanone

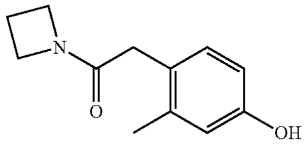

Step A: tert-butyl [4-(benzyloxy)-2-methylphenyl]acetate

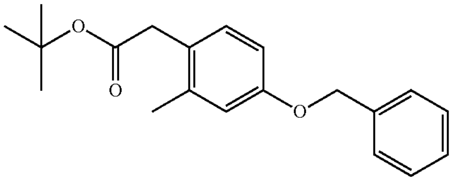 [SMILES: Cc1cc(OCc2ccccc2)ccc1CC(=O)OC(C)(C)C]

To a solution of 5-benzyloxy-2-bromotoluene (1 g, 3.61 mmol) in THF (10 ml) was added 2-tert-butoxy-2-oxoethylzinc chloride (18.04 ml, 9.02 mmol). Nitrogen gas bubbled through the mixture for 10 min. then $Pd_2(dba)_3$ (0.165 g, 0.180 mmol) and X-PHOS (0.172 g, 0.361 mmol) were added and the resulting mixture heated at 60° C. for 50 min. The mixture was cooled, diluted with ethyl acetate (20 mL), washed with aqueous ammonium chloride (saturated, 1×15 mL), dried over $MgSO_4$, filtered and the solvent evaporated under reduced pressure. The residue was purified by column chromatography on silica gel Biotage 50M, using a gradient eluant of EtOAc/Hexane (0-20%) %) to afford the title compound. LC/MS (m/z): 335$(M+Na)^+$.

Step B: [4-(benzyloxy)-2-methylphenyl]acetic acid

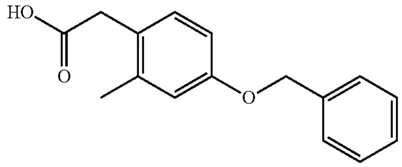 [SMILES: Cc1cc(OCc2ccccc2)ccc1CC(=O)O]

A solution of tert-butyl [4-(benzyloxy)-2-methylphenyl] acetate (1.05 g, 3.36 mmol) in DCM (8 ml) was treated with TFA (7.77 ml, 101 mmol) and the mixture stirred at RT for 30 min. The volatiles were removed in vacuo to afford the title compound. LC/MS (m/z): 257 $(M+H)^+$.

Step C: 1-(azetidin-1-yl)-2-[4-(benzyloxy)-2-methylphenyl]ethanone

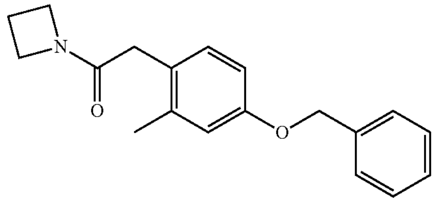 [SMILES: Cc1cc(OCc2ccccc2)ccc1CC(=O)N1CCC1]

[4-(benzyloxy)-2-methylphenyl]acetic acid (0.5 g, 1.951 mmol) was dissolved in DMF (1 ml) and azetidine (0.167 g, 2.93 mmol), DIEA (0.511 ml, 2.93 mmol), and HATU (1.484 g, 3.90 mmol) added. The mixture was stirred at RT for 1 hr. The reside was purified by column chromatography using a Biotage RP C18 cartridge (30 g) using a gradient eluant of 10-100% water:acetonitrile+0.05% formic acid. to afford the title compound. LC/MS (m/z): 296 $(M+H)^+$.

Step D: 1-(azetidin-1-yl)-2-(4-hydroxy-2-methylphenyl)ethanone

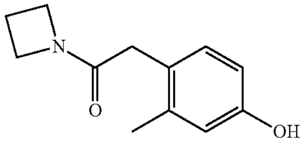

1-(azetidin-1-yl)-2-[4-(benzyloxy)-2-methylphenyl]ethanone (440 mg, 1.490 mmol) was dissolved in ethanol (3 ml). and palladium hydroxide on carbon (20%) (105 mg, 0.149 mmol) added. The mixture was stirred under an atmosphere of hydrogen gas at RT overnight. The mixture was filtered and the filtrate concentrated under reduced pressure to afford the title compound. LC/MS (m/z): 206 $(M+H)^+$.

Intermediate 10

Preparation of 1-(azetidin-1-yl)-2-(2-chloro-4-hydroxyphenyl)ethanone

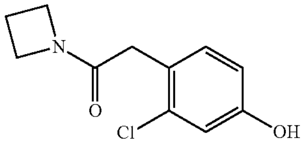 [SMILES: O=C(Cc1ccc(O)cc1Cl)N1CCC1]

Step A: 4-(benzyloxy)-1-bromo-2-chlorobenzene

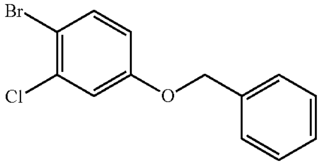 [SMILES: Clc1cc(OCc2ccccc2)ccc1Br]

4-bromo-3-chlorophenol (1 g, 4.82 mmol) was dissolved in DMF (10 ml) and K2CO3 (1.332 g, 9.64 mmol) and benzyl bromide (0.630 ml, 5.30 mmol) added. The mixture was stirred under N2 for 1 hr at RT. The mixture was diluted with water (15 mL) and extracted with EtOAc (2×10 mL). The organic fractions were combined, washed with brine (saturated, 1×8 mL), dried over $MgSO_4$, filtered and the volatiles removed in vacuo. The residue was purified by chromatography on silica gel Biotage 25M, using a gradient eluant of EtOAc/Hexane (0-50%) to afford the title compound. LC/MS (m/z): 297 $(M+H)^+$.

Step B: tert-butyl [4-(benzyloxy)-2-chlorophenyl]acetate

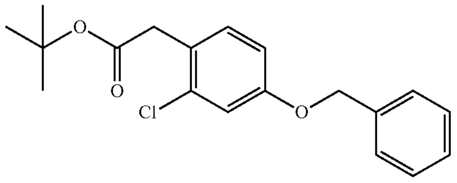 [SMILES: CC(C)(C)OC(=O)Cc1ccc(OCc2ccccc2)cc1Cl]

To a solution of 4-(benzyloxy)-1-bromo-2-chlorobenzene (1 g, 3.36 mmol) in THF (10 ml) was added 2-tert-butoxy-2-oxoethylzinc chloride (13.44 ml, 6.72 mmol). Nitrogen gas bubbled through the mixture for 10 min. then $Pd_2(dba)_3$ (0.154 g, 0.180 mmol) and X-PHOS (0.160 g, 0.336 mmol) were added and the resulting mixture heated at 60° C. for 50 min. The mixture was cooled, diluted with ethyl acetate (20 mL), washed with aqueous ammonium chloride (saturated, 1×15 mL), dried over $MgSO_4$, filtered and the solvent evaporated under reduced pressure. The residue was purified by column chromatography on silica gel Biotage 50M, using a gradient eluant of EtOAc/Hexane (0-20%) to afford the title compound. LC/MS (m/z): 333 $(M+H)^+$.

Step C: [4-(benzyloxy)-2-chlorophenyl]acetic acid

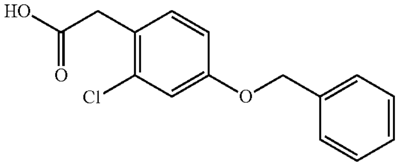 [SMILES: O=C(O)Cc1ccc(OCc2ccccc2)cc1Cl]

A solution of tert-butyl [4-(benzyloxy)-2-chlorophenyl] acetate (1.0 g, 3.00 mmol) in DCM (8 ml) was treated with TFA (6.94 ml, 90 mmol) and the mixture stirred at RT for 30 min. The volatiles were removed in vacuo to afford the title compound. LC/MS (m/z): 299 $(M+Na)^+$.

Step D: 1-(azetidin-1-yl)-2-[4-(benzyloxy)-2-chlorophenyl]ethanone

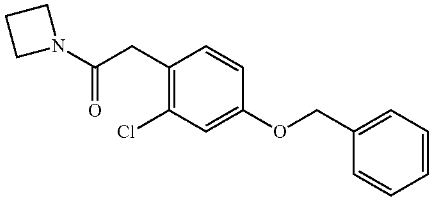

[4-(benzyloxy)-2-chlorophenyl]acetic acid (0.52 g, 1.88 mmol) was dissolved in DMF (1 ml) and azetidine (0.161 g, 2.82 mmol), DIEA (0.99 ml, 5.64 mmol), and HATU (1.43 g, 3.76 mmol) added. The mixture was stirred at RT for 1 hr. The solution was loaded directly onto a Biotage RP C18 cartridge (30 g) and purified using a gradient eluant of 10-100% water: acetonitrile+0.05% formic acid. The volatiles were removed in vacuo to afford the title compound. LC/MS (m/z): 316 $(M+H)^+$.

Step E: 1-(azetidin-1-yl)-2-(2-chloro-4-hydroxyphenyl) ethanone

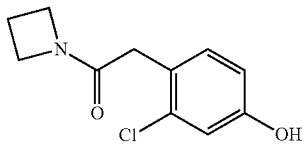 [SMILES: O=C(Cc1ccc(O)cc1Cl)N1CCC1]

1-(azetidin-1-yl)-2-[4-(benzyloxy)-2-chlorophenyl]ethanone (520 mg, 1.65 mmol) was dissolved in ethanol (2 ml). and palladium hydroxide on carbon (20%) (116 mg, 0.165 mmol) added. The mixture was stirred under an atmosphere of hydrogen gas at RT overnight. The mixture was filtered and the filtrate concentrated under reduced pressure. The reside was purified by column chromatography using a Biotage RP C18 cartridge (30 g) using a gradient eluant of 10-100% water:acetonitrile+0.05% formic acid. to afford the title compound. LC/MS (m/z): 226 $(M+H)^+$.

Intermediate 11

Preparation of 2-(4-hydroxy-2-methylphenyl)-N,N-dimethylacetamide

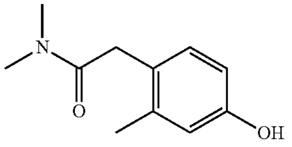

Step A: 2-(4-(benzyloxy)-2-methylphenyl)-N,N-dimethylacetamide

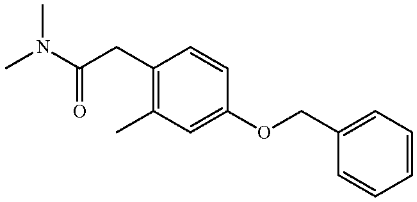 [SMILES: Cc1cc(OCc2ccccc2)ccc1CC(=O)N(C)C]

[4-(benzyloxy)-2-methylphenyl]acetic acid (1.1 g, 4.29 mmol) was dissolved in DMF (5 ml) and dimethylamine (6.44 ml, 12.88 mmol), DIEA (2.25 ml, 12.88 mmol), and HATU (3.26 g, 5.58 mmol) added. The mixture was stirred at RT for overnight. The residue was purified by column chromatography using a Biotage RP C18 cartridge (30 g) using a gradient eluant of 10-100% water:acetonitrile+0.05% formic acid. to afford the title compound. LC/MS (m/z): 284 $(M+H)^+$.

Step B: 2-(4-hydroxy-2-methylphenyl)-N,N-dimethylacetamide

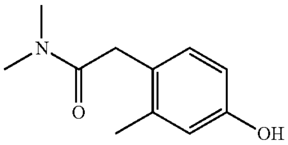

2-[4-(benzyloxy)-2-methylphenyl]-N,N-dimethylacetamide (680 mg, 2.40 mmol) was dissolved in ethanol (4 ml). and palladium hydroxide on carbon (20%) (169 mg, 0.240 mmol) added. The mixture was stirred under an atmosphere of hydrogen gas at RT overnight. The mixture was filtered and the filtrate concentrated under reduced pressure to afford the title compound. LC/MS (m/z): 194 $(M+H)^+$.

Intermediate 12

Preparation of 2-[2-(azetidin-1-yl)-2-oxoethyl]-5-hydroxybenzonitrile

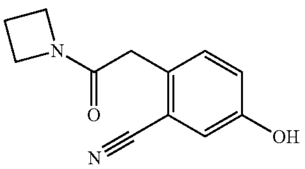 [SMILES: N#Cc1cc(O)ccc1CC(=O)N1CCC1]

Step A: 5-(benzyloxy)-2-bromobenzonitrile

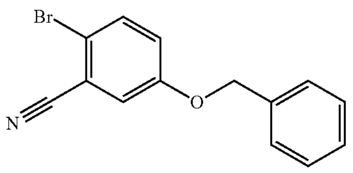 [SMILES: N#Cc1cc(OCc2ccccc2)ccc1Br]

4-bromo-3-cyanophenol (1 g, 5.05 mmol) was dissolved in DMF (10 ml) and K2CO3 (1.40 g, 10.10 mmol) and benzyl bromide (0.66 ml, 5.56 mmol) added. The mixture was stirred under N2 for 1 hr at RT. The mixture was diluted with water (15 mL) and extracted with EtOAc (2×10 mL). The organic fractions were combined, washed with brine (saturated, 1×8 mL), dried over $MgSO_4$, filtered and the volatiles removed in vacuo. The residue was purified by chromatography on silica gel Biotage 25M, using a gradient eluant of EtOAc/Hexane (0-50%) to afford the title compound. LC/MS (m/z): 289 $(M+H)^+$.

Step B: tert-butyl [4-(benzyloxy)-2-cyanophenyl]acetate

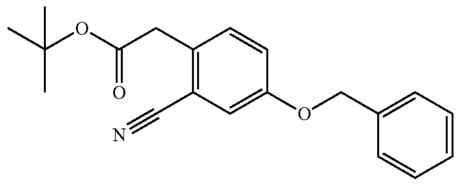 [SMILES: CC(C)(C)OC(=O)Cc1ccc(OCc2ccccc2)cc1C#N]

To a solution of 5-(benzyloxy)-2-bromobenzonitrile (0.73 g, 2.53 mmol) in THF (10 ml) was added 2-tert-butoxy-2-oxoethylzinc chloride (10.13 ml, 5.07 mmol). Nitrogen gas bubbled through the mixture for 10 min. then $Pd_2(dba)_3$ (0.116 g, 0.127 mmol) and X-PHOS (0.121 g, 0.253 mmol) were added and the resulting mixture heated at 60° C. for 50 min. The mixture was cooled, diluted with ethyl acetate (20 mL), washed with aqueous ammonium chloride (saturated, 1×15 mL), dried over $MgSO_4$, filtered and the solvent evaporated under reduced pressure. The residue was purified by column chromatography on silica gel Biotage 50M, using a gradient eluant of EtOAc/Hexane (0-15%) to afford the title compound. LC/MS (m/z): 346 $(M+H)^+$.

Step C: [4-(benzyloxy)-2-cyanophenyl]acetic acid

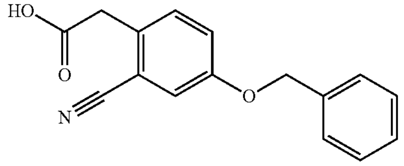 [SMILES: N#Cc1cc(OCc2ccccc2)ccc1CC(=O)O]

A solution of tert-butyl [4-(benzyloxy)-2-cyanophenyl]acetate (0.48 g, 1.48 mmol) in DCM (7 ml) was treated with TFA (3.43 ml, 44.5 mmol) and the mixture stirred at RT for 30 min. The volatiles were removed in vacuo to afford the title compound. LC/MS (m/z): 268 $(M+H)^+$.

Step D: 2-[2-(azetidin-1-yl)-2-oxoethyl]-5-(benzyloxy)benzonitrile

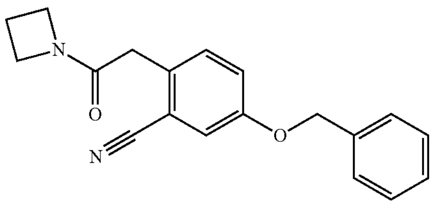 [SMILES: N#Cc1cc(OCc2ccccc2)ccc1CC(=O)N1CCC1]

[4-(benzyloxy)-2-cyanophenyl]acetic acid (0.40 g, 1.50 mmol) was dissolved in DMF (5 ml) and azetidine (0.128 g, 2.25 mmol), DIEA (0.78 ml, 4.49 mmol), and HATU (1.14 g, 2.99 mmol) added. The mixture was stirred at RT for 1 hr. The solution was loaded directly onto a Biotage RP C18 cartridge (30 g) and purified using a gradient eluant of 10-100% water: acetonitrile+0.05% formic acid. The volatiles were removed in vacuo to afford the title compound. LC/MS (m/z): 307 $(M+H)^+$.

Step E: 2-[2-(azetidin-1-yl)-2-oxoethyl]-5-hydroxybenzonitrile

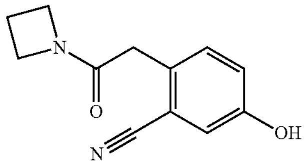 [SMILES: N#Cc1cc(O)ccc1CC(=O)N1CCC1]

2-[2-(azetidin-1-yl)-2-oxoethyl]-5-(benzyloxy)benzonitrile (410 mg, 1.34 mmol) was dissolved in ethanol (2 ml) and palladium hydroxide on carbon (20%) (94 mg, 0.134 mmol) added. The mixture was stirred under an atmosphere of hydrogen gas at RT overnight. The mixture was filtered and the filtrate concentrated under reduced pressure. The reside was purified by column chromatography using a Biotage RP C18 cartridge (30 g) using a gradient eluant of 0-25% water: acetonitrile+0.05% formic acid to afford the title compound. LC/MS (m/z): 217 $(M+H)^+$.

Intermediate 13

Preparation of 2-{(1S,2R)-2-[1-(3-isopropyl-1,2,4-oxadiazol-5-yl)piperidin-4-yl}cyclopropyl]ethanol

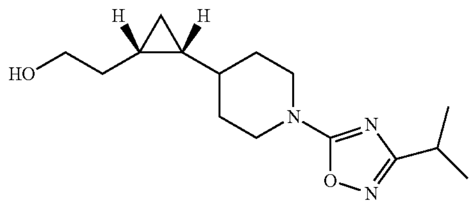 [SMILES: CC(C)c1noc(N2CCC([C@H]3C[C@H]3CCO)CC2)n1]

Step A: 2-((1S,2R)-2-(piperidin-4-yl)cyclopropyl)ethanol

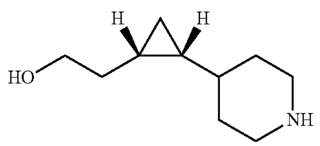 [SMILES: OCC[C@@H]1C[C@@H]1C1CCNCC1]

Benzyl 4-((1R,2S)-2-(2-hydroxyethyl)cyclopropyl)piperidine-1-carboxylate (75.0 g, 247 mmol) and palladium on activated carbon (10%, wet, 10.0 g) in methanol (1000 mL) were stirred under an atmosphere of hydrogen (1 atm) at RT for 48 h. The mixture was filtered through Celite® and the filter cake washed with methanol. The filtrate was concentrated to dryness under reduced pressure to afford the title compound as a white solid. $^1$H NMR (500 MHz, $CDCl_3$) δ 3.74 (m, 2H), 3.15-3.05 (m, 2H), 2.56 (m, 2H), 1.91-1.87 (m, 2H), 1.76-1.72 (m, 3H), 1.36-1.28 (m, 3H), 0.92-0.87 (m, 1H), 0.84-0.76 (m, 1H), 0.67-0.61 (m, 1H), 0.60-0.56 (m, 1H), −0.18 (q, J=4.5 Hz, 1H).

Step B: 4-[(1R,2S)-2-(2-hydroxylethyl)cyclopropyl]piperidine-1-carbonitrile

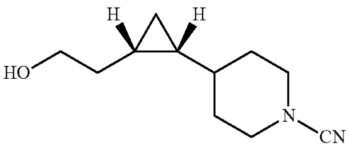 [SMILES: N#CN1CCC([C@H]2C[C@H]2CCO)CC1]

To a solution of 2-((1S,2R)-2-(piperidin-4-yl)cyclopropyl)ethanol (15.5 g, 81 mmol) in DCM (150 ml) was added a slurry of $K_2CO_3$ (55.9 g, 404 mmol) in water (55 ml) and the resulting solution was set to stir vigorously at room temperature. To the biphasic mixture, stirred rapidly at RT, was added a 3M solution of cyanogen bromide (27.0 ml, 81 mmol) in DCM dropwise via addition funnel. The mixture was stirred for 2 hours at RT.

The mixture was diluted with DCM (200 ml) and 150 ml of 1:1 water:saturated sodium bicarbonate added. The mixture was placed in a separatory funnel, shaken, and the layers separated. The aqueous phase was extracted with DCM (100 ml), the organics combined washed with brine, dried over Na2SO4, filtered through an 30 gram pad of silica, the silica washed with 200 ml of 1:1 DCM EtOAc, the organics combined, and the volatiles removed in vacuo. Dried overnight on high-vac to give the title compound as a clear oil. LC/MS (m/z): 195 $(M+H)^+$.

Step C: 2-{(1S,2R)-2-[1-(3-isopropyl-1,2,4-oxadiazol-5-yl)piperidin-4-yl}cyclopropyl]ethanol

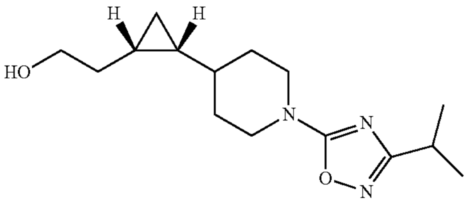 [SMILES: CC(C)c1noc(N2CCC([C@H]3C[C@H]3CCO)CC2)n1]

In a 500 ml RBF was added a solution of 4-[(1R,2S)-2-(2-hydroxyethyl)cyclopropyl]piperidine-1-carbonitrile (15.3 g, 85 mmol) in 1:1 THF:EtOAc (150 ml). To this solution was added N-hydroxy-2-methylpropanimidamide (9.93 g, 97 mmol) as a solid and the resulting mixture was stirred to yield a clear solution. An addition funnel was added to the flask and the whole set up was set under nitrogen atmosphere. The solution was placed in an oil bath heated to 70° C. A 0.5M solution of zinc chloride (204 ml, 102 mmol) in THF was placed in the addition funnel and added over a 5 minute period to the reaction mixture. Upon complete addition, the resulting mixture was stirred at 70° C. for 2 hours. After 30 minutes the clear solution became cloudy. After 1 hour at 70° C., a thick white precipitate formed. TLC indicates consumption of the all starting material. The mixture was cooled to RT and the white solid was filtered off and washed with 1:1 THF:EtOAc (200 mL) and dried. The white solid in the fitted funnel was dissolved in 100 mL of DMF and drawn through by vacuum into a 250 ml RBF. To this solution was then added Tosic Acid (8.07 g, 42.4 mmol) and the resulting mixture stirred at 80° C. overnight. (LCMS after 2.5 hrs showed the reaction was ~30-40% complete with no other by-products forming.) The mixture was allow to cool to room temperature and then was diluted with 150 mL of ethyl acetate. The mixture was placed in a separatory funnel and washed with sat'd sodium bicarbonate solution (150 mL). The aqueous was extracted once with ethyl acetate (100 mL) and the organics were combined. The organics were washed with 1M $Na_2CO_3$ (50 mL), followed by water (2×100 mL), and then brine (100 mL). The organics were dried over sodium sulfate, filtered, and the filtrate concentrated to dryness under reduced pressure. The residue was taken up in 50 mL DCM and loaded onto a Flash 75 system (silica gel column). Biotage Flash 75 purification was done eluting with 20-70% ethyl acetate/hexane for 4 column volumes followed by 70% ethyl acetate for 4 column volumes (total solvent 16 L). The fractions containing the product were collected and concentrated under reduced pressure to afford the pure product. LC/MS (m/z): 280 $(M+H)^+$.

Intermediate 14

Preparation of 2-((1S,2R)-2-{1-[3-(methoxymethyl)-1,2,4-oxadiazol-5-yl]piperidin-4-yl}cyclopropyl)ethanol

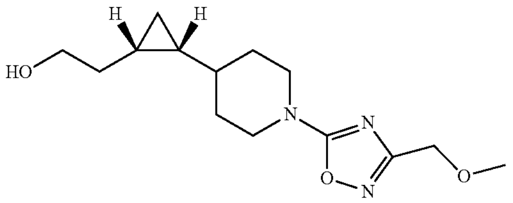 [SMILES: COCc1noc(N2CCC([C@H]3C[C@H]3CCO)CC2)n1]

In a 500 ml RBF was added a solution of 4-[(1R,2S)-2-(2-hydroxyethyl)cyclopropyl]piperidine-1-carbonitrile (from Step B, Intermediate 7; 7.5 g, 40 mmol) in 1:1 THF:EtOAc (150 ml). To this solution was added N-hydroxy-2-methoxyethanimidamide (5 g, 45 mmol) as a solid and the resulting mixture was stirred to yield a clear solution. An addition funnel was added to the flask and the whole set up was set under nitrogen atmosphere. The solution was placed in an oil bath heated to 70° C. A 0.5M solution of zinc chloride (100 ml, 50 mmol) in THF was placed in the addition funnel and added over a 5 minute period to the reaction mixture. Upon complete addition, the resulting mixture was stirred at 70° C. for 2 hours. After 30 minutes the clear solution became cloudy. After 1 hour at 70° C., a thick white precipitate formed. TLC indicates consumption of the all starting material. The mixture was cooled to RT and the white solid was filtered off and washed with 1:1 THF:EtOAc (200 mL) and dried. The white solid in the fritted funnel was dissolved in 50 mL of DMF and drawn through by vacuum into a 250 ml RBF.

To this solution was then added Tosic Acid (4 g, 20 mmol) and the resulting mixture stirred at 80° C. overnight. The mixture was allow to cool to room temperature and then was diluted with 150 mL of ethyl acetate. The mixture was placed in a separatory funnel and washed with sat'd sodium bicarbonate solution (150 mL). The aqueous was extracted once with ethyl acetate (100 mL) and the organics were combined. The organics were washed with 1M $Na_2CO_3$ (50 mL), followed by water (2×100 mL), and then brine (100 mL). The organics were dried over sodium sulfate, filtered, and the filtrate concentrated to dryness under reduced pressure. The residue was taken up in 50 mL DCM and loaded onto a Flash 75 system (silica gel column). Biotage Flash 75 purification was done eluting with 40-80% ethyl acetate/hexane for 4 column volumes followed by 80% ethyl acetate for 4 column volumes (total solvent 16 L). The fractions containing the product were collected and concentrated under reduced pressure to afford the pure product. LC/MS (m/z): 282 $(M+H)^+$.

Intermediate 15

Preparation of 1-methylcyclopropyl-4-[(1R,2S)-2-(2-hydroxyethyl)cyclopropyl]piperidine-1-carboxylate

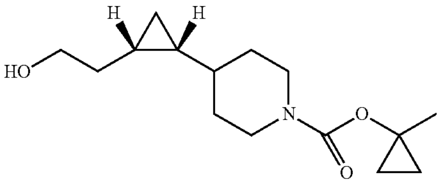 [SMILES: CC1(OC(=O)N2CCC([C@H]3C[C@H]3CCO)CC2)CC1]

To a solution of 2-((1S,2R)-2-(piperidin-4-yl)cyclopropyl)ethanol (Step A, Intermediate 7; 250 mg, 0.8 mmol) and triethylamine (3204, 2.3 mmol) were dissolved in dichloromethane (40 mL). 2,5-Dioxopyrrolidin-1-yl 1-methylcyclopropyl carbonate (170 mg, 0.8 mmol) was added. The mixture was stirred at RT for 30 minutes and concentrated to dryness under reduced pressure. The residue was purified by preparative TLC plate (1000 am, silica gel) developing with 75% ethyl acetate in hexane. The product was eluted off the silica gel using 5% methanol in DCM and the mixture was concentrated under reduced pressure to afford the title compound. LCMS (m/z): 268 $(M+H)^+$.

It is understood that in some cases the order of carrying out the foregoing reaction schemes may be varied to facilitate the reaction or to avoid unwanted reaction products. The following examples are provided for illustrative purposes and should not be construed as limiting the invention in any way.

EXAMPLES

Example 1

Preparation of isobutyl 4-((1R,2S)-2-(2-(4-(1H-tetrazol-1-yl)phenoxy)ethyl)cyclopropyl)piperidine-1-carboxylate

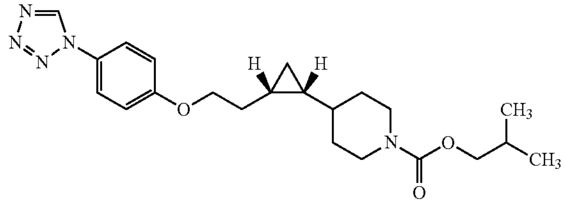 [SMILES: CC(C)COC(=O)N1CCC([C@H]2C[C@H]2CCOc2ccc(-n3cnnn3)cc2)CC1]

Step A: 4-((1R,2S)-2-(2-(4-(1H-tetrazol-1-yl)phenoxy)ethyl)cyclopropyl)piperidine

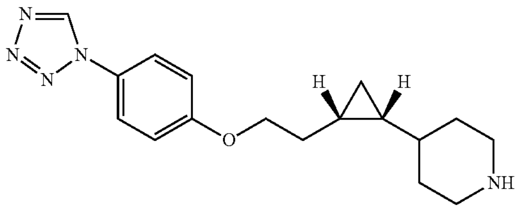 [SMILES: c1cc(-n2cnnn2)ccc1OCC[C@@H]1C[C@@H]1C1CCNCC1]

Benzyl 4-((1R,2S)-2-(2-(4-(1H-tetrazol-1-yl)phenoxy)ethyl)cyclopropyl)piperidine-1-carboxylate (Intermediate 13; 2.90 g, 6.49 mmol) and palladium on activated carbon (10%, wet, 600 mg) in ethanol (50 mL) were stirred under an atmosphere of hydrogen (1 atm) at RT for 2 h. The mixture was filtered (glass wool filter paper, Whatman 1821 110), and washed with ethanol. The filtrate was concentrated to dryness under reduced pressure. The residue was purified by silica gel chromatography (120 g RediSep, eluted with a gradient of dichloromethane/CMA, 9:1, 500 mL; 4:1, 1 L; 7:3, 3 L provide the title compound as an off-white solid. $^1$H NMR (300 MHz, $CDCl_3$) δ 8.90 (s, 1H), 7.59 (d, J=9.0 Hz, 2H), 7.07 (d, J=9.0 Hz, 2H), 4.12 (t, J=6.7 Hz, 2H), 3.17-3.00 (m, 2H), 2.65-2.45 (m, 2H), 2.25-2.05 (m, 1H), 1.90-1.70 (m, 3H), 1.63-1.47 (m, 1H), 1.43-1.23 (m, 2H), 1.02-0.84 (m, 2H), 0.74-0.57 (m, 2H), −0.12 (q, J=4.3 Hz, 1H). MS (Multimode) m/z 314 $[M+H]^+$.

Step B: isobutyl 4-((1R,2S)-2-(2-(4-(1H-tetrazol-1-yl)phenoxy)ethyl)cyclopropyl)piperidine-1-carboxylate

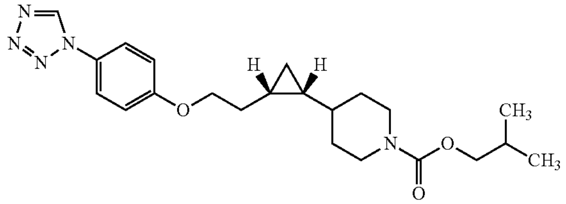 [SMILES: CC(C)COC(=O)N1CCC([C@H]2C[C@H]2CCOc2ccc(-n3cnnn3)cc2)CC1]

4-((1R,2S)-2-(2-(4-(1H-Tetrazol-1-yl)phenoxy)ethyl)cyclopropyl)piperidine (Step A, Example 1; 100 mg, 0.319 mmol) and triethylamine (97 mg, 0.96 mmol) were dissolved in dichloromethane (5 mL). Isobutyl chloroformate (52 mg, 0.38 mmol) was added. The mixture was stirred at RT for 30 min and concentrated to dryness under reduced pressure. The residue was purified by silica gel chromatography (12 g RediSep, eluted with dichloromethane/methanol, 199:1, 500 mL). The product containing fractions were combined and concentrated under reduced pressure. The compound was further purified by prep-HPLC (SunFire C18 OBD, 10 μm, 50×150 mm, 118 mL/min, acetonitrile/water 10:90 to 90:10 at 25 min, total run 30 min) provide the title compound as an off-white solid. $^1$H NMR (300 MHz, $CDCl_3$) δ 8.90 (s, 1H), 7.59 (d, J=9.0 Hz, 2H), 7.07 (d, J=9.0 Hz, 2H), 4.20-4.10 (m, 4H), 3.86 (d, J=6.6 Hz, 2H), 2.85-2.60 (m, 2H), 2.25-2.10 (m, 1H), 2.00-1.90 (m, 1H), 1.85-1.70 (m, 2H), 1.60-1.45 (m, 1H), 1.40-1.25 (m, 2H), 1.10-0.90 (m, 2H), 0.94 (d, J=6.7 Hz, 6H), 0.80-0.65 (m, 2H), −0.09 (q, J=5.2 Hz, 1H). MS (ESI) m/z 414 $[M+H]^+$. GPR119 Human EC50:1.6 nM Example 2

Preparation of 1-methylcyclopropyl 4-((1R,2S)-2-(2-(4-(1H-tetrazol-1-yl)phenoxy)ethyl)cyclopropyl)piperidine-1-carboxylate

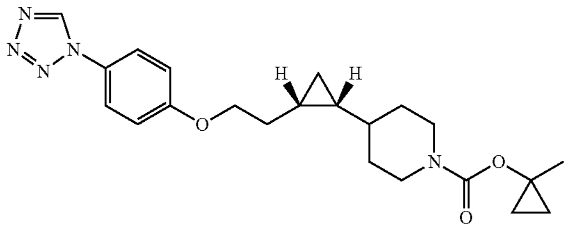 [SMILES: CC1(OC(=O)N2CCC([C@H]3C[C@H]3CCOc3ccc(-n4cnnn4)cc3)CC2)CC1]

Step A: 1-methylcyclopropyl 4-((1R,2S)-2-(2-(4-(1H-tetrazol-1-yl)phenoxy)ethyl)cyclopropyl)piperidine-1-carboxylate

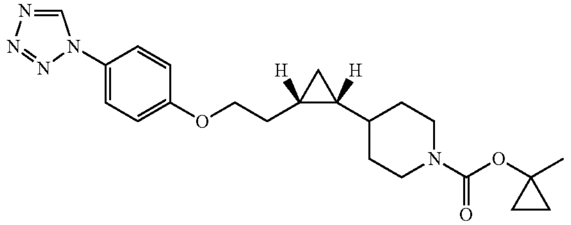 [SMILES: CC1(OC(=O)N2CCC([C@H]3C[C@H]3CCOc3ccc(-n4cnnn4)cc3)CC2)CC1]

4-((1R,2S)-2-(2-(4-(1H-Tetrazol-1-yl)phenoxy)ethyl)cyclopropyl)piperidine (Step B, Example 1; 100 mg, 0.319 mmol) and triethylamine (97 mg, 0.96 mmol) were dissolved in dichloromethane (5 mL). 2,5-Dioxopyrrolidin-1-yl 1-methylcyclopropyl carbonate (81 mg, 0.38 mmol) was added. The mixture was stirred at RT for 30 min and concentrated to dryness under reduced pressure. The residue was purified by silica gel chromatography (12 g RediSep, eluted with dichloromethane/methanol, 199:1, 1 L). The product containing fractions were combined and concentrated under reduced pressure. The compound was further purified by prep-HPLC (SunFire C18 OBD, 10 μm, 50×150 mm, 118 mL/min, acetonitrile/water 10:90 to 90:10 at 25 min, total run 30 min) to provide the title compound as an off-white solid. $^1$H NMR (300 MHz, $CDCl_3$) δ 8.90 (s, 1H), 7.59 (d, J=9.0 Hz, 2H), 7.07 (d, J=9.0 Hz, 2H), 4.30-3.90 (m, 4H), 2.80-2.60 (m, 2H), 2.25-2.10 (m, 1H), 1.85-1.70 (m, 2H), 1.60-1.45 (m, 1H), 1.55 (s, 3H), 1.40-1.20 (m, 2H), 1.10-0.80 (m, 4H), 0.80-0.55 (m, 4H), −0.09 (q, J=5.2 Hz, 1H). MS (ESI) m/z 412 [M+H]$^+$.

GPR119 Human EC50:1.0 nM

Example 3

Preparation of 1-(4-{2-[(1S,2R)-2-{1-[3-(1-methylethyl)-1,2,4-oxadiazol-5-yl]piperidin-4-yl}cyclopropyl]ethoxy}phenyl)imidazolidin-2-one

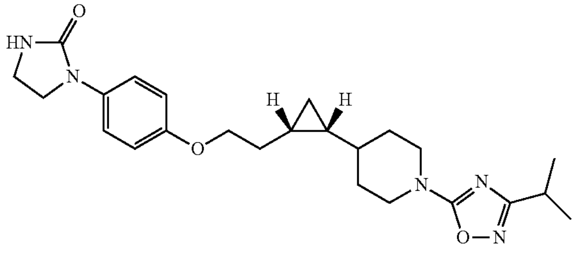 [SMILES: CC(C)c1noc(N2CCC([C@H]3C[C@H]3CCOc3ccc(N4CCNC4=O)cc3)CC2)n1]

Step A: 1-(3-isopropyl-1,2,4-oxadiazol-5-yl)-4-{(1R,2S)-2-[2-(4-nitrophenoxy)ethyl]cyclopropyl}piperidine

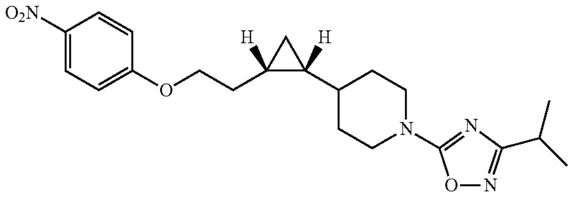 [SMILES: CC(C)c1noc(N2CCC([C@H]3C[C@H]3CCOc3ccc([N+](=O)[O-])cc3)CC2)n1]

To a solution of 2-{(1S,2R)-2-[1-(3-isopropyl-1,2,4-oxadiazol-5-yl)piperidin-4-yl]cyclopropyl}ethanol (367 mg, 0.943 mmol) in DMF (3 ml) at room temperature under nitrogen was added 4-nitrophenol (144 mg, 1.037 mmol), followed by cesium carbonate (614 mg, 1.886 mmol) and the resulting mixture stirred at room temperature overnight. Ethyl acetate (50 mL) was added and washed with water followed by brine. The organic layer was then dried over sodium sulfate, filtered, and the solvent was evaporated under reduced pressure to afford the crude product which was used for the next reaction without further purification. LCMS: retention 1.24 min/2.0 minute run: (ESI) m/z 401 [M+H]$^+$.

Step B: 4-(2-{(1S,2R)-2-[1-(3-isopropyl-1,2,4-oxadiazol-5-yl)piperidin-4-yl]cyclopropyl}ethoxy)aniline

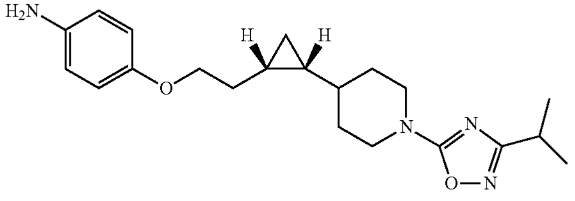

To a solution of 1-(3-isopropyl-1,2,4-oxadiazol-5-yl)-4-{(1R,2S)-2-[2-(4-nitrophenoxy)ethyl]cyclopropyl}piperidine (353 mg, 0.881 mmol) in DMF (5 ml) was added at tin(II) chloride dihydrate (994 mg, 4.41 mmol) and the resulting mixture stirred at room temperature for 2 hours, then heated to 50° C. for 13 hours. Ethyl acetate (50 mL) was added and the solution washed with saturated aqueous sodium hydrogen carbonate followed by brine. The organic layer was dried over sodium sulfate, filtered, and the solvent was evaporated under reduced pressure (328 mg). The residue was purified by flash chromatography on silica gel using a 25 g column, eluting with 1 column volume of DCM, followed by a linear gradient of ethyl acetate in DCM from 0% to 100% over 15 column volumes, to afford the title compound. LCMS: retention 0.79 min/2.0 minute run: (ESI) m/z 371 [M+H]$^+$.

Step C: 1-(4-{2-[(1S,2R)-2-{1-[3-(1-methylethyl)-1,2,4-oxadiazol-5-yl]piperidin-4-yl]cyclopropyl}ethoxy}phenyl)imidazolidin-2-one

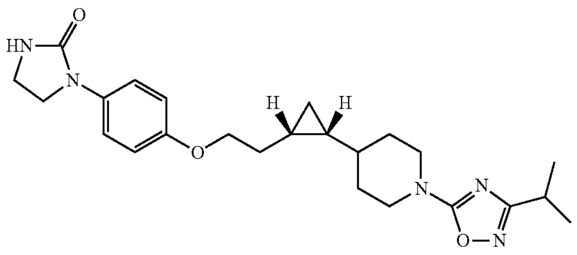 [SMILES: CC(C)c1noc(N2CCC([C@H]3C[C@H]3CCOc3ccc(N4CCNC4=O)cc3)CC2)n1]

To a solution of 4-(2-{(1S,2R)-2-[1-(3-isopropyl-1,2,4-oxadiazol-5-yl)piperidin-4-yl]cyclopropyl}ethoxy)aniline (82 mg, 0.221 mmol) in THF (2.5 ml) at room temperature under nitrogen was added DIPEA (0.155 ml, 0.885 mmol), followed by 2-chloroethyl isocyanate (0.038 ml, 0.443 mmol) and the resulting mixture stirred at room temperature for 1 hour. The mixture was then cooled to 0° C. and NaOtBu (2M solution in THF) (0.443 ml, 0.885 mmol) was added dropwise. The ice bath was removed and the mixture was stirred for 30 minutes at room temperature. The mixture was quenched with formic acid (0.068 ml, 1.771 mmol) and then concentrated under reduced pressure. The residue was dissolved in DMF and filtered. The residue in DMF was then purified by RP HPLC on a Gilson, SunFire-5C18 OBD 19×150 mm column, eluting with a gradient of MeCN in water (0.1% HCOOH) from 10% to 100% over 8 minutes, hold at 100% for 1 minute, at 20 ml/min flow rate. The fractions containing product were combined, frozen and then lyophilized from MeCN/water to afford the title compound.

Example 4

Preparation of 2-(2-{(1S,2R)-2-[1-(3-isopropyl-1,2,4-oxidiazol-5-yl)piperidin-4-yl]cyclopropyl}ethoxy]-3-methyl-5-(1H-tetrazol-1-yl)pyridine

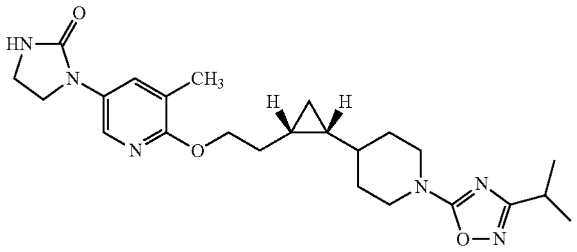 [SMILES: Cc1cc(N2CCNC2=O)cnc1OCC[C@@H]1C[C@@H]1C1CCN(c2nc(C(C)C)no2)CC1]

Step A: benzyl 4-((1R,2S)-2-{2-[(3-methyl-5-nitropyridin-2-yl)oxy]ethyl}cyclopropyl) piperidine-1-carboxylate

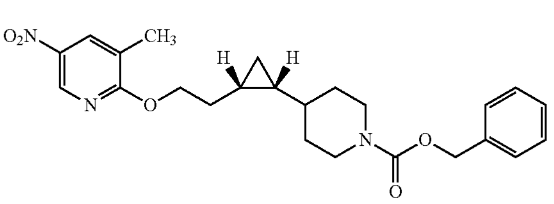 [SMILES: Cc1cc([N+](=O)[O-])cnc1OCC[C@@H]1C[C@@H]1C1CCN(C(=O)OCc2ccccc2)CC1]

To the solution of benzyl 4-[(1R,2S)-2-(2-hydroxyethyl)cyclopropyl]piperidine-1-carboxylate (1.84 g, 6.06 mmol) in 15 ml of DMSO was added NaH and the resulting solution was stirred at 45° C. for 15 min. The mixture was then cooled to 0° C. via an ice/water bath and 2-chloro-3-methyl-5-nitropyridine (1.05 g, 6.06 mmol) was added in portions. The reaction mixture turned dark and became a slurry. After 10 minutes, the ice/water bath was removed and 20 ml of DMSO was added. The resulting mixture was stirred for 40 minutes allowing to warm to room temperature. The reaction was quenched by water and extracted with ethyl acetate (3×100 mL). The organics were combined and washed with brine, dried on sodium sulfate, filtered and the filtrate concentrated under reduced pressure. The residue was purified via Biotage column (65M silica gel) using ethyl acetate in hexane (0-60%, 1000 ml) to afford the title compound. MS (ESI) m/z 440 $[M+H]^+$.

Step B: benzyl 4-((1R,2S)-2-{2-[(5-amino-3-methylpyridin-2-yl)oxy]ethyl}cyclopropyl)piperidine-1-carboxylate

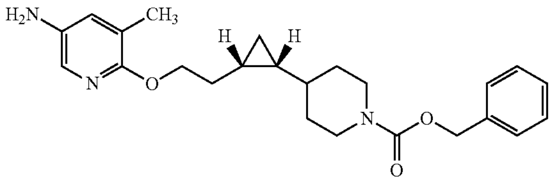

To the solution of $NiCl_2$ (Nickel (II) Chloride-hexahydrate) in 12 ml of methanol was added 50 mg of $NaBH_4$ (solution turned dark) at room temperature and the resulting mixture was stirred for 5 minutes. Benzyl 4-((1R,2S)-2-{2-[(3-methyl-5-nitropyridin-2-yl)oxy]ethyl}cyclopropyl)piperidine-1-carboxylate (from Step A; 550 mg, 1.25 mmol) in 5 ml of DCM was then added followed by the addition of 116 mg of $NaBH_4$ in 3 portions. The mixture was then stirred for 20 minutes and then diluted with DCM and filtered through a pad of sodium sulfate (messy). The solution was concentrated to dryness under reduced pressure and taken up in 15 mL DCM. This material was then filtered through a pad of silica gel (extracting with ethyl acetate) and the filtrate was then washed by saturated aq. $NaHCO_3$. The organics were then dried over sodium sulfate, filtered, and concentrated to dryness under reduced pressure to afford the title compound as a crude product which was used for next step. MS (ESI) m/z 410 $[M+H]^+$.

Step C: benzyl 4-[(1R,2S)-2-(2-{[3-methyl-5-(2-oxoimidazolidin-1-yl)pyridin-2-yl]oxy}ethyl)cyclopropyl]piperidine-1-carboxylate

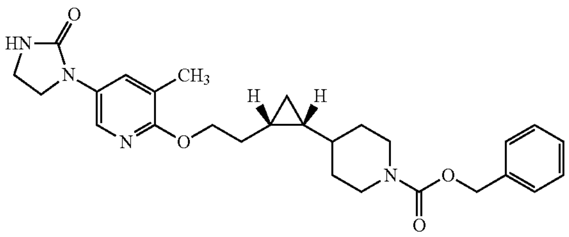 [SMILES: Cc1cc(N2CCNC2=O)cnc1OCC[C@@H]1C[C@@H]1C1CCN(C(=O)OCc2ccccc2)CC1]

To a solution of benzyl-4-((1R,2 S)-2-{2-[(5-amino-3-methylpyridin-2yl)oxy]ethyl}cyclopropyl)piperidine-1-carboxylate (39 mg, 0.106 mmol) in THF (2.5 ml) at RT under nitrogen was added DIPEA (0.037 ml, 0.213 mmol), followed by 2-chloroethyl isocyanate (0.014 ml, 0.160 mmol). And the resulting solution stirred at room temperature overnight. LC/MS showed clean conversion to the uncyclized urea intermediate. The mixture was cooled to 0° C. and NaH (8.51 mg, 0.213 mmol) was added. The mixture was removed from the ice bath after ca. 15 minutes. LC/MS at 1 h showed complete conversion to the desired product. Formic acid (50 μl) was added and the reaction mixture stirred for 30 minutes. The material was concentrated under reduced pressure and the residue was purified by RP HPLC on a Gilson, SunFire-5C18 OBD 19×150 mm column, eluting with a gradient of MeCN in water (0.1% HCOOH) from 10% to 100% over 8 minutes, hold at 100% for 1 minute, at 20 ml/min flow rate to afford the title compound. MS (ESI) m/z 479 $[M+H]^+$.

Step D: 1-(5-methyl-6-{2-[(1S,2R)-2-piperidin-4-ylcyclopropyl]ethoxy}pyridine-3-yl)imidazolidin-2-one

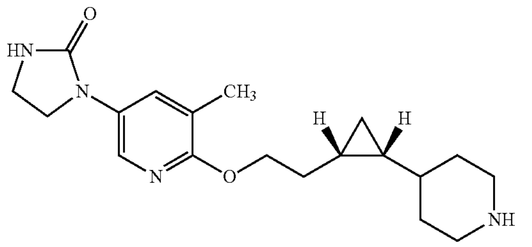 [SMILES: Cc1cc(N2CCNC2=O)cnc1OCC[C@@H]1C[C@@H]1C1CCNCC1]

Benzyl 4-[(1R,2S)-2-(2-{[3-methyl-5-(2-oxoimidazolidin-1-yl)pyridin-2-yl]oxy}ethyl)cyclopropyl]piperidine-1-carboxylate (18 mg, 0.041 mmol) in 1 mL of EtOH was treated with 10% palladium on carbon (10 mg) for 2.5 hrs under 1 atm. of hydrogen gas. The catalyst was filtered off via Gilsen 0.045 μM PTFE syringe filter and the filtrate was concentrated in vacuo to give the product used for the next reaction without further purification. LCMS (ESI) m/z 345 $[M+H]^+$.

Step E: 4-[(1R,2S)-2-(2-{[3-methyl-5-(2-oxoimidazolidin-1-yl)pyridine-2-yl]oxy}ethyl)cyclopropyl]piperidine-1-carbonitrile

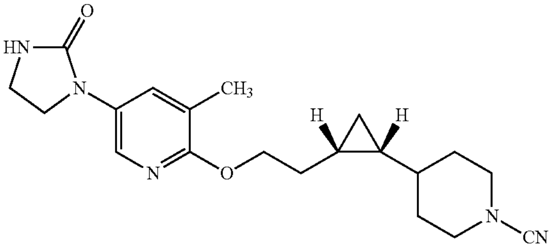 [SMILES: Cc1cc(N2CCNC2=O)cnc1OCC[C@@H]1C[C@@H]1C1CCN(C#N)CC1]

To a solution of 1-(5-methyl-6-{2-[(1S,2R)-2-piperidine-4-ylcyclopropyl]ethoxy}pyridine-3-yl)imidazolidin-2-one (12 mg, 0.035 mmol) in 1.5 mL of DCM was added $K_2CO_3$ (14.5 mg, 0.105 mmol, in 0.5 mL of water) at room temperature followed by addition of cyanogen bromide (0.014 mL of 3M soln in DCM, 0.042 mmol) via syringe at room temperature. The mixture was then stirred for 30 min at room temperature and then diluted with 2 mL DCM. The solution was washed with sat'd $NaHCO_3$ aq. soln, separated, dried over $Na_2SO_4$, filtered and the filtrate concentrated in vacuo. The crude product was used without further purification. LCMS (ESI) m/z 370 $[M+H]^+$.

Step F: 1-(5-methyl-6-{2-[(1S,2R)-2-{1-[3-(1-methylethyl)-1,2,4-oxadiazol-5-yl]piperidin-4-yl}cyclopropyl]ethoxy}pyridin-3-yl)imidazolidin-2-one

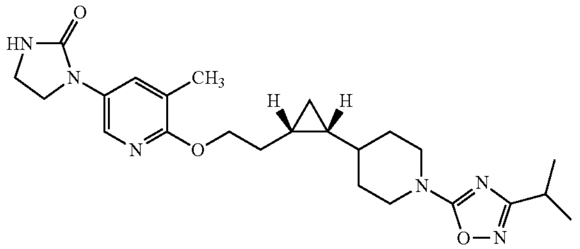 [SMILES: Cc1cc(N2CCNC2=O)cnc1OCC[C@@H]1C[C@@H]1C1CCN(c2nc(C(C)C)no2)CC1]

The mixture of 4-[(1R,2S)-2-(2-{[3-methyl-5-(2-oxoimidazolidin-1-yl)pyridine-2-yl]oxy}ethyl)cyclopropyl]piperidine-1-carbonitrile (13 mg, 0.035 mmol), N-hydroxy-2-methylpropanimidamide (5 mg., 0.05 mmol) and zinc chloride (0.1 mL., 0.05 mmol) in 1 mL of DMF was stirred 2 hrs at 80° C., then PTSA (7 mg, 0.037 mmol) was added and stirred for additional 2 hrs at 85° C. The mixture was cooled to room temperature and then quenched by sat'd aq soln of $NaHCO_3$. The mixture was extracted with EtOAc (2×5 mL), and the combined organics were then washed with brine, dried over sodium sulfate, filtered and the filtrate concentrated in vacuo. The residue was purified Gilson HPLC eluting with a gradient of 10-90% acetonitrile in water with 0.05% TFA as buffer. The fractions containing product were collected into a 20 mL scintillation vial and frozen via a dry ice/acetone bath. The frozen material was then lyophilized overnight to give the product as a white fluffy solid. LCMS (ESI) m/z 455 $[M+H]^+$.

The Examples in Table 2 were synthesized according to similar methods described in the prior examples (1-4).

TABLE 2
| Example # | Chemical Structure | Observed Mass [M + H]+ | GPR119 Human $EC_{50}$ (nM) |
|---|---|---|---|
| 5 | 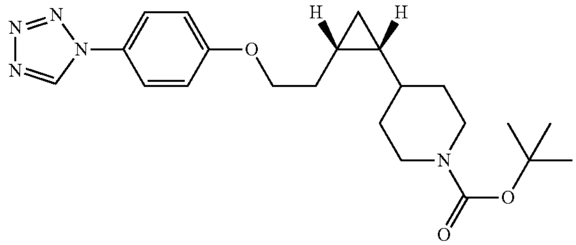 [SMILES: CC(C)(C)OC(=O)N1CCC([C@H]2C[C@H]2CCOc2ccc(-n3cnnn3)cc2)CC1] | 414 | 7 |
| 6 | 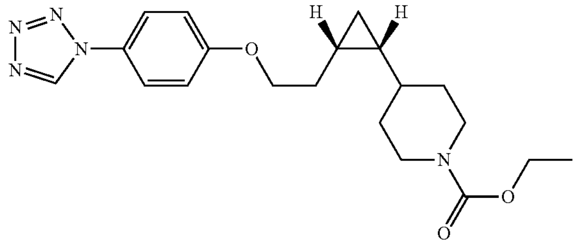 [SMILES: CCOC(=O)N1CCC([C@H]2C[C@H]2CCOc2ccc(-n3cnnn3)cc2)CC1] | 386 | 2 |
| 7 | 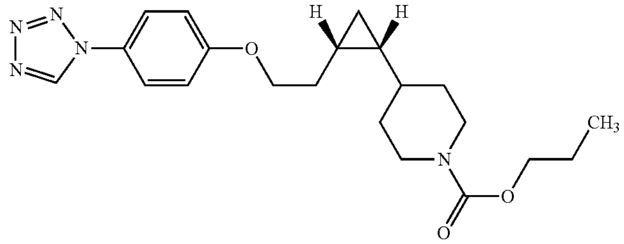 [SMILES: CCCOC(=O)N1CCC([C@H]2C[C@H]2CCOc2ccc(-n3cnnn3)cc2)CC1] | 400 | 0.8 |
| 8 | 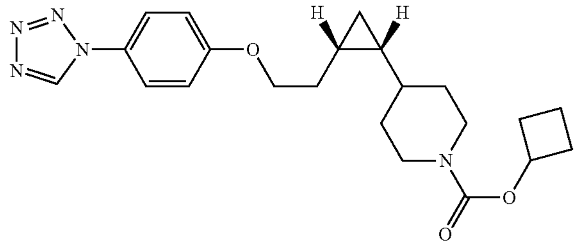 [SMILES: O=C(OC1CCC1)N1CCC([C@H]2C[C@H]2CCOc2ccc(-n3cnnn3)cc2)CC1] | 412 | 1 |
| 9 | 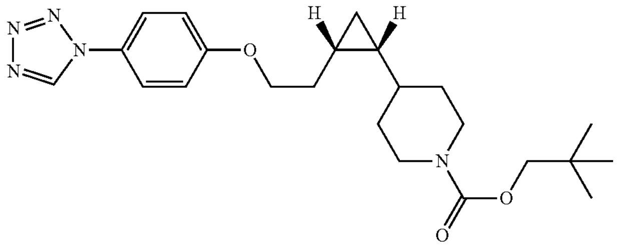 [SMILES: CC(C)(C)COC(=O)N1CCC([C@H]2C[C@H]2CCOc2ccc(-n3cnnn3)cc2)CC1] | 428 | 15 |
| 10 | 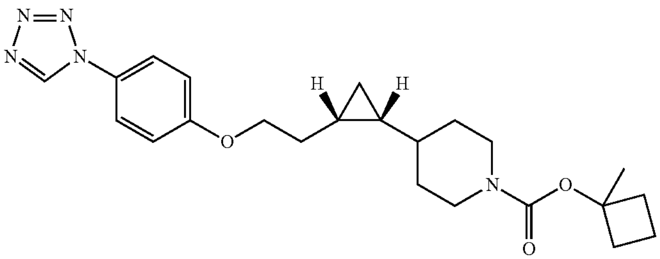 [SMILES: CC1(OC(=O)N2CCC([C@H]3C[C@H]3CCOc3ccc(-n4cnnn4)cc3)CC2)CCC1] | 426 | 0.3 |

TABLE 2-continued

| Example # | Chemical Structure | Observed Mass $[M + H]^+$ | GPR119 Human $EC_{50}$ (nM) |
|---|---|---|---|
| 11 | 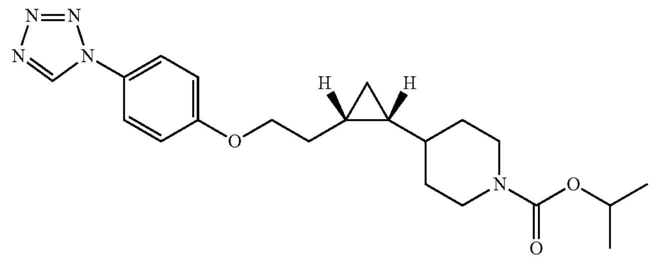 [SMILES: CC(C)OC(=O)N1CCC([C@H]2C[C@H]2CCOc2ccc(-n3cnnn3)cc2)CC1] | 400 | 1.5 |
| 12 | 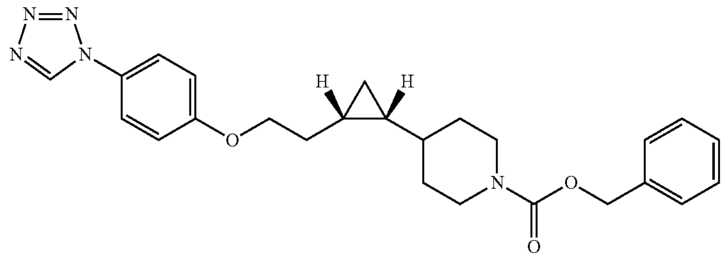 [SMILES: O=C(OCc1ccccc1)N1CCC([C@H]2C[C@H]2CCOc2ccc(-n3cnnn3)cc2)CC1] | 448 | 11.8 |

Example 13

Preparation of cyclopropylmethyl 4-((1R,2S)-2-(2-(5-(methylsulfonyl)pyridin-2-yloxy)ethyl)cyclopropyl)piperidine-1-carboxylate

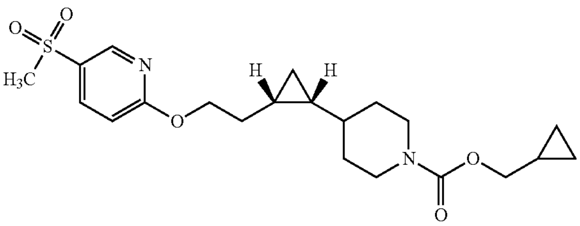 [SMILES: CS(=O)(=O)c1ccc(OCC[C@@H]2C[C@@H]2C2CCN(C(=O)OCC3CC3)CC2)nc1]

Step A: 5-(methylsulfonyl)-2-(2((1S,2R)-2-(piperidin-4-yl)cyclopropyl)ethoxy)pyridine

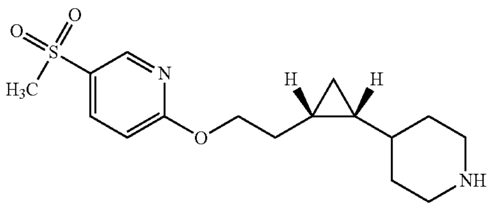 [SMILES: CS(=O)(=O)c1ccc(OCC[C@@H]2C[C@@H]2C2CCNCC2)nc1]

Benzyl 4-((1R,2S)-2-(2-(5-(methylsulfonyl)pyridin-2-yloxy)ethyl)cyclopropyl)piperidine-1-carboxylate (Intermediate 12; 1.20 g, 2.62 mmol) and palladium on activated carbon (10%, wet, 240 mg) in ethanol (50 mL) were stirred under an atmosphere of hydrogen (1 atm) at RT for 3 h. The mixture was filtered (glass wool filter paper, Whatman 1821 110), and washed with ethanol. The filtrate was concentrated to dryness under reduced pressure to provide the title compound as an off-white solid. $^1$H NMR (300 MHz, $CDCl_3$) δ 8.72 (dd, J=0.5, 2.5 Hz, 1H), 8.03 (dd, J=2.5, 8.7 Hz, 1H), 6.84 (dd, J=0.6, 8.7 Hz, 1H), 4.48 (t, J=7.2 Hz, 2H), 3.20-3.05 (m, 2H), 3.07 (s, 3H), 2.65-2.50 (m, 2H), 2.20-1.90 (m, 2H), 1.85-1.65 (m, 2H), 1.60-1.45 (m, 1H), 1.45-1.20 (m, 2H), 1.00-0.80 (m, 2H), 0.70-0.60 (m, 2H), −0.13 (q, J=4.2 Hz, 1H). MS (Multimode) m/z 325 $[M+H]^+$.

Step B: cyclopropylmethyl 4-((1R,2S)-2-(2-(5-(methylsulfonyl)pyridin-2-yloxy)ethyl)cyclopropyl)piperidine-1-carboxylate

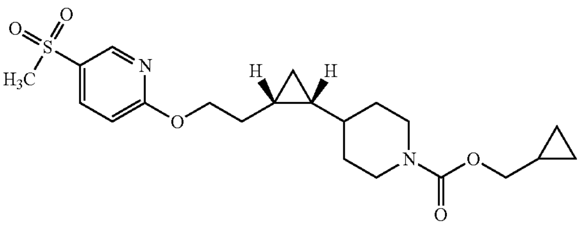 [SMILES: CS(=O)(=O)c1ccc(OCC[C@@H]2C[C@@H]2C2CCN(C(=O)OCC3CC3)CC2)nc1]

To a stirred solution of 5-(methylsulfonyl)-2-(2-((1S,2R)-2-(piperidin-4-yl)cyclopropyl)ethoxy)pyridine (Step A, Example 11; 0.30 g, 0.93 mmol) in dichloromethane (4.6 mL) under a nitrogen atmosphere was added triethylamine (0.36 mL, 2.6 mmol) and cyclopropylmethyl 2,5-dioxopyrrolidin-1-yl carbonate (0.35 g, 1.67 mmol). The resulting solution was stirred for 18 h at ambient temperature. The solution was diluted with saturated $NH_4Cl$(aq.) (10 mL). The resulting layers were separated and the aqueous phase extracted with dichloromethane (2×30 mL). The combined organic extracts were dried over sodium sulfate, filtered and concentrated under reduced pressure. Purification of the obtained residue by CombiFlash chromatography (12 g silica gel, 0 to 25%

EtOAc in heptane) provided the title compound as an off white semi-solid: $^1H$ NMR (500 MHz, $CDCl_3$) δ 8.72 (d, J=2.0 Hz, 1 h), 8.03 (m, 1H), 6.84 (d, J=8.5 Hz, 1H), 4.49 (m, 2H), 4.15 (m, 2H), 3.90 (d, J=7.0 Hz, 2H), 3.07 (s, 3H), 2.80-2.68 (m, 2H), 2.10 (m, 1H), 1.75 (m, 2H) 1.52 (m, 1H), 1.37-1.29 (m, 2H), 1.13 (m, 1H), 1.01-0.87 (m, 2H), 0.70-0.53 (m, 4H), 0.27 (m, 2H), −0.11 (q, J=5.0 Hz, 1H); MS (ESI) m/z 423 $[M+H]^+$.

GPR119 Human EC50: 0.3 nM

Example 14

Preparation of neopentyl 4-((1R,2S)-2-(2-(5-(methylsulfonyl)pyridin-2-yloxy)ethyl)cyclopropyl)piperidine-1-carboxylate

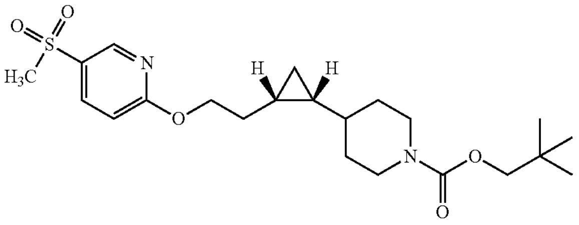 [SMILES: CC(C)(C)COC(=O)N1CCC([C@H]2C[C@H]2CCOc2ccc(S(C)(=O)=O)cn2)CC1]

Step A: neopentyl 4-((1R,2S)-2-(2-(5-(methylsulfonyl)pyridin-2-yloxy)ethyl)cyclopropyl)piperidine-1-carboxylate

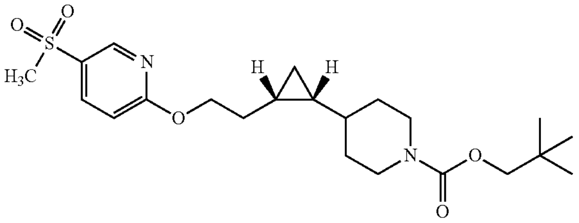 [SMILES: CC(C)(C)COC(=O)N1CCC([C@H]2C[C@H]2CCOc2ccc(S(C)(=O)=O)cn2)CC1]

To a stirred solution of 5-(methylsulfonyl)-2-(2-((1S,2R)-2-(piperidin-4-yl)cyclopropyl)ethoxy)pyridine (Step B, Example GJM10; 0.10 g, 0.32 mmol) in dichloromethane (3 mL) under a nitrogen atmosphere was added triethylamine (0.13 mL, 0.89 mmol) and neopentyl carbonochloridate (0.08 mL, 0.57 mmol). The resulting solution was stirred for 2 h at ambient temperature. The solution was diluted with saturated $NH_4Cl$(aq.) (20 mL). The resulting layers were separated and the aqueous phase extracted with dichloromethane (3×15 mL). The combined organic extracts were washed with brine (20 mL), dried over sodium sulfate, filtered and concentrated under reduced pressure. Purification of the obtained residue by CombiFlash chromatography (12 g silica gel, 0 to 50% EtOAc in hexanes) provided the title compound as an off white semi-solid: $^1H$ NMR (300 MHz, $CDCl_3$) δ 8.72 (m, 1 h), 8.03 (m, 1H), 6.84 (m, 1H), 4.49 (m, 2H), 4.14 (m, 2H), 3.77 (s, 2H), 3.07 (s, 3H), 2.75 (m, 2H), 2.11 (m, 1H), 1.82-1.71 (m, 2H) 1.59-1.47 (m, 1H), 1.39-1.25 (m, 2H), 1.04-0.85 (m, 11H), 0.73-0.54 (m, 2H), −0.11 (q, J=4.8 Hz, 1H); MS (ESI) m/z 439 $[M+H]^+$. GPR119 Human EC50: 2 nM Example 15

Preparation of 4-((1S,2R)-2-{2-[4-(ethylsulfonyl)-3-fluorophenoxy]ethyl}cyclopropyl)-1-[3-(methoxymethyl)-1,2,4-oxadiazol-5-yl]piperidine

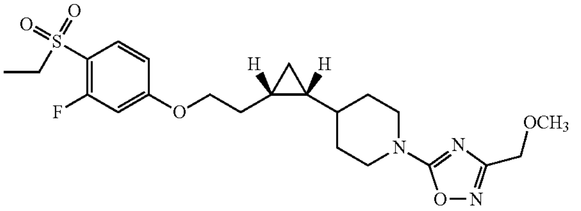 [SMILES: CCS(=O)(=O)c1ccc(OCC[C@@H]2C[C@@H]2C2CCN(c3nc(COC)no3)CC2)cc1F]

Step A: benzyl 4-[(1R,2S)-2-(2-{[4-(methylphenyl)sulfonyl]oxy}ethyl)cyclopropyl]piperidine-1-carboxylate

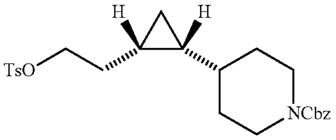

To a cooled solution of benzyl 4-((1R,2S)-2-(2-hydroxyethyl)cyclopropyl)piperidine-1-carboxylate (1.62 g, 5.34 mmol) in dichloromethane (30 mL) at 0° C. were added triethylamine (2.2 mL, 16.0 mmol), 4-dimethylaminopyridine (0.130 g, 1.07 mmol), and p-toluenesulfonyl chloride (1.53 g, 8.01 mmol). The reaction mixture was stirred at RT overnight. The reaction was quenched with saturated aqueous sodium hydrogen carbonate (100 mL) and extracted with dichloromethane (3×50 mL). The combined organics were washed with brine, dried over sodium sulfate, filtered, concentrated under reduced pressure, and the resulting residue purified by column chromatography, (40 g Redisep column, 5 to 50% ethyl acetate in heptane) to provide the tosylate as a clear oil. MS (ESI) m/z=458 $[M+H]^+$.

Step B: 2-[4-((1R,2S)-2-{2-{4-(ethylsulfonyl)-3-fluorophenoxy]ethyl}cyclopropyl)piperidine-1-yl]-1-phenylethanone

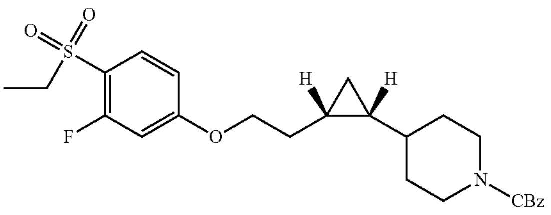

To a solution of the tosylate (1.61 g, 3.52 mmol) in DMF (35 mL) at RT was added sodium hydride (60% dispersion in mineral oil, 0.422 g, 10.55 mmol) and the mixture was stirred for 10 min. After this time, a solution of 3-fluoro-4-(methylsulfonyl)phenol (0.803 g, 4.22 mmol) in DMF (8 mL) was added and the reaction mixture was stirred at RT for 19 h, then heated at 50° C. for an additional 2 h. The reaction mixture was cooled to RT, quenched with water (100 mL) and extracted with ethyl acetate (6×100 mL). The combined organics were then washed with 5% aqueous lithium chloride solution, then brine, dried over sodium sulfate and concentrated under reduced pressure. The residue was purified by column chromatography, (40 g Redisep Gold column, 5 to 50% ethyl acetate in heptane) to afford the ether as a clear, sticky solid. MS (ESI) m/z=490 [M+H]$^+$.

Step C: 4-((1R,2S)-2-{2-{4-(ethylsulfonyl)-3-fluorophenoxy]ethyl}cyclopropyl)piperidine

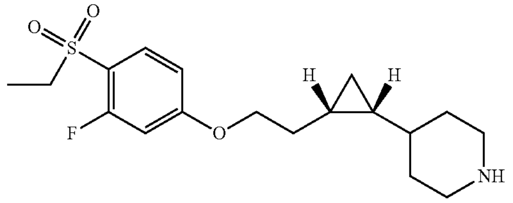 [SMILES: CCS(=O)(=O)c1ccc(OCC[C@@H]2C[C@@H]2C2CCNCC2)cc1F]

The ether, benzyl 4-[(1R,2S)-2-(2-{[4-methylphenyl)sulfonyl]oxy}ethyl)cyclopropyl]piperidine-1-carboxylate (740 mg, 1.62 mmol) in ethanol (25 mL) was added Palladium on carbon (10 wt. %, wet, 0.200 g), degassed (3× vacuum/$H_2$) again and stirred under $H_2$ at 1 atm for 64 h. The reaction mixture was filtered through a plug of celite, and the filter cake rinsed with ethanol (150 mL), ethyl acetate (150 mL), and the filtrate was concentrated under reduced pressure to provide the piperidine as a yellow oil. MS (ESI): 356 [M+H]$^+$.

Step D: 4-((1R,2S)-2-{2-[4-(ethylsulfonyl)-3-fluorophenoxy]ethyl}cyclopropyl)piperidine-1-carbonitrile

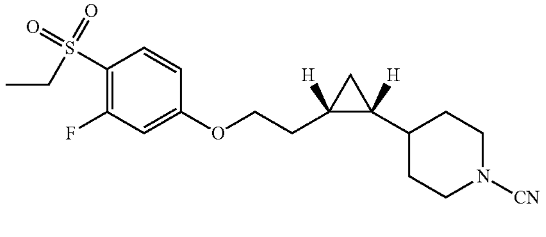 [SMILES: CCS(=O)(=O)c1ccc(OCC[C@@H]2C[C@@H]2C2CCN(C#N)CC2)cc1F]

4-((1R,2S)-2-{2-[4-(ethylsulfonyl)-3-fluorophenoxy]ethyl}cyclopropyl)piperidine (Step C, Example 111; 150 mg, 0.428 mmol) and potassium carbonate (244 mg, 1.77 mmol) were stirred in chloroform (7 mL). Cyanogen bromide (61 mg, 0.58 mmol) was added. The mixture was stirred at RT for 15 min and refluxed overnight. The mixture was cooled to RT, mixed with silica gel (5 g), and concentrated to dryness under reduced pressure. The residue was loaded on a silica gel column (15 g of silica gel) and eluted with dichloromethane/methanol (97.5:2.5, 1 L to provide the title compound as an white solid. MS (Multimode) m/z 381 [M+H]$^+$.

Step E: 4-((1S,2R)-2-{2-[4-(ethylsulfonyl)-3-fluorophenoxy]ethyl}cyclopropyl)-1-[3-(methoxymethyl)-1,2,4-oxadiazol-5-yl]piperidine

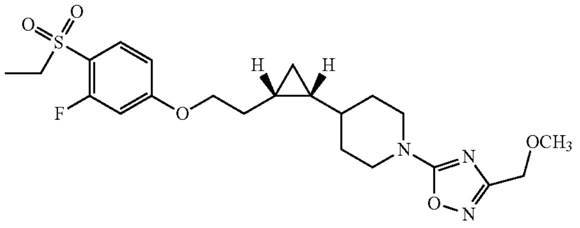 [SMILES: CCS(=O)(=O)c1ccc(OCC[C@@H]2C[C@@H]2C2CCN(c3nc(COC)no3)CC2)cc1F]

To a solution of 4-((1R,2S)-2-{2-{4-(ethylsulfonyl)-3-fluorophenoxy]ethyl}cyclopropyl)piperidine-1-carbonitrile (Step D; 100 mg, 0.27 mmol) and N-hydroxy-2-methoxyacetimidamide (38 mg, 0.37 mmol) in tetrahydrofuran (5 mL) was added zinc chloride (0.8 mL, 0.5 M in tetrahydrofuran, 0.4 mmol). The mixture was refluxed for 2 h, cooled to RT, and concentrated to dryness under reduced pressure. The residue was dissolved in 2 mL of 4N HCl ethanol and water (1:1). The solution was refluxed for 30 min, cooled to RT, and concentrated to dryness under reduced pressure. The residue was dissolved in methanol (5 mL), neutralized by the addition of excess potassium carbonate, mixed silica gel (2 g), and concentrated to dryness under reduced pressure. The residue was loaded on a silica gel column (10 g of silica gel) and eluted with a gradient of dichloromethane/CMA, 19:1, 500 mL; 4:1, 500 mL to provide the title compound. MS (ESI) m/z 468 [M+H]$^+$.

GPR119 Human EC50: 8.4 nM

The Examples in Table 3 were synthesized according to the methods described in the prior examples (13-15) employing the appropriate chloroformate or hydroxysuccinimide reagent.

TABLE 3
| Example # | Chemical Structure | Observed Mass [M + H]+ | GPR119 Human $EC_{50}$ (nM) |
|---|---|---|---|
| 16 | 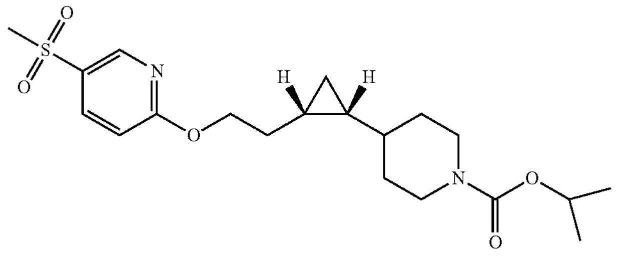 [SMILES: CC(C)OC(=O)N1CCC([C@H]2C[C@H]2CCOc2ccc(S(C)(=O)=O)cn2)CC1] | 411 | 46 |
| 17 | 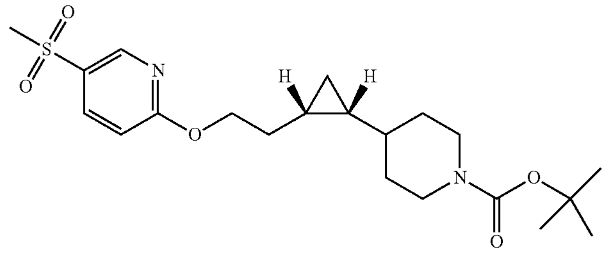 [SMILES: CC(C)(C)OC(=O)N1CCC([C@H]2C[C@H]2CCOc2ccc(S(C)(=O)=O)cn2)CC1] | 425 | 5.8 |
| 18 | 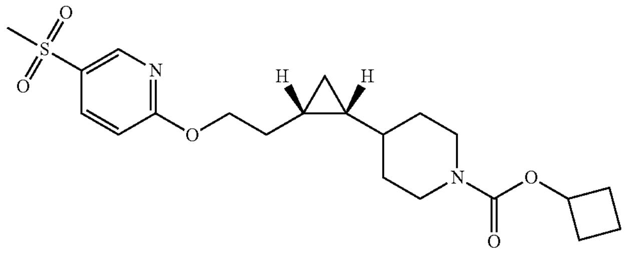 [SMILES: CS(=O)(=O)c1ccc(OCC[C@@H]2C[C@@H]2C2CCN(C(=O)OC3CCC3)CC2)nc1] | 423 | 0.4 |
| 19 | 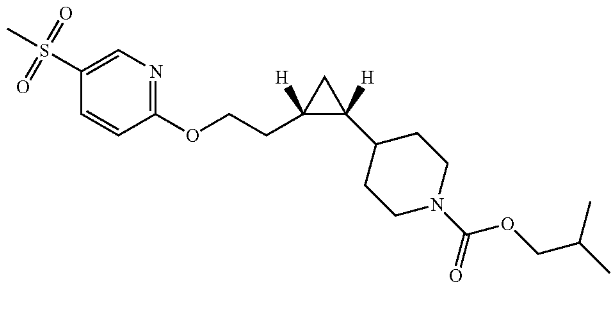 [SMILES: CC(C)COC(=O)N1CCC([C@H]2C[C@H]2CCOc2ccc(S(C)(=O)=O)cn2)CC1] | 425 | 12 |
| 20 | 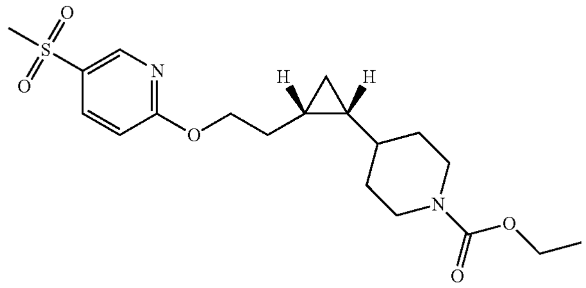 [SMILES: CCOC(=O)N1CCC([C@H]2C[C@H]2CCOc2ccc(S(C)(=O)=O)cn2)CC1] | 397 | 22 |

TABLE 3-continued
| Example # | Chemical Structure | Observed Mass $[M + H]^+$ | GPR119 Human $EC_{50}$ (nM) |
|---|---|---|---|
| 21 | 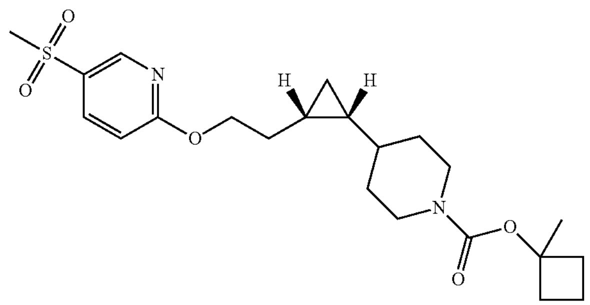 [SMILES: CC1(OC(=O)N2CCC([C@H]3C[C@H]3CCOc3ccc(S(C)(=O)=O)cn3)CC2)CCC1] | 437 | 0.6 |
| 22 | 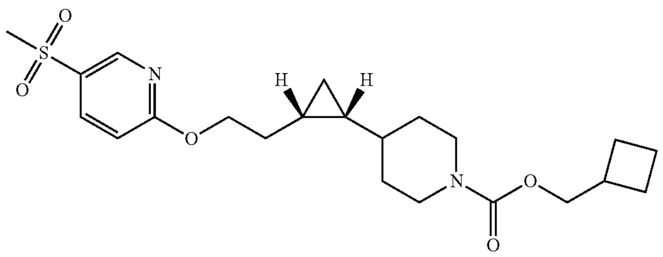 [SMILES: CS(=O)(=O)c1ccc(OCC[C@@H]2C[C@@H]2C2CCN(C(=O)OCC3CCC3)CC2)nc1] | 437 | 5 |
| 23 | 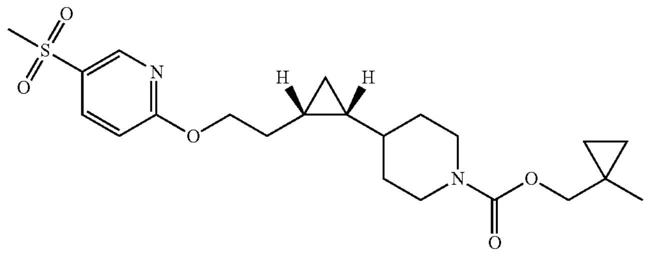 | 437 | 0.6 |
| 24 | 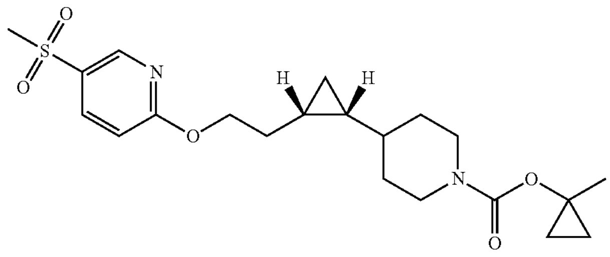 | 423 | 4.2 |
| 25 | 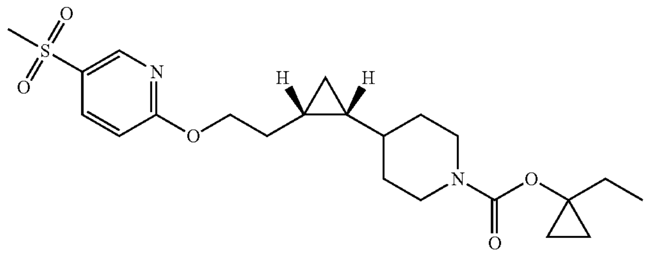 [SMILES: CCC1(OC(=O)N2CCC([C@H]3C[C@H]3CCOc3ccc(S(C)(=O)=O)cn3)CC2)CC1] | 437 | 2.2 |

TABLE 3-continued
| Example # | Chemical Structure | Observed Mass [M + H]+ | GPR119 Human $EC_{50}$ (nM) |
|---|---|---|---|
| 26 | 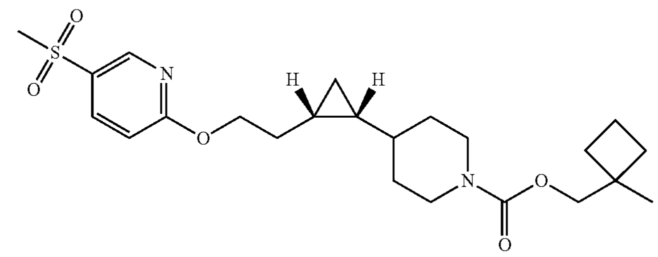 | 451 | 0.6 |
| 27 | 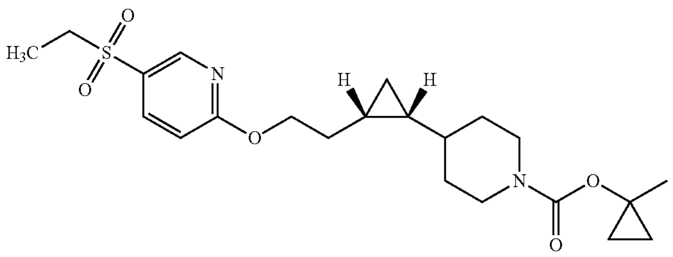 [SMILES: CCS(=O)(=O)c1ccc(OCC[C@@H]2C[C@@H]2C2CCN(C(=O)OC3(C)CC3)CC2)nc1] | 437 | 0.9 |
| 28 | 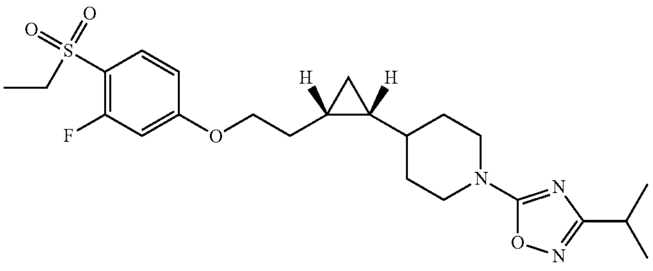 [SMILES: CCS(=O)(=O)c1ccc(OCC[C@@H]2C[C@@H]2C2CCN(c3nc(C(C)C)no3)CC2)cc1F] | 466 | 1.8 |
| 29 | 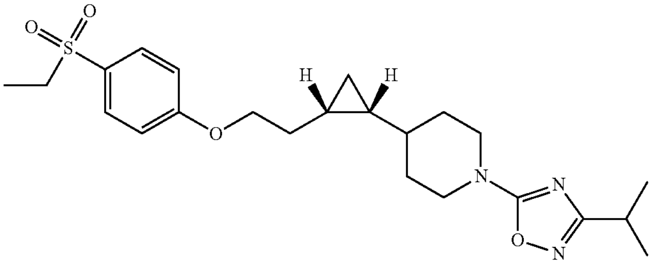 [SMILES: CCS(=O)(=O)c1ccc(OCC[C@@H]2C[C@@H]2C2CCN(c3nc(C(C)C)no3)CC2)cc1] | 448 | 7.7 |

Example 30

Preparation of 1-methylcyclopropyl 4-[(1R,2S)-2-(2-{[3-methyl-5-(1H-tetrazol-1 yl)pyridin-2-yl]oxy}ethyl)cyclopropyl]piperidine-1-carboxylate

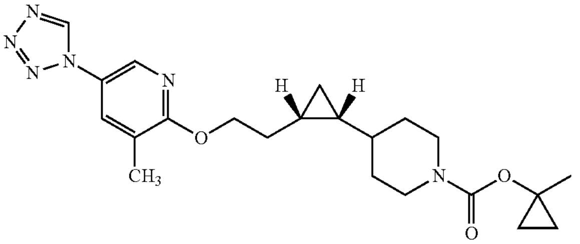 [SMILES: Cc1cc(-n2cnnn2)cnc1OCC[C@@H]1C[C@@H]1C1CCN(C(=O)OC2(C)CC2)CC1]

Step A: benzyl 4-((1R,2S)-2-{-[(3-methyl-5-nitropyridin-2-yl)oxy]ethyl}cyclopropyl)piperidine-1-carboxylate

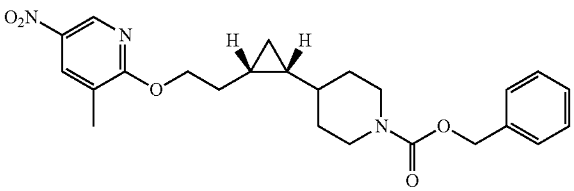 [SMILES: Cc1cc([N+](=O)[O-])cnc1OCC[C@@H]1C[C@@H]1C1CCN(C(=O)OCc2ccccc2)CC1]

To the solution of benzyl 4-[(1R,2S)-2-(2-hydroxyethyl) cyclopropyl)piperidine-1-carboxylate (3.0 g, 9.89 mmol) in 10 ml of anhydrous DMF was added NaH (0.40 g, 9.89 mmol) in small portions at RT and the final resulting solution was stirred for 15 min. Commercially available 2-chloro-3-methyl-5-nitropyridine (1.37 g, 7.91 mmol) was added in 10 portions over 2 minutes and the resulting mixture was stirred 3 hrs at RT. The reaction mixture was quenched with ice cooled aqueous sat'd $NH_4Cl$ solution and extracted with ethyl acetate/ether (1:1) (2×50 mL). The organics were combined, dried over sodium sulfate, filtered, and the filtrate concentrated under reduced pressure. The residue was purified on Biotage column (40M$^+$ silica gel) using a gradient eluant of 0-60% ethyl acetate in hexane (800 ml) to afford the title compound. LC/MS (m/z): 440 $(M+H)^+$.

Step B: benzyl 4-((1R,2S)-2-{-[(5-amino-3-methylpyridin-2-yl)oxy]ethyl}cyclopropyl)piperidine-1-carboxylate

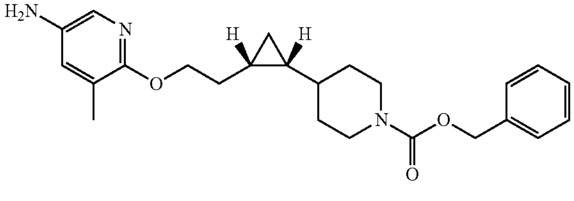

To the solution of $NiCl_2$ (Nickel (II) Chloride-hexahydrate, 1.03 g, 4.32 mmol) in 40 ml of methanol was added 150 mg of $NaBH_4$ (it turned dark) at RT and the mixture stirred 5 minutes. Benzyl 4-((1R,2S)-2-{-[(3-methyl-5-nitropyridin-2-yl)oxy]ethyl}cyclopropyl)piperidine-1-carboxylate (1.90 g, 4.32 mmol) in 15 ml of DCM was added followed by the addition of another 116 mg of $NaBH_4$ in 3 portions. The resulting mixture was then stirred for 40 minutes. The reaction was then diluted with DCM and filtered through a celite and silica gel pad. The filtrate was concentrated in vacuo and the residue was partitioned between saturated $NaHCO_3$ aqueous solution and DCM. The organics were separated, dried over sodium sulfate, filtered and the filtrate concentrated under reduced pressure to afford the title compound as a crude product which was used for the next step. LC/MS (m/z): 410 $(M+H)^+$.

Step C: benzyl 4-[(1R,2S)-2-(2-{[3-methyl-5-(1H-tetrazol-1-yl)pyridin-2-yl]oxy}ethyl)cyclopropyl]piperidine-1-carboxylate

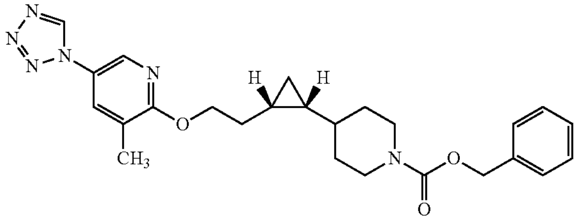 [SMILES: Cc1cc(-n2cnnn2)cnc1OCC[C@@H]1C[C@@H]1C1CCN(C(=O)OCc2ccccc2)CC1]

To a solution of benzyl 4-((1R,2S)-2-{-[(5-amino-3-methylpyridin-2-yl)oxy]ethyl}cyclopropyl)piperidine-1-carboxylate (1.20 g, 2.93 mmol) in acetic acid (50 mL) was added sodium azide (762 mg, 11.72 mmol) followed by triethyl orthoformate (1.95 mL, 11.72 mmol) and the resulting solution was heated to 60° C. and stirred for 3 hours. The volatiles were removed in vacuo and the residue was partitioned between $NaHCO_3$ and ethyl acetate. The aqueous was again extracted with ethyl acetate (100 mL). The organics were combined, washed by brine, dried on sodium sulfate, filtered, and the filtrate concentrated under reduced pressure. The residue was purified on Biotage column (40 M$^+$ silica gel) using a gradient eluant of 0-100% ethyl acetate in hexane (800 ml) to afford the title compound. LC/MS (m/z): 463 $(M+H)^+$.

Step D: 3-methyl-2-{2-[(1R,2S)-2-piperidin-4-yl)cyclopropyl]ethoxy}-5-(1H-tetrazol-1-yl)pyridine

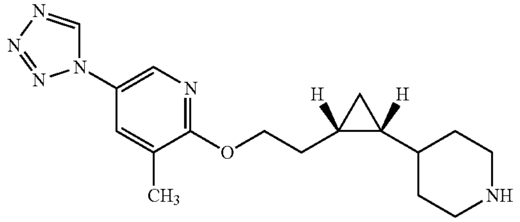 [SMILES: Cc1cc(-n2cnnn2)cnc1OCC[C@@H]1C[C@@H]1C1CCNCC1]

A solution of benzyl 4-[(1R,2S)-2-(2-{[3-methyl-5-(1H-tetrazol-1-yl)pyridin-2-yl]oxy}ethyl)cyclopropyl]piperidine-1-carboxylate (920 mg, 1.99 mmol) in 5 ml of EtOH was treated with 200 mg of Pd/C under a balloon of $H_2$ gas for 3.5 hours. The suspension was filtered through a plug of celite and the filtrate was concentrated to afford the title compound as a crude product to be used for the next step. LC/MS (m/z): 329 $(M+H)^+$.

Step E: 1-methylcyclopropyl 4-[(1R,2S)-2-(2-{[3-methyl-5-(1H-tetrazol-1 yl)pyridin-2-yl]oxy}ethyl) cyclopropyl]piperidine-1-carboxylate

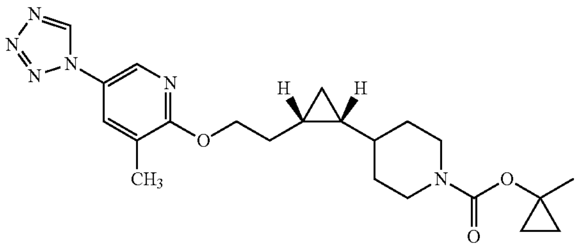 [SMILES: Cc1cc(-n2cnnn2)cnc1OCC[C@@H]1C[C@@H]1C1CCN(C(=O)OC2(C)CC2)CC1]

3-methyl-2-{2-[(1R,2S)-2-piperidin-4-yl)cyclopropyl] ethoxy}-5-(1H-tetrazol-1-yl)pyridine (25 mg, 0.08 mmol) and triethylamine (32 μL, 0.23 mmol) were dissolved in dichloromethane (4 mL). 2,5-Dioxopyrrolidin-1-yl 1-methylcyclopropyl carbonate (17 mg, 0.08 mmol) was added. The mixture was stirred at RT for 30 minutes and concentrated to dryness under reduced pressure. The residue was purified by preparative TLC plate (1000 am, silica gel) developing with 75% ethyl acetate in hexane The product was eluted off the silica gel using 5% methanol in DCM and the mixture was concentrated under reduced pressure to afford the title compound. The compound was further purified by prep-HPLC (SunFire C18 OBD, 10 μm, 50×150 mm, 118 mL/min, acetonitrile/water 10:90 to 90:10 at 25 min, total run 30 min) to provide the title compound. $^1$H NMR (500 MHz, $CDCl_3$) δ 8.96 (s, 1H), 8.31 (s, 1H), 7.77 (s, 1H), 4.60 (t, J=2.4 Hz, 2H), 2.78-2.64 (m, 2H), 2.38 (s, 3H), 2.20-2.16 (m, 1H), 1.80-1.70 (m, 2H), 1.55 (s, 3H), 1.38-1.20 (m, 2H), 1.02-0.95 (m, 2H), 0.94-0.80 (m, 2H), 0.70-0.64 (m, 1H), 0.62-0.55 (m, 2H), −0.10 (q, J=5.1 Hz, 1H). LC/MS (m/z): 427 $(M+H)^+$. GPR119 Human EC50: 0.7 nM The Examples in Table 4 were synthesized according to the methods described in the prior example (30) employing the appropriate reagents and solvents.

TABLE 4

| Example # | Chemical Structure | Observed Mass $[M+H]^+$ | GPR119 Human $EC_{50}$ (nM) |
|---|---|---|---|
| 31 | 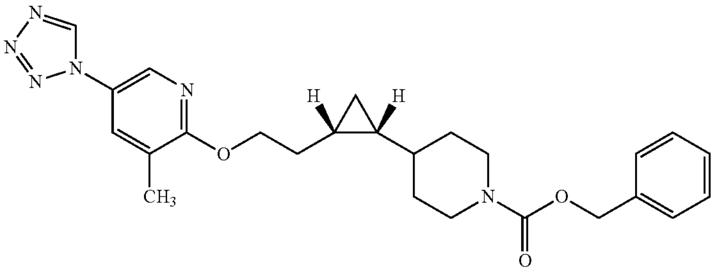 [SMILES: Cc1cc(-n2cnnn2)cnc1OCC[C@@H]1C[C@@H]1C1CCN(C(=O)OCc2ccccc2)CC1] | 463 | 2.8 |
| 32 | 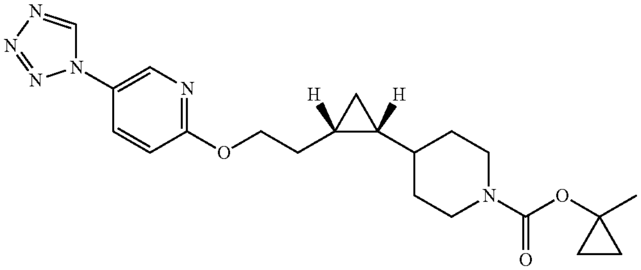 [SMILES: CC1(OC(=O)N2CCC([C@H]3C[C@H]3CCOc3ccc(-n4cnnn4)cn3)CC2)CC1] | 427 | 2.2 |
| 33 | 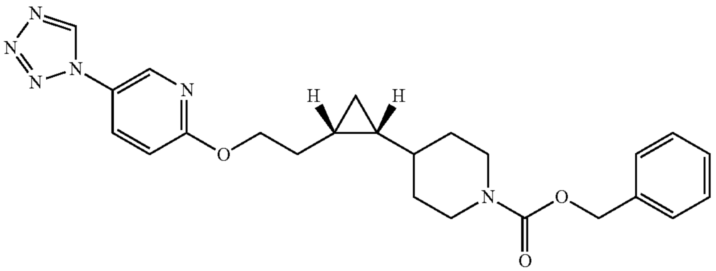 [SMILES: O=C(OCc1ccccc1)N1CCC([C@H]2C[C@H]2CCOc2ccc(-n3cnnn3)cn2)CC1] | 449 | 15 |

Example 34

Preparation of 1-methylcyclopropyl 4-[(1R,2S)-2-(2-{[5-(1H-1,2,4-triazol-1-yl)pyridin-2-yl]oxy}ethyl)cyclopropyl]piperidine-1-carboxylate

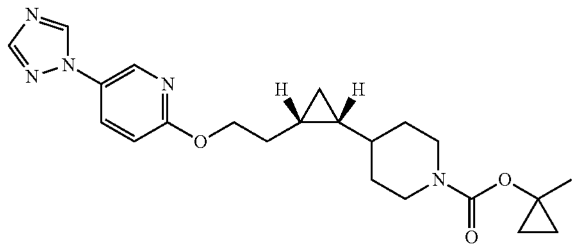 [SMILES: CC1(OC(=O)N2CCC([C@H]3C[C@H]3CCOc3ccc(-n4cncn4)cn3)CC2)CC1]

Step A: 1-methylcyclopropyl 4-[(1R,2S)-2-(2-{[5-(1H-1,2,4-triazol-1-yl)pyridin-2-yl]oxy}ethyl)cyclopropyl]piperidine-1-carboxylate To a stirred solution of 1-methylcyclopropyl 4-[(1R,2S)-2-(2-hydroxyethyl)cyclopropyl)piperidine-1-carboxylate (100 mg, 0.37 mmol) in DMF (5 mL) was added NaH (22 mg, 0.56 mmol) in small portions. After total addition, the grey solution was stirred at RT for 10 minutes and then cooled to −26° C. via dry ice/methanol bath. A solution of 5-(1H-1,2,4-triazole-1-yl)pyridin-2-ol (120 mg, 0.74 mmol) in DMF (0.5+0.5 mL) was added via syringe drop-wise and the resulting mixture was stirred for 30 minutes. The reaction was quenched with a cold solution of NH4Cl (10 mL) via syringe. Water (10 mL) was added and the mixture was extracted with EtOAc (2×30 mL). The organics were combined, dried by $MgSO_4$, filtered, and concentrated under reduced pressure. The residue was purified via flash column chromatography (80 g silica gel, ISCO, eluant 5% methanol in DCM) to afford the product after being concentrated to dryness under reduced pressure. LC/MS (m/z): 412 (M+H)±. LC/MS (m/z): 424 $(M+H)^+$. GPR119 Human EC50: 0.88 nM Example 35

Preparation of tert-butyl 4-((1R,2S)-2-{2-[4-(methylsulfonyl)phenoxy]ethyl}cyclopropyl) piperidine-1-carboxylate

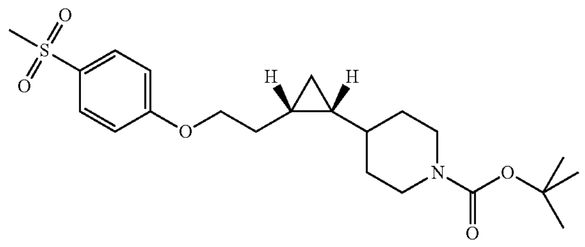 [SMILES: CC(C)(C)OC(=O)N1CCC([C@H]2C[C@H]2CCOc2ccc(S(C)(=O)=O)cc2)CC1]

Step A: tert-butyl 4-((1R,2S)-2-{2-[4-(methylsulfonyl)phenoxy]ethyl}cyclopropyl)piperidine-1-carboxylate 4-(methylsulfonyl)phenol (17 mg, 0.1 mmol), tert-butyl 4-[(1R,2S)-2-(2-hydroxyethyl)cyclopropyl)piperidine-1-carboxylate (27 mg, 0.1 mmol), and triphenylphosphine (70 mg, 0.21 mmol) were dissolved in tetrahydrofuran (1 mL) under an atmosphere of nitrogen and cooled at 0° C. DIAD (32 mg, 0.14 mmol) was added and the resulting mixture was warmed to RT and stirred overnight. The mixture was diluted with ethyl acetate (10 mL) and water (5 mL), and the layers were separated. The organic layer was washed with brine (2×10 mL), dried ($Na_2SO_4$), filtered, and concentrated under reduced pressure. The residue was purified by MS directed HPLC (30 minute, standard gradient 0-90% acetonitrile/water 0.1% formic acid buffer) and the fractions containing product combined. The solution was concentrated to dryness via GenoVac to afford the title compound. LC/MS (m/z): 424 $(M+H)^+$. GPR119 Human EC50: 0.9 nM The Examples in Table 5 were synthesized according to the methods described in the prior examples (34-35) employing the appropriate reagents and solvents.

TABLE 5
| Example # | Chemical Structure | Observed Mass $[M + H]^+$ | GPR119 Human $EC_{50}$ (nM) |
|---|---|---|---|
| 36 | 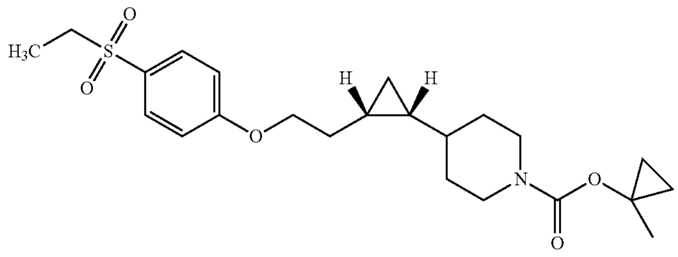 [SMILES: CCS(=O)(=O)c1ccc(OCC[C@@H]2C[C@@H]2C2CCN(C(=O)OC3(C)CC3)CC2)cc1] | 436 | 14.5 |
| 37 | 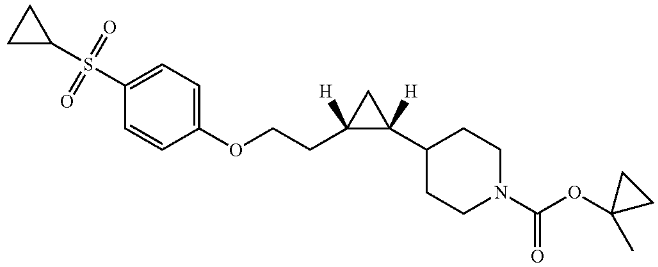 [SMILES: CC1(OC(=O)N2CCC([C@H]3C[C@H]3CCOc3ccc(S(=O)(=O)C4CC4)cc3)CC2)CC1] | 448 | 16 |
| 38 | 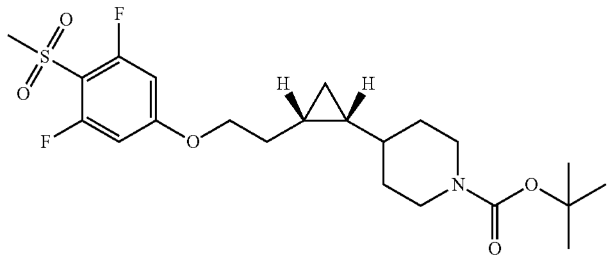 [SMILES: CC(C)(C)OC(=O)N1CCC([C@H]2C[C@H]2CCOc2cc(F)c(S(C)(=O)=O)c(F)c2)CC1] | 460 | 12 |
| 39 | 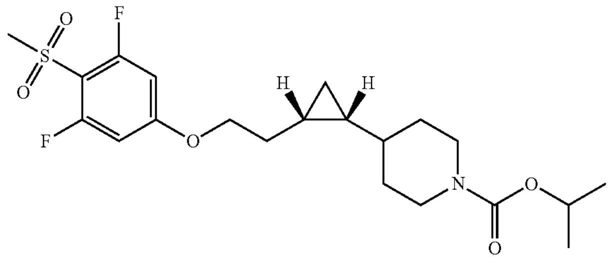 [SMILES: CC(C)OC(=O)N1CCC([C@H]2C[C@H]2CCOc2cc(F)c(S(C)(=O)=O)c(F)c2)CC1] | 446 | 6.6 |
| 40 | 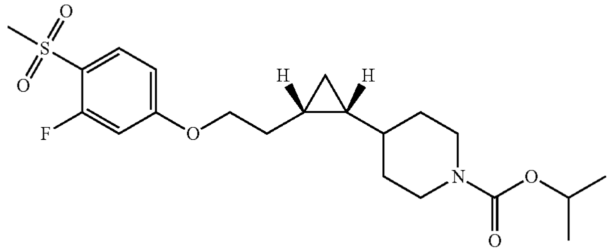 [SMILES: CC(C)OC(=O)N1CCC([C@H]2C[C@H]2CCOc2ccc(S(C)(=O)=O)c(F)c2)CC1] | 428 | 2.3 |

TABLE 5-continued

| Example # | Chemical Structure | Observed Mass $[M + H]^+$ | GPR119 Human $EC_{50}$ (nM) |
|---|---|---|---|
| 41 | 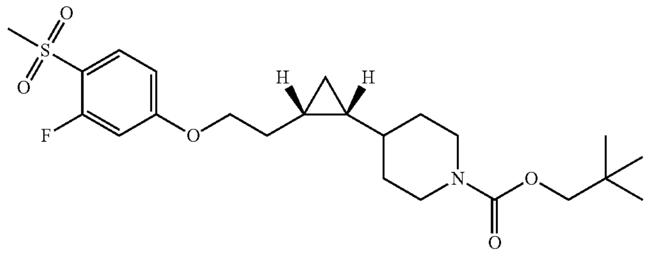 [SMILES: CC(C)(C)COC(=O)N1CCC([C@H]2C[C@H]2CCOc2ccc(S(C)(=O)=O)c(F)c2)CC1] | 456 | 0.4 |
| 42 | 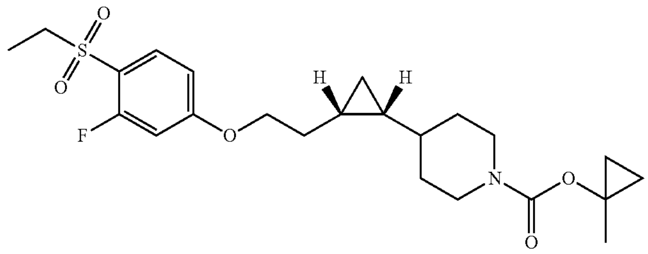 [SMILES: CCS(=O)(=O)c1ccc(OCC[C@@H]2C[C@@H]2C2CCN(C(=O)OC3(C)CC3)CC2)cc1F] | 454 | 2.5 |
| 43 | 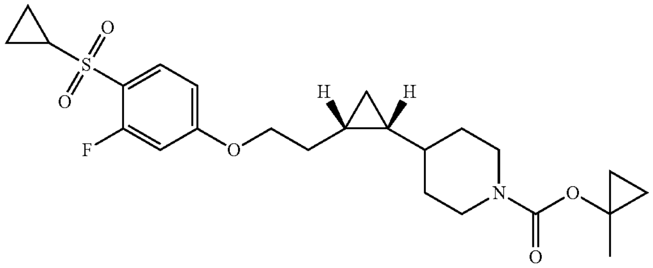 [SMILES: CC1(OC(=O)N2CCC([C@H]3C[C@H]3CCOc3ccc(S(=O)(=O)C4CC4)c(F)c3)CC2)CC1] | 466 | 1.0 |

Example 44

Preparation of methyl 4-((1R,2S-2-{2-[(6-cyano-2-methylpyrimidine-4-yl)oxy]ethyl}cyclopropyl)piperidine-1-carboxylate

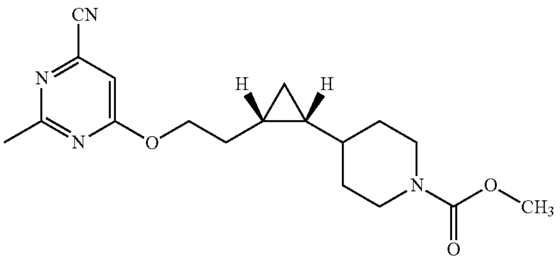

Step A: methyl 4-((1R,2S-2-{2-[(6-cyano-2-methylpyrimidine-4-yl)oxy]ethyl}cyclopropyl)piperidine-1-carboxylate To a stirred solution of methyl 4-[(1R,2S)-2-(2-hydroxyethyl)cyclopropyl)piperidine-1-carboxylate (270 mg, 1.0 mmol) in DMF (7 mL) was added NaH (60 mg, 1.5 mmol) in small portions. After total addition, the grey solution was stirred at RT for 10 minutes and then cooled to −26° C. via dry ice/methanol bath. A solution of commercially available 6-chloro-2-methylpyrimidine-4-carbonitrile (306 mg, 2.0 mmol) in DMF (1+0.5 mL) was added via syringe drop-wise and the resulting mixture was stirred for 30 minutes. The reaction was quenched with a cold solution of NH4Cl (10 mL) via syringe. Water (20 mL) was added and the mixture was extracted with EtOAc (50 mL). The aqueous was checked by TLC and back extracted with EtOAc (20 mL). The organics were combined, dried by MgSO4, filtered through a silica gel pad (1 in wide×2 in long to eliminate some color and baseline impurities) and the silica washed with ethyl acetate (100 mL). The organics were concentrated under vacuum and the residue was purified via flash column chromatography (RediSep Rf (80 g), CV125 mL, 60 mL/min, eluant EtOAc: Hexane=1:9, pdt F55-90) to afford the product as a white solid after being concentrated to dryness under reduced pressure. LC/MS (m/z): 345 $(M+H)^+$. GPR119 Human EC50: 34 nM The Examples in Table 6 were synthesized according to the methods described in the prior example (44) employing the appropriate reagents and solvents.

TABLE 6
| Example # | Chemical Structure | Observed Mass $[M+H]^+$ | GPR119 Human $EC_{50}$ (nM) |
|---|---|---|---|
| 45 | 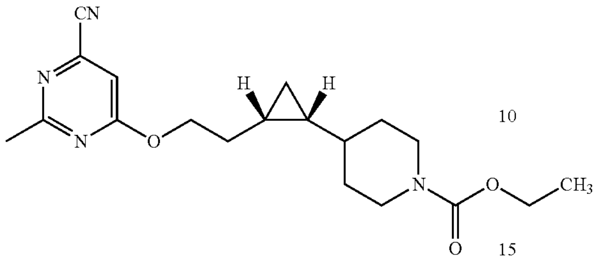 [SMILES: CCOC(=O)N1CCC([C@H]2C[C@H]2CCOc2cc(C#N)nc(C)n2)CC1] | 359 | 3.6 |
| 46 | 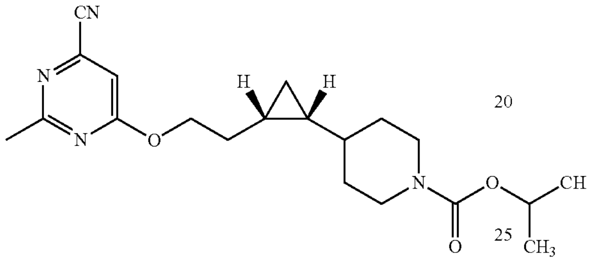 [SMILES: Cc1nc(C#N)cc(OCC[C@@H]2C[C@@H]2C2CCN(C(=O)OC(C)C)CC2)n1] | 373 | 1.2 |
| 47 | 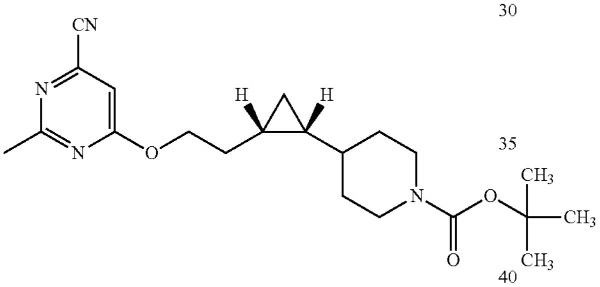 | 387 | 0.2 |
| 48 | 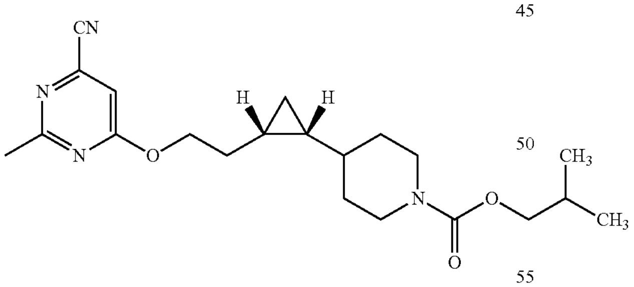 | 387 | 1.0 |
| 49 | 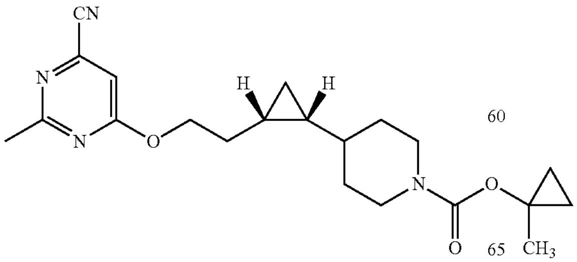 [SMILES: Cc1nc(C#N)cc(OCC[C@@H]2C[C@@H]2C2CCN(C(=O)OC3(C)CC3)CC2)n1] | 385 | 2.0 |

Example 50

Preparation of tert-butyl 4-((1R,2S-2-{2-[3-fluoro-4-(5-methyl-1,3,4-oxadiazol-2-yl)phenoxy]ethyl}cyclopropyl)piperidine-1-carboxylate

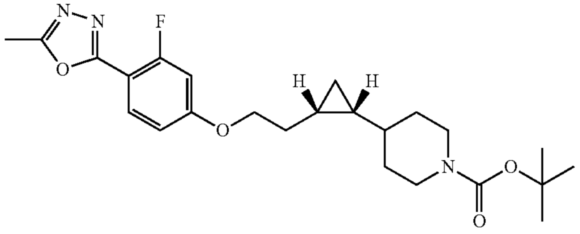 [SMILES: Cc1nnc(-c2ccc(OCC[C@@H]3C[C@@H]3C3CCN(C(=O)OC(C)(C)C)CC3)cc2F)o1]

Step A: tert-butyl 4-((1R,2S-2-{2-[3-fluoro-4-(5-methyl-1,3,4-oxadiazol-2-yl)phenoxy]ethyl}cyclopropyl)piperidine-1-carboxylate 3-fluoro-4-(5-methyl-1,3,4-oxadiazol-2-yl)phenol (40 mg, 0.21 mmol), tert-butyl 4-[(1R,2S)-2-(2-hydroxyethyl)cyclopropyl)piperidine-1-carboxylate (54 mg, 0.2 mmol), and triphenylphosphine (140 mg, 0.42 mmol) were dissolved in tetrahydrofuran (2 mL) under an atmosphere of nitrogen and cooled at 0° C. DIAD (64 mg, 0.28 mmol) was added and the resulting mixture was warmed to RT and stirred overnight. The mixture was diluted with ethyl acetate (10 mL) and water (5 mL), and the layers were separated. The organic layer was washed with brine (2×10 mL), dried ($Na_2SO_4$), filtered, and concentrated under reduced pressure. The residue was purified by MS directed HPLC (30 minute, standard gradient 0-90% acetonitrile/water 0.1% formic acid buffer) and the fractions containing product combined. The solution was concentrated to dryness by centrifugation at low pressure to afford the title compound. LC/MS (m/z): 446 $(M+H)^+$. GPR119 Human EC50: 1.8

Example 51

Preparation of isopropyl 4-((1R,2S-2-{2-[4-(cyclopropyl carbonyl)-3,5-difluorophenoxy]ethyl}cyclopropyl)piperidine-1-carboxylate

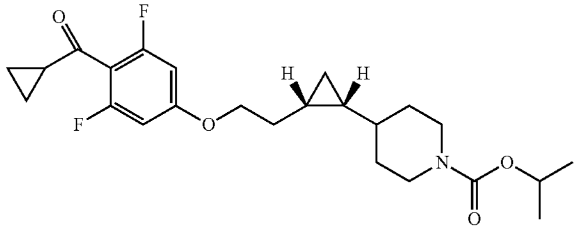 [SMILES: CC(C)OC(=O)N1CCC([C@H]2C[C@H]2CCOc2cc(F)c(C(=O)C3CC3)c(F)c2)CC1]

Step A: cyclopropyl{2,6-difluoro-4-[(4-methoxybenzyl)oxy]phenyl}methanol

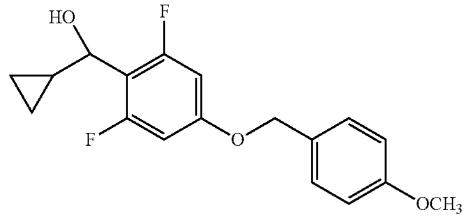 [SMILES: COc1ccc(COc2cc(F)c(C(O)C3CC3)c(F)c2)cc1]

To a stirred solution of commercially available cyclopropyl {2,6-difluoro-4-[(4-methoxybenzyl)oxy]phenyl}methanol (3.0 g, 12.0 mmol) under N2 in anhydrous THF (67 mL) cooled to −78° C. via dry ice/acetone bath was added dropwise n-BuLi (14.4 mL, 1.0M in THF, 14.4 mmol). After 1 hr at −78° C., the solution of cyclopropanecarbaldehyde in THF was added dropwise and the resulting mixture stirred for 2 hrs at this temperature and then slowly warmed up to RT. After stirring for an additional hour, the reaction mixture was quenched with water and extracted with EtOAc. The organics were combined, dried over sodium sulfate, filtered, and then concentrated under reduced pressure. The material was purified by flash chromatography (100 g silica gel, ISCO, eluting with 20/80 ethyl acetate/hexane to afford the title compound. LC/MS 343 $(M+Na)^+$.

Step B: cyclopropyl{2,6-difluoro-4-[(4-methoxybenzyl)oxy]phenyl}methanone

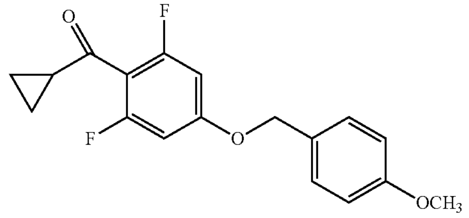 [SMILES: COc1ccc(COc2cc(F)c(C(=O)C3CC3)c(F)c2)cc1]

To a solution of cyclopropyl{2,6-difluoro-4-[(4-methoxybenzyl)oxy]phenyl}methanol (860 mg, 2.73 mmol) in DCM (137 mL) cooled to 0° C. via ice water bath was added 4-methoxylmorpholine N-oxide (481 mg, 4.10 mmol) followed by TPAP (96 mg, 0.27 mmol) and the resulting mixture was stirred for 20 minutes. The mixture was directly loaded onto a silica gel column (80 g, ISCO, eluting with a gradient of 10-30% ethyl acetate hexane) and purified to afford the title compound (728 mg, 85%). LC/MS 319 $(M+H)^+$.

Step C: cyclopropyl(2,6-difluoro-4-hydroxyphenyl)methanone

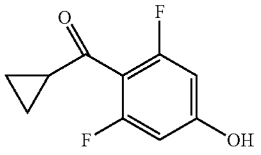 [SMILES: O=C(c1c(F)cc(O)cc1F)C1CC1]

A solution of cyclopropyl {2,6-difluoro-4-[(4-methoxybenzyl)oxy]phenyl}methanone (700 mg, 2.20 mmol) in DCM (10 ml) was added to TFA (3.0 mL) and the resulting solution stirred for 2 hour at RT. The material was concentrated under reduced pressure and the residue purified via flash column chromatography (80 g silica gel, ISCO, eluting with 30-100% ethyl acetate in hexane) to afford the title compound as an oil. $^1$H NMR ($CDCl_3$): δ 8.20 (s, 2H), δ 2.43-2.38 (m, 1H), δ 1.35-1.28 (m, 2H), δ 1.10-1.03 (m, 2H). LC/MS 221 $(M+Na)^+$.

Step D: isopropyl 4-[(1R,2S)-2-(2-hydroxyethyl) cyclopropyl)piperidine-1-carboxylate

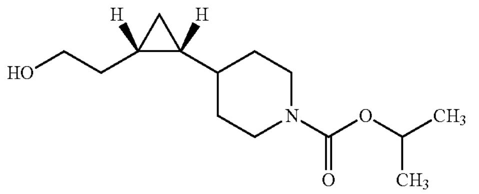 [SMILES: CC(C)OC(=O)N1CCC([C@H]2C[C@H]2CCO)CC1]

Isopropyl chloroformate (0.12 μL, 1.0 mmol) was added dropwise to a solution of 2-((1S,2R)-2-(piperidin-4-yl)cyclopropyl)ethanol (170 mg, 1.0 mmol) and cesium carbonate (650 mg, 2.0 mmol) in acetonitrile (5 mL). After total addition, the mixture was stirred for 2 hours at RT. The solution was concentrated under reduced pressure and the residue taken-up in 10 mL DCM. The solution was washed with water, the organics were collected, dried over sodium sulfate, filtered and the filtrate concentrated to dryness under reduced pressure. The residue by flash chromatography (20 g of silica gel, ISCO, eluted with a gradient 0-100% ethyl acetate in Hexane) to afford the title compound (189 mg, 74%). LC/MS 256 $(M+H)^+$.

Step E: isopropyl 4-((1R,2S-2-{2-[4-(cyclopropylcarbonyl)-3,5-difluorophenoxy]ethyl}cyclopropyl) piperidine-1-carboxylate

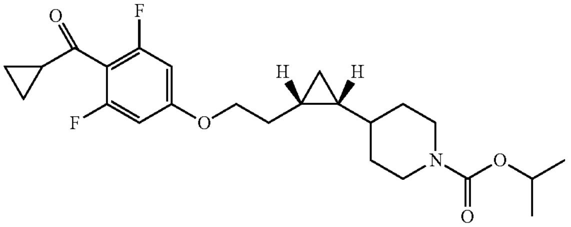 [SMILES: CC(C)OC(=O)N1CCC([C@H]2C[C@H]2CCOc2cc(F)c(C(=O)C3CC3)c(F)c2)CC1]

Cyclopropyl(2,6-difluoro-4-hydroxyphenyl)methanone (15 mg, 0.07 mmol), isopropyl 4-[(1R,2S)-2-(2-hydroxyethyl)cyclopropyl)piperidine-1-carboxylate (Step D, Example 48; 18 mg, 0.07 mmol), and triphenylphosphine (70 mg, 0.21 mmol) were dissolved in tetrahydrofuran (1 mL) under an atmosphere of nitrogen and cooled at 0° C. DIAD (32 mg, 0.14 mmol) was added and the resulting mixture was warmed to RT and stirred overnight. The mixture was diluted with ethyl acetate (10 mL) and water (5 mL), and the layers were separated. The organic layer was washed with brine (2×10 mL), dried ($Na_2SO_4$), filtered, and concentrated under reduced pressure. The residue was purified by MS directed HPLC (30 minute, standard gradient 0-90% acetonitrile/water 0.1% formic acid buffer) and the fractions containing product combined. The solution was concentrated to dryness via GenoVac to afford the title compound. HPLC/MS; 1.18 min, 451 $(M+H)^+$. GPR119 Human EC50: 0.8 nM The Examples in Table 7 were synthesized according to the methods described in the prior examples (50 and 51) employing the appropriate reagents and solvents.

TABLE 7

| Example # | Chemical Structure | Observed Mass $[M + H]^+$ | GPR119 Human $EC_{50}$ (nM) |
|---|---|---|---|
| 52 | 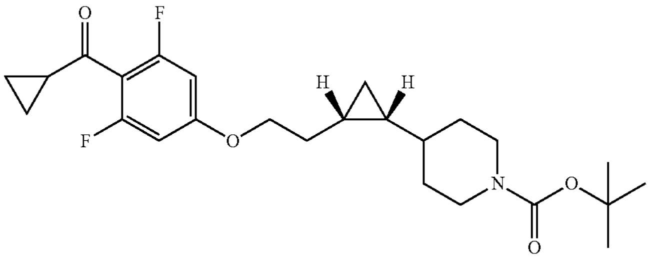 [SMILES: CC(C)(C)OC(=O)N1CCC([C@H]2C[C@H]2CCOc2cc(F)c(C(=O)C3CC3)c(F)c2)CC1] | 450 | 0.2 |
| 53 | 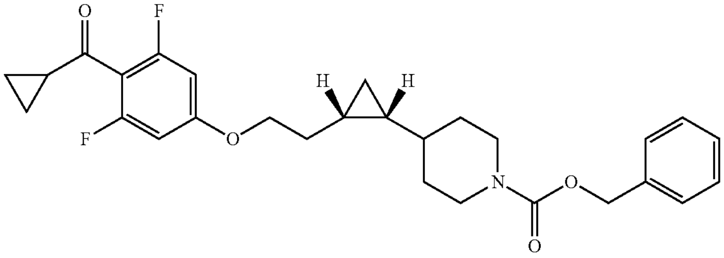 [SMILES: O=C(c1c(F)cc(OCC[C@@H]2C[C@@H]2C2CCN(C(=O)OCc3ccccc3)CC2)cc1F)C1CC1] | 484 | 18 |
| 54 | 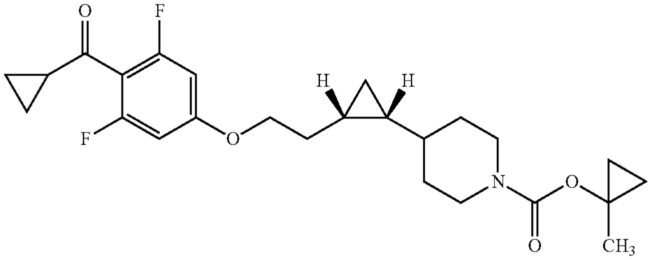 [SMILES: CC1(OC(=O)N2CCC([C@H]3C[C@H]3CCOc3cc(F)c(C(=O)C4CC4)c(F)c3)CC2)CC1] | 448 | 0.7 |
| 55 | 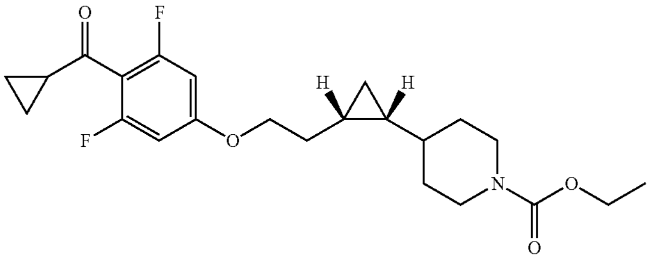 [SMILES: CCOC(=O)N1CCC([C@H]2C[C@H]2CCOc2cc(F)c(C(=O)C3CC3)c(F)c2)CC1] | 422 | 1.1 |

Example 56

Preparation of 1-methylcyclopropyl 4-((1R,2S-2-{2-[4-(2-oxo-2-pyrrolidin-1-ylethyl)phenoxy]ethyl}cyclopropyl)piperidine-1-carboxylate

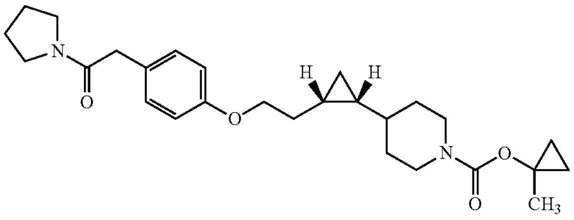 [SMILES: CC1(OC(=O)N2CCC([C@H]3C[C@H]3CCOc3ccc(CC(=O)N4CCCC4)cc3)CC2)CC1]

Step A: 1-methylcyclopropyl 4-((1R,2S)-2-{2-[4-(2-methoxy-2-oxoethyl)phenoxy]ethyl}cyclopropyl)piperidine-1-carboxylate

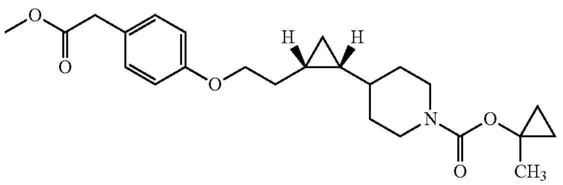 [SMILES: COC(=O)Cc1ccc(OCC[C@@H]2C[C@@H]2C2CCN(C(=O)OC3(C)CC3)CC2)cc1]

Methyl (4-hydroxyphenyl)acetate (37 mg, 0.22 mmol), 1-methylcyclopropyl 4-[(1R,2S)-2-(2-hydroxyethyl)cyclopropyl)piperidine-1-carboxylate (60 mg, 0.22 mmol), and triphenylphosphine (88 mg, 0.34 mmol) were dissolved in tetrahydrofuran (1 mL) under an atmosphere of nitrogen and cooled at 0° C. DIAD (68 mg, 0.34 mmol) was added and the resulting mixture was warmed to RT and stirred overnight. The mixture was diluted with ethyl acetate (10 mL) and water (5 mL), and the layers were separated. The organic layer was washed with brine (2×10 mL), dried ($Na_2SO_4$), filtered, and concentrated under reduced pressure. The residue was purified by silica gel chromatography (24 g of silica gel, ISCO, eluted with a gradient 0-100% ethyl acetate in Hexane) to afford the title compound. HPLC/MS; 1.27 min, 438 $(M+Na)^+$.

Step B: (4-{2-[(1S,2R)-2-(1-{[(1-methylcyclopropyl)oxy]carbonyl}piperidin-4-yl)cyclopropyl]ethoxy}phenyl)acetic acid

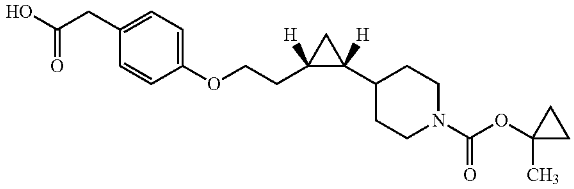 [SMILES: CC1(OC(=O)N2CCC([C@H]3C[C@H]3CCOc3ccc(CC(=O)O)cc3)CC2)CC1]

To a solution of 1-methylcyclopropyl 4-((1R,2S)-2-{2-[4-(2-methoxy-2-oxoethyl)phenoxy]ethyl}cyclopropyl)piperidine-1-carboxylate (Example 53, Step A, 88 mg, 0.21 mmol) in a 1:1:1 mixture of THF/methanol/water (3 mL) was added lithium hydroxide (10.7 mg, 0.44 mmol) and the resulting mixture stirred for 2 h at RT. The mixture was neutralized via addition of 1N aqueous HCl until pH of 7 was obtained. The solution was then extracted with ethyl acetate (3×10 mL). The organics were combined, dried over sodium sulfate, filtered and the filtrate concentrated under reduced pressure to afford the title compound used for the next reaction without further purification. HPLC/MS; 1.22 min, 401 $(M+H)^+$.

Step C: 1-methylcyclopropyl 4-((1R,2S-2-{2-[4-(2-oxo-2-pyrrolidin-1-ylethyl)phenoxy]ethyl}cyclopropyl)piperidine-1-carboxylate

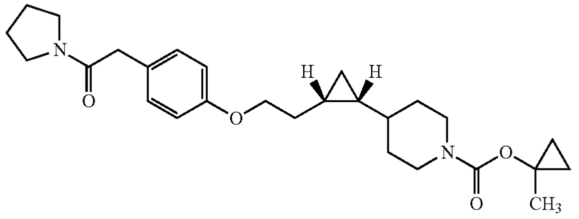 [SMILES: CC1(OC(=O)N2CCC([C@H]3C[C@H]3CCOc3ccc(CC(=O)N4CCCC4)cc3)CC2)CC1]

To a solution of (4-{2-[(1S,2R)-2-(1-{[(1-methylcyclopropyl)oxy]carbonyl}piperidin-4-yl)cyclopropyl]ethoxy}phenyl)acetic acid (50 mg, 0.12 mmol), HOBt (18.4 mg, 0.12 mmol) and EDC (23 mg, 0.12 mmol) in anhydrous DCM (1 mL) was added pyrrolidine (10 μL, 0.12 mmol) and the resulting mixture stirred at RT overnight. LC-MS showed formation of product with no starting material left over. The mixture was diluted with 10 mL of DCM and washed with water. The organics were dried over sodium sulfate, filtered, and the filtrate concentrated to dryness under reduced pressure. The residue was purified by flash column chromatography (10 g of silica gel, ISCO, eluted with a gradient 0-100% ethyl acetate in Hexane) to afford the title compound. HPLC/MS; 1.25 min, 455 $(M+H)^+$. GPR119 Human EC50: 4.7 nM Example 57

Preparation of 1-methylcyclopropyl 4-((1R,2S-2-{2-[4-(2-azetidin-1-yl-2-oxoethyl)phenoxy]ethyl}cyclopropyl)piperidine-1-carboxylate

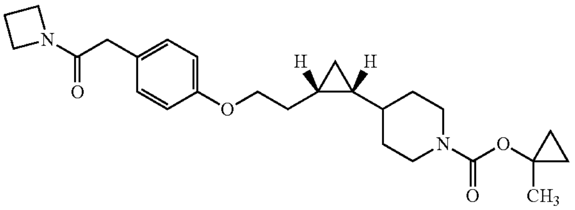 [SMILES: CC1(OC(=O)N2CCC([C@H]3C[C@H]3CCOc3ccc(CC(=O)N4CCC4)cc3)CC2)CC1]

Step A: 1-methylcyclopropyl 4-((1R,2S-2-{2-[4-(2-azetidin-1-yl-2-oxoethyl)phenoxy]ethyl}cyclopropyl)piperidine-1-carboxylate

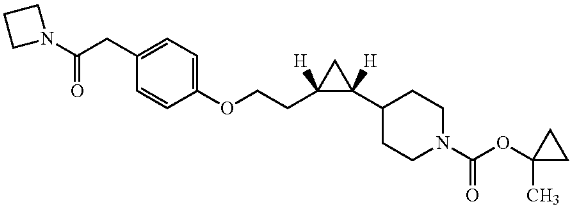 [SMILES: CC1(OC(=O)N2CCC([C@H]3C[C@H]3CCOc3ccc(CC(=O)N4CCC4)cc3)CC2)CC1]

To a solution of (4-{2-[(1S,2R)-2-(1-{[(1-methylcyclopropyl)oxy]carbonyl}piperidin-4-yl)cyclopropyl]ethoxy}phenyl)acetic acid (Step B, Example 53; 25 mg, 0.06 mmol), HOBt (9.2 mg, 0.06 mmol) and EDC (12 mg, 0.06 mmol) in anhydrous DCM (1 mL) was added azetidine (5 μL, 0.06 mmol) and the resulting mixture stirred at RT overnight. LC-MS showed formation of product with no starting material left over. The mixture was diluted with 10 mL of DCM and washed with water. The organics were dried over sodium sulfate, filtered, and the filtrate concentrated to dryness under reduced pressure. The residue was purified by flash column chromatography (10 g of silica gel, ISCO, eluted with a gradient 0-100% ethyl acetate in Hexane) to afford the title compound. HPLC/MS; 1.23 min, 441 (M+H)$^+$. GPR119 Human EC50: 5.9 nM Example 58

Preparation of isopropyl 4-[(1R,2S-2-(2-{4-[(cyclopropylamine)carbonyl]-3,5-difluorophenoxy}ethyl)cyclopropyl]piperidine-1-carboxylate

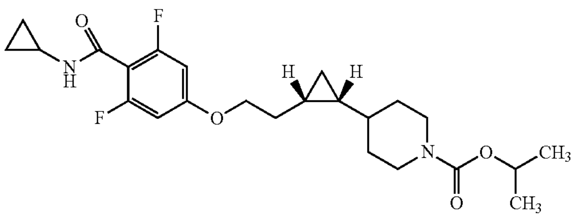 [SMILES: CC(C)OC(=O)N1CCC([C@H]2C[C@H]2CCOc2cc(F)c(C(=O)NC3CC3)c(F)c2)CC1]

Step A: isopropyl 4-[(1R,2S-2-(2-[4-[(cyclopropylamine)carbonyl]-3,5-difluorophenoxy]ethyl)cyclopropyl]piperidine-1-carboxylate

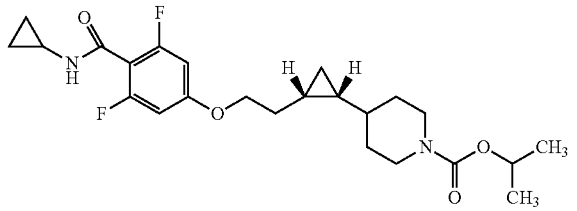 [SMILES: CC(C)OC(=O)N1CCC([C@H]2C[C@H]2CCOc2cc(F)c(C(=O)NC3CC3)c(F)c2)CC1]

N-cyclopropyl-2,6-difluoro-4-hydroxybenzamide (15 mg, 0.07 mmol), isopropyl 4-[(1R,2S)-2-(2-hydroxyethyl)cyclopropyl)piperidine-1-carboxylate (Step D, Example 48; 18 mg, 0.07 mmol), and triphenylphosphine (70 mg, 0.21 mmol) were dissolved in tetrahydrofuran (1 mL) under an atmosphere of nitrogen and cooled at 0° C. Diisopropyl azodicarboxylate, DIAD, (32 mg, 0.14 mmol) was added and the resulting mixture was warmed to RT and stirred overnight. The mixture was diluted with ethyl acetate (10 mL) and water (5 mL), and the layers were separated. The organic layer was washed with brine (2×10 mL), dried ($Na_2SO_4$), filtered, and concentrated under reduced pressure. The residue was purified by MS directed HPLC (30 minute, standard gradient 0-90% acetonitrile/water 0.1% formic acid buffer) and the fractions containing product combined. The solution was concentrated to dryness via GenoVac to afford the title compound. HPLC/MS; 1.18 min, 451 (M+H)$^+$. GPR119 Human EC50: 3.5 nM Example 59

Preparation of 1-methylcyclopropyl 4-[(1R,2S)-2-(2-{4-[2-(azetidin-1-yl)-2-oxoethyl]-3-fluorophenoxy}ethyl)cyclopropyl]piperidine-1-carboxylate

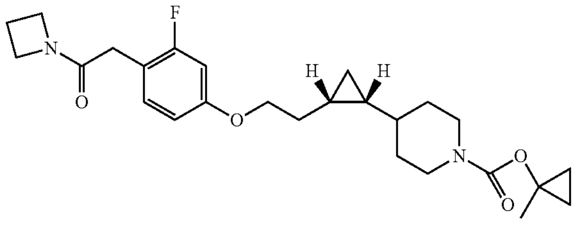 [SMILES: CC1(OC(=O)N2CCC([C@H]3C[C@H]3CCOc3ccc(CC(=O)N4CCC4)c(F)c3)CC2)CC1]

Step A: 1-methylcyclopropyl 4-[(1R,2S)-2-{2-[3-fluoro-4-(2-methoxy-2-oxoethyl)phenoxy]ethyl}cyclopropyl]piperidine-1-carboxylate

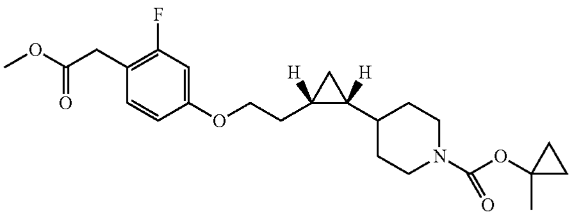 [SMILES: COC(=O)Cc1ccc(OCC[C@@H]2C[C@@H]2C2CCN(C(=O)OC3(C)CC3)CC2)cc1F]

To a solution of 1-methylcyclopropyl 4-[(1R,2S)-2-(2-hydroxyethyl)cyclopropyl]piperidine-1-carboxylate (Intermediate 9, 0.484 g, 1.81 mmol) in 5 ml anhydrous dichloromethane at RT was added a solution of methyl (2-fluoro-4-hydroxyphenyl)acetate (0.400 g, 2.17 mmol) in 10 ml anhydrous dichloromethane, triphenylphosphine, polymer-bound (1.42 g, 4.10 mmol), and di-tert-butyl azodicarboxylate (0.834 g, 3.61 mmol). The reaction mixture was stirred at RT for 3 hours. It was filtered by Celite and concentrated. The residue was purified on Biotage column (50 g silica gel) using a gradient eluent of 0-50% ethyl acetate in hexanes (1000 ml) to afford the title compound. LC/MS (m/z) 434.2 (M+H)$^+$.

Step B: (2-fluoro-4-{2-[(1S,2R)-2-(1-{[(1-methylcyclopropyl)oxy]carbonyl}piperidin-4-yl)cyclopropyl]ethoxy}phenyl)acetic acid

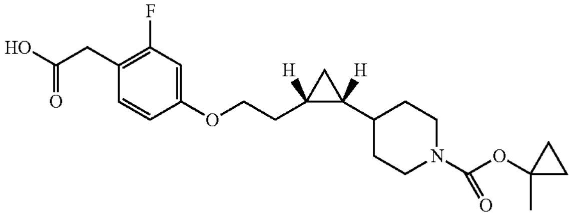 [SMILES: CC1(OC(=O)N2CCC([C@H]3C[C@H]3CCOc3ccc(CC(=O)O)c(F)c3)CC2)CC1]

To a solution of 1-methylcyclopropyl 4-[(1R,2S)-2-{2-[3-fluoro-4-(2-methoxy-2-oxoethyl)phenoxy]ethyl}cyclopropyl]piperidine-1-carboxylate (0.450 g, 1.04 mmol) in 14 ml anhydrous tetrahydrofuran was added by 7 ml methanol and 7 ml water. Lithium hydroxide (0.393 g, 16.39 mmol) was added into the reaction mixture, and the reaction was stirred at RT overnight. 1 M hydrochloric acid was added to adjust the pH to 4. The volatiles were removed under vacuum, and the remaining aqueous layer was extracted with dichloromethane (3×50 ml). The organics were combined, dried over magnesium sulphate, filtered, and the filtrate concentrated under reduced pressure. The residue was purified on Biotage column (50 g silica gel) using a gradient eluent of 0-70% ethyl acetate in hexanes (700 ml) to afford the title compound. LC/MS (m/z) 420.2 (M+H)$^+$.

Step C: 1-methylcyclopropyl 4-[(1R,2S)-2-(2-{4-[2-(azetidin-1-yl)-2-oxoethyl]-3-fluorophenoxy}ethyl)cyclopropyl]piperidine-1-carboxylate

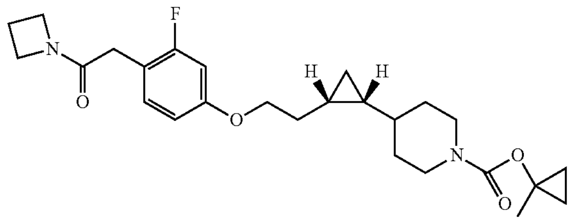 [SMILES: CC1(OC(=O)N2CCC([C@H]3C[C@H]3CCOc3ccc(CC(=O)N4CCC4)c(F)c3)CC2)CC1]

To a solution of (2-fluoro-4-{2-[(1S,2R)-2-(1-{[(1-methylcyclopropyl)oxy]carbonyl}piperidin-4-yl)cyclopropyl]ethoxy}phenyl)acetic acid (100 mg, 0.238 mmol) in 1 ml anhydrous DMF at RT was added azetidine (16.3 mg, 0.286 mmol) and N,N-diisopropylethylamine (0.125 ml, 0.715 mmol). o-(7-Azabenzotriazol-1-yl)-N,N,N',N'-tetramethyluronium hexafluorophosphate (181 mg, 0.477 mmol) was added into the solution and stirred at RT for 4 hrs. The reaction mixture was filtered and purified by reverse-phase HPLC (SunFire Prep C18 OBD 5 um 19×100 mm column; 35-95% acetonitrile in 0.1% formic acid in water gradient) to give the title compound. LC/MS (m/z): 459.3 $(M+H)^+$. GPR119 Human EC50: 3.3 nM Example 60

Preparation of 1-methylcyclopropyl-4-((1R,2S)-2-{2-[4-(2-azetidin-1-yl-2-oxoethyl)-3-methylphenoxy]ethyl}cyclopropyl)piperidine-1-carboxylate

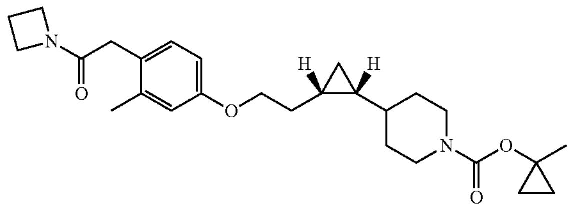 [SMILES: Cc1cc(OCC[C@@H]2C[C@@H]2C2CCN(C(=O)OC3(C)CC3)CC2)ccc1CC(=O)N1CCC1]

Step A: 1-methylcyclopropyl-4-((1R,2S)-2-{2-[4-(2-azetidin-1-yl-2-oxoethyl)-3-methylphenoxy]ethyl}cyclopropyl)piperidine-1-carboxylate

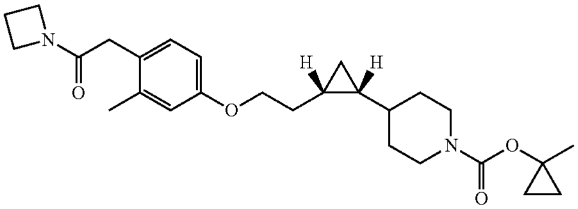 [SMILES: Cc1cc(OCC[C@@H]2C[C@@H]2C2CCN(C(=O)OC3(C)CC3)CC2)ccc1CC(=O)N1CCC1]

1-methylcyclopropyl-4-[(1R,2S)-2-(2-hydroxyethyl)cyclopropyl]piperidine-1-carboxylate (50 mg, 0.177 mmol) was dissolved in toluene (1 ml) and 1-(azetidin-1-yl)-2-(4-hydroxy-2-methylphenyl)ethanone (Intermediate 3, 36.4 mg, 0.177 mmol), triphenylphosphine (55.8 mg, 0.213 mmol), and DIAD (41.4 μl, 0.213 mmol) added and the mixture stirred at RT overnight. The mixture was diluted with ethyl acetate (20 mL), washed with brine (10 ml), dried over $MgSO_4$, filtered and the solvent removed in vacuo. The residue was purified by chromatography on silica gel, Biotage 25M, eluting with a gradient eluant of 0-100% EtOAc/Hexane to afford afford the title compound. LC/MS (m/z): 455 $(M+H)^+$. GPR119 Human EC50: 5.4 nM.

Example 61

Preparation of cyclopropylmethyl-4-((1R,2S)-2-{2-[4-(2-azetidin-1-yl-2-oxoethyl)-3-fluorophenoxy]ethyl}cyclopropyl)piperidine-1-carboxylate

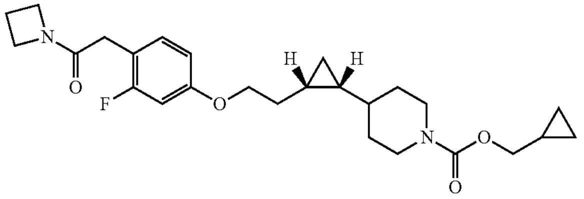 [SMILES: O=C(Cc1ccc(OCC[C@@H]2C[C@@H]2C2CCN(C(=O)OCC3CC3)CC2)cc1F)N1CCC1]

Step A: Benzyl 4-((1R,2S)-2-{2-[4-(2-azetidin-1-yl-2-oxoethyl)-3-fluorophenoxy]ethyl}cyclopropyl)piperidine-1-carboxylate

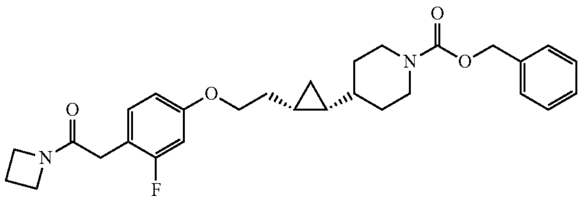 [SMILES: O=C(Cc1ccc(OCC[C@@H]2C[C@@H]2C2CCN(C(=O)OCc3ccccc3)CC2)cc1F)N1CCC1]

To a solution of benzyl 4-[(1R,2S)-2-(2-hydroxyethyl)cyclopropyl]piperidine-1-carboxylate (0.808 g, 2.66 mmol) in 24 ml anhydrous dichloromethane at ambient temperature was added 1-(azetidin-1-yl)-2-(3-fluoro-4-hydroxyphenyl)ethanone (0.518 g, 3.20 mmol) and triphenylphosphine polymer supported (2.64 g, 7.99 mmol). Di-tert-butyl azodicarboxylate (1.23 g, 5.33 mmol) was added into the solution. The solution was stirred at ambient temperature 3 hours. The solution was filtered, and the filtrate was concentrated. The crude product was dried and dissolved in acetonitrile. It was purified directly by reverse phase HPLC (TMC Pro-Pac C18; 30-100% acetonitrile/0.1% formic acid in water gradient). The pure fractions were lyophilized to give the title compound as colorless oil. LC/MS 495.4 $(M+H)^+$.

Step B: 4-((1R,2S)-2-{2-[4-(2-azetidin-1-yl-2-oxoethyl)-3-fluorophenoxy]ethyl}cyclopropyl)piperidine

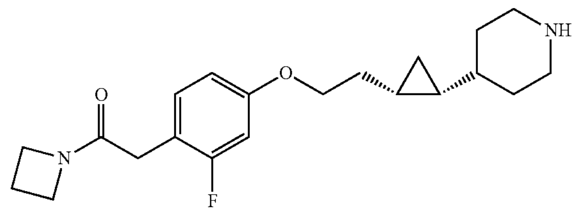 [SMILES: O=C(Cc1ccc(OCC[C@@H]2C[C@@H]2C2CCNCC2)cc1F)N1CCC1]

To a solution of benzyl 4-((1R,2S)-2-{2-[4-(2-azetidin-1-yl-2-oxoethyl)-3-fluorophenoxy]ethyl}cyclopropyl)piperidine-1-carboxylate (590 mg, 1.32 mmol) in 8 mL anhydrous methanol at ambient temperature was added palladium on carbon (80.0 mg, 0.676 mmol), 10% by weight. The solution was stirred under hydrogen for 4 hours and filtered. The crude product was concentrated to the title compound as white solid and used for the next step. LC/MS 361.3 $(M+H)^+$.

Step C: cyclopropylmethyl-4-((1R,2S)-2-{2-[4-(2-azetidin-1-yl-2-oxoethyl)-3-fluorophenoxy]ethyl}cyclopropyl)piperidine-1-carboxylate

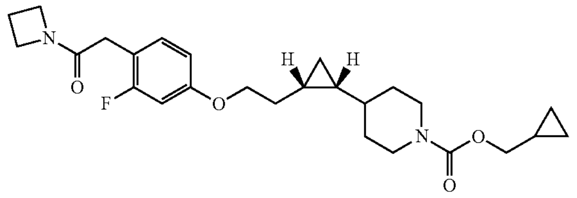 [SMILES: O=C(Cc1ccc(OCC[C@@H]2C[C@@H]2C2CCN(C(=O)OCC3CC3)CC2)cc1F)N1CCC1]

To a stirred solution of 4-((1R,2S)-2-{2-[4-(2-azetidin-1-yl-2-oxoethyl)-3-fluorophenoxy]ethyl)cyclopropyl)piperidine (Step B, Example 11; 0.30 g, 0.93 mmol) in dichloromethane (4.6 mL) under a nitrogen atmosphere was added triethylamine (0.36 mL, 2.6 mmol) and cyclopropylmethyl 2,5-dioxopyrrolidin-1-yl carbonate (0.35 g, 1.67 mmol). The resulting solution was stirred for 18 h at ambient temperature. The solution was diluted with saturated $NH_4Cl$(aq.) (10 mL). The resulting layers were separated and the aqueous phase extracted with dichloromethane (2×30 mL). The combined organic extracts were dried over sodium sulfate, filtered and concentrated under reduced pressure. Purification of the obtained residue by CombiFlash chromatography (12 g silica gel, 0 to 25% EtOAc in heptane) provided the title compound as an off white semi-solid. LC/MS (m/z): 459.3 $(M+H)^+$. GPR119 Human EC50: 2.0 nM.

Example 62

Preparation of 1-methylcyclopropyl 4-[(1R,2S)-2-(2-{4-[2-(dimethylamino)-2-oxoethyl]-2,5-difluorophenoxy}ethyl)cyclopropyl]piperidine-1-carboxylate

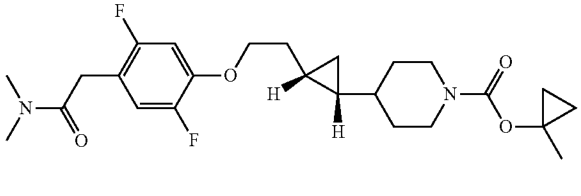 [SMILES: CN(C)C(=O)Cc1cc(F)c(OCC[C@@H]2C[C@@H]2C2CCN(C(=O)OC3(C)CC3)CC2)cc1F]

Step A: Benzyl 4-{(1R,2S)-2-[2-(4-bromo-2,5 difluorophenoxy)ethyl]cyclopropyl}piperidine-1-carboxylate

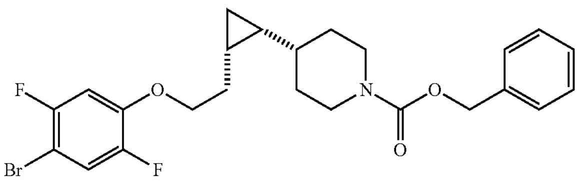

Benzyl 4-[(1R,2S)-2-(2-hydroxyethyl)cyclopropyl]piperidine-1-carboxylate (2.24 g, 7.38 mmol) in DCM (35 ml) was added 4-bromo-2,5-difluorophenol (1.62 g, 7.75 mmol), 3.93 g of triphenylphosphine (polymer-bound, 3.0 mmol/g) and di-tert-butyl diazene-1,2-dicarboxylate (2.21 g, 9.60 mmol). The reaction mixture was stirred at ambient temperature for 4 hours. The solid was filtered off through celite and the filtrate was concentrated. The residue was purified on Biotage column (50 g SNAP silica gel) using a gradient 0-20% then 20% EtOAc in hexanes to afford the title compound as colorless viscous oil. LC/MS (m/z): 496.2 $(M+H)^+$.

Step B: Benzyl 4-{(1R,2S)-2-{2-[4-(2-tert-butoxy-2-oxoethyl-2,5-difluorophenoxy)ethyl]cyclopropyl}piperidine-1-carboxylate

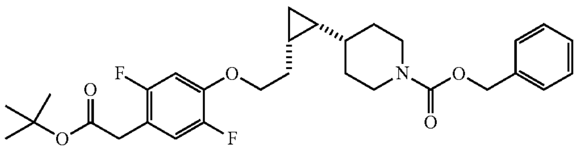

Benzyl 4-{(1R,2S)-2-[2-(4-bromo-2,5 difluorophenoxy)ethyl]cyclopropyl}piperidine-1-carboxylate (0.540 g, 1.09 mmol) from Step A in THF (5 ml) was added 0.5 M 2-tert-butoxy-2-oxoethylzinc chloride in diethyl ether (5.46 ml, 2.73 mmol), followed by $Pd_2(dba)_3$ (50 mg, 0.055 mmol) and 52 mg X-Phos. After vacuum and back filled with nitrogen three times, the reaction mixture was heated at 65° C. overnight. Then it was quenched with saturated ammonium chloride (10 ml) and extracted with EtOAc (15 ml). The organic layer was separated, dried over $Na_2SO_4$, and concentrated. The residue was purified on Biotage column (25 g SNAP silica gel) using a gradient 0-15% then 15% EtOAc in hexanes to afford the title compound as viscous oil. LC/MS (m/z): 552.4 $(M+Na)^+$.

Step C: {4-[2-((1S,2R)-2-{1-[(benzyloxy)carbonyl]piperidin-4-yl}cyclopropyl)ethoxy]-2,5-difluorophenyl}acetic acid

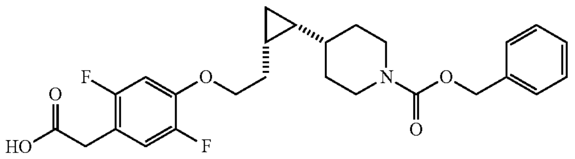

Benzyl 4-{(1R,2S)-2-{2-[4-(2-tert-butoxy-2-oxoethyl-2,5-difluorophenoxy)ethyl]cyclopropyl}piperidine-1-carboxylate (0.350 g, 0.661 ml) from Step B in dichloromethane (1.5 ml) was added TFA (1.5 ml). The reaction mixture was stirred at ambient temperature for 3.5 h. The volatiles were removed under vacuum. The resulting viscous oil was used without further purification. LC/MS (m/z): 474.3 $(M+H)^+$.

Step D: benzyl 4-[(1R,2S)-2-(2-{4-[2-(dimethylamino)-2-oxoethyl]-2,5-difluorophenoxy}ethyl)cyclopropyl]piperidine-1-carboxylate

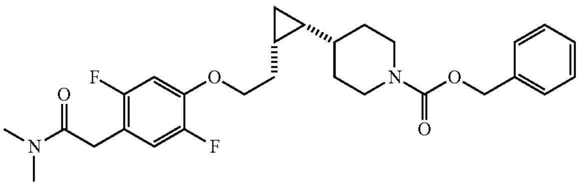

To a solution of {4-[2-((1S,2R)-2-{1-[(benzyloxy)carbonyl]piperidin-4-yl}cyclopropyl)ethoxy]-2,5-difluorophenyl}acetic acid (313 mg, 0.661 mmol) in 2.5 ml anhydrous DMF at RT was added dimethylamine, 2.0 M solution in THF (0.661 ml, 1.32 mmol) and N,N-diisopropylethylamine (0.562 ml, 3.31 mmol). O-(7-Azabenzotriazol-1-yl)-N,N,N',N'-tetramethyluronium hexafluorophosphate (503 mg, 1.32 mmol) was added into the solution and stirred at RT overnight. The reaction mixture in 12 ml water was extracted with 12 ml ethyl acetate. The organic layer was dried over sodium sulfate, filtered, and the filtrate was concentrated under reduced pressure. The residue was purified on Biotage column (25 g silica gel) using a gradient eluent of 0-50% ethyl acetate in hexanes (800 ml) to afford the title compound. LC/MS (m/z): 501.4 $(M+H)^+$.

Step E: 2-(2,5-difluoro-4-{2-[(1S,2R)-2-piperidin-4-ylcyclopropyl]ethoxy}phenyl-)-N,N-dimethylacetamide

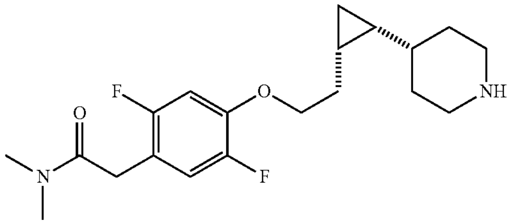

To a solution of benzyl 4-[(1R,2S)-2-(2-{4-[2-(dimethylamino)-2-oxoethyl]-2,5-difluorophenoxy}ethyl)cyclopropyl]piperidine-1-carboxylate (226 mg, 0.451 mmol) in 2 ml anhydrous methanol at RT was added 10% Palladium on carbon (25.0 mg, 0.211 mmol). The reaction was stirred with hydrogen balloon for 2 hours. It was filtered by Celite, and the filtrate was concentrated to give the title compound (160 mg, 97%). LC/MS (m/z): 368.4 $(M+H)^+$.

Step F: 1-methylcyclopropyl 4-[(1R,2S)-2-(2-{4-[2-(dimethylamino)-2-oxoethyl]-2,5-difluorophenoxy}ethyl)cyclopropyl]piperidine-1-carboxylate

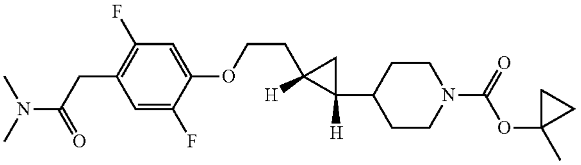 [SMILES: CN(C)C(=O)Cc1cc(F)c(OCC[C@@H]2C[C@@H]2C2CCN(C(=O)OC3(C)CC3)CC2)cc1F]

To a solution of 2-(2,5-difluoro-4-{2-[(1S,2R)-2-piperidin-4 ylcyclopropyl]ethoxy}phenyl-)-N,N-dimethylacetamide (40.0 mg, 0.109 mmol) in 1 ml anhydrous dichloromethane at 0° C. was added triethylamine (0.0300 ml, 0.218 mmol) and 1-({[(1-methylcyclopropyl)oxy]carbonyl}oxy)pyrrolidine-2,5-dione (27.9 mg, 0.131 mmol). The reaction was stirred at RT for 2 hours. The solvent was evaporated, and the residue was purified by reverse-phase HPLC (SunFire Prep C18 OBD 5 um 19×100 mm column; 25-85% acetonitrile in 0.1% formic acid in water gradient) to give the title compound. LC/MS (m/z): 465.4 $(M+H)^+$. Human EC50: 2.2 nM The Examples in Table 1 were synthesized according to the methods described in the prior examples (56-62) employing the appropriate reagents and solvents.

TABLE 1

| Example # | Chemical Structure | Observed Mass $[M+H]^+$ | GPR119 HumC $EC_{50}$ (nM) |
|---|---|---|---|
| 63 | 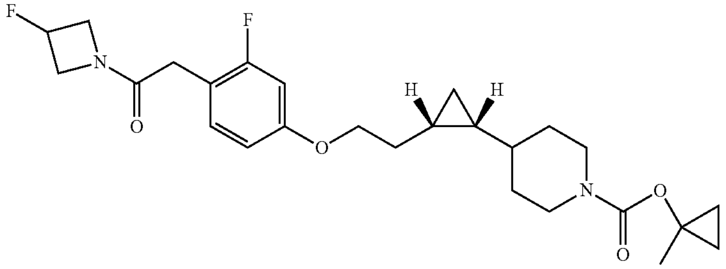 [SMILES: CC1(OC(=O)N2CCC([C@H]3C[C@H]3CCOc3ccc(CC(=O)N4CC(F)C4)c(F)c3)CC2)CC1] | 477 | 0.88 |

TABLE 1-continued
| Example # | Chemical Structure | Observed Mass $[M+H]^+$ | GPR119 HumC $EC_{50}$ (nM) |
|---|---|---|---|
| 64 | 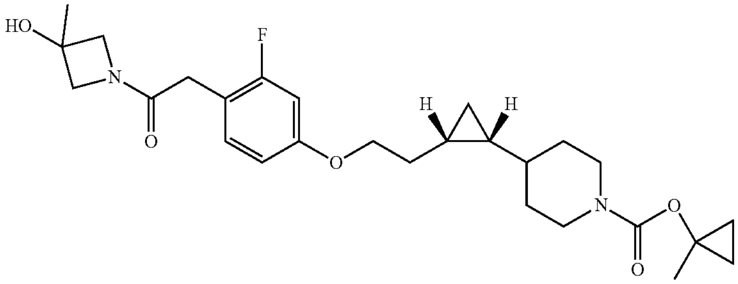 [SMILES: CC1(O)CN(C(=O)Cc2ccc(OCC[C@@H]3C[C@@H]3C3CCN(C(=O)OC4(C)CC4)CC3)cc2F)C1] | 489 | 9.5 |
| 65 | 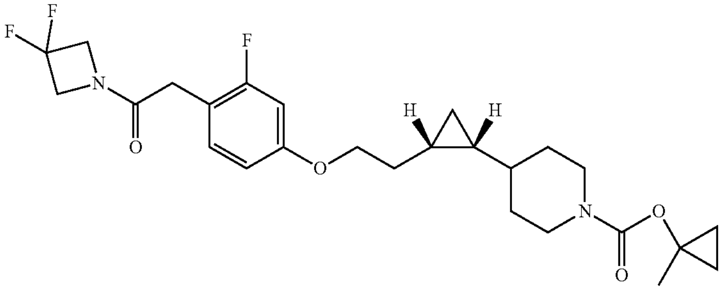 [SMILES: CC1(OC(=O)N2CCC([C@H]3C[C@H]3CCOc3ccc(CC(=O)N4CC(F)(F)C4)c(F)c3)CC2)CC1] | 495 | 0.49 |
| 66 | 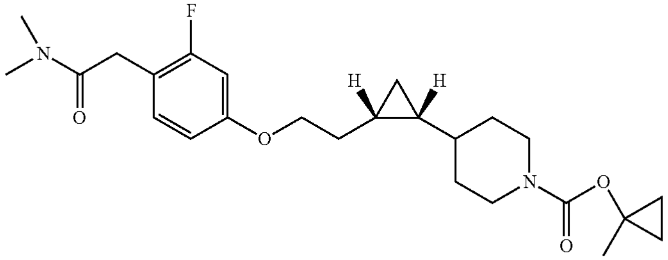 [SMILES: CN(C)C(=O)Cc1ccc(OCC[C@@H]2C[C@@H]2C2CCN(C(=O)OC3(C)CC3)CC2)cc1F] | 447 | 2.4 |
| 67 | 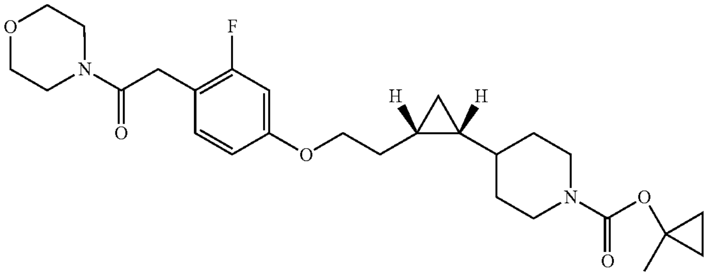 [SMILES: CC1(OC(=O)N2CCC([C@H]3C[C@H]3CCOc3ccc(CC(=O)N4CCOCC4)c(F)c3)CC2)CC1] | 489 | 8.5 |
| 68 | 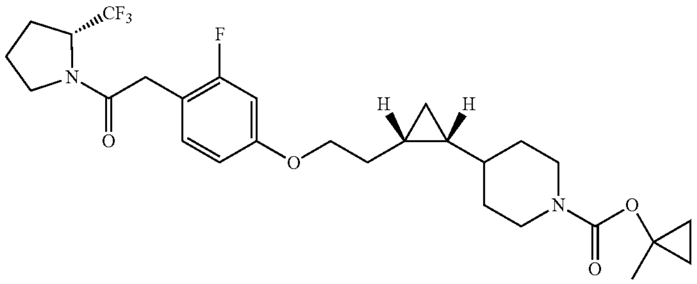 [SMILES: CC1(OC(=O)N2CCC([C@H]3C[C@H]3CCOc3ccc(CC(=O)N4CCC[C@@H]4C(F)(F)F)c(F)c3)CC2)CC1] | 541 | 5.1 |

TABLE 1-continued
| Example # | Chemical Structure | Observed Mass [M + H]+ | GPR119 HumC $EC_{50}$ (nM) |
|---|---|---|---|
| 69 | 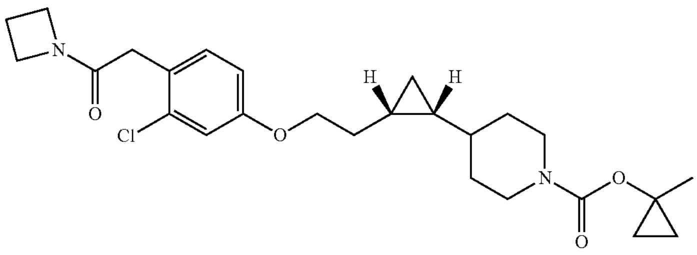 [SMILES: CC1(OC(=O)N2CCC([C@H]3C[C@H]3CCOc3ccc(CC(=O)N4CCC4)c(Cl)c3)CC2)CC1] | 475 | 1.5 |
| 70 | 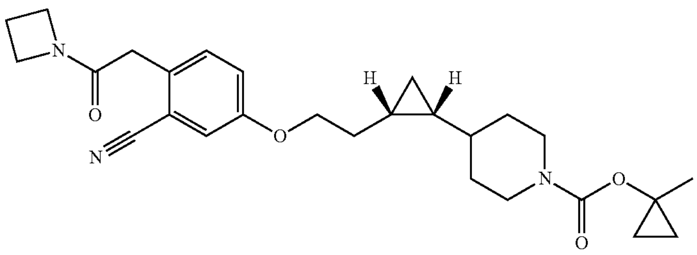 [SMILES: CC1(OC(=O)N2CCC([C@H]3C[C@H]3CCOc3ccc(CC(=O)N4CCC4)c(C#N)c3)CC2)CC1] | 466 | 2.7 |
| 71 | 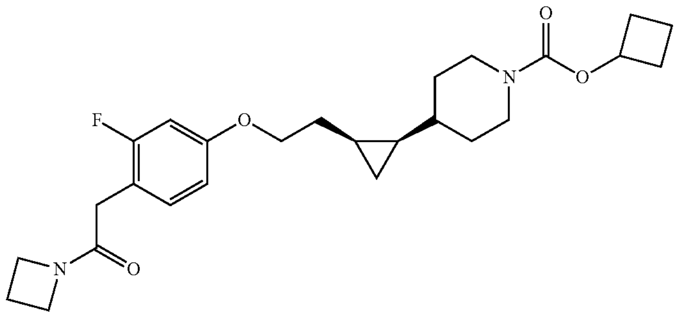 [SMILES: O=C(Cc1ccc(OCC[C@@H]2C[C@@H]2C2CCN(C(=O)OC3CCC3)CC2)cc1F)N1CCC1] | 459 | 1.4 |
| 72 | 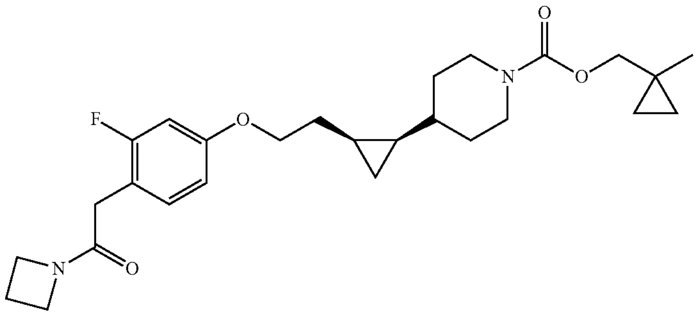 [SMILES: CC1(COC(=O)N2CCC([C@H]3C[C@H]3CCOc3ccc(CC(=O)N4CCC4)c(F)c3)CC2)CC1] | 473 | 3.6 |
| 73 | 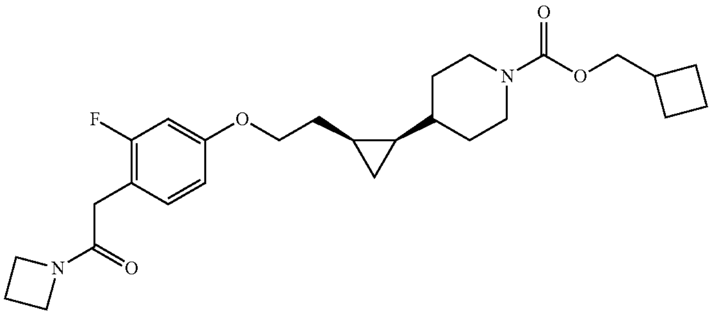 [SMILES: O=C(Cc1ccc(OCC[C@@H]2C[C@@H]2C2CCN(C(=O)OCC3CCC3)CC2)cc1F)N1CCC1] | 473 | 2.2 |

TABLE 1-continued

| Example # | Chemical Structure | Observed Mass $[M + H]^+$ | GPR119 HumC $EC_{50}$ (nM) |
|---|---|---|---|
| 74 | 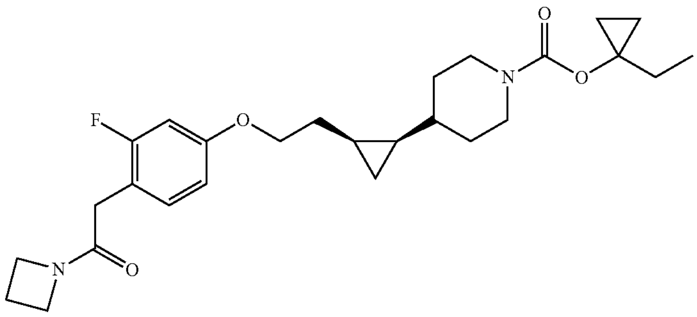 [SMILES: CCC1(OC(=O)N2CCC([C@H]3C[C@H]3CCOc3ccc(CC(=O)N4CCC4)c(F)c3)CC2)CC1] | 473 | 2.7 |
| 75 | 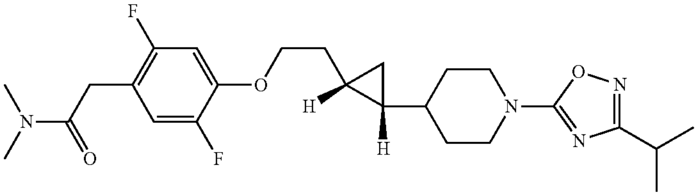 [SMILES: CC(C)c1noc(N2CCC([C@H]3C[C@H]3CCOc3cc(F)c(CC(=O)N(C)C)cc3F)CC2)n1] | 478 | 0.6 |

Example 76

Preparation of N-(tert-butyl)-4-((1R,2S)-2-(2-(4-(1H-tetrazol-1-yl)phenoxy)ethyl)cyclopropyl)piperidine-1-carboxamide

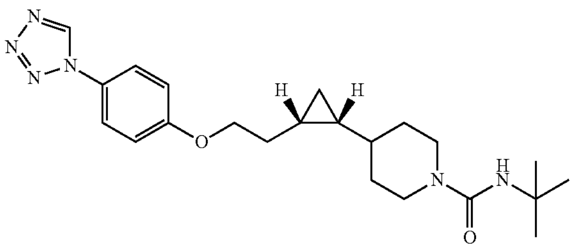 [SMILES: CC(C)(C)NC(=O)N1CCC([C@H]2C[C@H]2CCOc2ccc(-n3cnnn3)cc2)CC1]

To a solution of 4-((1R,2S)-2-(2-(4-(1H-tetrazol-1-yl)phenoxy)ethyl)cyclopropyl)piperidine (20 mg, 0.064 mmol) in DMF (0.7 ml) under nitrogen at RT was added DIPEA (0.022 ml, 0.128 mmol) followed by t-butyl isocyanate (drop). At 20 minutes, LC/MS showed no SM left. Quenched with formic acid (4.90 μl, 0. The fractions containing product were collected and dried via GenoVac to afford the title compound. GPR119 Human EC50: 14.7 nM Example 77

Preparation of 1-(cyclohexylacetyl)-4-((1R,2S)-2-{2-[4-(1H-tetrazol-1-yl)phenoxy]ethyl}cyclopropyl)piperidine

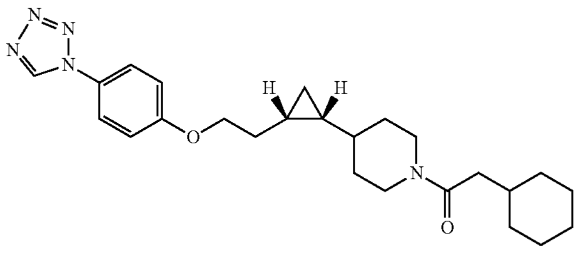 [SMILES: O=C(CC1CCCCC1)N1CCC([C@H]2C[C@H]2CCOc2ccc(-n3cnnn3)cc2)CC1]

Step A: Benzyl 4-((1R,2S-2-{2-[4-(1H-tetrazol-1-yl)phenoxy]ethyl}cyclopropyl)piperidine-1-carboxylate

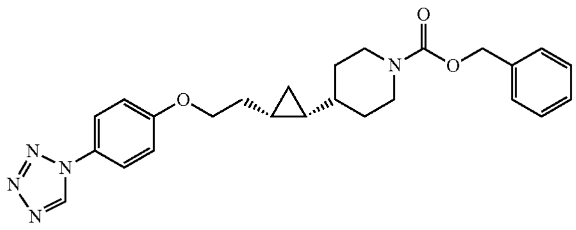 [SMILES: O=C(OCc1ccccc1)N1CCC([C@H]2C[C@H]2CCOc2ccc(-n3cnnn3)cc2)CC1]

To a solution of 0.808 g (2.66 mmol) benzyl 4-[(1R,2S)-2-(2-hydroxyethyl)cyclopropyl]piperidine-1-carboxylate in 24 ml anhydrous dichloromethane at ambient temperature was added 0.518 g (3.20 mmol) 4-(1H-tetrazol-1-yl)phenol and 2.64 g (7.99 mmol) triphenylphosphine polymer supported. 1.23 g (5.33 mmol) di-tert-butyl azodicarboxylate was added into the solution. The solution was stirred at ambient temperature 3 hours. The solution was filtered, and the filtrate was concentrated. The crude product was dried and dissolved in acetonitrile. It was purified directly by reverse phase HPLC (TMC Pro-Pac C18; 30-100% acetonitrile/0.1% formic acid in water gradient). The pure fractions were lyophilized to yield the title compound as colorless oil. $^1$H NMR (DMSO): δ 9.70 (s, 1H), δ 7.78 (d, J=8.9 Hz, 2H), δ 7.29-7.38 (m, 5H), δ 7.17 (d, J=9.0 Hz, 2H), δ 5.06 (s, 2H), δ 4.13 (t, J=6.8 Hz, 2H), δ 3.99 (t, J=13.4 Hz, 2H), δ 3.29 (s, 2H), δ 2.68-2.87 (m, 2H), δ 2.01-2.08 (m, 1H), δ 1.70 (t, J=16.4 Hz, 2H), δ 1.49-1.56 (m, 1H), δ 1.16-1.25 (m, 2H), δ 1.01-1.08 (m, 1H), δ 0.86-0.94 (m, 1H), δ 0.54-0.61 (m, 2H). LC/MS 448.6 (M+1).

Step B: 4-((1R,2S)-2-{2-[4-(1H-tetrazol-1-yl)phenoxy]ethyl}cyclopropyl)piperidine

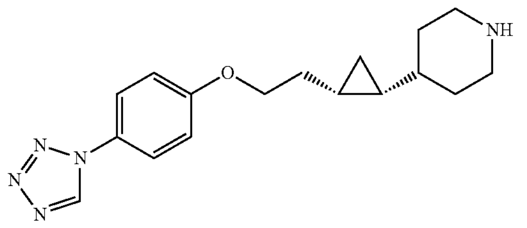 [SMILES: c1cc(-n2cnnn2)ccc1OCC[C@@H]1C[C@@H]1C1CCNCC1]

To a solution of 590 mg (1.32 mmol) Benzyl 2S-2-{2-[4-(1H-tetrazol-1-yl)phenoxy]ethyl}cyclopropyl)piperidine-1-carboxylate in 8 ml anhydrous methanol at ambient temperature was added 80.0 mg (0.676 mmol) palladium on carbon, 10% by weight. The solution was stirred under hydrogen for 4 hours and filtered. The crude product was concentrated to give the title compound as white solid and used for the next step. LC/MS 314.5 (M+1).

Step C: 1-(cyclohexylacetyl)-4-((1R,2S)-2-{2-[4-(1H-tetrazol-1-yl)phenoxy]ethyl}cyclopropyl) piperidine

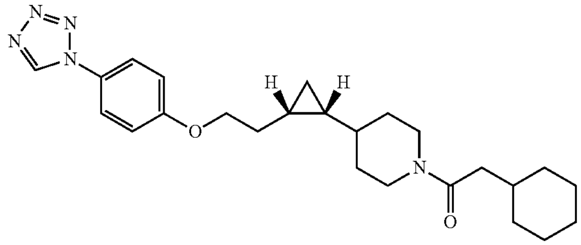 [SMILES: O=C(CC1CCCCC1)N1CCC([C@H]2C[C@H]2CCOc2ccc(-n3cnnn3)cc2)CC1]

To a solution of 23 mg (0.071 mmol) of 4-((1R,2S)-2-{2-[4-(1H-tetrazol-1-yl)phenoxy]ethyl}cyclopropyl)piperidine in 0.6 ml anhydrous N,N-dimethylformamide at ambient temperature was added 0.020 ml (0.14 mmol) cyclohexylacetic acid, followed by 27 mg (0.14 mmol) EDC, 9.6 mg (0.071 mmol) HOBt, and 0.062 ml (0.35 mmol) diisopropylethylamine. The solution was stirred overnight at ambient temperature. The crude in N,N-dimethylformamide was purified directly by reverse phase HPLC (TMC Pro-Pac C18; 30-100% acetonitrile/0.1% formic acid in water gradient). The pure fractions were lyophilized to yield the title compound as white solid.

GPR119 Human EC50: 11.8 nM

The Examples in Table 8 were synthesized according to the methods described in the prior examples (76-77) employing the appropriate acetyl chlorides or carboxylic acids for standard acetylation of the piperidine amine.

TABLE 8

| Example # | Chemical Structure | Observed Mass $[M + H]^+$ | GPR119 Human $EC_{50}$ (nM) |
|---|---|---|---|
| 78 | 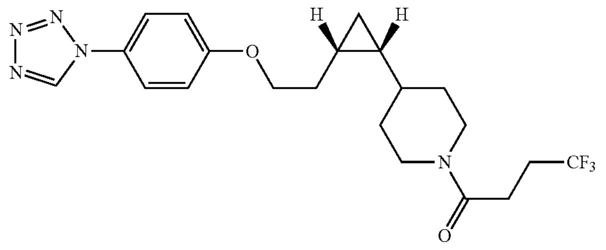 [SMILES: O=C(CCC(F)(F)F)N1CCC([C@H]2C[C@H]2CCOc2ccc(-n3cnnn3)cc2)CC1] | 438 | 8.5 |
| 79 | 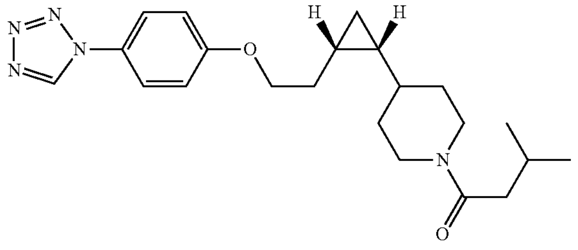 [SMILES: CC(C)CC(=O)N1CCC([C@H]2C[C@H]2CCOc2ccc(-n3cnnn3)cc2)CC1] | 398 | 7.7 |

TABLE 8-continued
| Example # | Chemical Structure | Observed Mass [M + H]+ | GPR119 Human $EC_{50}$ (nM) |
|---|---|---|---|
| 80 | 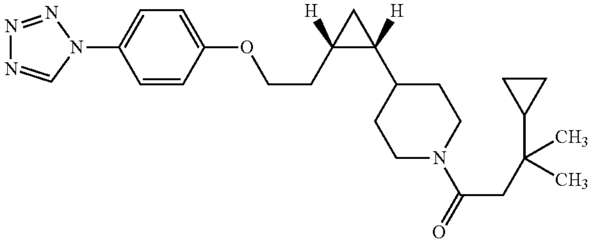 [SMILES: CC(C)(CC(=O)N1CCC([C@H]2C[C@H]2CCOc2ccc(-n3cnnn3)cc2)CC1)C1CC1] | 438 | 4 |
| 81 | 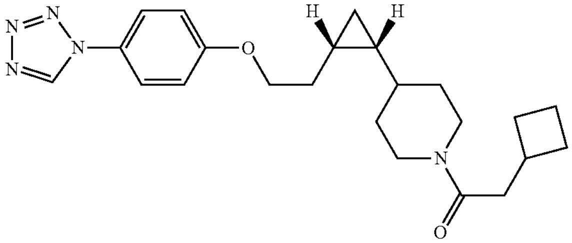 [SMILES: O=C(CC1CCC1)N1CCC([C@H]2C[C@H]2CCOc2ccc(-n3cnnn3)cc2)CC1] | 410 | 15 |
| 82 | 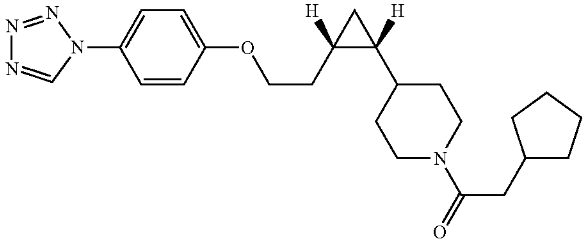 [SMILES: O=C(CC1CCCC1)N1CCC([C@H]2C[C@H]2CCOc2ccc(-n3cnnn3)cc2)CC1] | 424 | 16 |
| 83 | 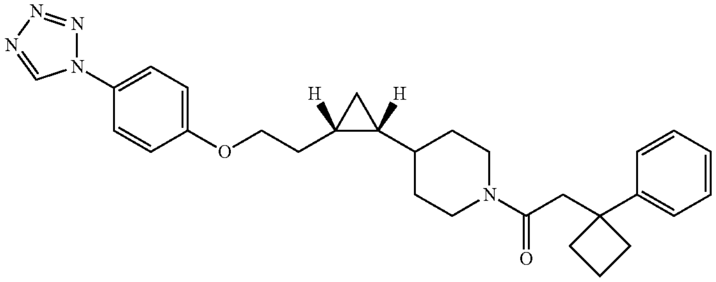 [SMILES: O=C(CC1(c2ccccc2)CCC1)N1CCC([C@H]2C[C@H]2CCOc2ccc(-n3cnnn3)cc2)CC1] | 486 | 15 |
| 84 | 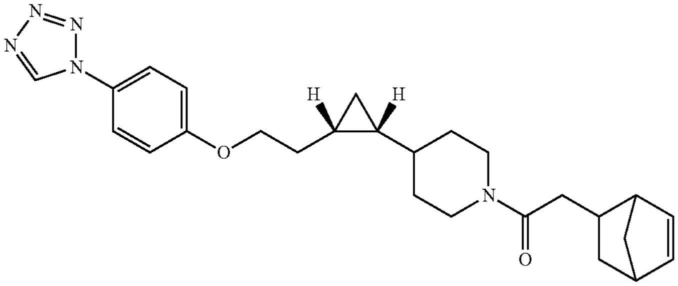 [SMILES: O=C(CC1CC2C=CC1C2)N1CCC([C@H]2C[C@H]2CCOc2ccc(-n3cnnn3)cc2)CC1] | 448 | 3.7 |

Example 85

Preparation of 2-(2-{(1S,2R)-2-[1-(cyclohexylacetyl) piperidin-4-yl]cyclopropyl}ethoxy)-5-(methylsulfonyl)pyridine

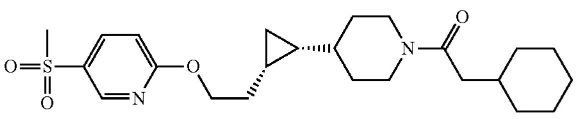 [SMILES: CS(=O)(=O)c1ccc(OCC[C@@H]2C[C@@H]2C2CCN(C(=O)CC3CCCCC3)CC2)nc1]

Step A: Benzyl 4-[(1R,2S)-2-(2-{[5-(methylsulfonyl) pyridin-2-yl]oxy}ethyl)cyclopropyl]piperidine-1-carboxylate

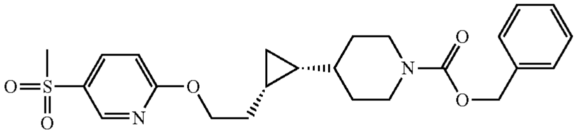 [SMILES: CS(=O)(=O)c1ccc(OCC[C@@H]2C[C@@H]2C2CCN(C(=O)OCc3ccccc3)CC2)nc1]

To a solution of 860 mg (2.83 mmol) benzyl 4-[(1R,2S)-2-(2-hydroxyethyl)cyclopropyl]piperidine-1-carboxylate in 14.5 ml anhydrous N,N-dimethylformamide at ambient temperature was added 147 mg (3.68 mmol) sodium hydride. The solution was stirred for 20 minutes. 669 mg (2.83 mmol) 2-bromo-5-(methylsulfonyl)pyridine was added into the solution. It was heated to 50° C., and stirred for 3 hours. 100 ml water was added into the mixture, and it was extracted with 50 ml ethyl acetate three times. The crude product was dried and purified using a Biotage Horizon® system (0-50% ethyl acetate/hexanes mixture) to give the title compound as colorless oil. $^1$H NMR ($CDCl_3$): δ 8.71 (d, J=2.4 Hz, 1H), δ 8.03 (dd, J=8.8 Hz, 2.5 Hz, 1H), δ 7.30-7.37 (m, 5H), δ 6.84 (d, J=8.7 Hz, 1H), δ 5.13 (s, 2H), δ 4.49 (t, J=7.1 Hz, 2H), δ 4.10-4.16 (m, 2H), δ 3.07 (s, 2H), δ 2.75-2.76 (m, 2H), δ 2.08-2.12 (m, 1H), δ 1.74-1.75 (m, 2H), δ 1.50-1.56 (m, 2H), δ 1.29-1.40 (m, 2H), δ 0.88-0.99 (m, 2H), δ 0.56-0.70 (m, 2H). LC/MS 459.2 (M+1).

Step B: 5-(methylsulfonyl)-2-{2-[(1S,2R)-2-piperidin-4-ylcyclopropyl]ethoxy}pyridine

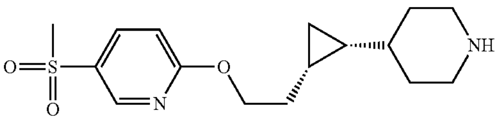 [SMILES: CS(=O)(=O)c1ccc(OCC[C@@H]2C[C@@H]2C2CCNCC2)nc1]

To a solution of 1.16 g (2.53 mmol) benzyl 4-[(1R,2S)-2-(2-{[5-(methylsulfonyl)pyridin-2-yl]oxy}ethyl)cyclopropyl]piperidine-1-carboxylate in 15 ml anhydrous methanol at ambient temperature was added 0.12 g (1.13 mmol) palladium on carbon, 10% by weight. The solution was stirred under hydrogen for 4 hours and filtered. The crude product was concentrated to give the title compound as white solid and used for the next step. LC/MS 325.5 (M+1).

Step C: 2-(2-{(1S,2R)-2-[1-(cyclohexylacetyl)piperidin-4-yl]cyclopropyl}ethoxy)-5-(methylsulfonyl) pyridine

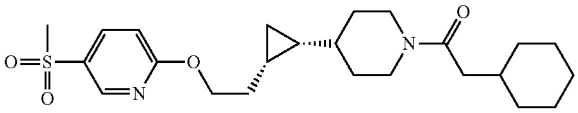 [SMILES: CS(=O)(=O)c1ccc(OCC[C@@H]2C[C@@H]2C2CCN(C(=O)CC3CCCCC3)CC2)nc1]

To a solution of 23 mg (0.071 mmol) of 5-(methylsulfonyl)-2-{2-[(1S,2R)-2-piperidin-4-ylcyclopropyl] ethoxy}pyridine in 0.6 ml anhydrous N,N-dimethylformamide at ambient temperature was added 0.020 ml (0.14 mmol) cyclohexylacetic acid, followed by 27 mg (0.14 mmol) EDCl, 9.6 mg (0.071 mmol) HOBt, and 0.062 ml (0.35 mmol) diisopropylethylamine. The solution was stirred overnight at ambient temperature. The crude in N,N-dimethylformamide was purified directly by reverse phase HPLC (TMC Pro-Pac C18; 30-100% acetonitrile/0.1% formic acid in water gradient). The pure fractions were lyophilized to yield the title compound as white solid. $^1$H NMR (DMSO): δ 8.65 (d, J=2.1 Hz, 1H), δ 8.15 (dd, J=8.8 Hz, 2.5 Hz, 1H), δ 7.01 (d, J=8.7 Hz, 1H), δ 4.43 (t, J=6.8 Hz, 2H), δ 4.36 (t, J=12.0 Hz, 1H), δ 3.85 (t, J=13.7 Hz, 1H), δ 3.31 (s, 1H), δ 3.28 (s, 1H), δ 3.24 (s, 3H), δ 2.94 (t, J=12.7 Hz, 1H), δ 2.15 (d, J=6.5 Hz, 2H), δ 2.00-2.04 (m, 1H), δ 1.51-1.75 (m, 9H), δ 1.08-1.23 (m, 6H), δ 0.83-0.94 (m, 3H), δ 0.53-0.59 (m, 2H). LC/MS 589.3 (M+1). GPR119 Human EC50: 11.8 nM The Examples in Table 9 were synthesized according to the methods described in the prior example (85) employing the appropriate acetyl chlorides or carboxylic acids for standard acetylation of the piperidine amine.

TABLE 9
| Example # | Chemical Structure | Observed Mass $[M + H]^+$ | GPR119 Human $EC_{50}$ (nM) |
|---|---|---|---|
| 86 | 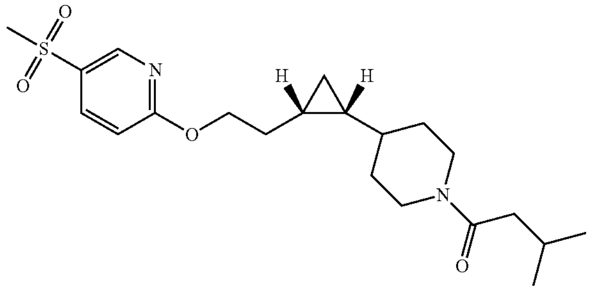 [SMILES: CC(C)CC(=O)N1CCC([C@H]2C[C@H]2CCOc2ccc(S(C)(=O)=O)cn2)CC1] | 409 | 29 |
| 87 | 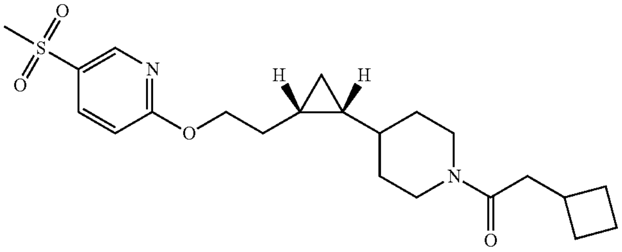 | 421 | 13 |
| 88 | 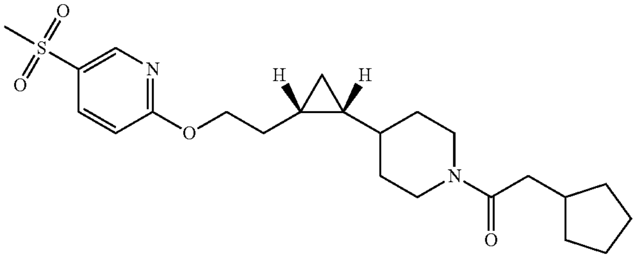 [SMILES: CS(=O)(=O)c1ccc(OCC[C@@H]2C[C@@H]2C2CCN(C(=O)CC3CCCC3)CC2)nc1] | 435 | 4.6 |
| 89 | 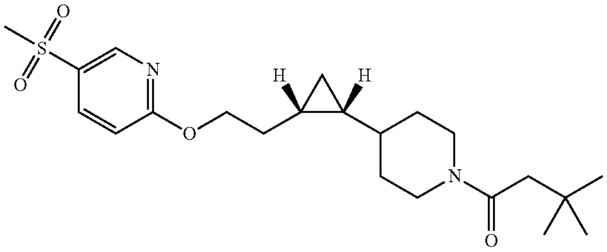 [SMILES: CC(C)(C)CC(=O)N1CCC([C@H]2C[C@H]2CCOc2ccc(S(C)(=O)=O)cn2)CC1] | 423 | 16 |
| 90 | 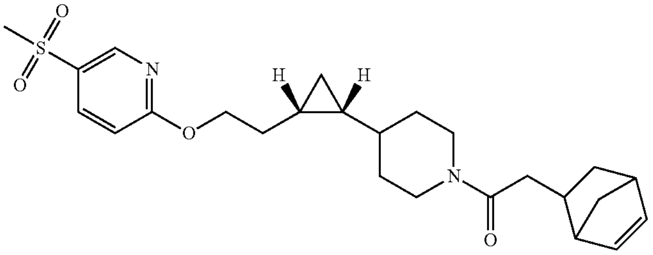 [SMILES: CS(=O)(=O)c1ccc(OCC[C@@H]2C[C@@H]2C2CCN(C(=O)CC3CC4C=CC3C4)CC2)nc1] | 459 | 16 |

TABLE 9-continued
| Example # | Chemical Structure | Observed Mass $[M + H]^+$ | GPR119 Human $EC_{50}$ (nM) |
|---|---|---|---|
| 91 | 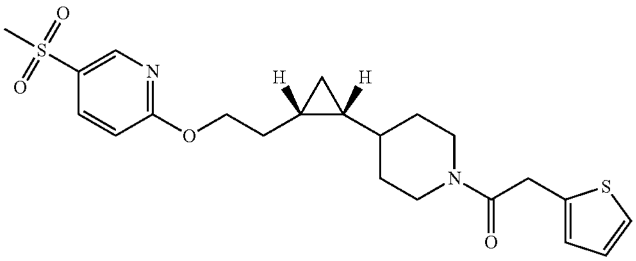 [SMILES: CS(=O)(=O)c1ccc(OCC[C@@H]2C[C@@H]2C2CCN(C(=O)Cc3cccs3)CC2)nc1] | 449 | 36 |
| 92 | 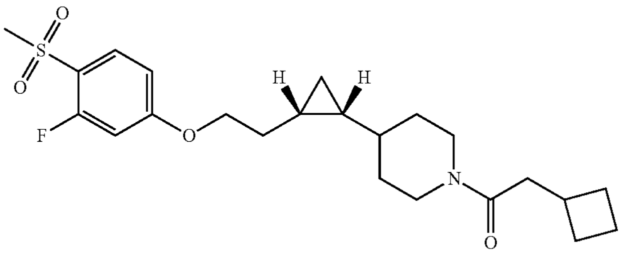 [SMILES: CS(=O)(=O)c1ccc(OCC[C@@H]2C[C@@H]2C2CCN(C(=O)CC3CCC3)CC2)cc1F] | 438 | 10 |
| 93 | 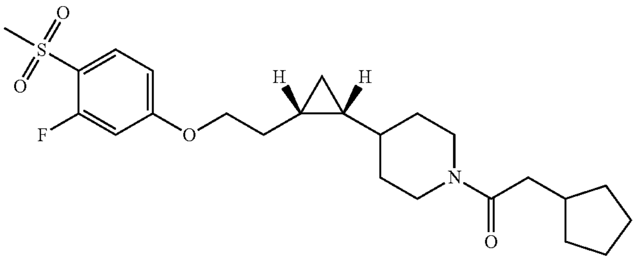 [SMILES: CS(=O)(=O)c1ccc(OCC[C@@H]2C[C@@H]2C2CCN(C(=O)CC3CCCC3)CC2)cc1F] | 452 | 4.6 |
| 94 | 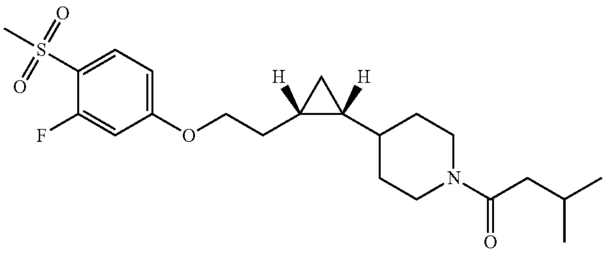 | 426 | 19 |
| 95 | 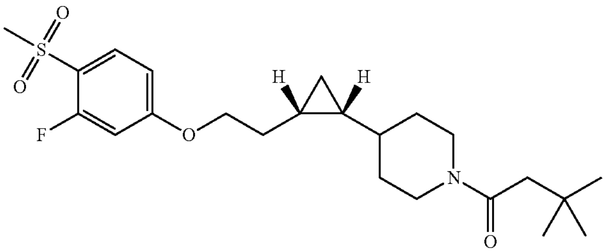 [SMILES: CC(C)(C)CC(=O)N1CCC([C@H]2C[C@H]2CCOc2ccc(S(C)(=O)=O)c(F)c2)CC1] | 440 | 5.4 |

TABLE 9-continued

| Example # | Chemical Structure | Observed Mass $[M + H]^+$ | GPR119 Human $EC_{50}$ (nM) |
|---|---|---|---|
| 96 | 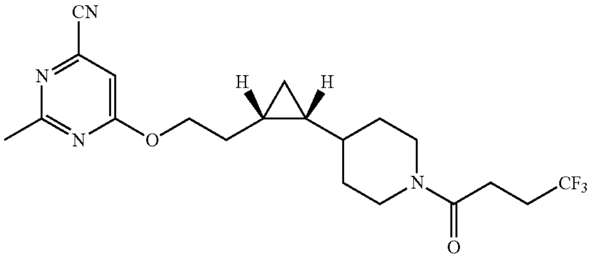 [SMILES: Cc1nc(C#N)cc(OCC[C@@H]2C[C@@H]2C2CCN(C(=O)CCC(F)(F)F)CC2)n1] | 411 | 43 |
| 97 | 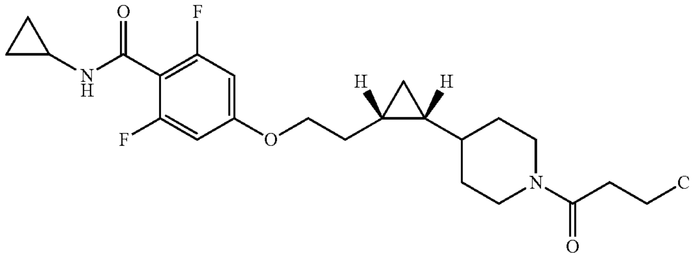 [SMILES: CCCC(=O)N1CCC([C@H]2C[C@H]2CCOc2cc(F)c(C(=O)NC3CC3)c(F)c2)CC1] | 489 | 3.5 |

Example 98

Preparation of 5-(4-((1R,2S)-2-(2-(4-(1H-tetrazol-1-yl)phenoxy)ethyl)cyclopropyl)piperidin-1-yl)-3-isopropyl-1,2,4-oxadiazole

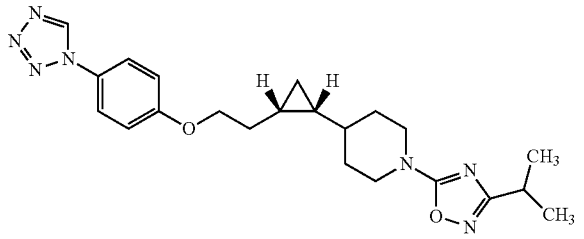 [SMILES: CC(C)c1noc(N2CCC([C@H]3C[C@H]3CCOc3ccc(-n4cnnn4)cc3)CC2)n1]

Step A: 4-((1R,2S)-2-(2-(4-(1H-tetrazol-1-yl)phenoxy)ethyl)cyclopropyl)piperidine-1-carbonitrile

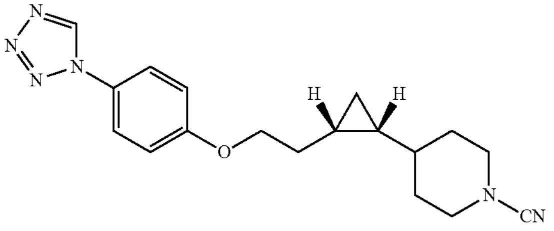 [SMILES: N#CN1CCC([C@H]2C[C@H]2CCOc2ccc(-n3cnnn3)cc2)CC1]

4-((1R,2S)-2-(2-(4-(1H-Tetrazol-1-yl)phenoxy)ethyl)cyclopropyl)piperidine (Step B, Example 1; 300 mg, 0.958 mmol) and potassium carbonate (492 mg, 3.57 mmol) were stirred in chloroform (10 mL). Cyanogen bromide (122 mg, 1.15 mmol) was added. The mixture was stirred at RT for 15 min and refluxed overnight. The mixture was cooled to RT, mixed with silica gel (5 g), and concentrated to dryness under reduced pressure. The residue was loaded on a silica gel column (15 g of silica gel) and eluted with dichloromethane/methanol (99:1, 1 L) to provide the title compound as an off-white solid. $^1H$ NMR (300 MHz, $CDCl_3$) δ 8.89 (s, 1H), 7.60 (d, J=9.0 Hz, 2H), 7.06 (d, J=9.0 Hz, 2H), 4.11 (t, J=6.5 Hz, 2H), 3.50-3.25 (m, 2H), 3.10-2.90 (m, 2H), 2.25-2.10 (m, 1H), 1.90-1.75 (m, 2H), 1.65-1.40 (m, 3H), 1.10-0.80 (m, 2H), 0.80-0.60 (m, 2H), −0.09 (q, J=4.7 Hz, 1H). MS (Multimode) m/z 339 $[M+H]^+$.

Step B: 5-(4-((1R,2S)-2-(2-(4-(1H-tetrazol-1-yl)phenoxy)ethyl)cyclopropyl)piperidin-1-yl)-3-isopropyl-1,2,4-oxadiazole

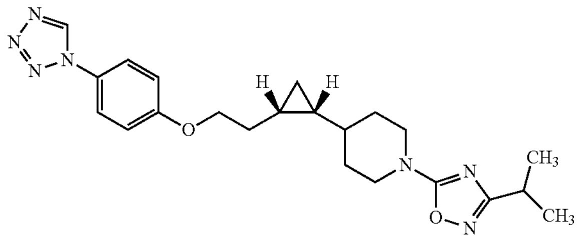 [SMILES: CC(C)c1noc(N2CCC([C@H]3C[C@H]3CCOc3ccc(-n4cnnn4)cc3)CC2)n1]

To a solution of 4-((1R,2S)-2-(2-(4-(1H-tetrazol-1-yl)phenoxy)ethyl)cyclopropyl)piperidine-1-carbonitrile (Step A, Example 83; 150 mg, 0.444 mmol) and N-hydroxyisobutyrimidamide (54 mg, 0.53 mmol) in tetrahydrofuran (5 mL) was added zinc chloride (1.1 mL, 0.5 M in tetrahydrofuran, 0.53 mmol). The mixture was refluxed for 2 h, cooled to RT, and concentrated to dryness under reduced pressure. The residue was dissolved in 2 mL of 4N HCl ethanol and water (1:1). The solution was refluxed for 1 hour, cooled to RT, and concentrated to dryness under reduced pressure. The residue was dissolved in methanol (5 mL), neutralized by the addition of excess potassium carbonate, mixed with silica gel (2 g), and concentrated to dryness under reduced pressure. The residue was loaded on a silica gel column (15 g of silica gel) and eluted with dichloromethane/methanol (199:1, 1 L) to provide impure product (72 mg).

The compound was further purified by prep-HPLC (SunFire C18 OBD, 10 50×150 mm, 118 mL/min, acetonitrile/water 10:90 to 90:10 at 25 min, total run 30 min) to provide the title compound as an off-white solid. $^{1}$H NMR (300 MHz, $CDCl_3$) δ 8.89 (s, 1H), 7.60 (d, J=9.0 Hz, 2H), 7.07 (d, J=9.0 Hz, 2H), 4.20-4.05 (m, 4H), 3.12-2.95 (m, 2H), 2.95-2.80 (m, 1H), 2.30-2.10 (m, 1H), 1.95-1.80 (m, 2H), 1.65-1.40 (m, 3H), 1.29 (d, J=6.9 Hz, 6H), 1.15-0.90 (m, 2H), 0.80-0.55 (m, 2H), −0.06 (q, J=4.5 Hz, 1H). MS (ESI) m/z 424 $[M+H]^+$.

GPR119 Human EC50: 11.8 nM

Example 99

Preparation of 4-[(1R,2S)-2-{2-[4-(2-azetidin-1-yl-2-oxoethyl)phenoxy]ethyl}cyclopropyl]-1-[3-(1-methylethyl)-1,2,4-oxadiazol-5-yl]piperidine

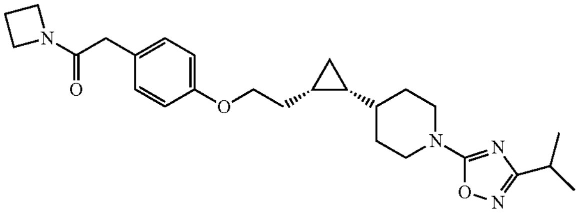 [SMILES: CC(C)c1noc(N2CCC([C@H]3C[C@H]3CCOc3ccc(CC(=O)N4CCC4)cc3)CC2)n1]

Step A: Methyl 2-(4-(2-((1S,2R)-2-(1-(3-isopropyl-1,2,4-oxadiazol-5-yl)piperidin-4-yl)cyclopropyl)ethoxy)phenyl)acetate

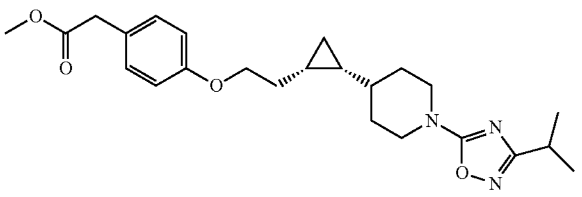 [SMILES: COC(=O)Cc1ccc(OCC[C@@H]2C[C@@H]2C2CCN(c3nc(C(C)C)no3)CC2)cc1]

2-((1S,2R)-2-(1-(3-isopropyl-1,2,4-oxadiazol-5-yl)piperidin-4-yl)cyclopropyl)ethanol (1.7 g, 6.08 mmol), methyl 2-(4-hydroxyphenyl)acetate (1.5 g, 9.1 mmol) and triphenylphosphine (2.4 g, 9.1 mmol) were dissolved in THF (30 ml). The mixture was stirred at RT under N2 for 5 min and disisopropyl azodicarboxylate (1.78 ml, 9.1 mmol) was added. The mixture was stirred at RT overnight. The mixture was diluted with DCM (50 ml), washed with water, dried and evaporated. The crude material was purified by silica gel column (100 g SNAP, 5-25% EtOAc in hexane) to afford the desired product. LC/MS (m/z): 428 $(M+H)^+$.

Step B: 2-(4-(2-((1S,2R)-2-(1-(3-isopropyl-1,2,4-oxadiazol-5-yl)piperidin-4-yl)cyclopropyl)ethoxy)phenyl)acetic acid

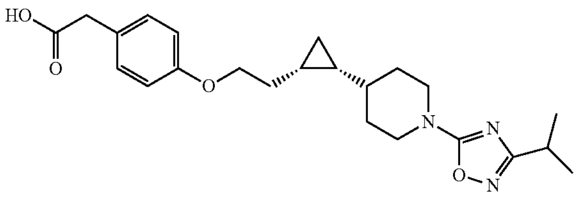 [SMILES: CC(C)c1noc(N2CCC([C@H]3C[C@H]3CCOc3ccc(CC(=O)O)cc3)CC2)n1]

Methyl 2-(4-(2-((1S,2R)-2-(1-(3-isopropyl-1,2,4-oxadiazol-5-yl)piperidin-4-yl)cyclopropyl)ethoxy)phenyl)acetate (0.55 g, 1.28 mmol) was dissolved in MeOH (5 ml) and lithium hydroxide (154 mg, 6.43 mmol) in 2 mL of water was added. The mixture was stirred at RT for 1 h and neutralized to pH 6 with 5 N HCl, extracted with EtOAc (50 ml). The EtOAc phase was dried over MgSO4, and evaporated to afford 514 mg (97%) of the desired product. LC/MS (m/z): 414 $(M+H)^+$.

Step C: 4-[(1R,2S)-2-{2-[4-(2-azetidin-1-yl-2-oxoethyl)phenoxy]ethyl}cyclopropyl]-1-[3-(1-methylethyl)-1,2,4-oxadiazol-5-yl]piperidine

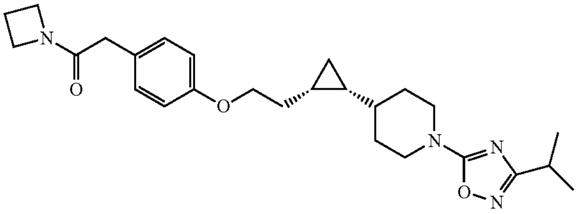 [SMILES: CC(C)c1noc(N2CCC([C@H]3C[C@H]3CCOc3ccc(CC(=O)N4CCC4)cc3)CC2)n1]

2-(4-(2-((1S,2R)-2-(1-(3-isopropyl-1,2,4-oxadiazol-5-yl)piperidin-4-yl)cyclopropyl)ethoxy)phenyl)acetic acid (100 mg, 0.242 mmol), 1-hydroxybenzotriazole hydrate (55 mg, 0.363 mmol), and (E)-3-(ethyldiazenyl)-N,N-dimethylpropan-1-amine hydrochloride (70.0 mg, 0.363 mmol) were dissolved in CH2Cl2 (4 ml). The mixture was stirred at RT for 5 min. and azetidine (21 mg, 0.363 mmol) was added. The mixture was stirred at RT overnight and loaded directly on Preparative TLC that was developed with 5% MeOH in DCM. The desired product (Rf=0.35 @ 5% MeOH in DCM) was collected to give the title compound. $^{1}$H NMR (500 MHz, $CDCl_3$) δ 7.20 (d, 2H), 6.90 (d, 2H), 4.05-4.15 (m, 8H), 3.41 (s, 2H), 3.05 (m, 2H), 2.96 (m, 1H), 2.26 (m, 2H), 2.18 (m, 1H), 1.95 (m, 2H), 1.50 (m, 3H), 1.35 (d, 6H), 0.95-1.05 (m, 2H), 0.68 (m, 2H), −0.40 (m, 1H). LC/MS (m/z): 453 $(M+H)^+$, GPR119 Human $EC_{50}$: 1.8 nM.

Example 100

Preparation of 4-[(1R,2S)-2-(2-{3-fluoro-4-[2-(3-fluoroazetidin-1-yl)-2-oxoethyl]phenoxy}ethyl)cyclopropyl]-1-(3-isopropyl-1,2,4-oxadiazol-5-yl)piperidine

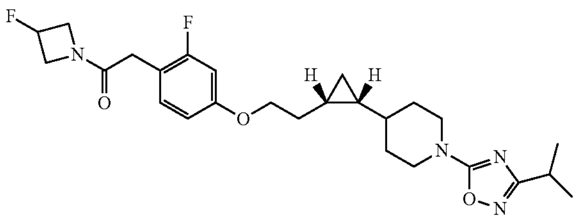 [SMILES: CC(C)c1noc(N2CCC([C@H]3C[C@H]3CCOc3ccc(CC(=O)N4CC(F)C4)c(F)c3)CC2)n1]

Step A: Methyl[2-fluoro-4-(2-{(1S,2R)-[1-(3-isopropyl-1,2,4-oxadiazol-5-yl)piperidin-4-yl]cyclopropyl}ethoxy)phenyl]acetate

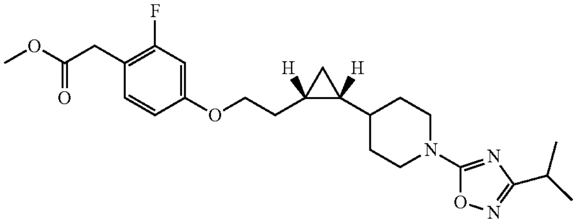 [SMILES: COC(=O)Cc1ccc(OCC[C@@H]2C[C@@H]2C2CCN(c3nc(C(C)C)no3)CC2)cc1F]

A solution of methyl (2-fluoro-4-hydroxyphenyl)acetate (Intermediate 1, 5 g, 27.10 mmol) and 2-{(1S,2R)-2-[1-(3-isopropyl-1,2,4-oxadiazol-5-yl)piperidin-4-yl]cyclopropyl}ethanol (7.96 g, 28.50 mmol) in anhydrous DCM (100 mL) was set under an atmosphere of nitrogen and cooled at 0° C. Triphenylphosphine on polymer bead (14.24 g, 54.3 mmol) was added followed by DIAD (7.92 mL, 40.7 mmol) and the resulting mixture was warmed to RT and stirred overnight. The mixture was filtered through a fitted funnel to remove the polymer bound triphenylphosphine and the organics concentrated under reduced pressure. The residue was purified by silica gel chromatography (220 g of silica gel, ISCO, eluted with a gradient 0-60% ethyl acetate in Hexane) to afford the title compound. HPLC/MS; 1.27 min (2 minute run), 468 $(M+Na)^+$.

Step B: 2-fluoro-4-(2-{(1S,2R)-[1-(3-isopropyl-1,2,4-oxadiazol-5-yl)piperidin-4-yl]cyclopropyl}ethoxy)phenyl]acetic acid

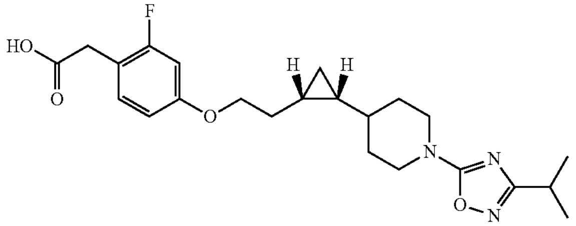 [SMILES: CC(C)c1noc(N2CCC([C@H]3C[C@H]3CCOc3ccc(CC(=O)O)c(F)c3)CC2)n1]

To a solution of methyl [2-fluoro-4-(2-{(1S,2R)-[1-(3-isopropyl-1,2,4-oxadiazol-5-yl)piperidin-4-yl]cyclopropyl}ethoxy)phenyl]acetate (Example GJM-1, Step A, 9.00 g, 20.20 mmol) in a 1.5:1:1 mixture of THF/methanol/water (60/40/40 mL) was added 10 mL of a 5M aqueous solution of NaOH and the resulting mixture stirred for 16 h at RT. The mixture was neutralized via addition of 1N aqueous HCl until pH of 5 was obtained. The solution was then extracted with DCM (3×100 mL). The organics were combined, dried over sodium sulfate, filtered and the filtrate concentrated under reduced pressure. The residue was purified via column chromatography (ISCO, 220 g silica gel column, 60 ml/min) eluting with 0-5% methanol in DCM. The fractions containing the product were combined and concentrated to dryness under reduce pressure to afford the title compound as a white solid. HPLC/MS; 2.20 min (4 minute run), 432 $(M+H)^+$.

Step C: 4-[(1R,2S)-2-(2-{3-fluoro-4-[2-(3-fluoroazetidin-1-yl)-2-oxoethyl]phenoxy}ethyl)cyclopropyl]-1-(3-isopropyl-1,2,4-oxadiazol-5-yl)piperidine

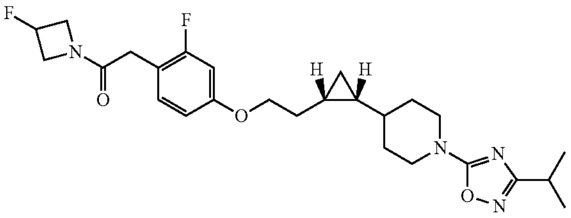 [SMILES: CC(C)c1noc(N2CCC([C@H]3C[C@H]3CCOc3ccc(CC(=O)N4CC(F)C4)c(F)c3)CC2)n1]

To a solution of 2-fluoro-4-(2-1(1S,2R)-[1-(3-isopropyl-1,2,4-oxadiazol-5-yl)piperidin-4-yl]cyclopropyl}ethoxy)phenyl]acetic acid (6.70 g, 15.53 mmol) and 3-fluoroazetidine (2.00 g, 17.93 mmol) in anhydrous DMF (100 mL) was added DIEA (13.56 mL, 78 mmol) followed by HATU (8.86 g, 23.29 mmol) and the resulting mixture stirred at RT overnight. LC-MS showed formation of product with no starting material left over. The mixture was diluted with 250 mL of ethyl acetate and washed with water (2×100 mL). The organics were dried over sodium sulfate, filtered, and the filtrate concentrated to dryness under reduced pressure. The residue was purified by flash column chromatography (220 g of silica gel, ISCO, eluted with a gradient of 0-80% ethyl acetate in hexanes) to afford the title compound (7.13 g, 89%, 94.3% purity). The product was purified again by flash column chromatography (220 g of silica gel, ISCO, eluted with a gradient of 0-5% methanol in DCM) to afford the title compound. HPLC/MS; 2.25 min (4 minute run), 489 $(M+H)^+$. $^1$HNMR: ($CD_3OD$, 500 MHz) δ: 7.20 (t, J=8.5 Hz, 1H), 6.75-6.67 (m, 2H), 5.42 (sept, J=3.2 Hz, 0.5H), 5.29 (sept, J=3.4 Hz, 0.5H). 4.60-4.49 (m, 1H), 4.36-4.22 (m, 2H), 4.12-3.98 (m, 5H), 3.48 (s, 2H), 3.16-3.06 (m, 2H), 2.84 (sept, J=7.0 Hz, 1H), 2.16-2.08 (m, 1H), 1.90 (br t, J=15.2 Hz, 2H), 1.62-1.52 (m, 1H), 1.50-1.41 (m, 2H), 1.27 (d, J=7.0, 6H), 1.20-1.12 (m, 1H), 1.02-0.96 (m, 1H), 0.72-0.64 (m, 2H), −0.04 (dd, J=5.0, 9.6 Hz, 1H).

GPR119 Human EC50: 0.4 nM

Example 101

Preparation of 4-((1R,2S)-2-{2-[4-(2-azetidin-1-yl-2-oxoethyl)-2-fluorophenoxy]ethyl}cyclopropyl)-1-(3-isopropyl-1,2,4-oxadiazol-5-yl)piperidine

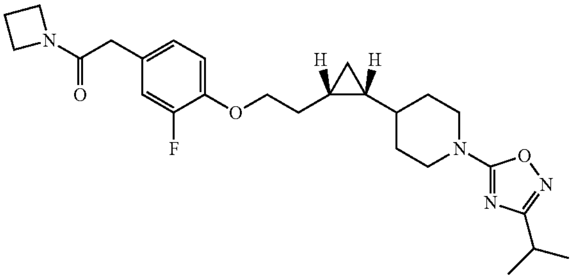 [SMILES: CC(C)c1noc(N2CCC([C@H]3C[C@H]3CCOc3ccc(CC(=O)N4CCC4)cc3F)CC2)n1]

Step A: 1-(azetidin-1-yl)-2-(3-fluoro-4-hydroxyphenyl)ethanone

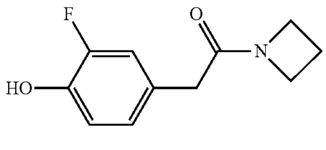 [SMILES: O=C(Cc1ccc(O)c(F)c1)N1CCC1]

To a solution of (3-fluoro-4-methoxyphenyl)acetic acid (0.94 g, 5.52 mmol) in 8 ml anhydrous DMF at RT was added azetidine (0.379 g, 6.63 mmol) and N,N-diisopropylethylamine (2.89 ml, 16.6 mmol), and EDC (1.59 g, 8.29 mmol) was added into the solution and stirred at RT for 4 hrs. The residue was purified by reverse-phase HPLC (SunFire Prep C18 OBD 5 um 19×100 mm column; 10-100% acetonitrile in 0.1% formic acid in water gradient), to give the title compound. LC/MS (m/z) 210.2 $(M+15)^+$.

Step B: 4-((1R,2S)-2-{2-[4-(2-azetidin-1-yl-2-oxoethyl)-2-fluorophenoxy]ethyl}cyclopropyl)-1-(3-isopropyl-1,2,4-oxadiazol-5-yl)piperidine

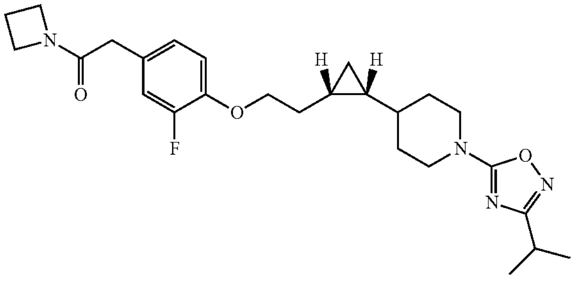 [SMILES: CC(C)c1noc(N2CCC([C@H]3C[C@H]3CCOc3ccc(CC(=O)N4CCC4)cc3F)CC2)n1]

To a solution of 1-(azetidin-1-yl)-2-(3-fluoro-4-hydroxyphenyl)ethanone (65.0 mg, 0.236 mmol) in 5 ml anhydrous dichloromethane at RT was added a solution of 2-{(1S,2R)-2-[1-(3-isopropyl-1,2,4-oxadiazol-5-yl)piperidin-4-yl]cyclopropyl}ethanol (59.0 mg, 0.283 mmol), triphenylphosphine, polymer-bound (186 mg, 0.534 mmol), and di-tert-butyl azodicarboxylate (109 mg, 0.472 mmol). The reaction mixture as stirred at RT for 3 hours. The mixture was filtered by Celite and concentrated. The residue The reaction mixture was filtered and purified by reverse-phase HPLC (SunFire Prep C18 OBD 5 um 19×100 mm column; 35-100% acetonitrile in 0.1% formic acid in water gradient), to give the title compound. LC/MS (m/z) 471.3 $(M+H)^+$. Human $EC_{50}$: 5.3 nM The Examples in Table 7 were synthesized according to the methods described in the prior examples (98-101) employing the appropriate reagents, intermediates, and solvents.

TABLE 7

| Example # | Chemical Structure | Observed Mass $[M + H]^+$ | GPR119 HumC $EC_{50}$ (nM) |
|---|---|---|---|
| 102 | 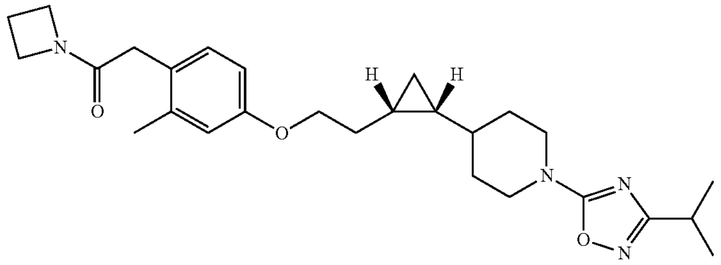 [SMILES: Cc1cc(OCC[C@@H]2C[C@@H]2C2CCN(c3nc(C(C)C)no3)CC2)ccc1CC(=O)N1CCC1] | 467 | 1.1 |
| 103 | 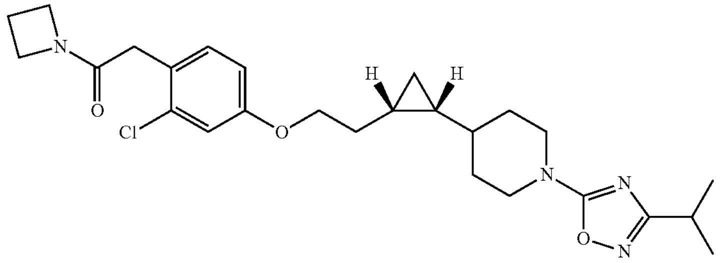 [SMILES: CC(C)c1noc(N2CCC([C@H]3C[C@H]3CCOc3ccc(CC(=O)N4CCC4)c(Cl)c3)CC2)n1] | 487 | 0.58 |
| 104 | 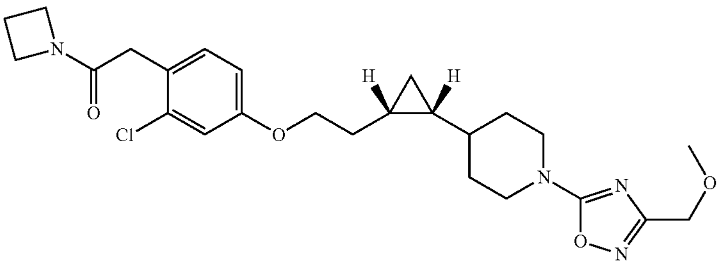 [SMILES: COCc1noc(N2CCC([C@H]3C[C@H]3CCOc3ccc(CC(=O)N4CCC4)c(Cl)c3)CC2)n1] | 489 | 2.6 |

TABLE 7-continued
| Example # | Chemical Structure | Observed Mass $[M + H]^+$ | GPR119 HumC $EC_{50}$ (nM) |
|---|---|---|---|
| 105 | 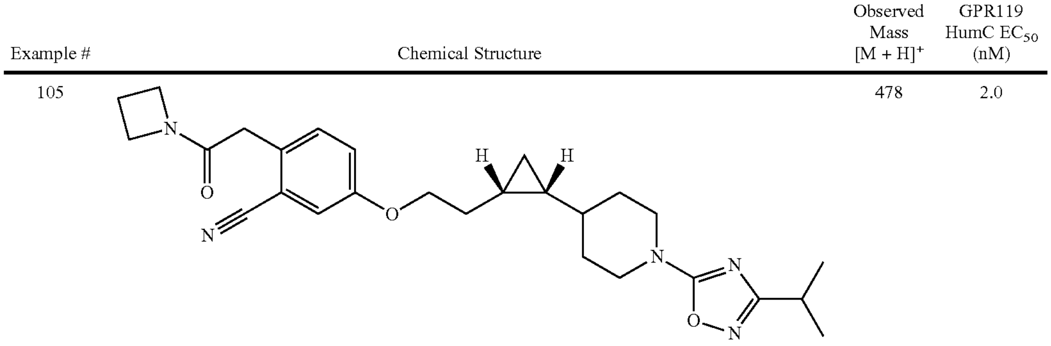 | 478 | 2.0 |
| 106 | 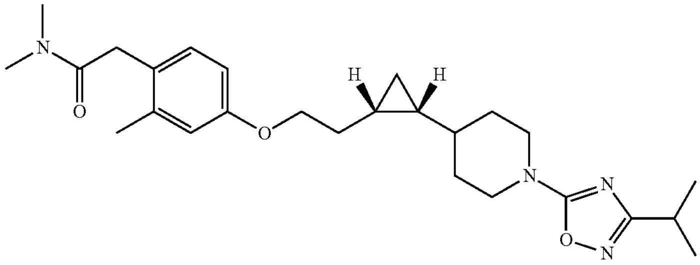 [SMILES: Cc1cc(OCC[C@@H]2C[C@@H]2C2CCN(c3nc(C(C)C)no3)CC2)ccc1CC(=O)N(C)C] | 455 | 3.4 |
| 107 | 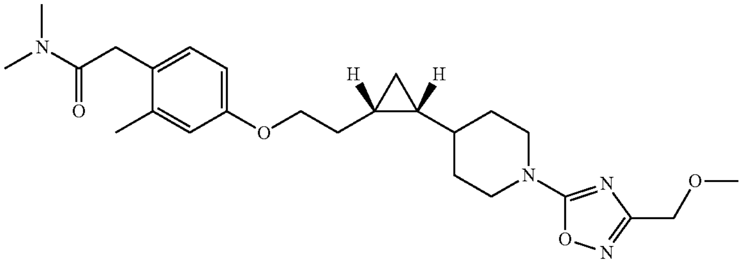 | 457 | 5.2 |

Example 108

Preparation of 1-[(2,6-difluoro-4-{2-[(1S,2R)-2-{1-[3-(1-methylethyl)-1,2,4-oxadiazol-5-yl]piperidin-4-yl}cyclopropyl]ethoxy}phenyl)acetyl]azetidin-3-ol

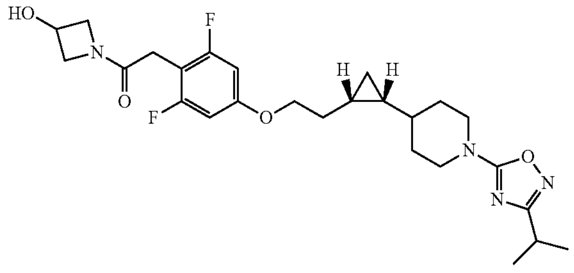 [SMILES: CC(C)c1noc(N2CCC([C@H]3C[C@H]3CCOc3cc(F)c(CC(=O)N4CC(O)C4)c(F)c3)CC2)n1]

Step A: methyl (2,6-difluoro-4-{24(1S,2R)-2-{1-[3-(propan-2-yl)-1,2,4-oxadiazol-5-yl]piperidin-4-yl}cyclopropyl]ethoxy}phenyl)acetate

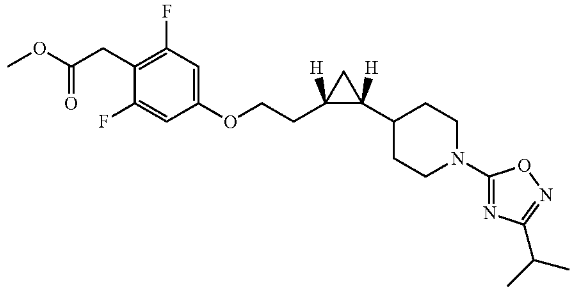 [SMILES: COC(=O)Cc1c(F)cc(OCC[C@@H]2C[C@@H]2C2CCN(c3nc(C(C)C)no3)CC2)cc1F]

To a solution of methyl (2-fluoro-4-hydroxyphenyl)acetate (450 mg, 1.61 mmol) (from Example 1, step A) in 5 ml anhydrous dichloromethane at RT was added a solution of 2-[(1S,2R)-2-{1-[3-(propan-2-yl)-1,2,4-oxadiazol-5-yl]piperidin-4-yl}cyclopropyl]ethanol (326 mg, 1.61 mmol) in 10 ml anhydrous dichloromethane, triphenylphosphine, polymer-bound (1.27 g, 3.69 mmol), and di-tert-butyl azodicarboxylate (724 mg, 3.22 mmol). The reaction mixture was stirred at RT for 3 hours. It was filtered by Celite and concentrated. The residue was purified on Biotage column (50 g silica gel) using a gradient eluent of 0-50% ethyl acetate in hexanes (1000 ml) to afford the title compound. LC/MS (m/z) 464.2 $(M+H)^+$.

Step B: [(2,6-difluoro-4-{2-[(1S,2R)-2-{1-[3-(propan-2-yl)-1,2,4-oxadiazol-5-yl]piperidin-4-yl}cyclopropyl]ethoxy}phenyl)acetic acid

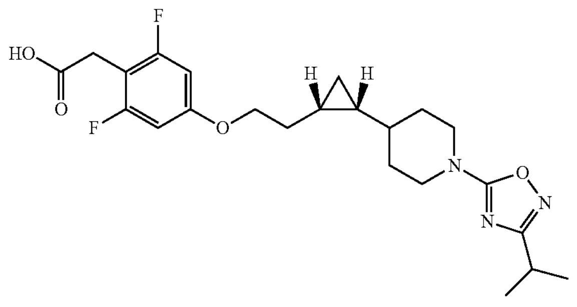 [SMILES: CC(C)c1noc(N2CCC([C@H]3C[C@H]3CCOc3cc(F)c(CC(=O)O)c(F)c3)CC2)n1]

To a solution of methyl [4-(2-{(1S,2R)-2-[1-(5-chloropyrimidin-2-yl)piperidin-4-yl]cyclopropyl}ethoxy)-2-fluorophenyl]acetate (626 g, 1.35 mmol) in 14 ml anhydrous tetrahydrofuran was added by 7 ml methanol and 7 ml water. Lithium hydroxide (193 mg, 8.05 mmol) was added into the reaction mixture, and the reaction was stirred at RT overnight. 1 M hydrochloric acid was added to adjust the pH to 4. The volatiles were removed under vacuum, and the remaining aqueous layer was extracted with dichloromethane (3×20 ml). The organics were combined, dried over magnesium sulphate, filtered, and the filtrate concentrated under reduced pressure to afford the title compound. LC/MS (m/z) 450.3 $(M+H)^+$.

Step C: 1-[(2,6-difluoro-4-{2-[(1S,2R)-2-{1-[3-(1-methylethyl)-1,2,4-oxadiazol-5-yl]piperidin-4-yl}cyclopropyl]ethoxy}phenyl)acetyl]azetidin-3-ol

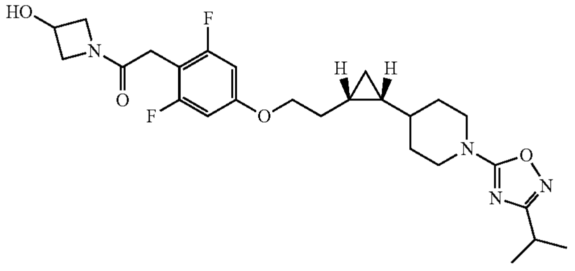 [SMILES: CC(C)c1noc(N2CCC([C@H]3C[C@H]3CCOc3cc(F)c(CC(=O)N4CC(O)C4)c(F)c3)CC2)n1]

To a solution of [(2,6-difluoro-4-{2-[(1S,2R)-2-{1-[3-(propan-2-yl)-1,2,4-oxadiazol-5-yl]piperidin-4-yl}cyclopropyl]ethoxy}phenyl)acetic acid (35.0 mg, 0.078 mmol) (from example 2, step B) in 1 ml anhydrous DMF at RT was added azetidin-3-ol hydrochloride salt (8.53 mg, 0.078 mmol) and N,N-diisopropylethylamine (0.041 ml, 0.234 mmol). o-(7-Azabenzotriazol-1-yl)-N,N,N',N'-tetramethyluronium hexafluorophosphate (59.2 mg, 0.156 mmol) was added into the solution and stirred at RT for 4 hrs. The reaction mixture was filtered and purified by reverse-phase HPLC (SunFire Prep C18 OBD 5 um 19×100 mm column; 35-95% acetonitrile in 0.1% formic acid in water gradient) to give the title compound. LC/MS (m/z): 505.4 $(M+H)^+$. GPR119 Human EC50: 0.96 nM The Examples in Table 8 were synthesized according to the methods described in the prior example (108) employing the appropriate reagents and solvents.

TABLE 8
| Example # | Chemical Structure | Observed Mass $[M + H]^+$ | GPR119 HumC $EC_{50}$ (nM) |
|---|---|---|---|
| 109 | 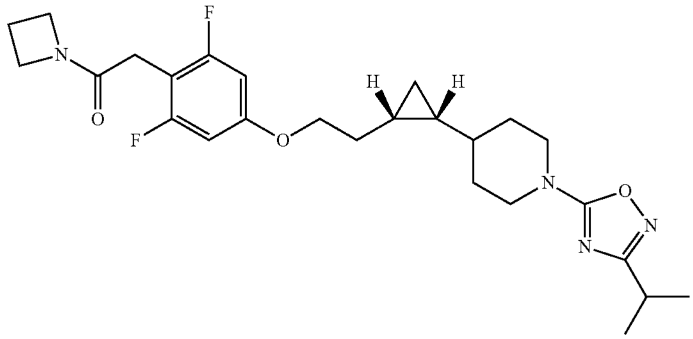 [SMILES: CC(C)c1noc(N2CCC([C@H]3C[C@H]3CCOc3cc(F)c(CC(=O)N4CCC4)c(F)c3)CC2)n1] | 489 | 0.24 |
| 110 | 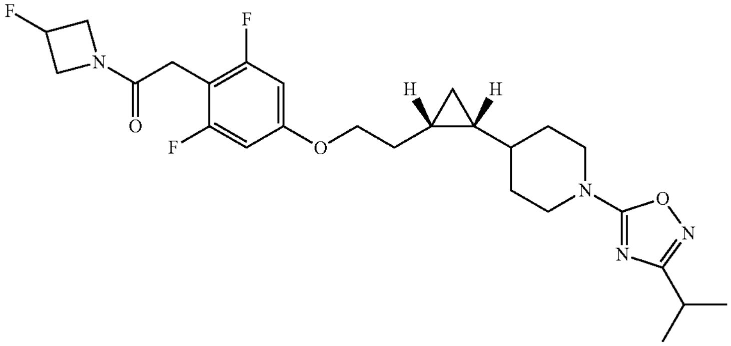 [SMILES: CC(C)c1noc(N2CCC([C@H]3C[C@H]3CCOc3cc(F)c(CC(=O)N4CC(F)C4)c(F)c3)CC2)n1] | 507 | 0.12 |
| 111 | 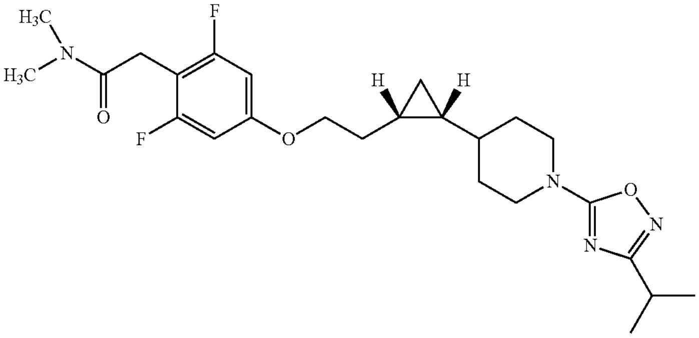 [SMILES: CC(C)c1noc(N2CCC([C@H]3C[C@H]3CCOc3cc(F)c(CC(=O)N(C)C)c(F)c3)CC2)n1] | 477 | 0.26 |
| 112 | 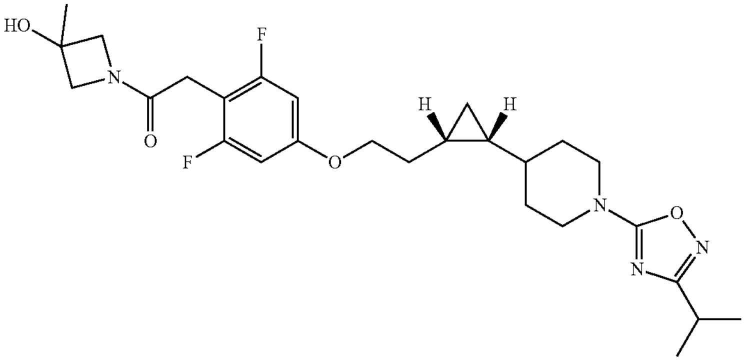 [SMILES: CC(C)c1noc(N2CCC([C@H]3C[C@H]3CCOc3cc(F)c(CC(=O)N4CC(C)(O)C4)c(F)c3)CC2)n1] | 519 | 2.4 |

TABLE 8-continued

| Example # | Chemical Structure | Observed Mass $[M + H]^+$ | GPR119 HumC $EC_{50}$ (nM) |
|---|---|---|---|
| 113 | 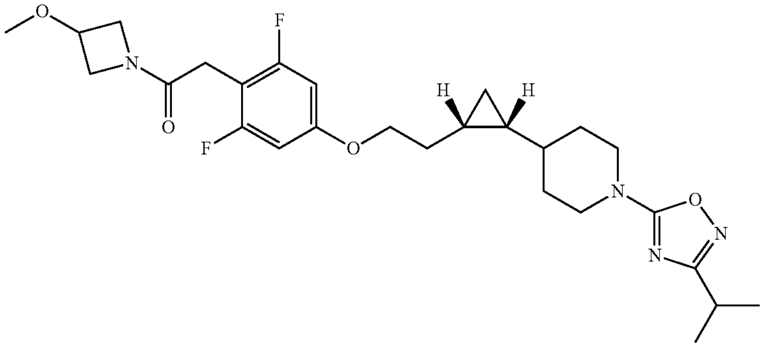 [SMILES: COC1CN(C(=O)Cc2c(F)cc(OCC[C@@H]3C[C@@H]3C3CCN(c4nc(C(C)C)no4)CC3)cc2F)C1] | 519 | 0.33 |
| 114 | 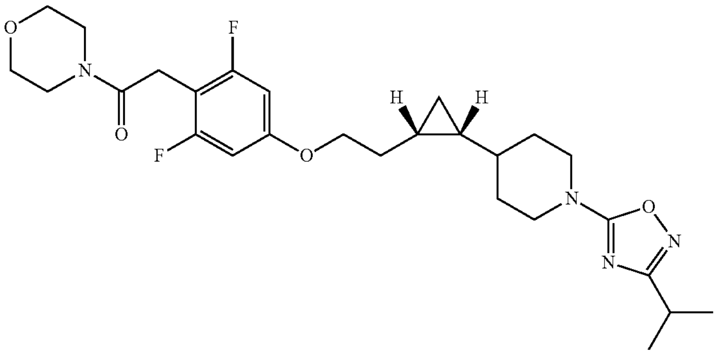 [SMILES: CC(C)c1noc(N2CCC([C@H]3C[C@H]3CCOc3cc(F)c(CC(=O)N4CCOCC4)c(F)c3)CC2)n1] | 519 | 0.19 |

Example 115

Preparation of 4-[(1R,2S)-2-{2-[4-(2-azetidin-1-yl-2-oxoethyl)-3-fluorophenoxy]ethyl}cyclopropyl]-1-[3-(methoxymethyl)-1,2,4-oxadiazol-5-yl]piperidine

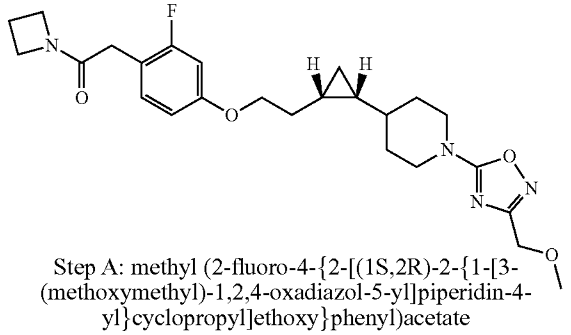

Step A: methyl (2-fluoro-4-{2-[(1S,2R)-2-{1-[3-(methoxymethyl)-1,2,4-oxadiazol-5-yl]piperidin-4-yl}cyclopropyl]ethoxy}phenyl)acetate

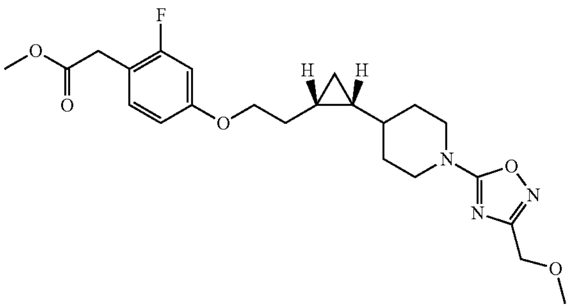

To a solution of 2-[(1S,2R)-2-{1-[3-(methoxymethyl)-1,2,4-oxadiazol-5-yl]piperidin-4-yl}cyclopropyl]ethanol (0.900 g, 3.20 mmol) in 5 ml anhydrous dichloromethane at RT was added a solution of methyl (2-fluoro-4-hydroxyphenyl)acetate (Intermediate 1, 0.707 g, 3.84 mmol) in 10 ml anhydrous dichloromethane, triphenylphosphine, polymer-bound (2.52 g, 12.6 mmol), and di-tert-butyl azodicarboxylate (1.47 g, 6.40 mmol). The reaction mixture was stirred at RT for 3 hours. It was filtered by Celite and concentrated. The residue was purified on Biotage column (100 g silica gel) using a gradient eluent of 0-50% ethyl acetate in hexanes (700 ml) to afford the title compound. LC/MS (m/z) 448.2 $(M+H)^+$.

Step B: (2-fluoro-4-{2-[(1S,2R)-2-{1-[3-(methoxymethyl)-1,2,4-oxadiazol-5-yl]piperidin-4-yl}cyclopropyl]ethoxy}phenyl)acetic acid

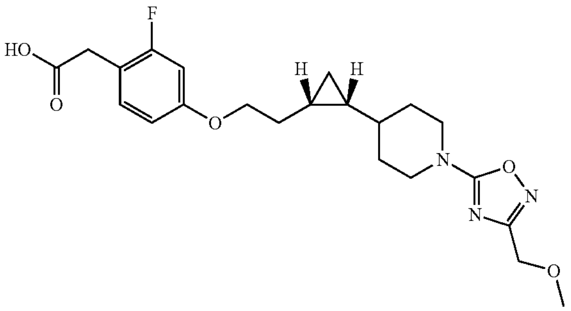 [SMILES: COCc1noc(N2CCC([C@H]3C[C@H]3CCOc3ccc(CC(=O)O)c(F)c3)CC2)n1]

To a solution of methyl methyl (2-fluoro-4-{2-[(1S,2R)-2-{1-[3-(methoxymethyl)-1,2,4-oxadiazol-5-yl]piperidin-4-yl}cyclopropyl]ethoxy}phenyl)acetate (1.00 g, 2.24 mmol) in 21 ml anhydrous tetrahydrofuran was added by 14 ml methanol and 14 ml water. Lithium hydroxide (0.456 g, 11.2 mmol) was added into the reaction mixture, and the reaction was stirred at RT overnight. 1 M hydrochloric acid was added to adjust the pH to 4. The volatiles were removed under vacuum, and the remaining aqueous layer was extracted with dichloromethane (3×50 ml). The organics were combined, dried over magnesium sulphate, filtered, and the filtrate concentrated under reduced pressure. The residue was purified on Biotage column (100 g silica gel) using a gradient eluent of 0-70% ethyl acetate in hexanes (1000 ml) to afford the title compound. LC/MS (m/z) 434.1 $(M+H)^+$.

Step C: 4-[(1R,2S)-2-{2-[4-(2-azetidin-1-yl-2-oxoethyl)-3-fluorophenoxy]ethyl}cyclopropyl]-1-[3-(methoxymethyl)-1,2,4-oxadiazol-5-yl]piperidine

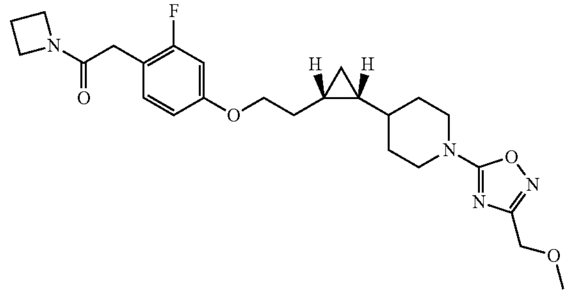 [SMILES: COCc1noc(N2CCC([C@H]3C[C@H]3CCOc3ccc(CC(=O)N4CCC4)c(F)c3)CC2)n1]

To a solution of (2-fluoro-4-{2-[(1S,2R)-2-{1-[3-(methoxymethyl)-1,2,4-oxadiazol-5-yl]piperidin-4-yl}cyclopropyl]ethoxy}phenyl)acetic acid (80.0 mg, 0.185 mmol) in 1 ml anhydrous DMF at RT was added azetidine (12.6.2 mg, 0.221 mmol) and N,N-diisopropylethylamine (0.097 ml, 0.554 mmol). o-(7-Azabenzotriazol-1-yl)-N,N,N',N'-tetramethyluronium hexafluorophosphate (140 mg, 0.369 mmol) was added into the solution and stirred at RT for 4 hrs. The reaction mixture was filtered and purified by reverse-phase HPLC (SunFire Prep C18 OBD 5 um 19×100 mm column; 35-95% acetonitrile in 0.1% formic acid in water gradient) to give the title compound. LC/MS (m/z): 473.2 $(M+H)^+$. GPR119 Human EC50: 5.8 nM Example 116

Preparation of 4-[(1R,2S)-2-(2-{3,5-difluoro-4-[2-(3-fluoroazetidin-1-yl)-2-oxoethyl]phenoxy}ethyl)cyclopropyl]-1-[3-(methoxymethyl)-1,2,4-oxadiazol-5-yl]piperidine

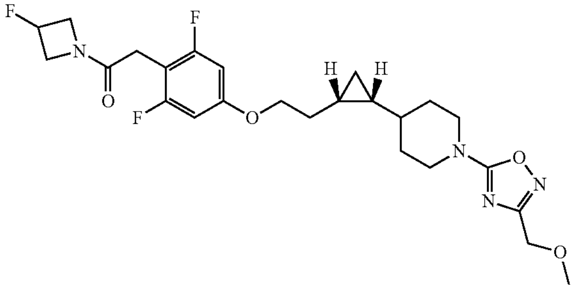 [SMILES: COCc1noc(N2CCC([C@H]3C[C@H]3CCOc3cc(F)c(CC(=O)N4CC(F)C4)c(F)c3)CC2)n1]

Step A: methyl (2,6-difluoro-4-{2-[(1S,2R)-2-{1-[3-(methoxymethyl)-1,2,4-oxadiazol-5-yl]piperidin-4-yl}cyclopropyl]ethoxy}phenyl)acetate

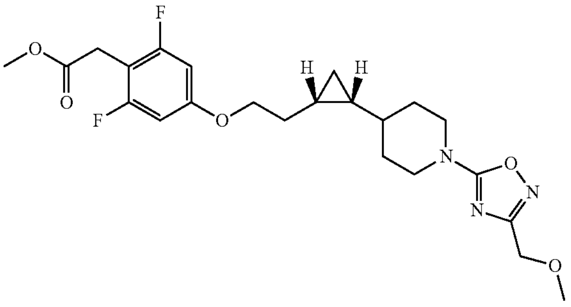

To a solution of methyl (2-fluoro-4-hydroxyphenyl)acetate (450 mg, 1.60 mmol) in 5 ml anhydrous dichloromethane at RT was added a solution of 2-[(1S,2R)-2-{1-[3-(methoxymethyl)-1,2,4-oxadiazol-5-yl]piperidin-4-yl}cyclopropyl]ethanol (322 mg, 1.60 mmol) in 10 ml anhydrous dichloromethane, triphenylphosphine, polymer-bound (1.26 g, 363 mmol), and di-tert-butyl azodicarboxylate (737 mg, 3.20 mmol). The reaction mixture was stirred at RT for 3 hours. It was filtered by Celite and concentrated. The residue was purified on Biotage column (50 g silica gel) using a gradient eluent of 0-50% ethyl acetate in hexanes (700 ml) to afford the title compound. LC/MS (m/z) 466.5 $(M+H)^+$.

Step B: (2,6-difluoro-4-{2-[(1S,2R)-2-{1-[3-(methoxymethyl)-1,2,4-oxadiazol-5-yl]piperidin-4-yl}cyclopropyl]ethoxy}phenyl)acetic acid

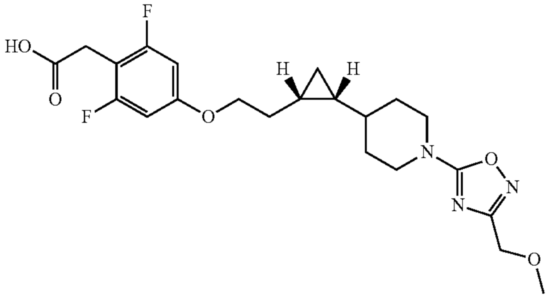 [SMILES: COCc1noc(N2CCC([C@H]3C[C@H]3CCOc3cc(F)c(CC(=O)O)c(F)c3)CC2)n1]

To a solution of methyl (2,6-difluoro-4-{2-[(1S,2R)-2-{1-[3-(methoxymethyl)-1,2,4-oxadiazol-5-yl]piperidin-4-yl}cyclopropyl]ethoxy}phenyl)acetate (0.500 g, 10.7 mmol) in 14 ml anhydrous tetrahydrofuran was added by 7 ml methanol and 7 ml water. Lithium hydroxide (0.3129 g, 5.37 mmol) was added into the reaction mixture, and the reaction was stirred at RT overnight. 1 M hydrochloric acid was added to adjust the pH to 4. The volatiles were removed under vacuum, and the remaining aqueous layer was extracted with dichloromethane (3×20 ml). The organics were combined, dried over magnesium sulphate, filtered, and the filtrate concentrated under reduced pressure. The residue was purified on Biotage column (50 g silica gel) using a gradient eluent of 0-70% ethyl acetate in hexanes (700 ml) to afford the title compound. LC/MS (m/z) 432.3 $(M+H)^+$.

Step C: 4-[(1R,2S)-2-(2-{3,5-difluoro-4-[2-(3-fluoroazetidin-1-yl)-2-oxoethyl]phenoxy}ethyl)cyclopropyl]-1-[3-(methoxymethyl)-1,2,4-oxadiazol-5-yl] piperidine

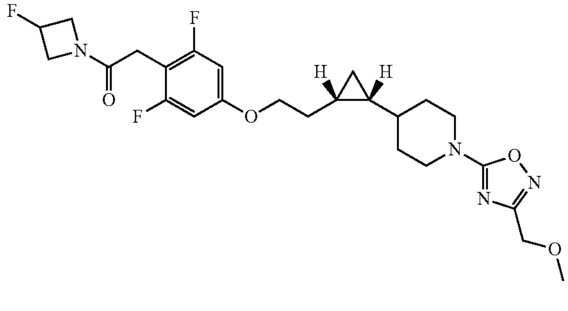 [SMILES: COCc1noc(N2CCC([C@H]3C[C@H]3CCOc3cc(F)c(CC(=O)N4CC(F)C4)c(F)c3)CC2)n1]

To a solution of (2,6-difluoro-4-{2-[(1S,2R)-2-{1-[3-(methoxymethyl)-1,2,4-oxadiazol-5-yl]piperidin-4-yl}cyclopropyl]ethoxy}phenyl)acetic acid (100 mg, 0.230 mmol) (from example 1, step C) in 1 ml anhydrous DMF at RT was added azetidine (13.2 mg, 0.230 mmol) and N,N-diisopropylethylamine (0.201 ml, 1.15 mmol). o-(7-Azabenzotriazol-1-yl)-N,N,N',N'-tetramethyluronium hexafluorophosphate (175 mg, 0.461 mmol) was added into the solution and stirred at RT for 4 hrs. The reaction mixture was filtered and purified by reverse-phase HPLC (SunFire Prep C18 OBD 5 um 19×100 mm column; 35-100% acetonitrile in 0.1% formic acid in water gradient) to give the title compound. LC/MS (m/z): 509.4.2 $(M+H)^+$. GPR119 Human EC50:1.4 nM.

The Examples in Table 11 were synthesized according to the methods described in the prior examples (115-116) employing the appropriate reagents and solvents.

TABLE 11

| Example # | Chemical Structure | Observed Mass $[M + H]^+$ | GPR119 Human $EC_{50}$ (nM) |
|---|---|---|---|
| 117 | 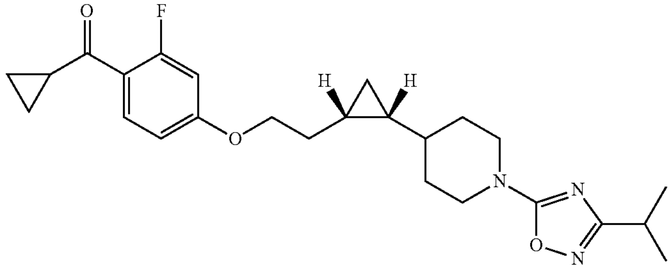 [SMILES: CC(C)c1noc(N2CCC([C@H]3C[C@H]3CCOc3ccc(C(=O)C4CC4)c(F)c3)CC2)n1] | 442 | 0.6 |
| 118 | 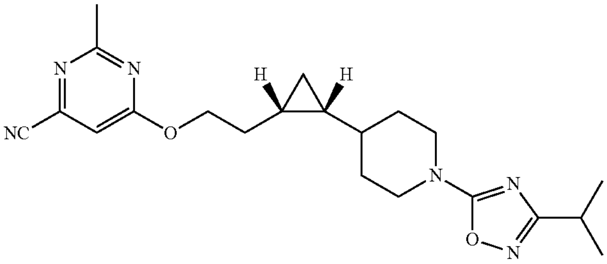 [SMILES: Cc1nc(C#N)cc(OCC[C@@H]2C[C@@H]2C2CCN(c3nc(C(C)C)no3)CC2)n1] | 397 | 0.4 |
| 119 | 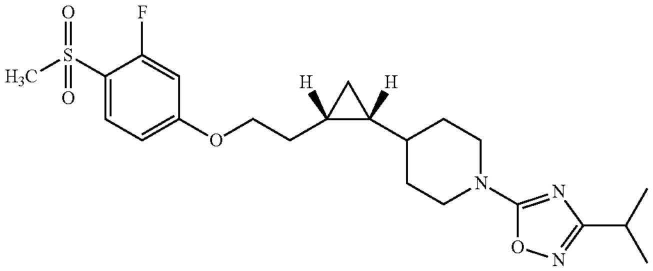 [SMILES: CC(C)c1noc(N2CCC([C@H]3C[C@H]3CCOc3ccc(S(C)(=O)=O)c(F)c3)CC2)n1] | 452 | 1.3 |

TABLE 11-continued
| Example # | Chemical Structure | Observed Mass [M + H]$^+$ | GPR119 Human $EC_{50}$ (nM) |
|---|---|---|---|
| 120 | 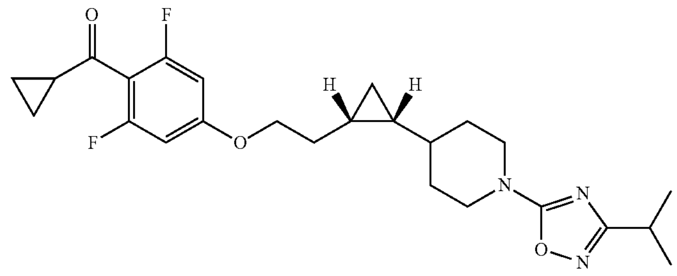 [SMILES: CC(C)c1noc(N2CCC([C@H]3C[C@H]3CCOc3cc(F)c(C(=O)C4CC4)c(F)c3)CC2)n1] | 460 | 0.1 |
| 121 | 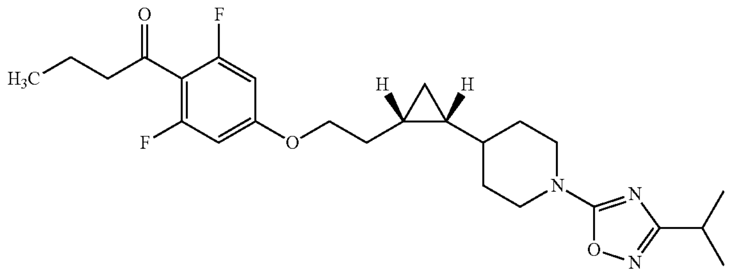 [SMILES: CCCC(=O)c1c(F)cc(OCC[C@@H]2C[C@@H]2C2CCN(c3nc(C(C)C)no3)CC2)cc1F] | 462 | 0.1 |
| 122 | 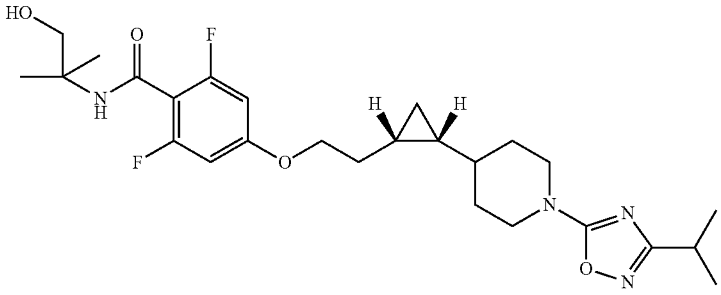 [SMILES: CC(C)c1noc(N2CCC([C@H]3C[C@H]3CCOc3cc(F)c(C(=O)NC(C)(C)CO)c(F)c3)CC2)n1] | 507 | 10 |
| 123 | 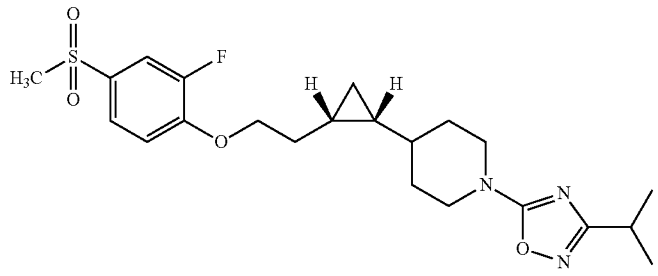 [SMILES: CC(C)c1noc(N2CCC([C@H]3C[C@H]3CCOc3ccc(S(C)(=O)=O)cc3F)CC2)n1] | 452 | 3.8 |
| 124 | 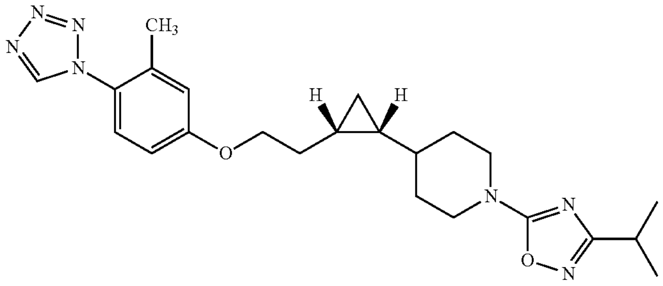 [SMILES: Cc1cc(OCC[C@@H]2C[C@@H]2C2CCN(c3nc(C(C)C)no3)CC2)ccc1-n1cnnn1] | 438 | 2.6 |

TABLE 11-continued
| Example # | Chemical Structure | Observed Mass [M + H]$^+$ | GPR119 Human $EC_{50}$ (nM) |
|---|---|---|---|
| 125 | 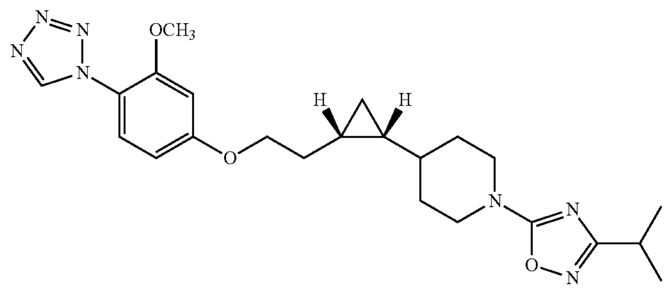 [SMILES: COc1cc(OCC[C@@H]2C[C@@H]2C2CCN(c3nc(C(C)C)no3)CC2)ccc1-n1cnnn1] | 454 | 11 |
| 126 | 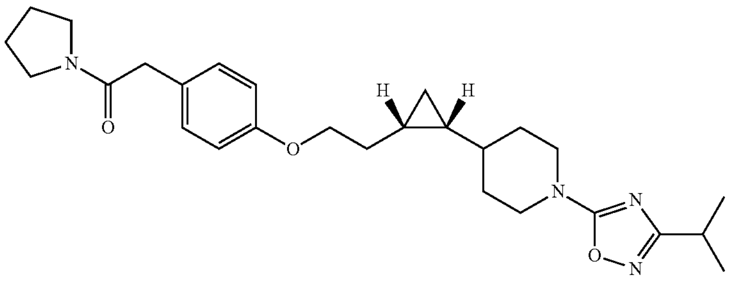 [SMILES: CC(C)c1noc(N2CCC([C@H]3C[C@H]3CCOc3ccc(CC(=O)N4CCCC4)cc3)CC2)n1] | 467 | 1.4 |
| 127 | 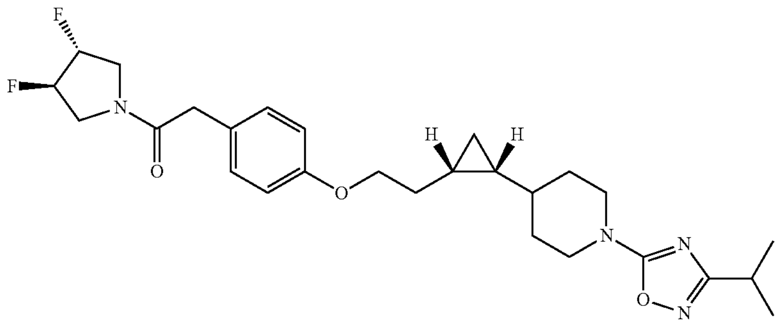 [SMILES: CC(C)c1noc(N2CCC([C@H]3C[C@H]3CCOc3ccc(CC(=O)N4C[C@@H](F)[C@H](F)C4)cc3)CC2)n1] | 503 | 1.1 |
| 128 | 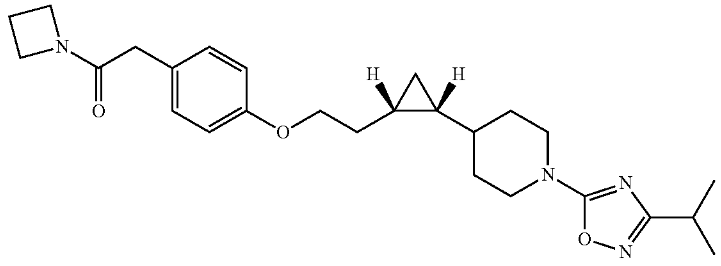 [SMILES: CC(C)c1noc(N2CCC([C@H]3C[C@H]3CCOc3ccc(CC(=O)N4CCC4)cc3)CC2)n1] | 453 | 1.8 |
| 129 | 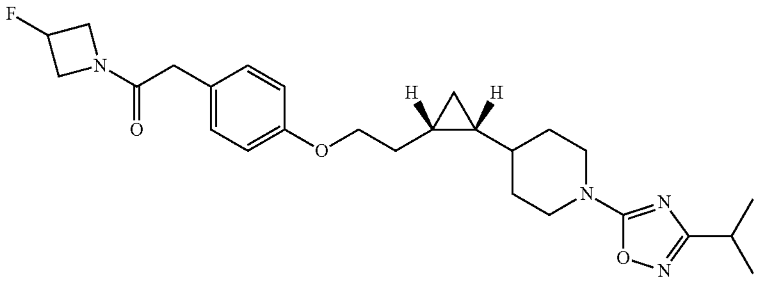 [SMILES: CC(C)c1noc(N2CCC([C@H]3C[C@H]3CCOc3ccc(CC(=O)N4CC(F)C4)cc3)CC2)n1] | 471 | 1.5 |

TABLE 11-continued
| Example # | Chemical Structure | Observed Mass [M + H]+ | GPR119 Human $EC_{50}$ (nM) |
|---|---|---|---|
| 130 | 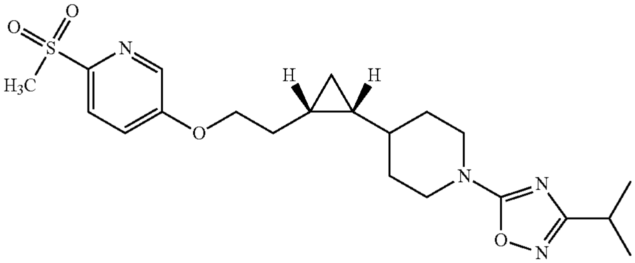 [SMILES: CC(C)c1noc(N2CCC([C@H]3C[C@H]3CCOc3ccc(S(C)(=O)=O)nc3)CC2)n1] | 435 | 10.6 |
| 131 | 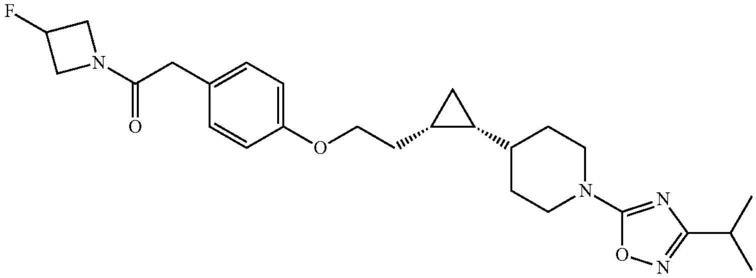 [SMILES: CC(C)c1noc(N2CCC([C@H]3C[C@H]3CCOc3ccc(CC(=O)N4CC(F)C4)cc3)CC2)n1] | 471 | 1.5 |
| 132 | 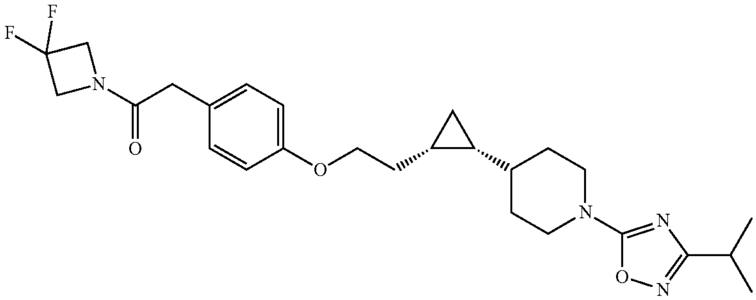 [SMILES: CC(C)c1noc(N2CCC([C@H]3C[C@H]3CCOc3ccc(CC(=O)N4CC(F)(F)C4)cc3)CC2)n1] | 489 | 2.7 |
| 133 | 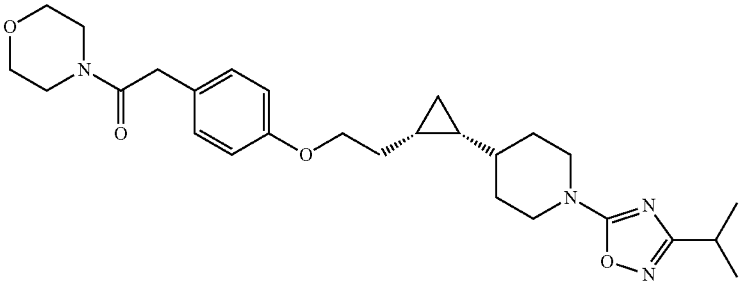 [SMILES: CC(C)c1noc(N2CCC([C@H]3C[C@H]3CCOc3ccc(CC(=O)N4CCOCC4)cc3)CC2)n1] | 483 | 6.0 |
| 134 | 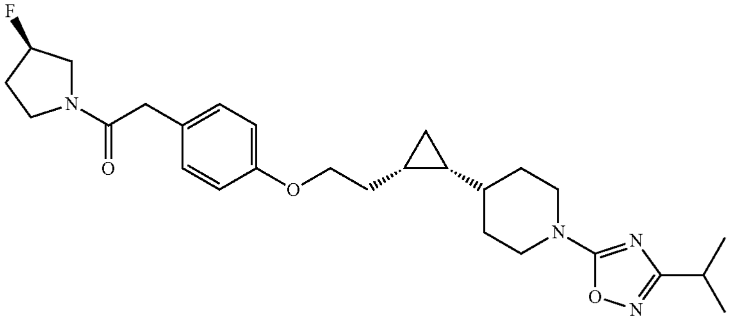 [SMILES: CC(C)c1noc(N2CCC([C@H]3C[C@H]3CCOc3ccc(CC(=O)N4CC[C@@H](F)C4)cc3)CC2)n1] | 484 | 5.3 |

TABLE 11-continued
| Example # | Chemical Structure | Observed Mass $[M + H]^+$ | GPR119 Human $EC_{50}$ (nM) |
|---|---|---|---|
| 135 | 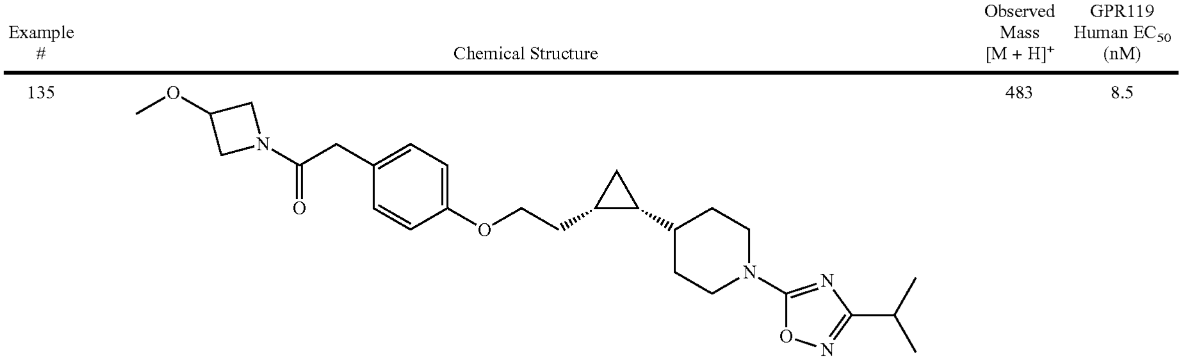 | 483 | 8.5 |
| 136 | 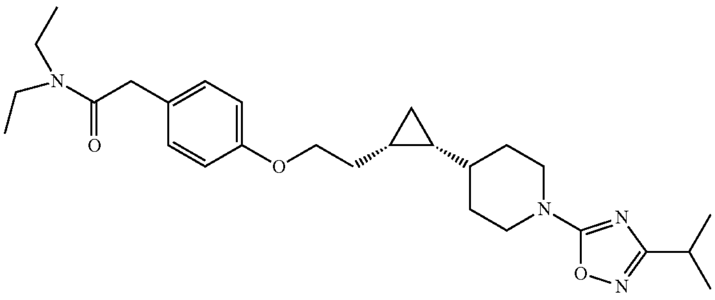 [SMILES: CCN(CC)C(=O)Cc1ccc(OCC[C@@H]2C[C@@H]2C2CCN(c3nc(C(C)C)no3)CC2)cc1] | 469 | 3.9 |
| 137 | 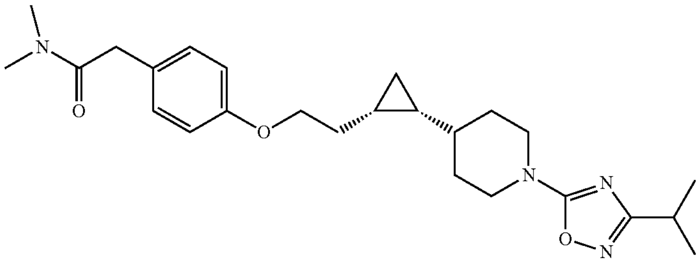 [SMILES: CC(C)c1noc(N2CCC([C@H]3C[C@H]3CCOc3ccc(CC(=O)N(C)C)cc3)CC2)n1] | 441 | 6.7 |
| 138 | 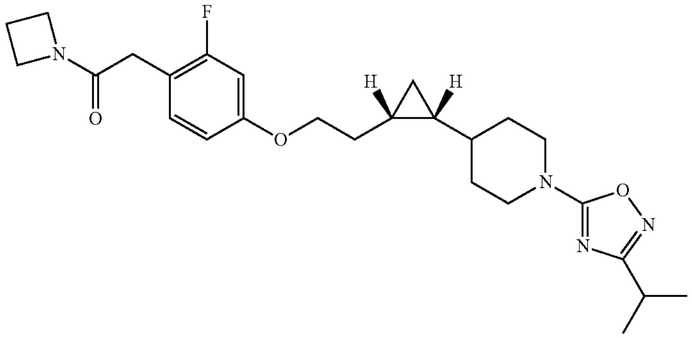 [SMILES: CC(C)c1noc(N2CCC([C@H]3C[C@H]3CCOc3ccc(CC(=O)N4CCC4)c(F)c3)CC2)n1] | 471 | 2.0 |
| 139 | 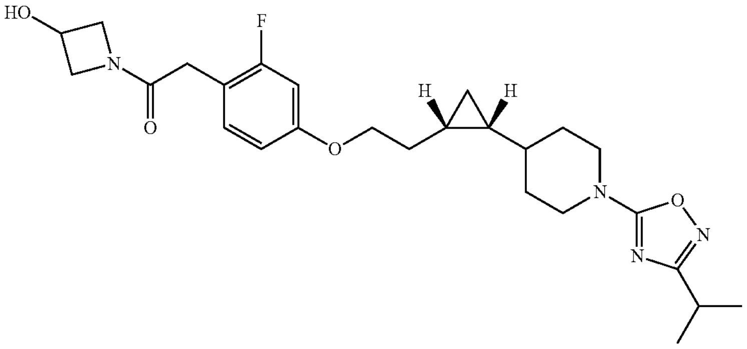 [SMILES: CC(C)c1noc(N2CCC([C@H]3C[C@H]3CCOc3ccc(CC(=O)N4CC(O)C4)c(F)c3)CC2)n1] | 487 | 6.0 |

TABLE 11-continued
| Example # | Chemical Structure | Observed Mass [M + H]+ | GPR119 Human $EC_{50}$ (nM) |
|---|---|---|---|
| 140 | 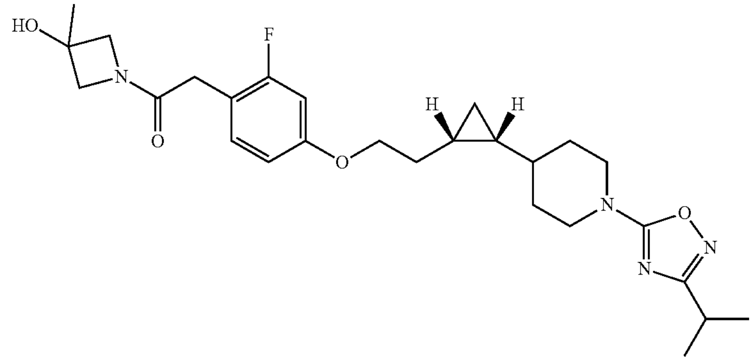 [SMILES: CC(C)c1noc(N2CCC([C@H]3C[C@H]3CCOc3ccc(CC(=O)N4CC(C)(O)C4)c(F)c3)CC2)n1] | 501 | 3.6 |
| 141 | 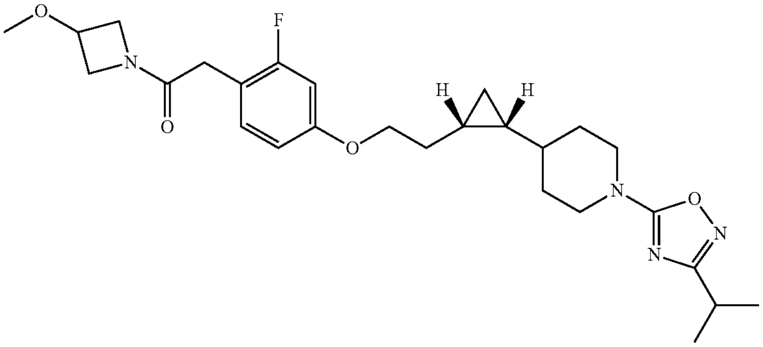 [SMILES: COC1CN(C(=O)Cc2ccc(OCC[C@@H]3C[C@@H]3C3CCN(c4nc(C(C)C)no4)CC3)cc2F)C1] | 501 | 0.93 |
| 142 | 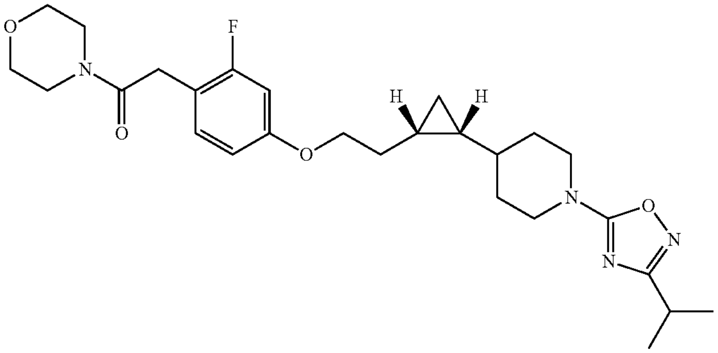 [SMILES: CC(C)c1noc(N2CCC([C@H]3C[C@H]3CCOc3ccc(CC(=O)N4CCOCC4)c(F)c3)CC2)n1] | 501 | 0.84 |
| 143 | 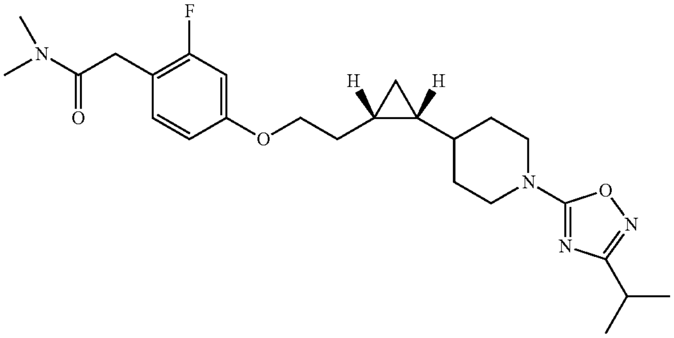 [SMILES: CC(C)c1noc(N2CCC([C@H]3C[C@H]3CCOc3ccc(CC(=O)N(C)C)c(F)c3)CC2)n1] | 459 | 0.94 |

TABLE 11-continued
| Example # | Chemical Structure | Observed Mass [M + H]+ | GPR119 Human $EC_{50}$ (nM) |
|---|---|---|---|
| 144 | 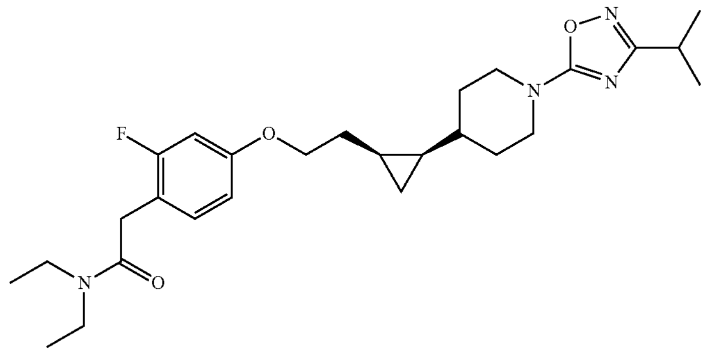 [SMILES: CCN(CC)C(=O)Cc1ccc(OCC[C@@H]2C[C@@H]2C2CCN(c3nc(C(C)C)no3)CC2)cc1F] | 487 | 1.8 |
| 145 | 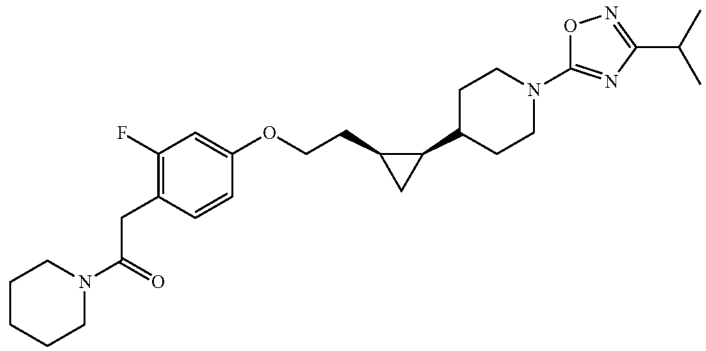 [SMILES: CC(C)c1noc(N2CCC([C@H]3C[C@H]3CCOc3ccc(CC(=O)N4CCCCC4)c(F)c3)CC2)n1] | 499 | 1.7 |
| 146 | 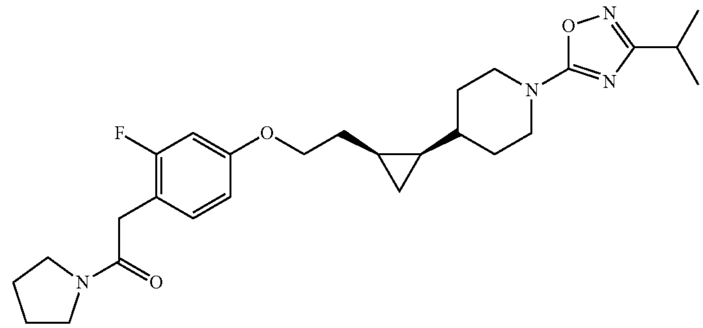 [SMILES: CC(C)c1noc(N2CCC([C@H]3C[C@H]3CCOc3ccc(CC(=O)N4CCCC4)c(F)c3)CC2)n1] | 485 | 1.2 |
| 147 | 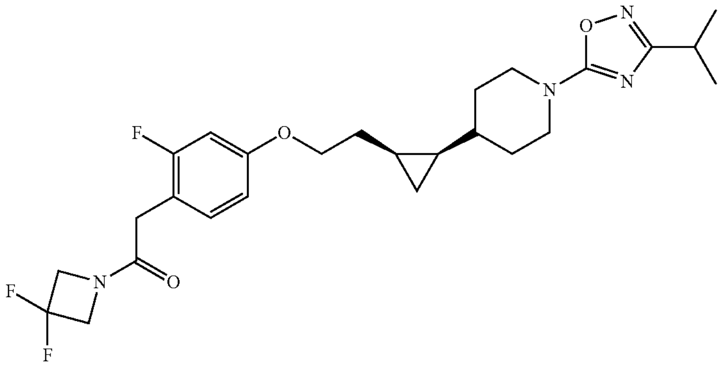 [SMILES: CC(C)c1noc(N2CCC([C@H]3C[C@H]3CCOc3ccc(CC(=O)N4CC(F)(F)C4)c(F)c3)CC2)n1] | 507 | 0.55 |

TABLE 11-continued
| Example # | Chemical Structure | Observed Mass [M + H]$^+$ | GPR119 Human $EC_{50}$ (nM) |
|---|---|---|---|
| 148 | 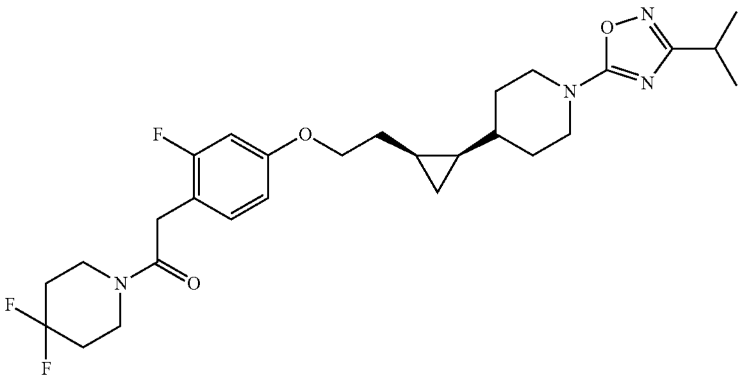 [SMILES: CC(C)c1noc(N2CCC([C@H]3C[C@H]3CCOc3ccc(CC(=O)N4CCC(F)(F)CC4)c(F)c3)CC2)n1] | 535 | 1.7 |
| 149 | 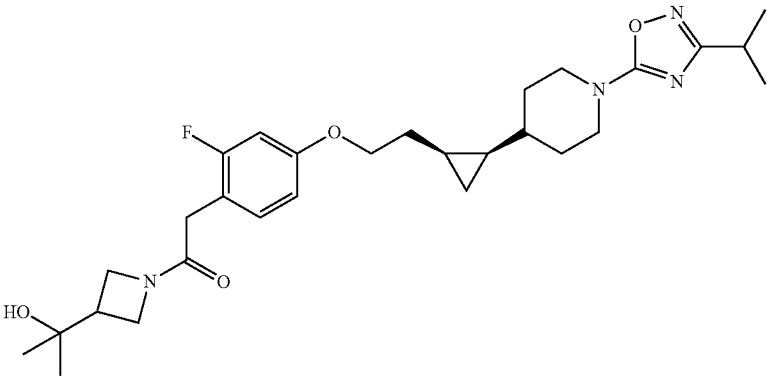 [SMILES: CC(C)c1noc(N2CCC([C@H]3C[C@H]3CCOc3ccc(CC(=O)N4CC(C(C)(C)O)C4)c(F)c3)CC2)n1] | 529 | 8.2 |
| 150 | 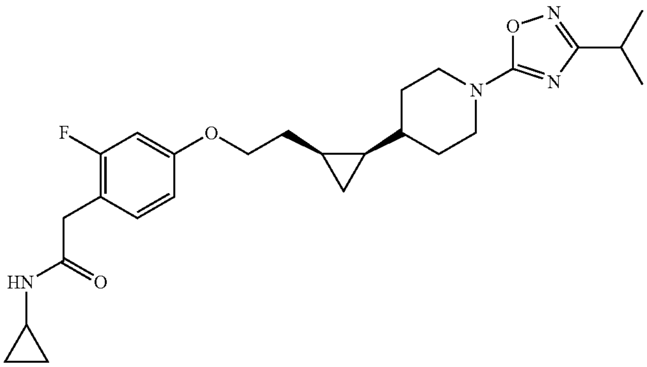 [SMILES: CC(C)c1noc(N2CCC([C@H]3C[C@H]3CCOc3ccc(CC(=O)NC4CC4)c(F)c3)CC2)n1] | 471 | 2.1 |
| 151 | 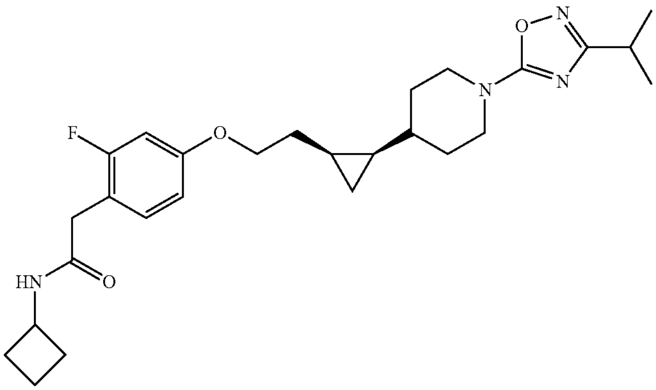 [SMILES: CC(C)c1noc(N2CCC([C@H]3C[C@H]3CCOc3ccc(CC(=O)NC4CCC4)c(F)c3)CC2)n1] | 485 | 3.2 |

TABLE 11-continued
| Example # | Chemical Structure | Observed Mass [M + H]+ | GPR119 Human $EC_{50}$ (nM) |
|---|---|---|---|
| 152 | 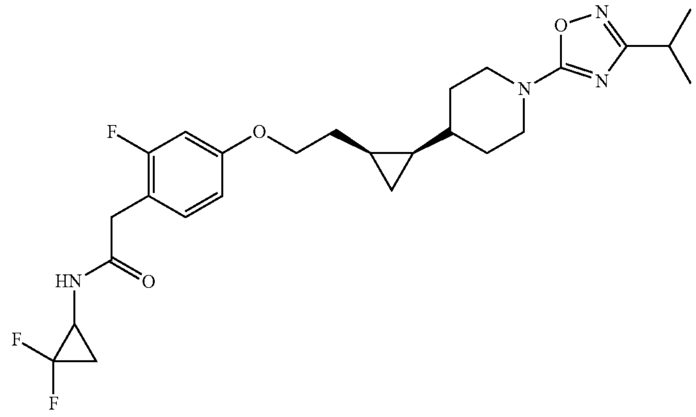 [SMILES: CC(C)c1noc(N2CCC([C@H]3C[C@H]3CCOc3ccc(CC(=O)NC4CC4(F)F)c(F)c3)CC2)n1] | 507 | 6.3 |
| 153 | 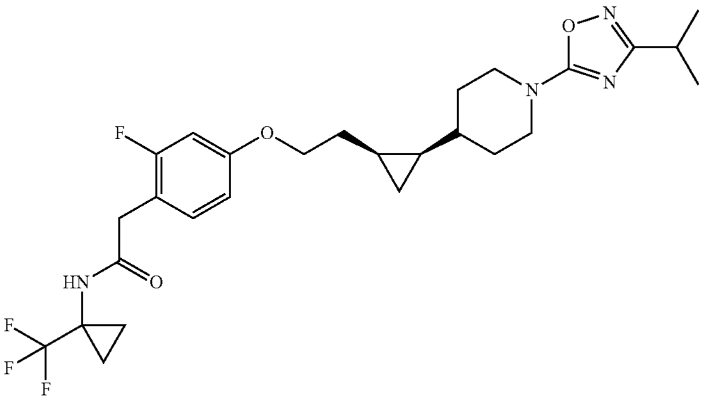 [SMILES: CC(C)c1noc(N2CCC([C@H]3C[C@H]3CCOc3ccc(CC(=O)NC4(C(F)(F)F)CC4)c(F)c3)CC2)n1] | 539 | 4.3 |
| 154 | 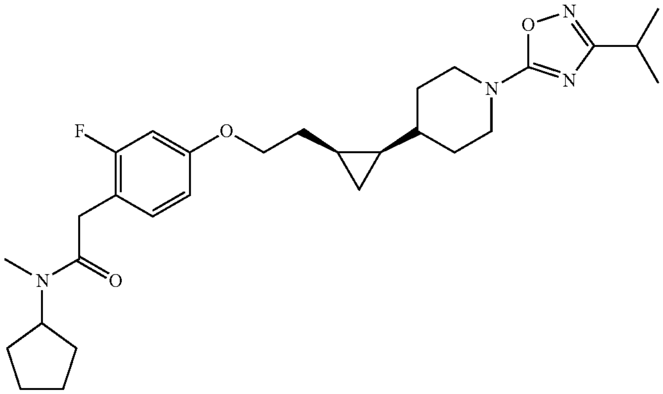 [SMILES: CC(C)c1noc(N2CCC([C@H]3C[C@H]3CCOc3ccc(CC(=O)N(C)C4CCCC4)c(F)c3)CC2)n1] | 513 | 5.0 |

TABLE 11-continued
| Example # | Chemical Structure | Observed Mass $[M + H]^+$ | GPR119 Human $EC_{50}$ (nM) |
|---|---|---|---|
| 155 | 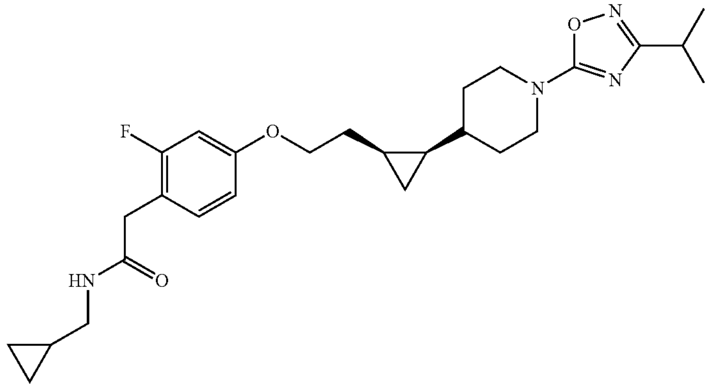 [SMILES: CC(C)c1noc(N2CCC([C@H]3C[C@H]3CCOc3ccc(CC(=O)NCC4CC4)c(F)c3)CC2)n1] | 485 | 7.5 |
| 156 | 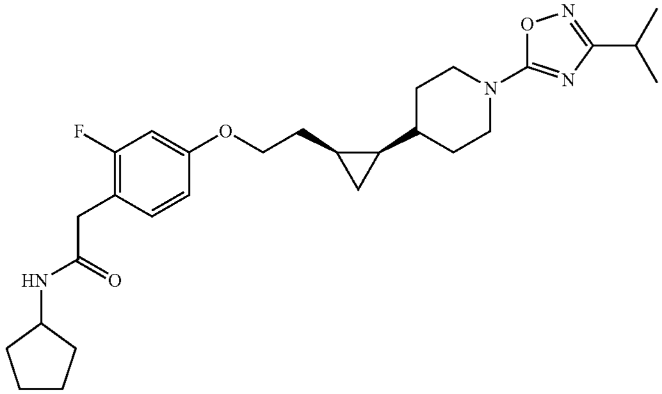 [SMILES: CC(C)c1noc(N2CCC([C@H]3C[C@H]3CCOc3ccc(CC(=O)NC4CCCC4)c(F)c3)CC2)n1] | 499 | 5.4 |
| 157 | 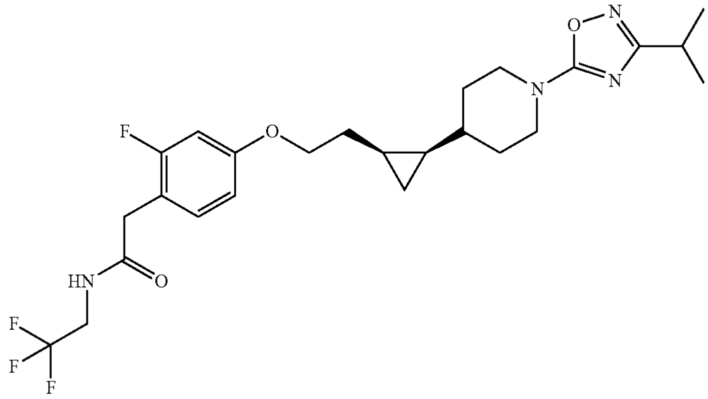 [SMILES: CC(C)c1noc(N2CCC([C@H]3C[C@H]3CCOc3ccc(CC(=O)NCC(F)(F)F)c(F)c3)CC2)n1] | 513 | 3.9 |
| 158 | 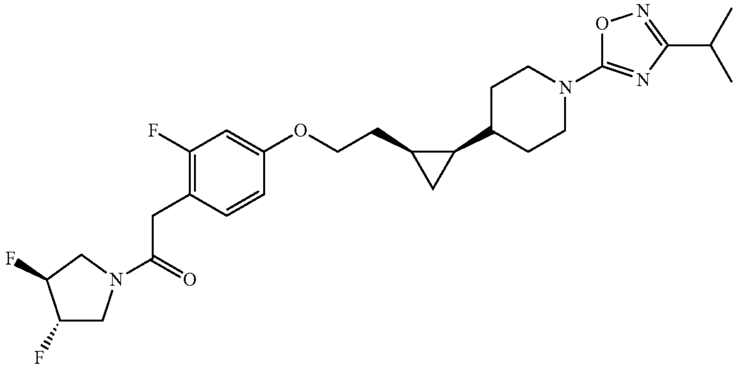 [SMILES: CC(C)c1noc(N2CCC([C@H]3C[C@H]3CCOc3ccc(CC(=O)N4C[C@H](F)[C@@H](F)C4)c(F)c3)CC2)n1] | 521 | 1.1 |

TABLE 11-continued
| Example # | Chemical Structure | Observed Mass [M + H]+ | GPR119 Human $EC_{50}$ (nM) |
|---|---|---|---|
| 159 | 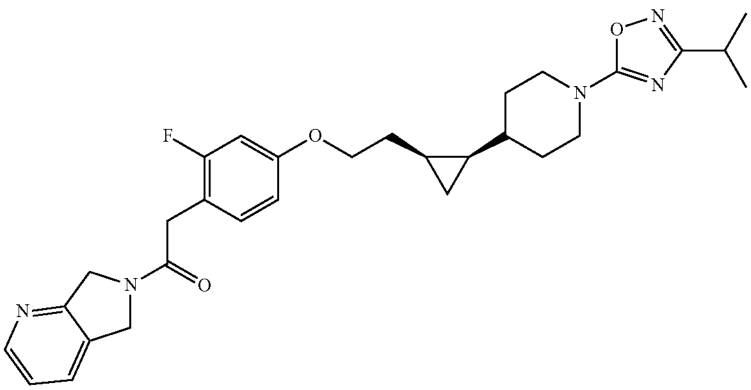 [SMILES: CC(C)c1noc(N2CCC([C@H]3C[C@H]3CCOc3ccc(CC(=O)N4Cc5cccnc5C4)c(F)c3)CC2)n1] | 534 | 0.93 |
| 160 | 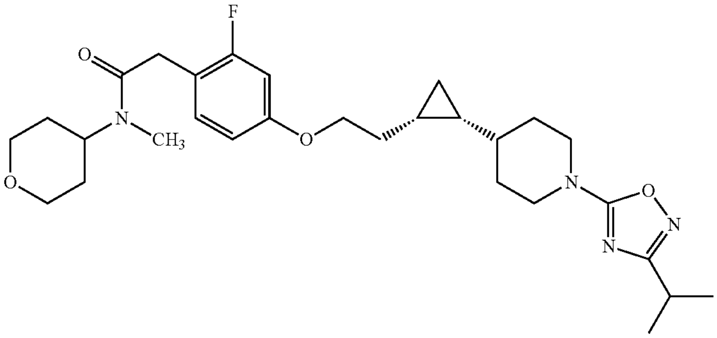 [SMILES: CC(C)c1noc(N2CCC([C@H]3C[C@H]3CCOc3ccc(CC(=O)N(C)C4CCOCC4)c(F)c3)CC2)n1] | 529 | 4.8 |
| 161 | 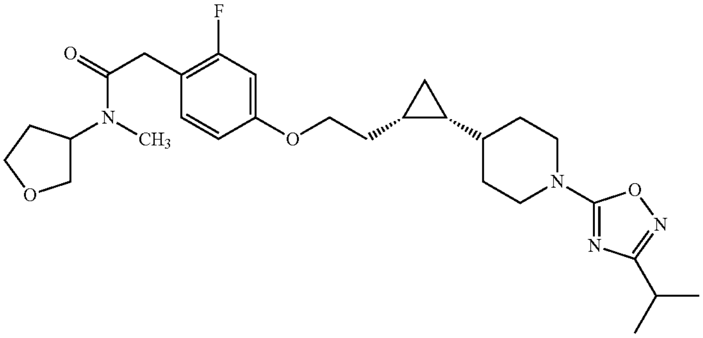 [SMILES: CC(C)c1noc(N2CCC([C@H]3C[C@H]3CCOc3ccc(CC(=O)N(C)C4CCOC4)c(F)c3)CC2)n1] | 515 | 1.1 |
| 162 | 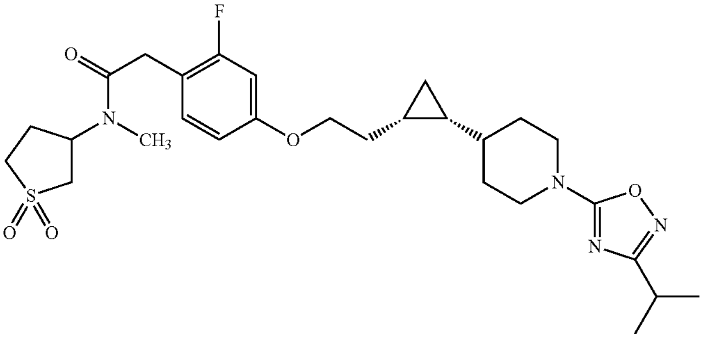 [SMILES: CC(C)c1noc(N2CCC([C@H]3C[C@H]3CCOc3ccc(CC(=O)N(C)C4CCS(=O)(=O)C4)c(F)c3)CC2)n1] | 563 | 2.0 |

TABLE 11-continued
| Example # | Chemical Structure | Observed Mass [M + H]+ | GPR119 Human $EC_{50}$ (nM) |
|---|---|---|---|
| 163 | 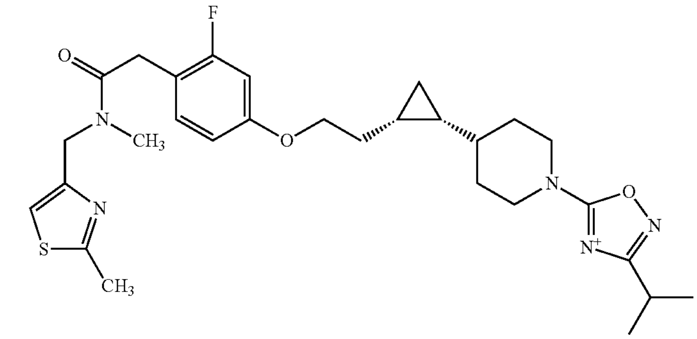 [SMILES: Cc1nc(CN(C)C(=O)Cc2ccc(OCC[C@@H]3C[C@@H]3C3CCN(c4[nH+]c(C(C)C)no4)CC3)cc2F)cs1] | 556 | 2.3 |
| 164 | 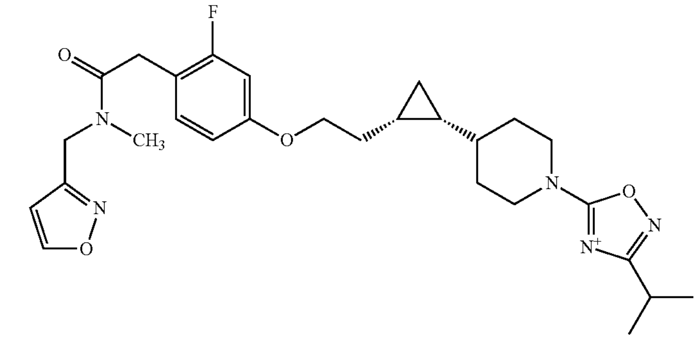 [SMILES: CC(C)c1noc(N2CCC([C@H]3C[C@H]3CCOc3ccc(CC(=O)N(C)Cc4ccon4)c(F)c3)CC2)[nH+]1] | 526 | 1.7 |
| 165 | 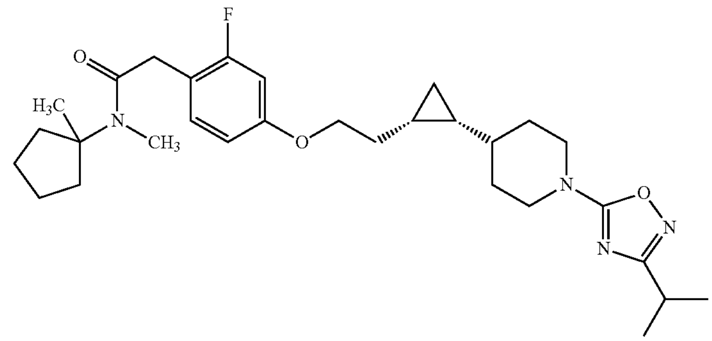 [SMILES: CC(C)c1noc(N2CCC([C@H]3C[C@H]3CCOc3ccc(CC(=O)N(C)C4(C)CCCC4)c(F)c3)CC2)n1] | 527 | 8.1 |
| 166 | 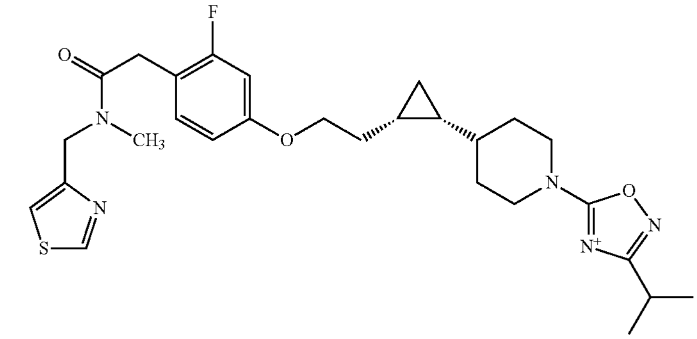 [SMILES: CC(C)c1noc(N2CCC([C@H]3C[C@H]3CCOc3ccc(CC(=O)N(C)Cc4cscn4)c(F)c3)CC2)[nH+]1] | 542 | 2.6 |

TABLE 11-continued
| Example # | Chemical Structure | Observed Mass [M + H]+ | GPR119 Human $EC_{50}$ (nM) |
|---|---|---|---|
| 167 | 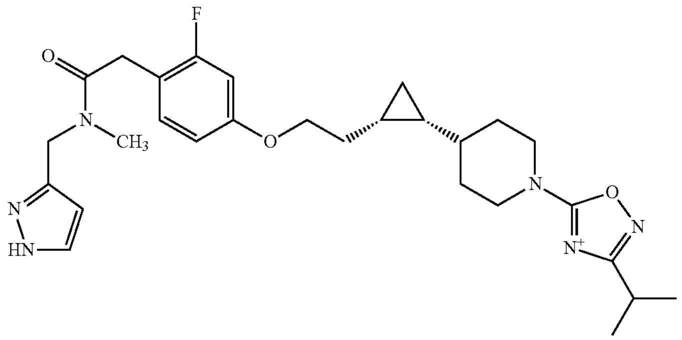 [SMILES: CC(C)c1noc(N2CCC([C@H]3C[C@H]3CCOc3ccc(CC(=O)N(C)Cc4cc[nH]n4)c(F)c3)CC2)[nH+]1] | 525 | 3.1 |
| 168 | 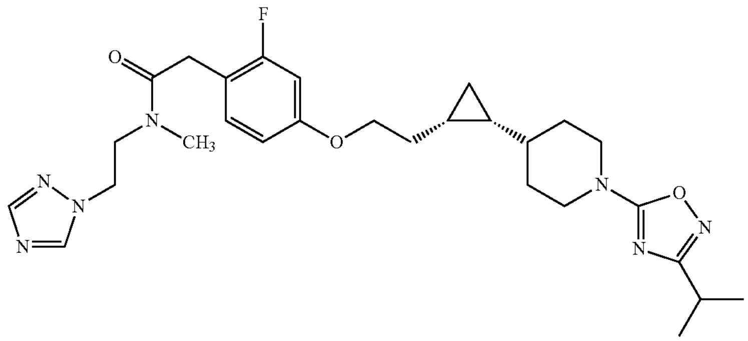 [SMILES: CC(C)c1noc(N2CCC([C@H]3C[C@H]3CCOc3ccc(CC(=O)N(C)CCn4cncn4)c(F)c3)CC2)n1] | 540 | 7.9 |
| 169 | 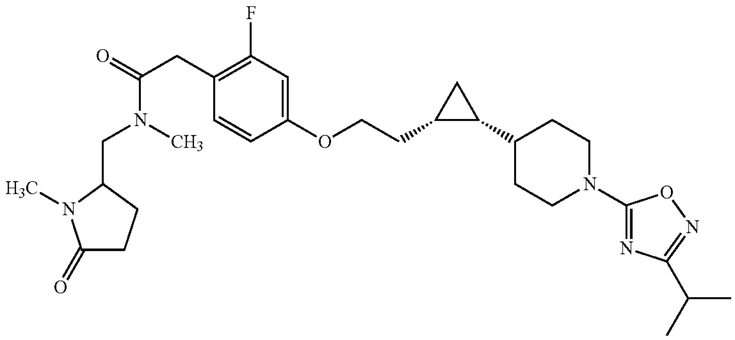 [SMILES: CC(C)c1noc(N2CCC([C@H]3C[C@H]3CCOc3ccc(CC(=O)N(C)CC4CCC(=O)N4C)c(F)c3)CC2)n1] | 556 | 7.7 |
| 170 | 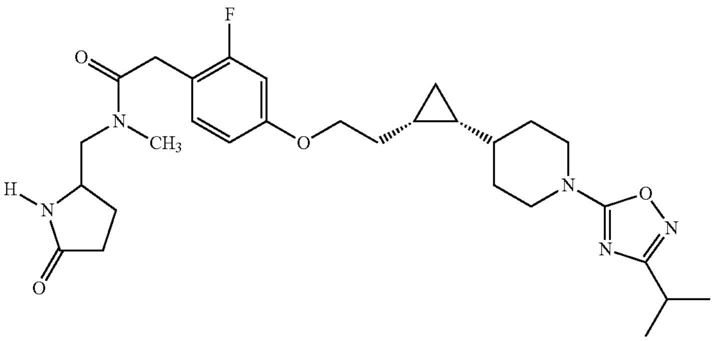 [SMILES: CC(C)c1noc(N2CCC([C@H]3C[C@H]3CCOc3ccc(CC(=O)N(C)CC4CCC(=O)N4)c(F)c3)CC2)n1] | 542 | 7.9 |

TABLE 11-continued
| Example # | Chemical Structure | Observed Mass $[M + H]^+$ | GPR119 Human $EC_{50}$ (nM) |
|---|---|---|---|
| 171 | 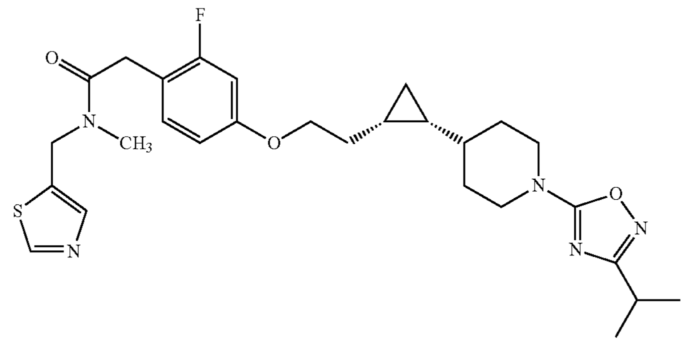 [SMILES: CC(C)c1noc(N2CCC([C@H]3C[C@H]3CCOc3ccc(CC(=O)N(C)Cc4cncs4)c(F)c3)CC2)n1] | 542 | 1.5 |
| 172 | 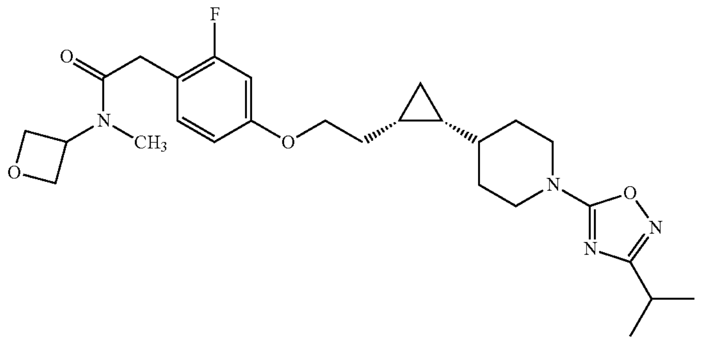 [SMILES: CC(C)c1noc(N2CCC([C@H]3C[C@H]3CCOc3ccc(CC(=O)N(C)C4COC4)c(F)c3)CC2)n1] | 501 | 0.88 |
| 173 | 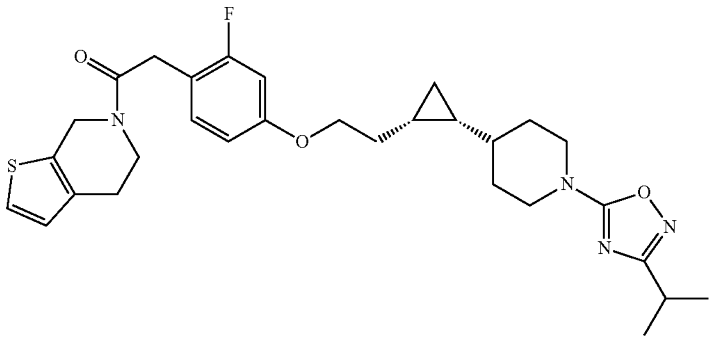 [SMILES: CC(C)c1noc(N2CCC([C@H]3C[C@H]3CCOc3ccc(CC(=O)N4CCc5ccsc5C4)c(F)c3)CC2)n1] | 553 | 2.2 |
| 174 | 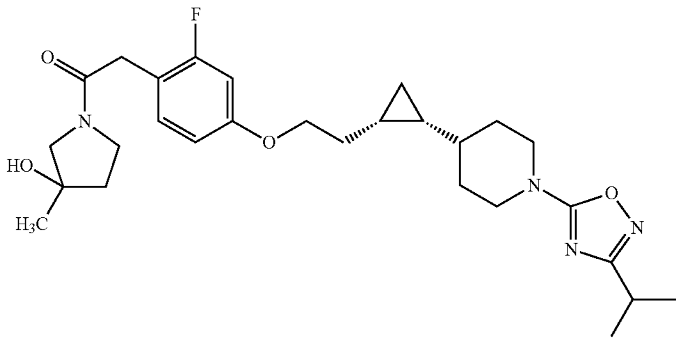 [SMILES: CC(C)c1noc(N2CCC([C@H]3C[C@H]3CCOc3ccc(CC(=O)N4CCC(C)(O)C4)c(F)c3)CC2)n1] | 515 | 11.4 |

TABLE 11-continued
| Example # | Chemical Structure | Observed Mass [M + H]+ | GPR119 Human $EC_{50}$ (nM) |
|---|---|---|---|
| 175 | 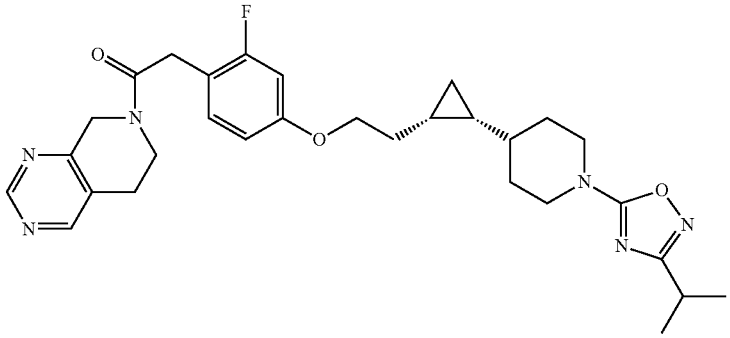 [SMILES: CC(C)c1noc(N2CCC([C@H]3C[C@H]3CCOc3ccc(CC(=O)N4CCc5cncnc5C4)c(F)c3)CC2)n1] | 549 | 3.2 |
| 176 | 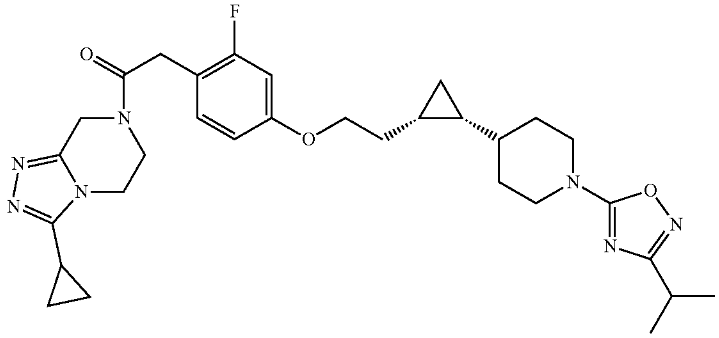 [SMILES: CC(C)c1noc(N2CCC([C@H]3C[C@H]3CCOc3ccc(CC(=O)N4CCn5c(nnc5C5CC5)C4)c(F)c3)CC2)n1] | 578 | 5.7 |
| 177 | 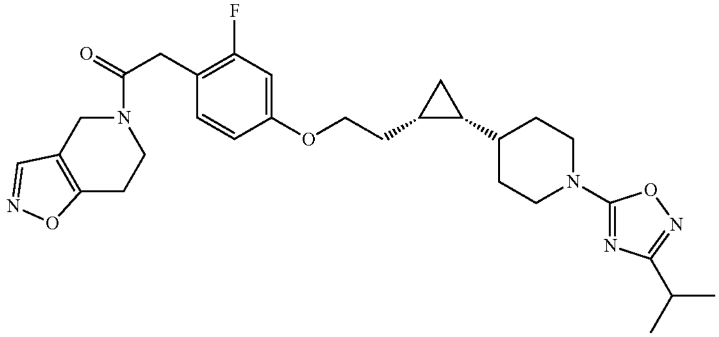 [SMILES: CC(C)c1noc(N2CCC([C@H]3C[C@H]3CCOc3ccc(CC(=O)N4CCc5oncc5C4)c(F)c3)CC2)n1] | 538 | 1.8 |
| 178 | 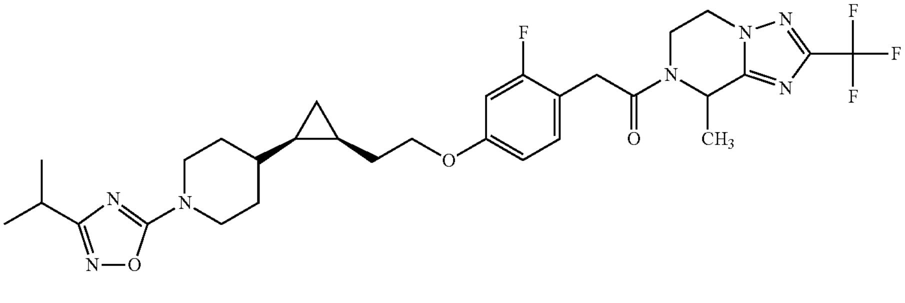 [SMILES: CC(C)c1noc(N2CCC([C@H]3C[C@H]3CCOc3ccc(CC(=O)N4CCn5nc(C(F)(F)F)nc5C4C)c(F)c3)CC2)n1] | 620 | 14 |

TABLE 11-continued
| Example # | Chemical Structure | Observed Mass [M + H]+ | GPR119 Human $EC_{50}$ (nM) |
|---|---|---|---|
| 179 | 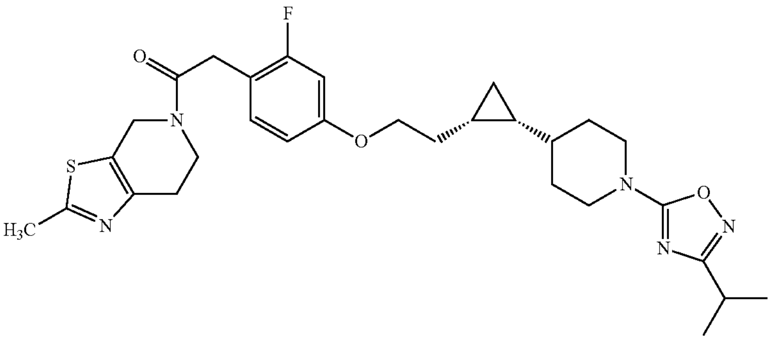 | 568 | 2.6 |
| 180 | 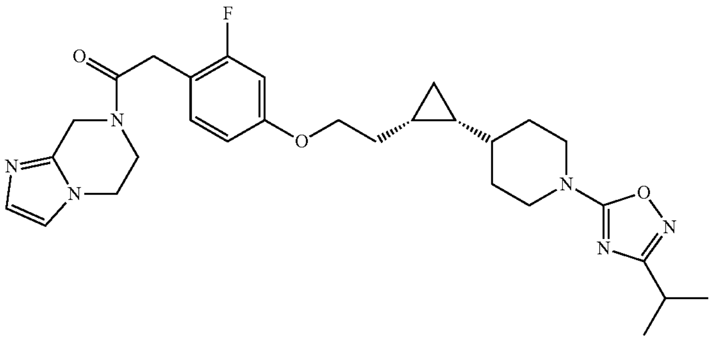 [SMILES: CC(C)c1noc(N2CCC([C@H]3C[C@H]3CCOc3ccc(CC(=O)N4CCn5ccnc5C4)c(F)c3)CC2)n1] | 537 | 4.9 |
| 181 | 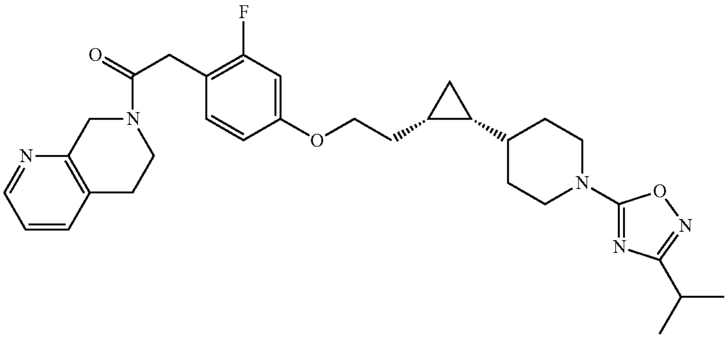 | 548 | 3.7 |
| 182 | 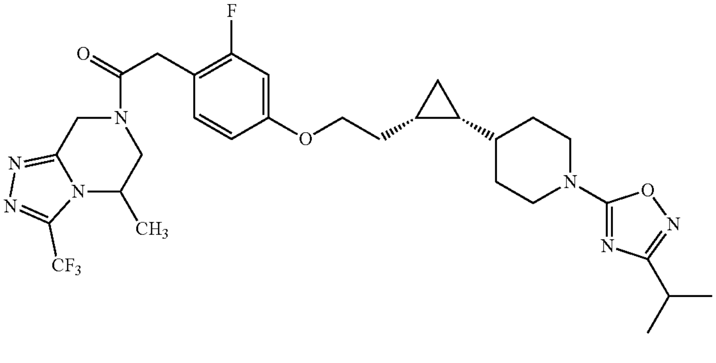 [SMILES: CC(C)c1noc(N2CCC([C@H]3C[C@H]3CCOc3ccc(CC(=O)N4Cc5nnc(C(F)(F)F)n5C(C)C4)c(F)c3)CC2)n1] | 620 | 8.7 |

TABLE 11-continued
| Example # | Chemical Structure | Observed Mass [M + H]+ | GPR119 Human $EC_{50}$ (nM) |
|---|---|---|---|
| 183 | 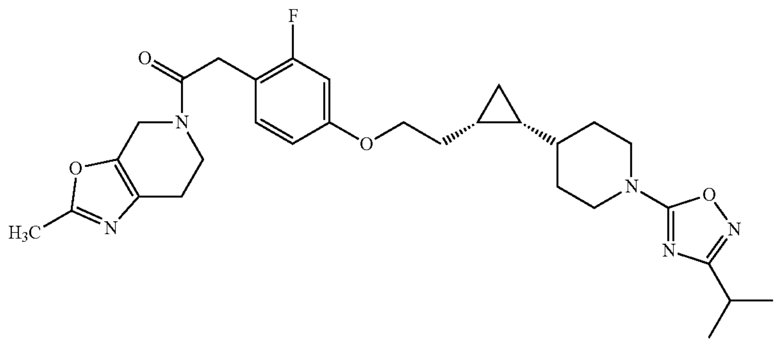 | 552 | 2.1 |
| 184 | 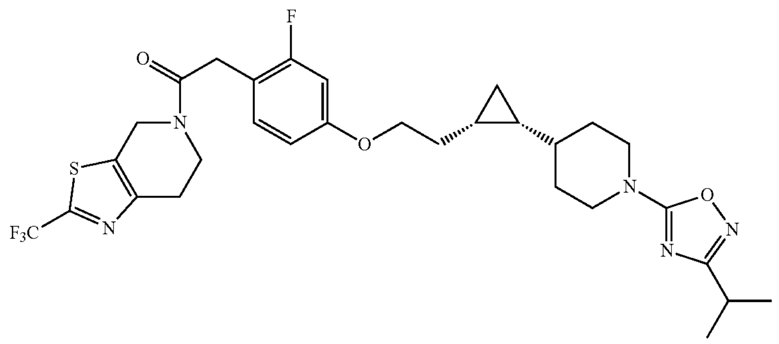 [SMILES: CC(C)c1noc(N2CCC([C@H]3C[C@H]3CCOc3ccc(CC(=O)N4CCc5nc(C(F)(F)F)sc5C4)c(F)c3)CC2)n1] | 622 | 3.5 |
| 185 | 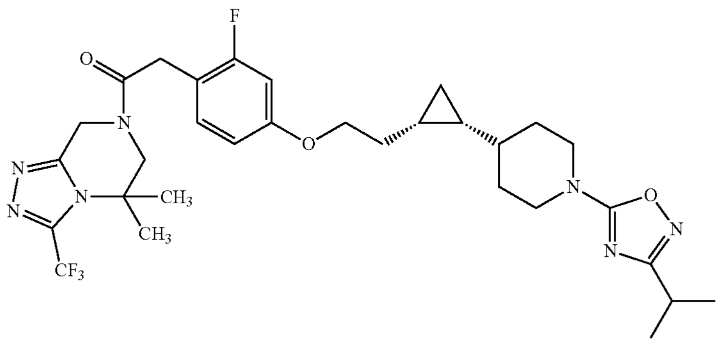 [SMILES: CC(C)c1noc(N2CCC([C@H]3C[C@H]3CCOc3ccc(CC(=O)N4Cc5nnc(C(F)(F)F)n5C(C)(C)C4)c(F)c3)CC2)n1] | 634 | 8.8 |
| 186 | 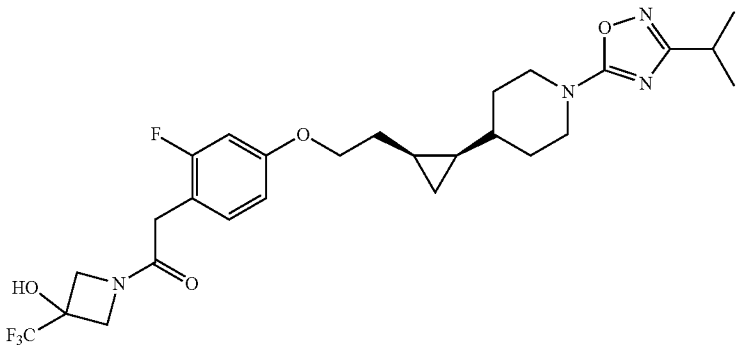 [SMILES: CC(C)c1noc(N2CCC([C@H]3C[C@H]3CCOc3ccc(CC(=O)N4CC(O)(C(F)(F)F)C4)c(F)c3)CC2)n1] | 555 | 2.6 |

TABLE 11-continued
| Example # | Chemical Structure | Observed Mass [M + H]$^+$ | GPR119 Human $EC_{50}$ (nM) |
|---|---|---|---|
| 187 | 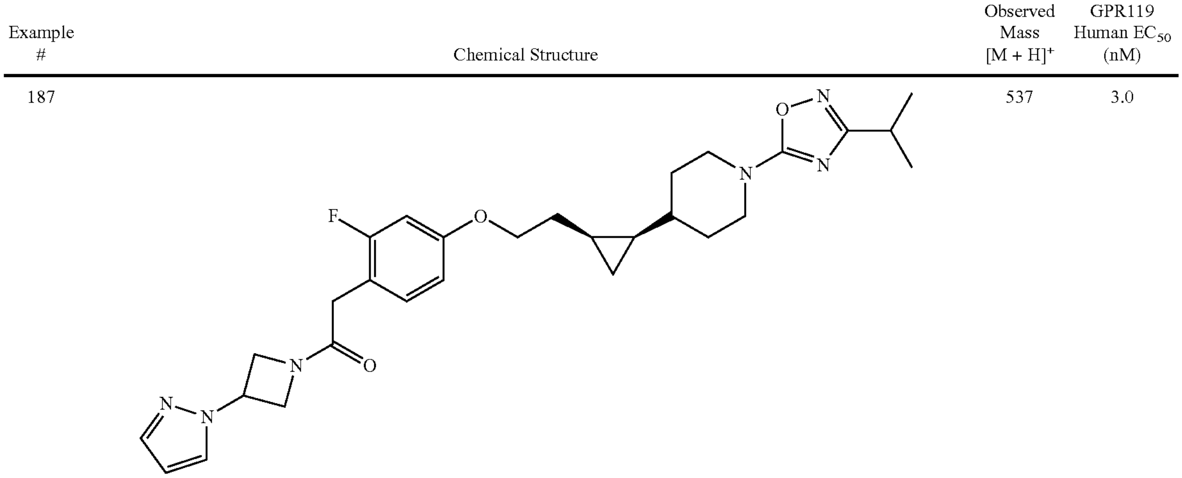 | 537 | 3.0 |
| 188 | 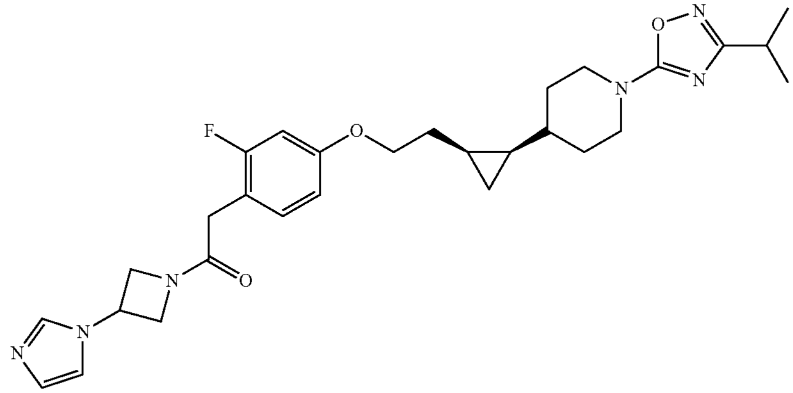 [SMILES: CC(C)c1noc(N2CCC([C@H]3C[C@H]3CCOc3ccc(CC(=O)N4CC(n5ccnc5)C4)c(F)c3)CC2)n1] | 537 | 6.4 |
| 189 | 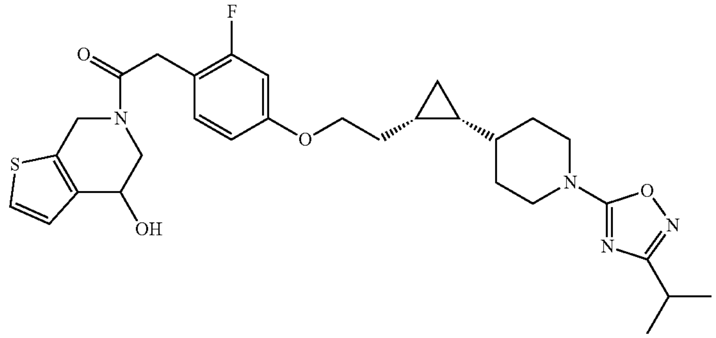 [SMILES: CC(C)c1noc(N2CCC([C@H]3C[C@H]3CCOc3ccc(CC(=O)N4Cc5sccc5C(O)C4)c(F)c3)CC2)n1] | 569 | 4.7 |
| 190 | 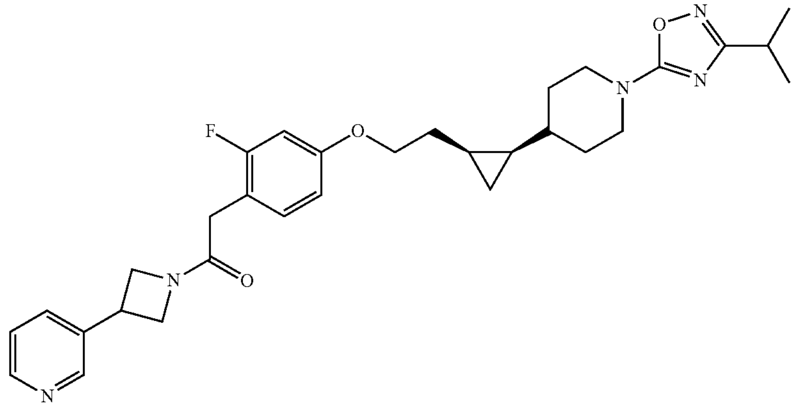 [SMILES: CC(C)c1noc(N2CCC([C@H]3C[C@H]3CCOc3ccc(CC(=O)N4CC(c5cccnc5)C4)c(F)c3)CC2)n1] | 548 | 3.6 |

TABLE 11-continued
| Example # | Chemical Structure | Observed Mass [M + H]+ | GPR119 Human $EC_{50}$ (nM) |
|---|---|---|---|
| 191 | 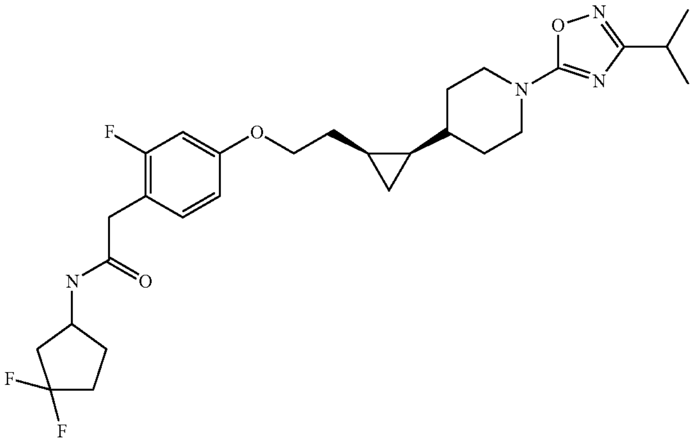 [SMILES: CC(C)c1noc(N2CCC([C@H]3C[C@H]3CCOc3ccc(CC(=O)NC4CCC(F)(F)C4)c(F)c3)CC2)n1] | 535 | 2.8 |
| 192 | 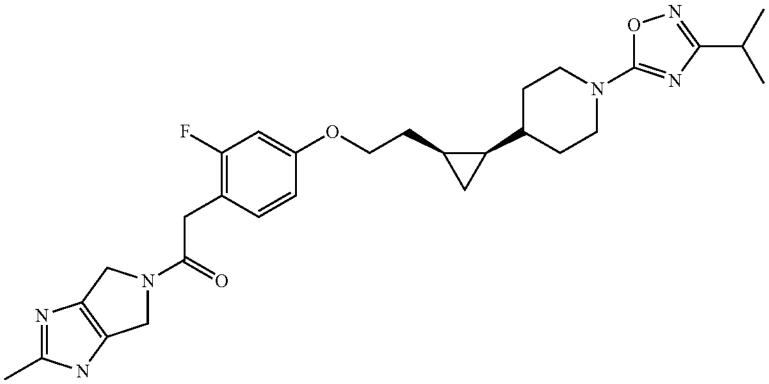 [SMILES: Cc1nc2c([nH]1)CN(C(=O)Cc1ccc(OCC[C@@H]3C[C@@H]3C3CCN(c4nc(C(C)C)no4)CC3)cc1F)C2] | 537 | 4.2 |
| 193 | 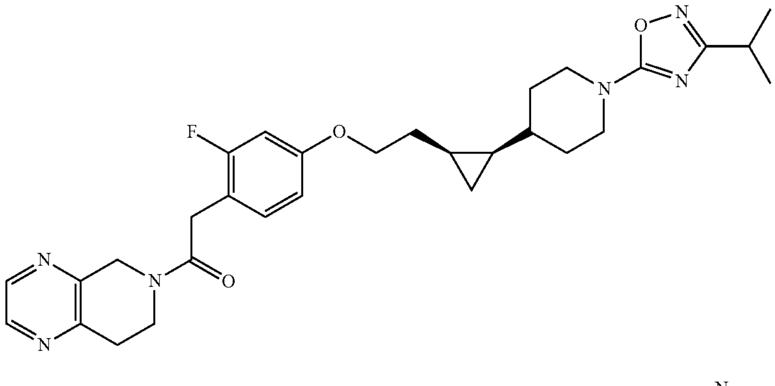 | 549 | 1.3 |
| 194 | 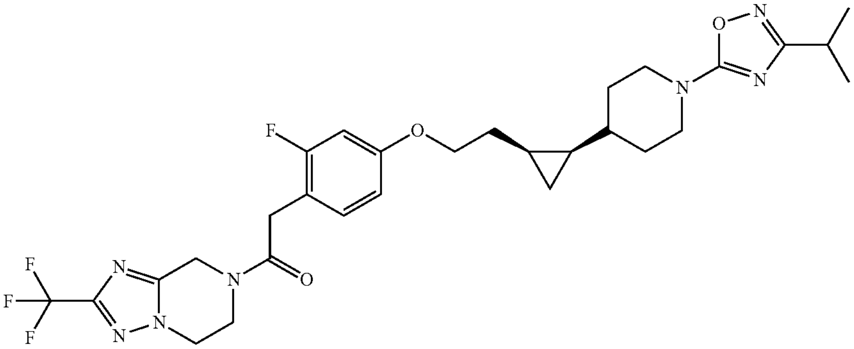 [SMILES: CC(C)c1noc(N2CCC([C@H]3C[C@H]3CCOc3ccc(CC(=O)N4CCn5nc(C(F)(F)F)nc5C4)c(F)c3)CC2)n1] | 606 | 1.5 |

TABLE 11-continued
| Example # | Chemical Structure | Observed Mass $[M + H]^+$ | GPR119 Human $EC_{50}$ (nM) |
|---|---|---|---|
| 195 | 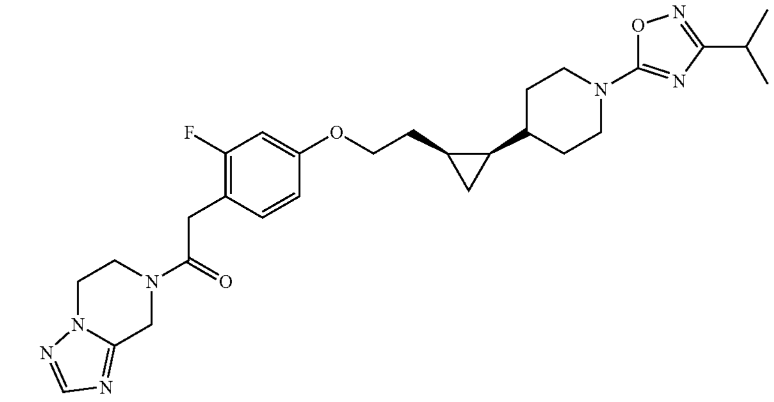 [SMILES: CC(C)c1noc(N2CCC([C@H]3C[C@H]3CCOc3ccc(CC(=O)N4CCn5ncnc5C4)c(F)c3)CC2)n1] | 538 | 1.6 |
| 196 | 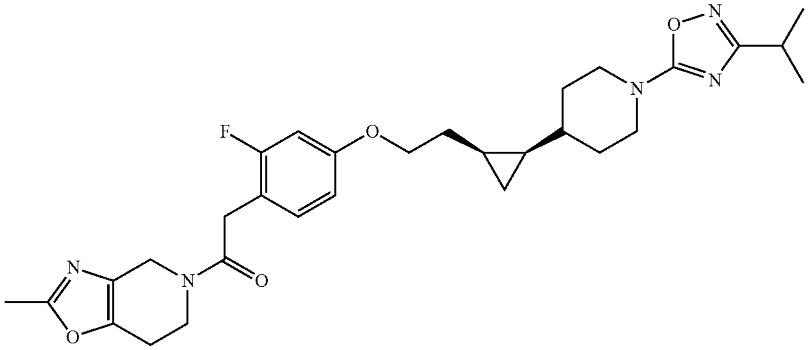 [SMILES: Cc1nc2c(o1)CCN(C(=O)Cc1ccc(OCC[C@@H]3C[C@@H]3C3CCN(c4nc(C(C)C)no4)CC3)cc1F)C2] | 552 | 1.4 |
| 197 | 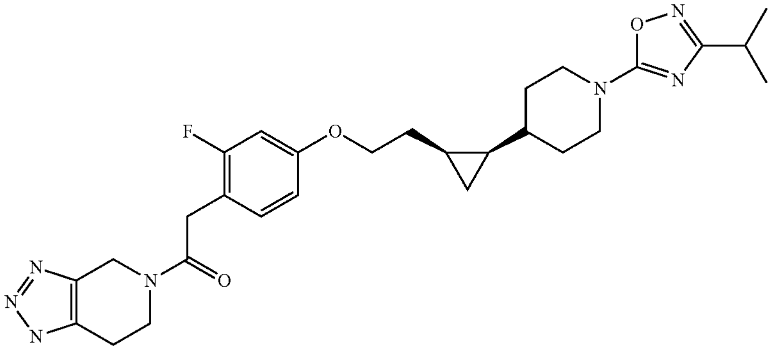 [SMILES: CC(C)c1noc(N2CCC([C@H]3C[C@H]3CCOc3ccc(CC(=O)N4CCc5[nH]nnc5C4)c(F)c3)CC2)n1] | 538 | 2.9 |
| 198 | 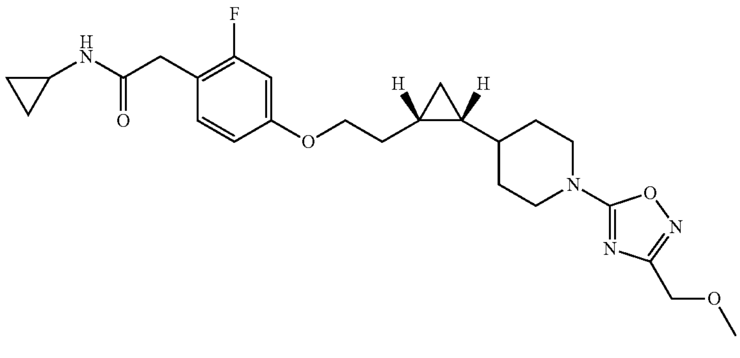 [SMILES: COCc1noc(N2CCC([C@H]3C[C@H]3CCOc3ccc(CC(=O)NC4CC4)c(F)c3)CC2)n1] | 473 | 13 |

TABLE 11-continued
| Example # | Chemical Structure | Observed Mass [M + H]+ | GPR119 Human $EC_{50}$ (nM) |
|---|---|---|---|
| 199 | 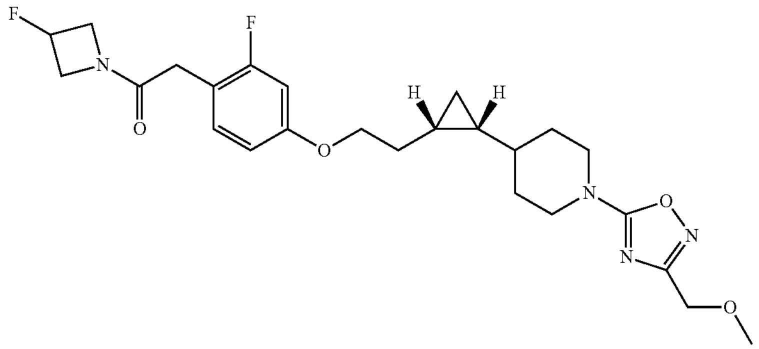 [SMILES: COCc1noc(N2CCC([C@H]3C[C@H]3CCOc3ccc(CC(=O)N4CC(F)C4)c(F)c3)CC2)n1] | 491 | 2.0 |
| 200 | 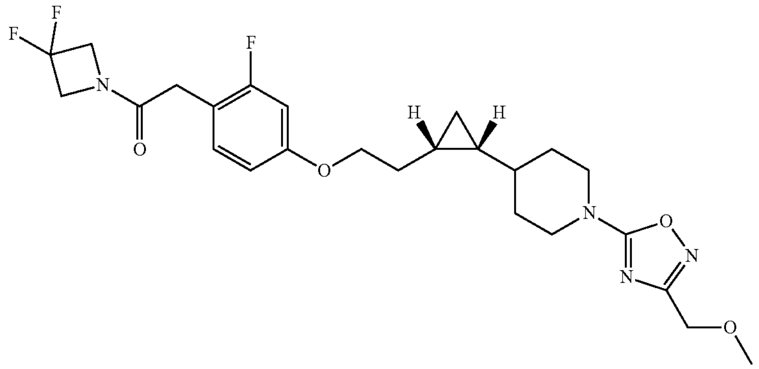 [SMILES: COCc1noc(N2CCC([C@H]3C[C@H]3CCOc3ccc(CC(=O)N4CC(F)(F)C4)c(F)c3)CC2)n1] | 509 | 1.2 |
| 201 | 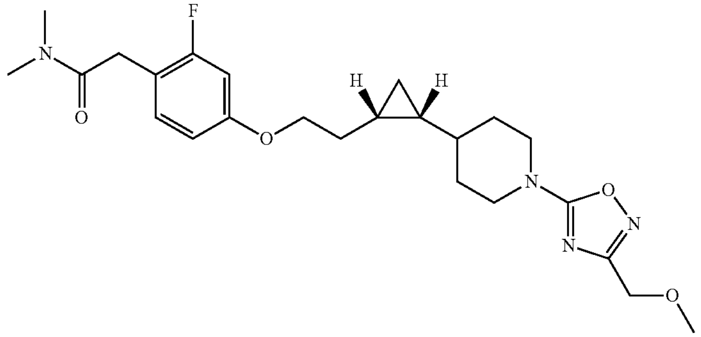 | 461 | 5.9 |
| 202 | 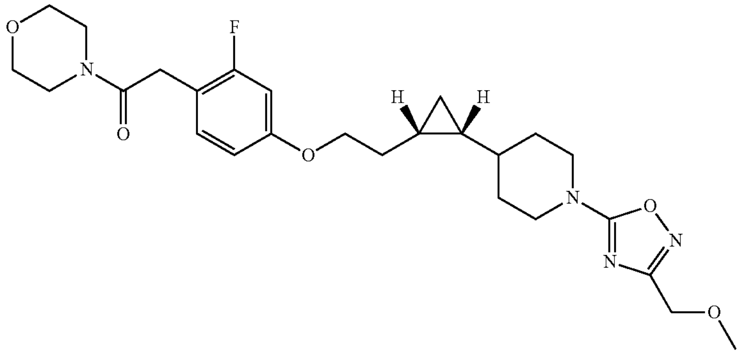 [SMILES: COCc1noc(N2CCC([C@H]3C[C@H]3CCOc3ccc(CC(=O)N4CCOCC4)c(F)c3)CC2)n1] | 503 | 9.8 |

TABLE 11-continued
| Example # | Chemical Structure | Observed Mass [M + H]$^+$ | GPR119 Human $EC_{50}$ (nM) |
|---|---|---|---|
| 203 | 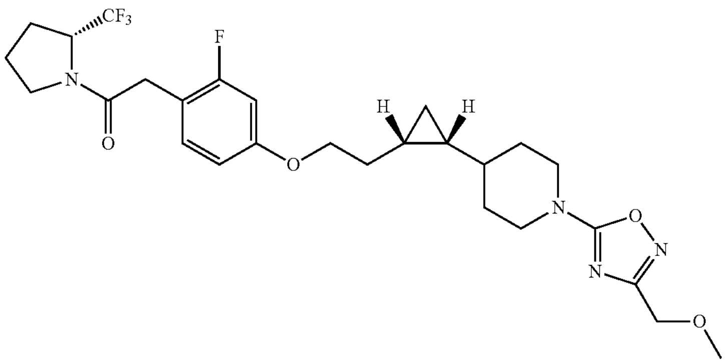 [SMILES: COCc1noc(N2CCC([C@H]3C[C@H]3CCOc3ccc(CC(=O)N4CCC[C@@H]4C(F)(F)F)c(F)c3)CC2)n1] | 555 | 5.1 |
| 204 | 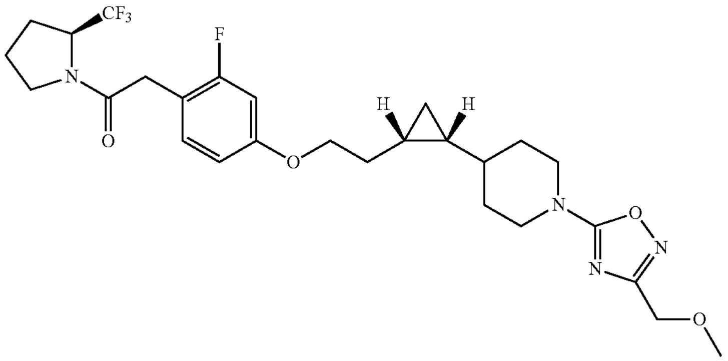 [SMILES: COCc1noc(N2CCC([C@H]3C[C@H]3CCOc3ccc(CC(=O)N4CCC[C@H]4C(F)(F)F)c(F)c3)CC2)n1] | 555 | 3.6 |
| 205 | 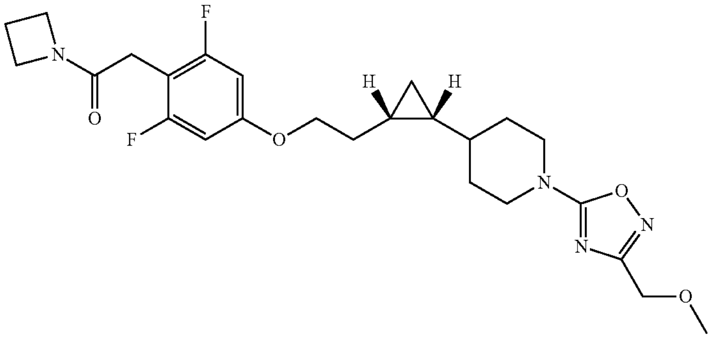 [SMILES: COCc1noc(N2CCC([C@H]3C[C@H]3CCOc3cc(F)c(CC(=O)N4CCC4)c(F)c3)CC2)n1] | 491 | 1.2 |
| 206 | 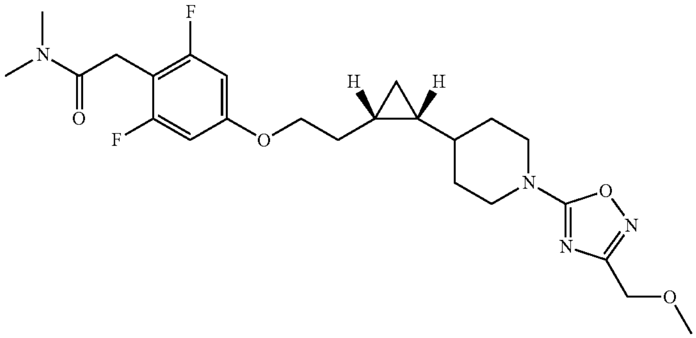 | 479 | 2.5 |

TABLE 11-continued

| Example # | Chemical Structure | Observed Mass $[M + H]^+$ | GPR119 Human $EC_{50}$ (nM) |
|---|---|---|---|
| 207 | 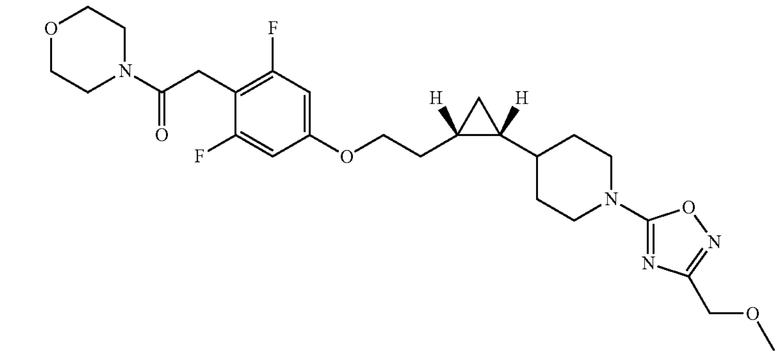 [SMILES: COCc1noc(N2CCC([C@H]3C[C@H]3CCOc3cc(F)c(CC(=O)N4CCOCC4)c(F)c3)CC2)n1] | 521 | 3.1 |

Example 208

Preparation of 3-(methoxymethyl)-5-(4-((1R,2S)-2-(2-(5-(methylsulfonyl)pyridin-2-yloxy)ethyl)cyclopropyl)piperidin-1-yl)-1,2,4-oxadiazole

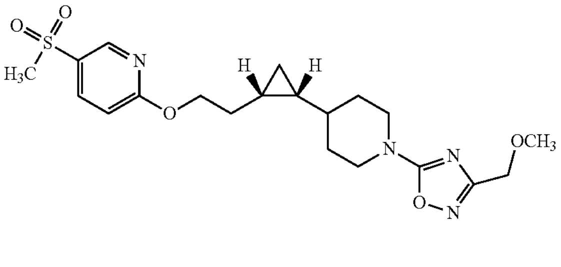 [SMILES: COCc1noc(N2CCC([C@H]3C[C@H]3CCOc3ccc(S(C)(=O)=O)cn3)CC2)n1]

Step A: 4-((1R,2S)-2-(2-(5-(methylsulfonyl)pyridin-2-yloxy)ethyl)cyclopropyl)piperidine-1-carbonitrile

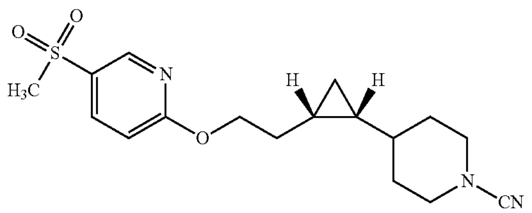 [SMILES: CS(=O)(=O)c1ccc(OCC[C@@H]2C[C@@H]2C2CCN(C#N)CC2)nc1]

5-(Methylsulfonyl)-2-(2-((1S,2R)-2-(piperidin-4-yl)cyclopropyl)ethoxy)pyridine (Step A, Example 11; 310 mg, 0.957 mmol) and potassium carbonate (489 mg, 3.54 mmol) were stirred in chloroform (15 mL). Cyanogen bromide (122 mg, 1.15 mmol) was added. The mixture was stirred at RT for 15 min and refluxed overnight. The mixture was cooled to RT, mixed with silica gel (5 g), and concentrated to dryness under reduced pressure. The residue was loaded on a silica gel column (15 g of silica gel) and eluted with dichloromethane/methanol (99:1, 1 L to provide the title compound as an off-white solid. $^1H$ NMR (300 MHz, $CDCl_3$) δ 8.71 (dd, J=0.5, 2.5 Hz, 1H), 8.03 (dd, J=2.5, 8.7 Hz, 1H), 6.84 (dd, J=0.6, 8.7 Hz, 1H), 4.48 (t, J=7.2 Hz, 2H), 3.50-3.35 (m, 2H), 3.07 (s, 3H), 3.05-2.90 (m, 2H), 2.15-2.00 (m, 1H), 1.85-1.75 (m, 2H), 1.60-1.35 (m, 3H), 1.00-0.85 (m, 2H), 0.80-0.50 (m, 2H), −0.12 (q, J=5.0 Hz, 1H). MS (Multimode) m/z 339 $[M+H]^+$.

Step B: 3-(methoxymethyl)-5-(4-((1R,2S)-2-(2-(5-(methylsulfonyl)pyridin-2-yloxy)ethyl)cyclopropyl)piperidin-1-yl)-1,2,4-oxadiazole

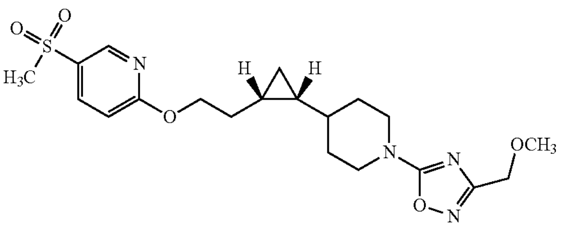 [SMILES: COCc1noc(N2CCC([C@H]3C[C@H]3CCOc3ccc(S(C)(=O)=O)cn3)CC2)n1]

To a solution of 4-((1R,2S)-2-(2-(5-(methylsulfonyl)pyridin-2-yloxy)ethyl)cyclopropyl)piperidine-1-carbonitrile (Step A, Example 98; 80 mg, 0.23 mmol) and N-hydroxy-2-methoxyacetimidamide (38 mg, 0.37 mmol) in tetrahydrofuran (5 mL) was added zinc chloride (0.6 mL, 0.5 M in tetrahydrofuran, 0.3 mmol). The mixture was refluxed for 2 h, cooled to RT, and concentrated to dryness under reduced pressure. The residue was dissolved in 2 mL of 4N HCl ethanol and water (1:1). The solution was refluxed for 30 min, cooled to RT, and concentrated to dryness under reduced pressure. The residue was dissolved in methanol (5 mL), neutralized by the addition of excess potassium carbonate, mixed silica gel (2 g), and concentrated to dryness under reduced pressure. The residue was loaded on a silica gel column (10 g of silica gel) and eluted with a gradient of dichloromethane/CMA, 19:1, 500 mL; 4:1, 500 mL to provide the title compound as an off-white solid, $^1H$ NMR (300 MHz, $CDCl_3$) δ 8.72 (d, J=2.4 Hz, 1H), 8.03 (dd, J=2.5, 8.7 Hz, 1H), 6.85 (d, J=8.7 Hz, 1H), 4.50 (t, J=7.2 Hz, 2H), 4.38 (s, 2H), 4.25-4.10 (m, 2H), 3.46 (s, 3H), 3.15-2.95 (m, 2H), 3.08 (s, 3H), 2.20-2.05 (m, 1H), 1.95-1.80 (m, 2H), 1.60-1.40 (m, 3H), 1.20-0.85 (m, 2H), 0.80-0.55 (m, 2H), −0.08 (q, J=4.6 Hz, 1H). MS (ESI) m/z 437 $[M+H]^+$. MP: 68-70° C. GPR119 Human EC50: 7 nM The Examples in Table 12 were synthesized according to the methods described in the prior example (208) employing the appropriate reagents and solvents.

TABLE 12
| Example # | Chemical Structure | Observed Mass [M + H]$^+$ | GPR119 Human $EC_{50}$ (nM) |
|---|---|---|---|
| 209 | 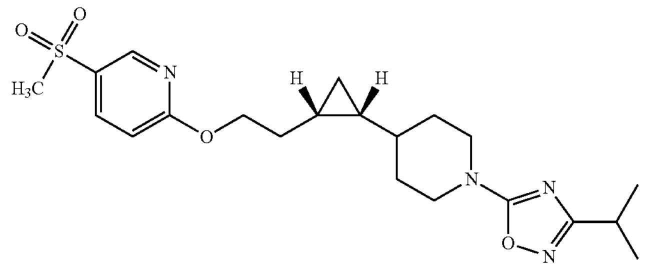 [SMILES: CC(C)c1noc(N2CCC([C@H]3C[C@H]3CCOc3ccc(S(C)(=O)=O)cn3)CC2)n1] | 435 | 2 |
| 210 | 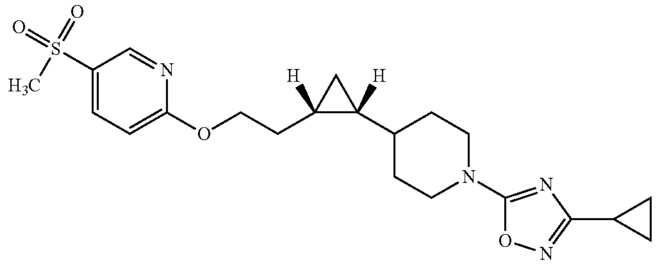 [SMILES: CS(=O)(=O)c1ccc(OCC[C@@H]2C[C@@H]2C2CCN(c3nc(C4CC4)no3)CC2)nc1] | 433 | 6 |
| 211 | 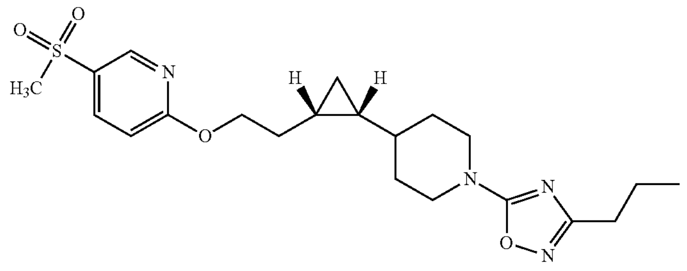 [SMILES: CCCc1noc(N2CCC([C@H]3C[C@H]3CCOc3ccc(S(C)(=O)=O)cn3)CC2)n1] | 435 | 8 |
| 212 | 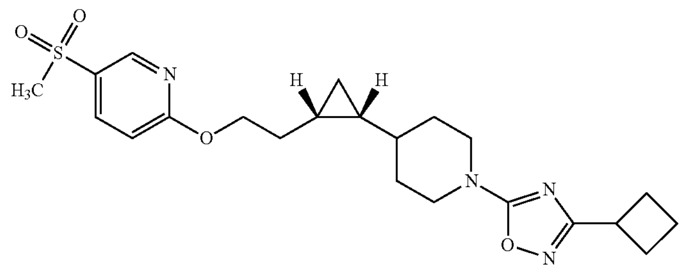 [SMILES: CS(=O)(=O)c1ccc(OCC[C@@H]2C[C@@H]2C2CCN(c3nc(C4CCC4)no3)CC2)nc1] | 447 | 4.8 |
| 213 | 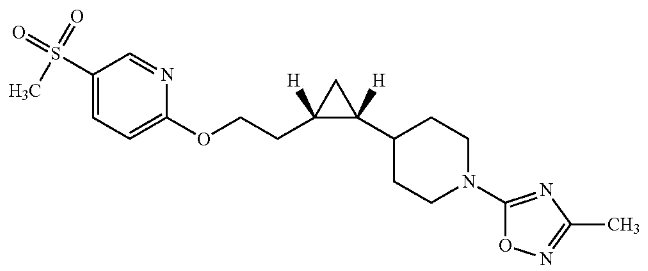 [SMILES: Cc1noc(N2CCC([C@H]3C[C@H]3CCOc3ccc(S(C)(=O)=O)cn3)CC2)n1] | 407 | 11 |

TABLE 12-continued
| Example # | Chemical Structure | Observed Mass [M + H]+ | GPR119 Human $EC_{50}$ (nM) |
|---|---|---|---|
| 214 | 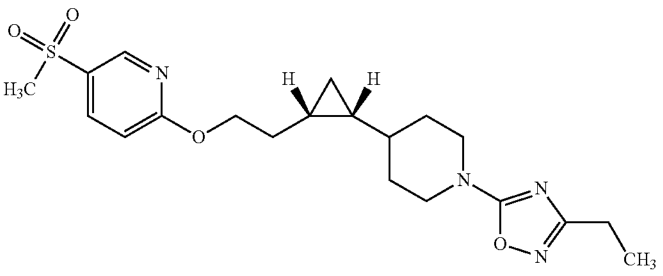 [SMILES: CCc1noc(N2CCC([C@H]3C[C@H]3CCOc3ccc(S(C)(=O)=O)cn3)CC2)n1] | 421 | 3.2 |
| 215 | 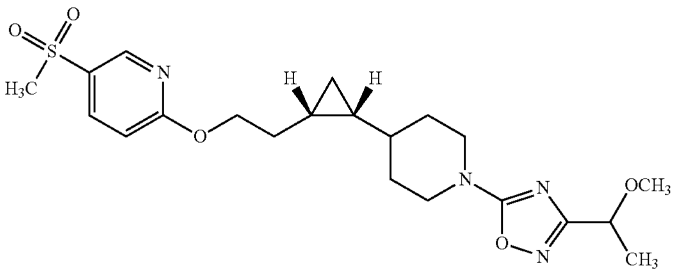 [SMILES: COC(C)c1noc(N2CCC([C@H]3C[C@H]3CCOc3ccc(S(C)(=O)=O)cn3)CC2)n1] | 451 | 5.8 |
| 216 | 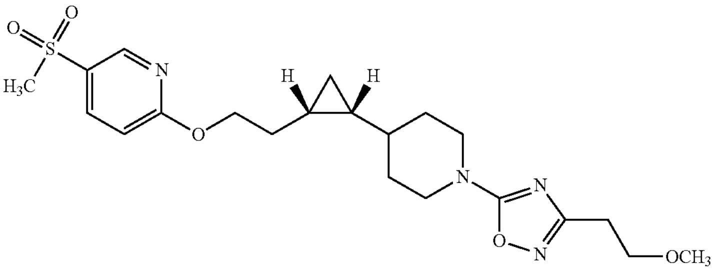 [SMILES: COCCc1noc(N2CCC([C@H]3C[C@H]3CCOc3ccc(S(C)(=O)=O)cn3)CC2)n1] | 451 | 26 |
| 217 | 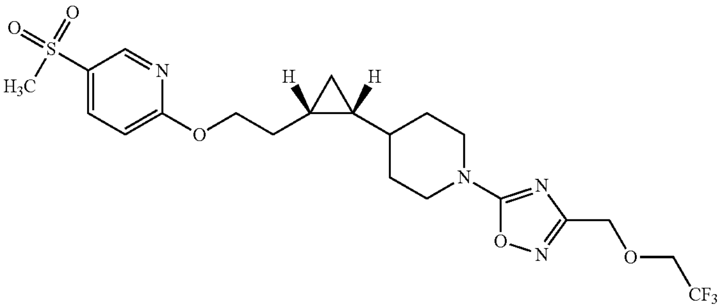 [SMILES: CS(=O)(=O)c1ccc(OCC[C@@H]2C[C@@H]2C2CCN(c3nc(COCC(F)(F)F)no3)CC2)nc1] | 505 | 7.8 |
| 218 | 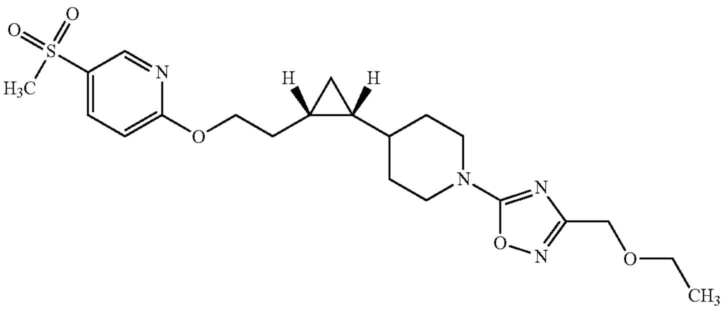 [SMILES: CCOCc1noc(N2CCC([C@H]3C[C@H]3CCOc3ccc(S(C)(=O)=O)cn3)CC2)n1] | 451 | 14 |

TABLE 12-continued

| Example # | Chemical Structure | Observed Mass $[M + H]^+$ | GPR119 Human $EC_{50}$ (nM) |
| --- | --- | --- | --- |
| 219 | 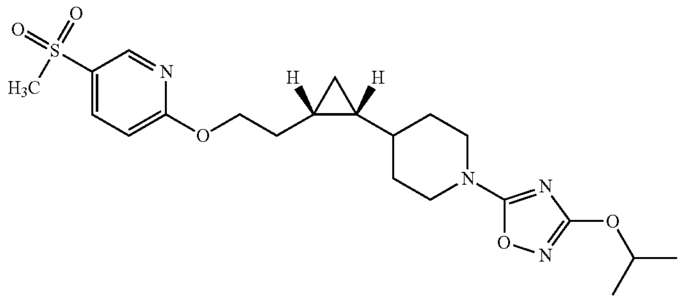 [SMILES: CC(C)Oc1noc(N2CCC([C@H]3C[C@H]3CCOc3ccc(S(C)(=O)=O)cn3)CC2)n1] | 465 | 4.7 |

Example 220

Preparation of 4-((1S,2R)-2-{2-[2-fluoro-4-(methylsulfonyl)phenoxy]ethyl}cyclopropyl)-1-[3-(methoxymethyl)-1,2,4-oxadiazol-5-yl]piperidine

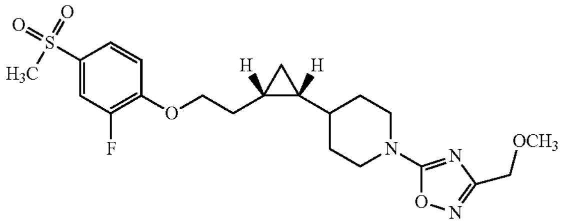 [SMILES: COCc1noc(N2CCC([C@H]3C[C@H]3CCOc3ccc(S(C)(=O)=O)cc3F)CC2)n1]

Step A: benzyl 4-[(1R,2S)-2-(2-{[4-methylphenyl)sulfonyl]oxy}ethyl)cyclopropyl]piperidine-1-carboxylate

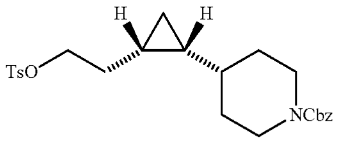

To a cooled solution of benzyl 4-((1R,2S)-2-(2-hydroxyethyl)cyclopropyl)piperidine-1-carboxylate (1.62 g, 5.34 mmol) in dichloromethane (30 mL) at 0° C. were added triethylamine (2.2 mL, 16.0 mmol), 4-dimethylaminopyridine (0.130 g, 1.07 mmol), and p-toluenesulfonyl chloride (1.53 g, 8.01 mmol). The reaction mixture was stirred at RT overnight. The reaction was quenched with saturated aqueous sodium hydrogen carbonate (100 mL) and extracted with dichloromethane (3×50 mL). The combined organics were washed with brine, dried over sodium sulfate, filtered, concentrated under reduced pressure, and the resulting residue purified by column chromatography, (40 g Redisep column, 5 to 50% ethyl acetate in heptane) to provide the tosylate as a clear oil. MS (ESI) m/z=458 $[M+H]^+$.

Step B: 2-[4-((1R,2S)-2-{2-{2-fluoro-4-(methylsulfonyl)phenoxy]ethyl}cyclopropyl)piperidine-1-yl]-1-phenylethanone

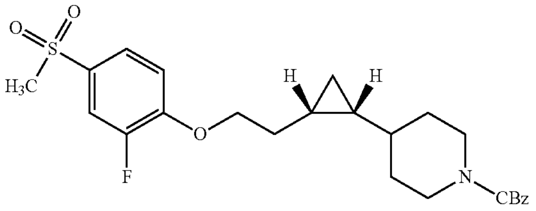

To a solution of the tosylate (1.61 g, 3.52 mmol) in DMF (35 mL) at RT was added sodium hydride (60% dispersion in mineral oil, 0.422 g, 10.55 mmol) and the mixture was stirred for 10 min. After this time, a solution of 3-fluoro-4-(methylsulfonyl)phenol (0.803 g, 4.22 mmol) in DMF (8 mL) was added and the reaction mixture was stirred at RT for 19 h, then heated at 50° C. for an additional 2 h. The reaction mixture was cooled to RT, quenched with water (100 mL) and extracted with ethyl acetate (6×100 mL). The combined organics were then washed with 5% aqueous lithium chloride solution, then brine, dried over sodium sulfate and concentrated under reduced pressure. The residue was purified by column chromatography, (40 g Redisep Gold column, 5 to 50% ethyl acetate in heptane) to afford the ether as a clear, sticky solid. MS (ESI) m/z=476 $[M+H]^+$.

Step C: 4-((1R,2S)-2-{2-{2-fluoro-4-(methylsulfonyl)phenoxy]ethyl}cyclopropyl)piperidine

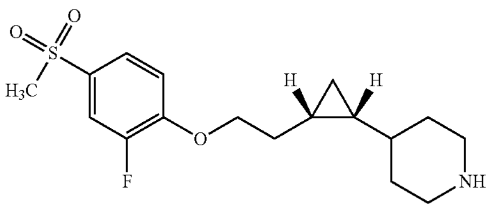 [SMILES: CS(=O)(=O)c1ccc(OCC[C@@H]2C[C@@H]2C2CCNCC2)c(F)c1]

The ether, 2-[4-((1R,2S)-2-{2-{2-fluoro-4-(methylsulfonyl)phenoxy]ethyl}cyclopropyl)piperidine-1-yl]-1-phenylethanone (740 mg, 1.62 mmol) in ethanol (25 mL) was added Palladium on carbon (10 wt. %, wet, 0.200 g), degassed (3× vacuum/$H_2$) again and stirred under $H_2$ at 1 atm for 64 h. The reaction mixture was filtered through a plug of celite, and the filter cake rinsed with ethanol (150 mL), ethyl acetate (150 mL), and the filtrate was concentrated under reduced pressure to provide the piperidine as a yellow oil. MS (ESI): 342 $[M+H]^+$.

Step D: 4-((1R,2S)-2-{2-{2-fluoro-4-(methylsulfonyl)phenoxy]ethyl}cyclopropyl)piperidine-1-carbonitrile

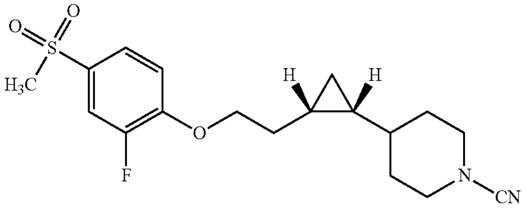 [SMILES: CS(=O)(=O)c1ccc(OCC[C@@H]2C[C@@H]2C2CCN(C#N)CC2)c(F)c1]

4-((1R,2S)-2-{2-{2-fluoro-4-(methylsulfonyl)phenoxy]ethyl}cyclopropyl)piperidine (Step C, Example 111; 150 mg, 0.428 mmol) and potassium carbonate (244 mg, 1.77 mmol) were stirred in chloroform (7 mL). Cyanogen bromide (61 mg, 0.58 mmol) was added. The mixture was stirred at RT for 15 min and refluxed overnight. The mixture was cooled to RT, mixed with silica gel (5 g), and concentrated to dryness under reduced pressure. The residue was loaded on a silica gel column (15 g of silica gel) and eluted with dichloromethane/methanol (97.5:2.5, 1 L to provide the title compound as an white solid. MS (Multimode) m/z 367 [M+H]$^+$.

Step E: 4-((1S,2R)-2-{2-[2-fluoro-4-(methylsulfonyl)phenoxy]ethyl}cyclopropyl)-1-[3-(methoxymethyl)-1,2,4-oxadiazol-5-yl]piperidine

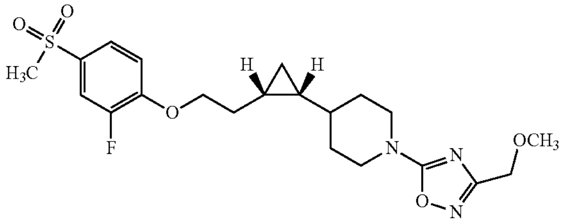 [SMILES: COCc1noc(N2CCC([C@H]3C[C@H]3CCOc3ccc(S(C)(=O)=O)cc3F)CC2)n1]

To a solution of 4-((1R,2S)-2-{2-{2-fluoro-4-(methylsulfonyl)phenoxy]ethyl}cyclopropyl)piperidine-1-carbonitrile (Step D, Example 111; 100 mg, 0.27 mmol) and N-hydroxy-2-methoxyacetimidamide (38 mg, 0.37 mmol) in tetrahydrofuran (5 mL) was added zinc chloride (0.8 mL, 0.5 M in tetrahydrofuran, 0.4 mmol). The mixture was refluxed for 2 h, cooled to RT, and concentrated to dryness under reduced pressure. The residue was dissolved in 2 mL of 4N HCl ethanol and water (1:1). The solution was refluxed for 30 min, cooled to RT, and concentrated to dryness under reduced pressure. The residue was dissolved in methanol (5 mL), neutralized by the addition of excess potassium carbonate, mixed silica gel (2 g), and concentrated to dryness under reduced pressure. The residue was loaded on a silica gel column (10 g of silica gel) and eluted with a gradient of dichloromethane/CMA, 19:1, 500 mL; 4:1, 500 mL to provide the title compound. MS (ESI) m/z 454 [M+H]$^+$.

GPR119 Human EC50: 0.9 nM

The Examples in Table 13 were synthesized according to the methods described in the prior example (220) employing the appropriate reagents and solvents.

TABLE 13

| Example # | Chemical Structure | Observed Mass [M + H]$^+$ | GPR119 Human $EC_{50}$ (nM) |
|---|---|---|---|
| 221 | 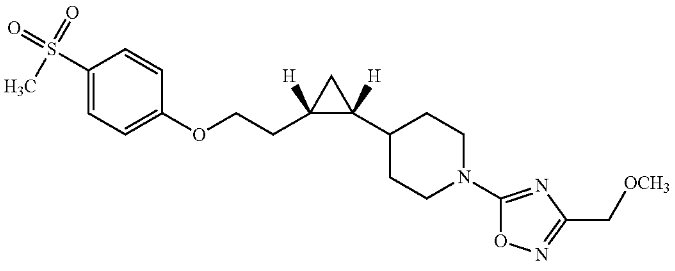 [SMILES: COCc1noc(N2CCC([C@H]3C[C@H]3CCOc3ccc(S(C)(=O)=O)cc3)CC2)n1] | 436 | 3.4 |
| 222 | 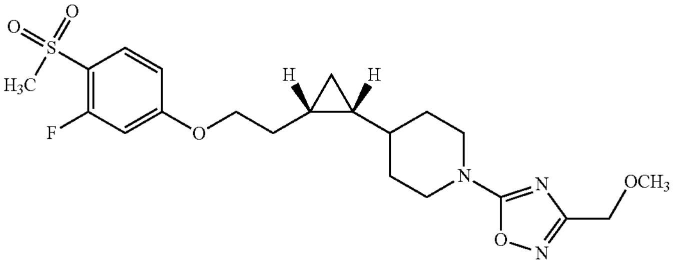 [SMILES: COCc1noc(N2CCC([C@H]3C[C@H]3CCOc3ccc(S(C)(=O)=O)c(F)c3)CC2)n1] | 454 | 0.9 |

TABLE 13-continued

| Example # | Chemical Structure | Observed Mass $[M + H]^+$ | GPR119 Human $EC_{50}$ (nM) |
|---|---|---|---|
| 223 | 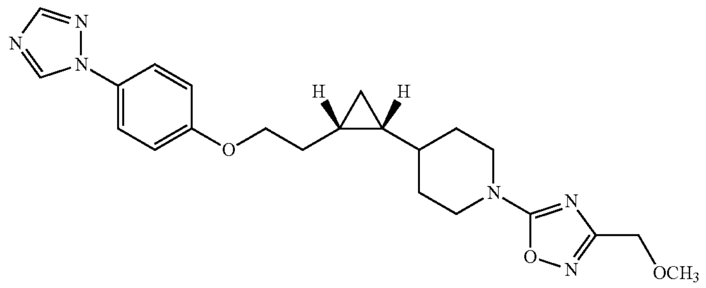 [SMILES: COCc1noc(N2CCC([C@H]3C[C@H]3CCOc3ccc(-n4cncn4)cc3)CC2)n1] | 425 | 7.2 |
| 224 | 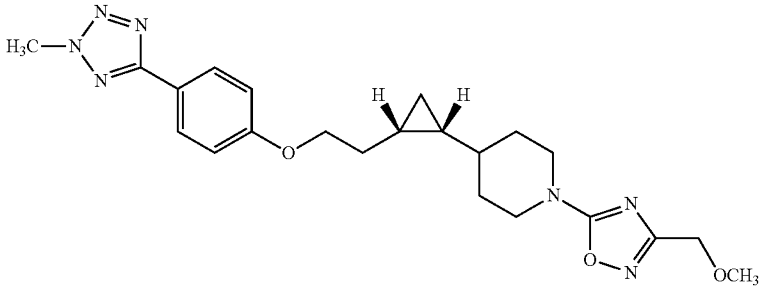 [SMILES: COCc1noc(N2CCC([C@H]3C[C@H]3CCOc3ccc(-c4nnn(C)n4)cc3)CC2)n1] | 440 | 6.4 |

Example 225

Preparation of 2-(2-{(1S,2R)-2-[1-(3-isopropyl-1,2,4-oxidiazol-5-yl)piperidin-4-yl]cyclopropyl}ethoxy]-3-methyl-5-(1H-tetrazol-1-yl)pyridine

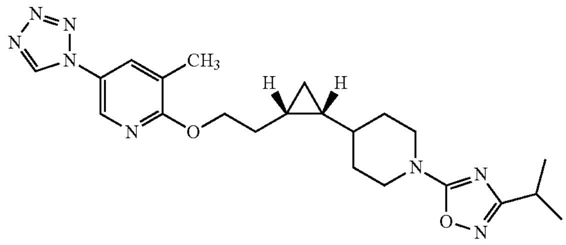 [SMILES: Cc1cc(-n2cnnn2)cnc1OCC[C@@H]1C[C@@H]1C1CCN(c2nc(C(C)C)no2)CC1]

Step A: benzyl 4-((1R,2S)-2-{2-[(3-methyl-5-nitropyridin-2-yl)oxy]ethyl}cyclopropyl)piperidine-1-carboxylate

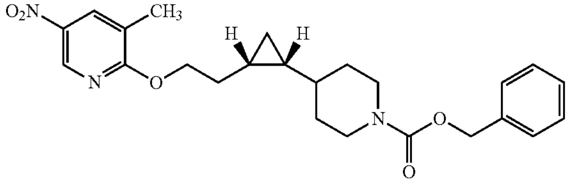

To the solution of benzyl 4-[(1R,2S)-2-(2-hydroxyethyl)cyclopropyl]piperidine-1-carboxylate (Intermediate 10, 1.84 g, 6.06 mmol) in 15 ml of DMSO was added NaH and the resulting solution was stirred at 45° C. for 15 min. The mixture was then cooled to 0° C. via an ice/water bath and 2-chloro-3-methyl-5-nitropyridine (1.05 g, 6.06 mmol) was added in portions. The reaction mixture turned dark and became a slurry. After 10 minutes, the ice/water bath was removed and 20 ml of DMSO was added. The resulting mixture was stirred for 40 minutes allowing to warm to room temperature. The reaction was quenched by water and extracted with ethyl acetate (3×100 mL). The organics were combined and washed with brine, dried on sodium sulfate, filtered and the filtrate concentrated under reduced pressure. The residue was purified via Biotage column (65M silica gel) using ethyl acetate in hexane (0-60%, 1000 ml) to afford the title compound. MS (ESI) m/z 440 $[M+H]^+$.

Step B: benzyl 4-((1R,2S)-2-{2-[(5-amino-3-methylpyridin-2-yl)oxy]ethyl}cyclopropyl)piperidine-1-carboxylate

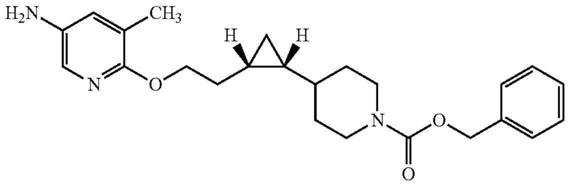 [SMILES: Cc1cc([N+](=O)[O-])cnc1OCC[C@@H]1C[C@@H]1C1CCN(C(=O)OCc2ccccc2)CC1]

To the solution of $NiCl_2$ (Nickel (II) Chloride-hexahydrate) in 12 ml of methanol was added 50 mg of $NaBH_4$ (solution turned dark) at room temperature and the resulting mixture was stirred for 5 minutes. Benzyl 4-((1R,2S)-2-{24 (3-methyl-5-nitropyridin-2-yl)oxy]ethyl}cyclopropyl)piperidine-1-carboxylate (Example 4, Step A; 550 mg, 1.25 mmol) in 5 ml of DCM was then added followed by the addition. of 116 mg of $NaBH_4$ in 3 portions. The mixture was then stirred for 20 minutes and then diluted with DCM and filtered through a pad of sodium sulfate (messy). The solution was concentrated to dryness under reduced pressure and taken up in 15 mL DCM. This material was then filtered through a pad of silica gel (extracting with ethyl acetate) and the filtrate was then washed by saturated aq. $NaHCO_3$. The organics were then dried over sodium sulfate, filtered, and concentrated to dryness under reduced pressure to afford the title compound as a crude product which was used for next step. MS (ESI) m/z 410 $[M+H]^+$.

Step C: benzyl 4-[(1R,2S)-2-(2-{[3-methyl-5-(1H-tetrazol-1-yl)pyridin-2-yl]oxy}ethyl)cyclopropyl] piperidine-1-carboxylate

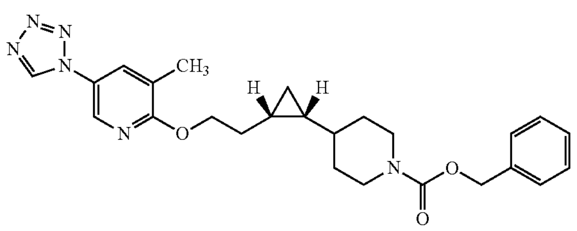 [SMILES: Cc1cc(-n2cnnn2)cnc1OCC[C@@H]1C[C@@H]1C1CCN(C(=O)OCc2ccccc2)CC1]

To a solution of benzyl 4-((1R,2S)-2-{2-[(5-amino-3-methylpyridin-2-yl)oxy]ethyl}cyclopropyl)piperidine-1-carboxylate (Example 116, Step B; 310 mg, 0.76 mmol) in 10 ml of AcOH was added triethyl orthoformate (0.5 mL, 3.03 mmol) and sodium azide (197 mg, 3.03 mmol) and the resulting mixture was stirred at 35° C. for 1.5 hrs. The mixture was then allowed to cool to room temperature and was stirred overnight. The volatiles were removed in vacuo and the residue was partitioned between aqueous sodium carbonate and ethyl acetate. The aqueous was then extracted with ethyl acetate (2×15 mL) and then all the organics were combined and washed with brine. The organics were then dried over sodium sulfate, filtered, and concentrated under reduced pressure to afford the title compound as a crude product which was used as is for the next reaction. MS (ESI) m/z 463 $[M+H]^+$.

Step D: 3-methyl-2-{2-[(1S,2R)-2-piperidin-4-ylcyclopropyl]ethoxy}-5-(1H-tetrazol-1-yl) pyridine

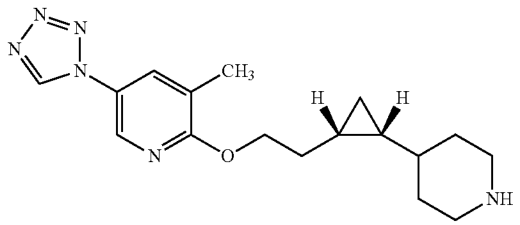 [SMILES: Cc1cc(-n2cnnn2)cnc1OCC[C@@H]1C[C@@H]1C1CCNCC1]

To a solution of benzyl 4-[(1R,2S)-2-(2-{[3-methyl-5-(1H-tetrazol-1-yl)pyridin-2-yl]oxy ethyl)cyclopropyl]piperidine-1-carboxylate (Example 116, Step C; 285 mg, 0.62 mmol) in 5 mL ethanol was added 75 mg of 10% palladium on carbon and the resulting suspension set under hydrogen atmosphere using a balloon of hydrogen gas. The mixture was stirred under hydrogen for 4 hours, filtered through a pad of celite to remove all catalyst and the filtrate concentrated to dryness under reduced pressure to afford the title compound as a crude product which was used as is for the next reaction. MS (ESI) m/z 329 $[M+H]^+$.

Step E: 4-[(1R,2S)-2-(2-[3-methyl-5-(1H-tetrazol-1-yl)pyridin-2-yl]oxy}ethyl)cyclopropyl]piperidine-1-carbonitrile

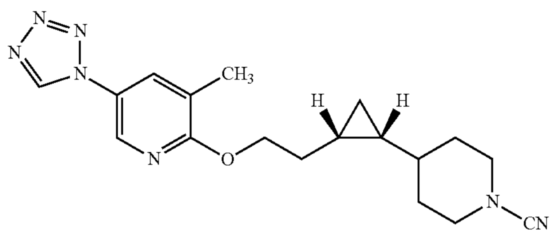 [SMILES: Cc1cc(-n2cnnn2)cnc1OCC[C@@H]1C[C@@H]1C1CCN(C#N)CC1]

To the solution of 3-methyl-2-{2-[(1S,2R)-2-piperidin-4-ylcyclopropyl]ethoxy}-5-(1H-tetrazol-1-yl)pyridine (Example 116, Step D; 160 mg, 0.34 mmol) in 5 ml of DCM was added a slurry of sodium bicarbonate in 1 ml of water at 0° C. followed by the addition of cyanogen bromide in 1 ml of DCM. The resulting mixture was stirred at 0° C. for 40 min. and then an additional 20 min. at room temperature. The mixture was diluted with DCM and then washed with saturated aqueous $NaHCO_3$ solution. The organics were separated, dried over sodium sulfate, and the filtrate concentrated to dryness to afford the title compound as a crude product which was used as is for the next reaction. MS (ESI) m/z 354 $[M+H]^+$.

Step F: 2-(2-(1S,2R)-2-[1-(3-isopropyl-1,2,4-oxidiazol-5-yl)piperidin-4-yl]cyclopropyl}ethoxy]-3-methyl-5-(1H-tetrazol-1-yl)pyridine

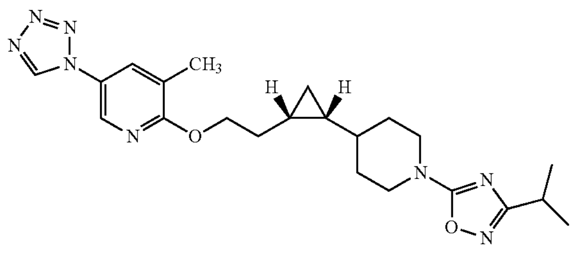 [SMILES: Cc1cc(-n2cnnn2)cnc1OCC[C@@H]1C[C@@H]1C1CCN(c2nc(C(C)C)no2)CC1]

To a solution of 4-[(1R,2S)-2-(2-{[3-methyl-5-(1H-tetrazol-1-yl)pyridin-2-yl]oxy}ethyl)cyclopropyl]piperidine-1-carbonitrile (Example 116, Step E; 110 mg, 0.22 mmol) and N-hydroxy-2-methylpropanimidamide (27 mg, 0.26 mmol) in tetrahydrofuran (5 mL) was added zinc chloride (0.5 mL, 0.5 M in tetrahydrofuran, 0.25 mmol). The mixture was refluxed for 2 h, cooled to room temperature, and concentrated to dryness under reduced pressure. The residue was dissolved in 2 mL of 4N HCl ethanol and water (1:1). The solution was refluxed for 30 min, cooled to room temperature, and concentrated to dryness under reduced pressure. The residue was dissolved in methanol (5 mL), neutralized by the addition of excess potassium carbonate, filtered, and the filtrate concentrated to dryness under reduced pressure. The residue was loaded onto two preparative TLC plates (silica gel, 1000 μM) and developed with dichloromethane/ethyl acetate, 1:2. The band containing the product was stripped from the TLC plates and the product eluted off with 100% ethyl acetate. The organics were concentrated to dryness under reduced pressure to afford the title compound. MS (ESI) m/z 439 [M+H]$^+$.

GPR119 Human EC50: 0.1 nM

The Examples in Table 14 were synthesized according to the methods described in the prior example (225) employing the appropriate reagents and solvents.

TABLE 14

| Example # | Chemical Structure | Observed Mass [M + H]$^+$ | GPR119 Human $EC_{50}$ (nM) |
|---|---|---|---|
| 226 | 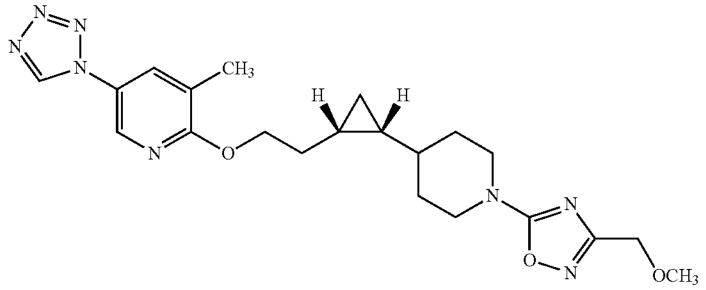 [SMILES: COCc1noc(N2CCC([C@H]3C[C@H]3CCOc3ncc(-n4cnnn4)cc3C)CC2)n1] | 441 | 2.3 |
| 227 | 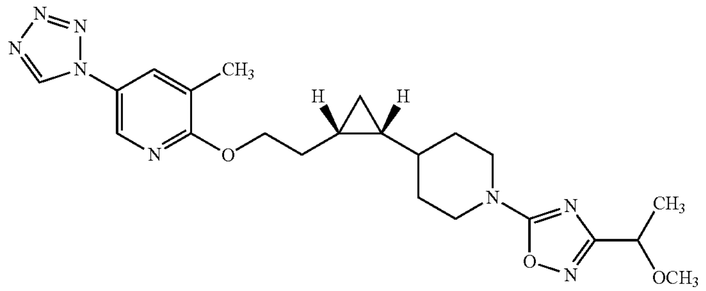 [SMILES: COC(C)c1noc(N2CCC([C@H]3C[C@H]3CCOc3ncc(-n4cnnn4)cc3C)CC2)n1] | 455 | 0.9 |
| 228 | 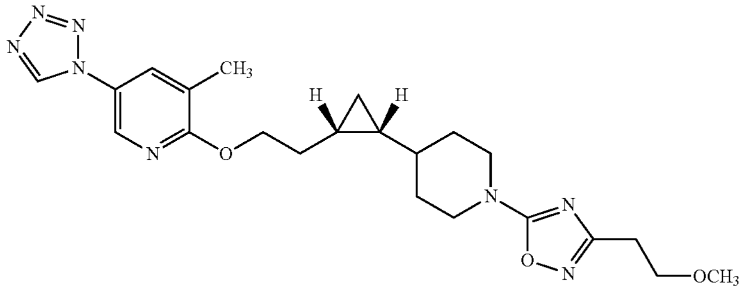 [SMILES: COCCc1noc(N2CCC([C@H]3C[C@H]3CCOc3ncc(-n4cnnn4)cc3C)CC2)n1] | 455 | 2.0 |
| 229 | 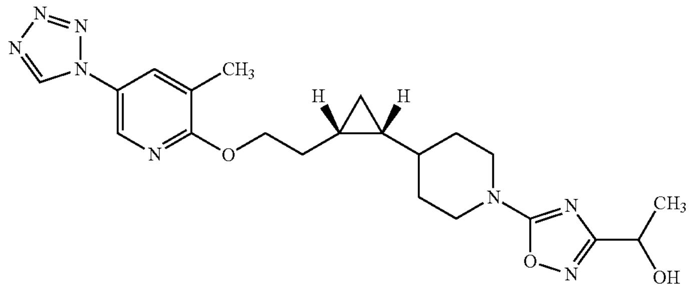 [SMILES: Cc1cc(-n2cnnn2)cnc1OCC[C@@H]1C[C@@H]1C1CCN(c2nc(C(C)O)no2)CC1] | 441 | 5 |

TABLE 14-continued

| Example # | Chemical Structure | Observed Mass [M + H]+ | GPR119 Human $EC_{50}$ (nM) |
|---|---|---|---|
| 230 | 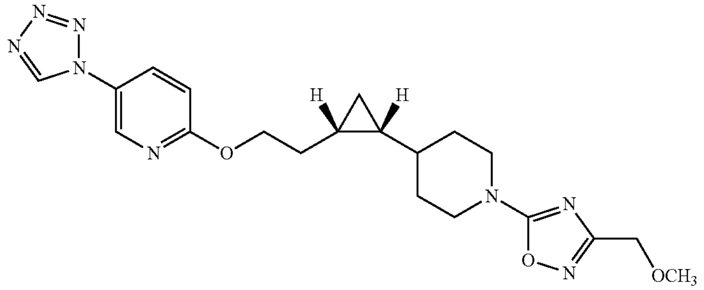 [SMILES: COCc1noc(N2CCC([C@H]3C[C@H]3CCOc3ccc(-n4cnnn4)cn3)CC2)n1] | 427 | 1.6 |
| 231 | 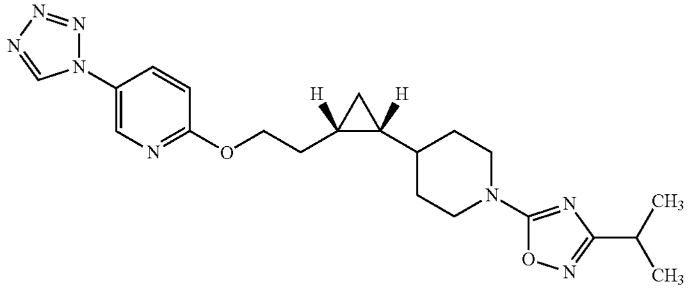 [SMILES: CC(C)c1noc(N2CCC([C@H]3C[C@H]3CCOc3ccc(-n4cnnn4)cn3)CC2)n1] | 425 | 0.4 |
| 232 | 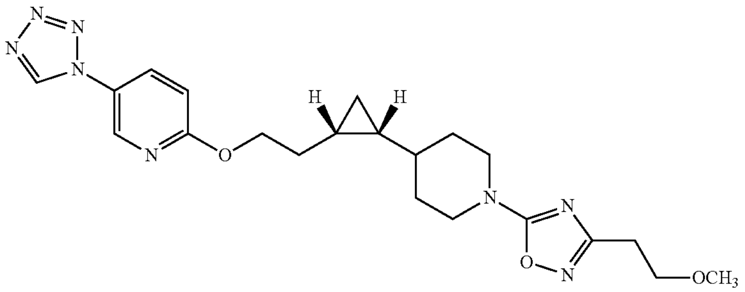 [SMILES: COCCc1noc(N2CCC([C@H]3C[C@H]3CCOc3ccc(-n4cnnn4)cn3)CC2)n1] | 441 | 10.6 |

Example 233

Preparation of 2-(2-{(1S,2R)-2-[1-(5-ethyl-1,2,4-oxidiazol-5-yl)piperidin-4-yl]cyclopropyl}ethoxy)-5-(methylsulfonyl)pyridine

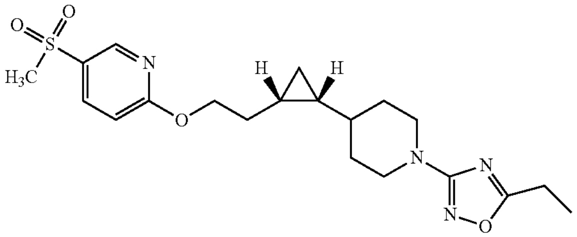 [SMILES: CCc1nc(N2CCC([C@H]3C[C@H]3CCOc3ccc(S(C)(=O)=O)cn3)CC2)no1]

Step A: N'-hydroxy-4-[(1R,2S)-2-(2-{[5-(methylsulfonyl)pyridin-2-yl]oxy}ethyl)cyclopropyl]piperidine-1-carboximidamide

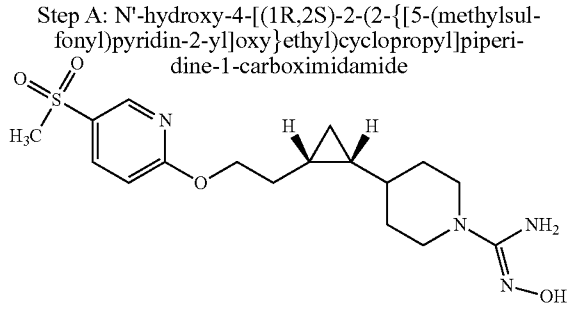

5-(methylsulfonyl)-2-(2-((1S,2R)-2-(piperidin-4-yl)cyclopropyl)ethoxy)pyridine (320 mg, 0.98 mmol) was combined with cyanogen bromide (0.395 mL of a 3.0M solution, 1.19 mmol) and sodium bicarbonate (250 mg, 3.0 mmol) at 0° C. in a 10:1 mixture of DCM/water (5 mL), and the resulting slurry stirred for 30 min and warmed to ambient temperature. After 3 hr, HPLC/MS indicated no starting material. The reaction mixture was diluted with dichloromethane (10 mL), water (3 mL) and the layers separated. The organic layer was dried over magnesium sulfate, filtered, concentrated in vacuo and purified by flash chromatography (10-40% acetone/hexanes, 25S+ column) to afford a white film (not weighed). The material was dissolved in 3 mL of methanol and to this solution was added hydroxylamine (82 mg, 1.19 mmol) and triethylamine (0.2 mL, 1.48 mmol). The mixture was then heated to reflux for 2 hrs and then cooled to ambient temperature. The mixture was concentrated under reduced pressure and the residue was purified by flash chromatography (3.5% methanol/95.5% dichloromethane/1% $NH_4OH$, 25S+ column) to afford title compound as a white foam. HPLC/MS; 0.99 min, 383 $(M+H)^+$.

Step B: 2-(2-{(1S,2R)-2-[1-(5-ethyl-1,2,4-oxidiazol-5-yl)piperidin-4-yl]cyclopropyl}ethoxy)-5-(methylsulfonyl)pyridine

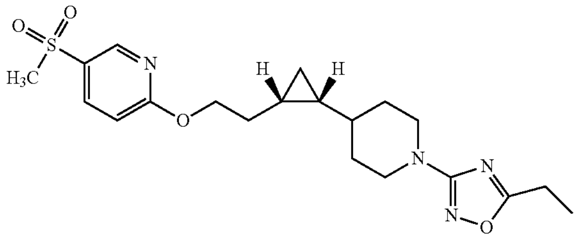 [SMILES: CCc1nc(N2CCC([C@H]3C[C@H]3CCOc3ccc(S(C)(=O)=O)cn3)CC2)no1]

To a solution of N'-hydroxy-4-[(1R,2S)-2-(2-{[5-(methylsulfonyl)pyridin-2-yl]oxy}ethyl)cyclopropyl]piperidine-1-carboximidamide (180 mg, 0.47 mmol) and propionic acid (38 mg, 0.52 mmol) in acetonitrile (1 mL) was added BOP (250 mg, 0.57 mmol) and the resulting mixture heated via microwave reactor to 150° C. for 20 minutes. The material cooled to RT and was concentrated to dryness under reduced pressure. The material was dissolved in 0.5 mL DMSO and purified via Mass spectra directed HPLC. The pure fractions were combined and GenoVac dried to afford the title compound as a white solid. $^1$H NMR (500 MHz, $CDCl_3$) δ 8.65 (d, J=2.4 Hz, 1H), 8.03 (dd, J=2.5, 8.7 Hz, 1H), 6.50 (d, J=8.7 Hz, 1H), 4.42 (t, J=7.2 Hz, 2H), 3.92-3.85 (m, 2H), 3.05-2.95 (m, 2H), 2.43-2.38 (m, 1H), 2.25 (q, J=7.6 Hz, 2H), 2.05-1.92 (m, 1H), 1.78-1.55 (m, 2H), 1.45-1.32 (m, 4H), 1.30 (t, J=7.6 Hz 3H), 1.06-0.98 (m, 1H), 0.85-0.72 (m, 1H), −0.07 (q, J=4.6 Hz, 1H). HPLC/MS; 0.88 min, 421 (M+H)±. GPR119 Human EC50: 9.2 nM The Examples in Table 15 were synthesized according to the methods described in the prior example (233) employing the appropriate reagents and solvents.

TABLE 15

| Example # | Chemical Structure | Observed Mass [M + H]$^+$ | GPR119 Human $EC_{50}$ (nM) |
|---|---|---|---|
| 234 | 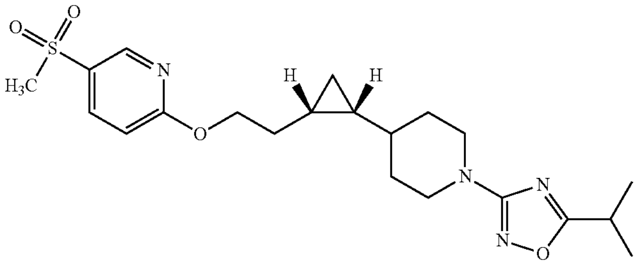 [SMILES: CC(C)c1nc(N2CCC([C@H]3C[C@H]3CCOc3ccc(S(C)(=O)=O)cn3)CC2)no1] | 435 | 3.5 |
| 235 | 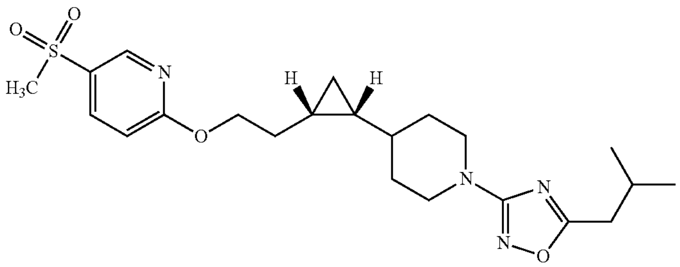 [SMILES: CC(C)Cc1nc(N2CCC([C@H]3C[C@H]3CCOc3ccc(S(C)(=O)=O)cn3)CC2)no1] | 449 | 6.5 |
| 236 | 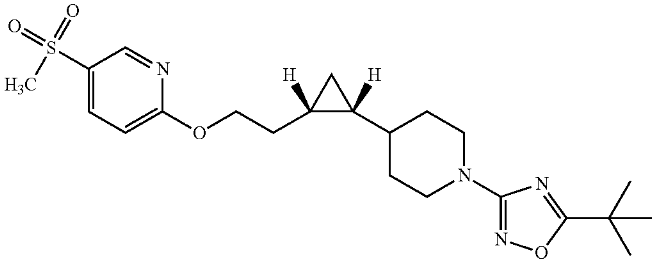 [SMILES: CC(C)(C)c1nc(N2CCC([C@H]3C[C@H]3CCOc3ccc(S(C)(=O)=O)cn3)CC2)no1] | 449 | 1.7 |

TABLE 15-continued
| Example # | Chemical Structure | Observed Mass [M + H]+ | GPR119 Human $EC_{50}$ (nM) |
|---|---|---|---|
| 237 | 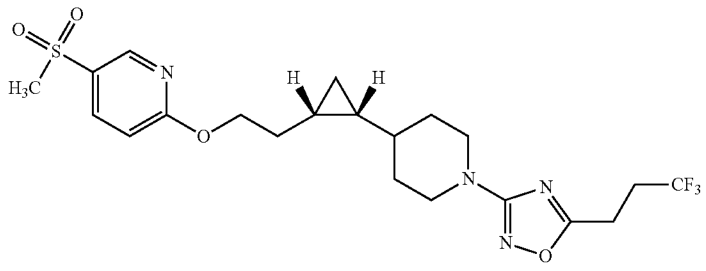 [SMILES: CS(=O)(=O)c1ccc(OCC[C@@H]2C[C@@H]2C2CCN(c3noc(CCC(F)(F)F)n3)CC2)nc1] | 489 | 18 |
| 238 | 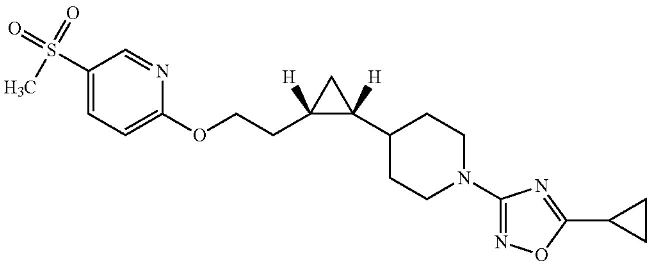 [SMILES: CS(=O)(=O)c1ccc(OCC[C@@H]2C[C@@H]2C2CCN(c3noc(C4CC4)n3)CC2)nc1] | 433 | 22 |
| 239 | 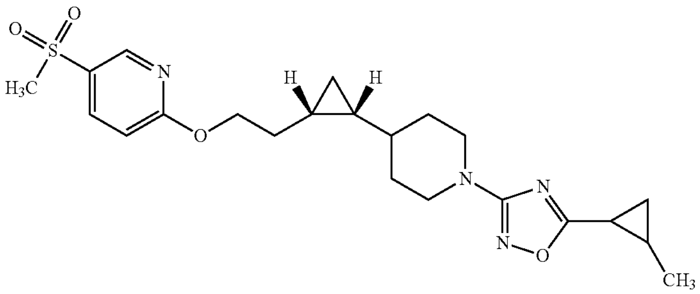 [SMILES: CC1CC1c1nc(N2CCC([C@H]3C[C@H]3CCOc3ccc(S(C)(=O)=O)cn3)CC2)no1] | 447 | 7 |
| 240 | 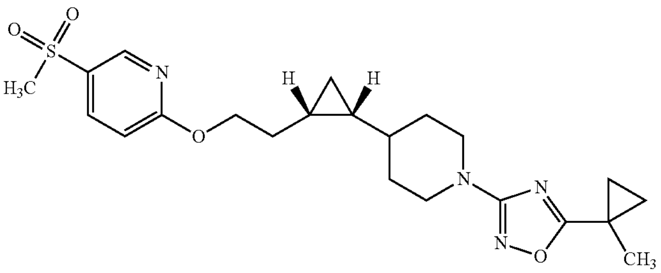 [SMILES: CC1(c2nc(N3CCC([C@H]4C[C@H]4CCOc4ccc(S(C)(=O)=O)cn4)CC3)no2)CC1] | 447 | 5.2 |
| 241 | 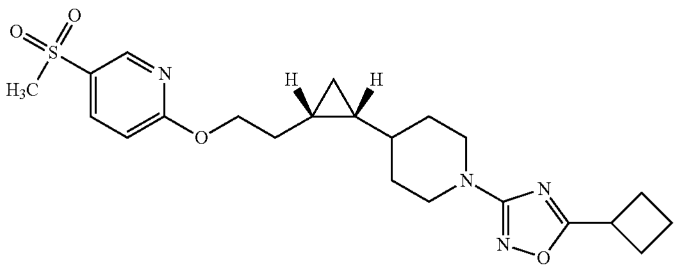 [SMILES: CS(=O)(=O)c1ccc(OCC[C@@H]2C[C@@H]2C2CCN(c3noc(C4CCC4)n3)CC2)nc1] | 447 | 4 |

TABLE 15-continued
| Example # | Chemical Structure | Observed Mass [M + H]+ | GPR119 Human $EC_{50}$ (nM) |
|---|---|---|---|
| 242 | 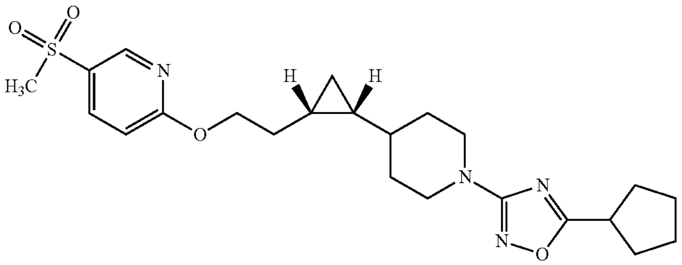 [SMILES: CS(=O)(=O)c1ccc(OCC[C@@H]2C[C@@H]2C2CCN(c3noc(C4CCCC4)n3)CC2)nc1] | 461 | 11.6 |
| 243 | 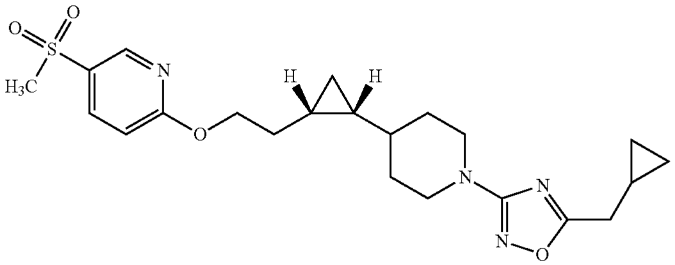 [SMILES: CS(=O)(=O)c1ccc(OCC[C@@H]2C[C@@H]2C2CCN(c3noc(CC4CC4)n3)CC2)nc1] | 447 | 9.8 |
| 244 | 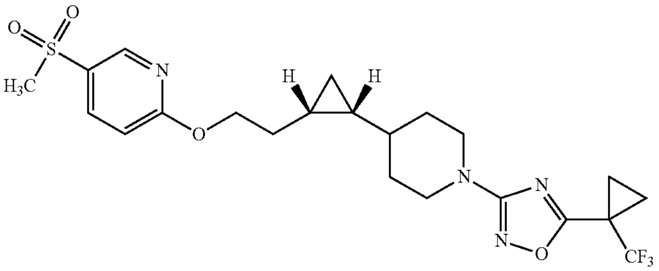 [SMILES: CS(=O)(=O)c1ccc(OCC[C@@H]2C[C@@H]2C2CCN(c3noc(C4(C(F)(F)F)CC4)n3)CC2)nc1] | 501 | 2.1 |
| 245 | 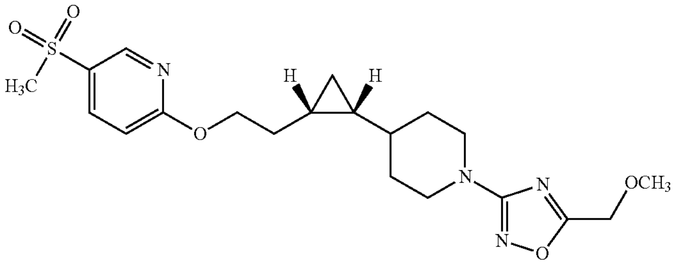 [SMILES: COCc1nc(N2CCC([C@H]3C[C@H]3CCOc3ccc(S(C)(=O)=O)cn3)CC2)no1] | 437 | 8.1 |
| 246 | 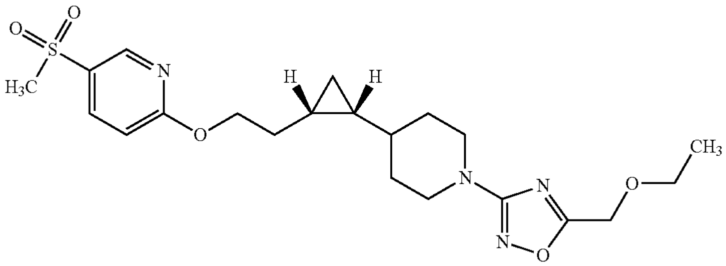 [SMILES: CCOCc1nc(N2CCC([C@H]3C[C@H]3CCOc3ccc(S(C)(=O)=O)cn3)CC2)no1] | 451 | 7.9 |

Example 247

Preparation of 2-(2-{(1S,2R)-2-[1-(5-butyl-1,3,4-oxidiazol-2-yl)piperidin-4-yl]cyclopropyl}ethoxy)-5-(methylsulfonyl)pyridine

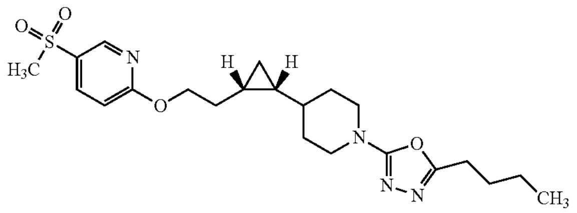 [SMILES: CCCCc1nnc(N2CCC([C@H]3C[C@H]3CCOc3ccc(S(C)(=O)=O)cn3)CC2)o1]

Step A: 2-(2-(1S,2R)-2-[1-(5-butyl-1,3,4-oxidiazol-2-yl)piperidin-4-yl]cyclopropyl}ethoxy)-5-(methylsulfonyl)pyridine

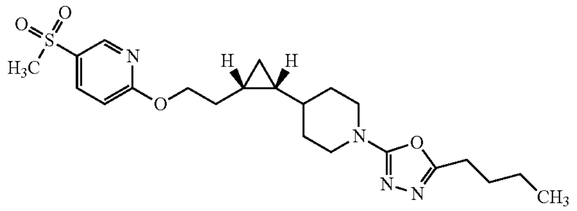 [SMILES: CCCCc1nnc(N2CCC([C@H]3C[C@H]3CCOc3ccc(S(C)(=O)=O)cn3)CC2)o1]

To a mixture of 5-(methylsulfonyl)-2-(2-((1S,2R)-2-(piperidin-4-yl)cyclopropyl)ethoxy)pyridine in DMF (2 mL) cooled to 0° C. via ice/water bath was added 60% oil dispersed solid sodium hydride (26 mg, 0.67 mmol) in portions over 15 minutes. The resulting grey suspension was stirred at 0° C. for one hour. (2-bromo-5-butyl-1,3,4-oxadiazole (68 mg, 0.33 mmol) was then added to the slurry and the resulting mixture was stirred overnight allowing to warm to RT. The mixture was quenched with cold water and extracted with ethyl acetate (3×15 mL). The organics were combined, dried over sodium sulfate, filtered and concentrated to dryness under reduced pressure. The resulting residue was then purified via preparative TLC plates (2×1000 μM silica gel) eluting with 5% methanol in DCM. The product was removed from the silica gel by extracting with 10% methanol in DCM and the solvent was removed under reduced pressure to afford the title compound. $^1$H NMR (500 MHz, $CDCl_3$) δ 8.55 (d, J=2.4 Hz, 1H), 6.82 (d, J=8.7 Hz, 1H), 6.46 (dd, J=2.5, 8.7 Hz, 1H), 4.40 (t, J=7.2 Hz, 2H), 4.15-4.04 (m, 2H), 3.05-2.95 (m, 2H), 2.43-2.38 (m, 1H), 2.25-2.18 (m, 1H), 1.95-1.82 (m, 2H), 1.58-1.40 (m, 5H), 1.30-1.20 (m, 3H), 1.08-1.00 (m, 4H), 0.95-0.80 (m, 1H), 0.75-0.60 (m, 1H), −0.08 (q, J=4.6 Hz, 1H). MS (ESI) m/z 449 $[M+H]^+$. GPR119 Human EC50: 28 nM The Examples in Table 16 were synthesized according to the methods described in the prior example (247) employing the appropriate reagents and solvents.

TABLE 16

| Example # | Chemical Structure | Observed Mass $[M + H]^+$ | GPR119 Human $EC_{50}$ (nM) |
|---|---|---|---|
| 248 | 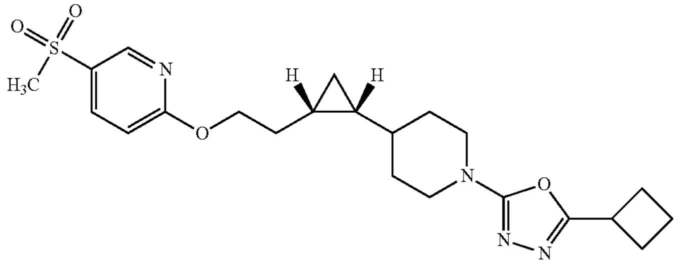 [SMILES: CS(=O)(=O)c1ccc(OCC[C@@H]2C[C@@H]2C2CCN(c3nnc(C4CCC4)o3)CC2)nc1] | 447 | 39 |
| 249 | 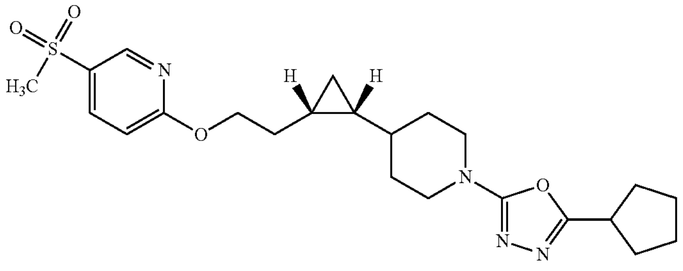 [SMILES: CS(=O)(=O)c1ccc(OCC[C@@H]2C[C@@H]2C2CCN(c3nnc(C4CCCC4)o3)CC2)nc1] | 461 | 32 |

TABLE 16-continued

| Example # | Chemical Structure | Observed Mass $[M + H]^+$ | GPR119 Human $EC_{50}$ (nM) |
|---|---|---|---|
| 250 | 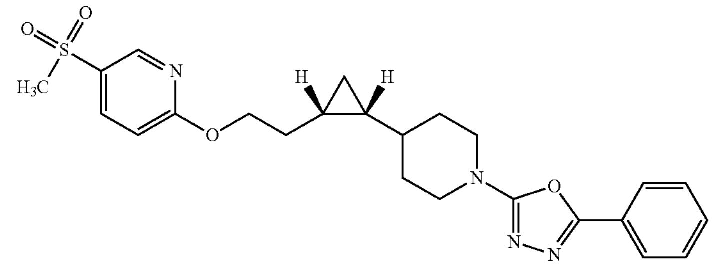 [SMILES: CS(=O)(=O)c1ccc(OCC[C@@H]2C[C@@H]2C2CCN(c3nnc(-c4ccccc4)o3)CC2)nc1] | 469 | 49 |

Example 251

Preparation of cyclopropyl(2,6-difluoro-4-{2-[(1S,2R)-2-[1,2,4]triazolo[1,5-a]pyrimidin-2-ylpiperidin-4-yl)cyclopropyl]ethoxy)phenyl)methanone

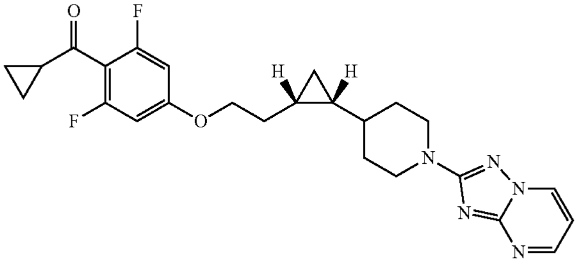 [SMILES: O=C(c1c(F)cc(OCC[C@@H]2C[C@@H]2C2CCN(c3nc4ncccn4n3)CC2)cc1F)C1CC1]

Step A: 2-[(1S,2R)-2-(1-[1,2,4]triazolo[1,5-a]pyrimidin-2-ylpiperidin-4-yl)cyclopropyl]ethanol

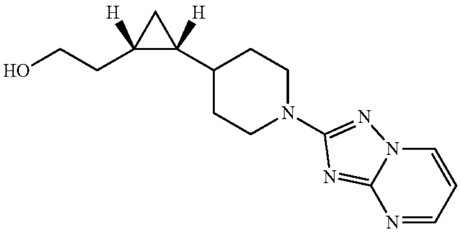 [SMILES: OCC[C@@H]1C[C@@H]1C1CCN(c2nc3ncccn3n2)CC1]

To a mixture of 2-((1S,2R)-2-(piperidin-4-yl)cyclopropyl) ethanol (Intermediate 11; 70 mg, 0.4 mmol) and 2-bromo[1,2,4]triazolo[1,5-a]pyrimidine (9 mg, 0.496 mmol) in ethanol (2 mL) was added DIEA (0.22 mL, 1.21 mmol) and the resulting mixture heated via microwave to 120° C. for 1 hr. HPLC of the reaction mixture proved the reaction was complete with the absence of Intermediate 11. The mixture was filtered (glass wool filter paper, Whatman 1821 110), and washed with ethanol. The filtrate was concentrated to dryness under reduced pressure and the resulting residue purified via preparative TLC plates (2×1000 μM silica gel) eluting with 50% ethyl acetate in hexane. The product was removed from the silica gel by extracting with ethyl acetate and the solvent was removed under reduced pressure to afford the title compound as an off-white solid. MS (Multimode) m/z 288 $[M+H]^+$.

Step B: cyclopropylmethyl 4-((1R,2S)-2-(2-(5-(methylsulfonyl)pyridin-2-yloxy)ethyl)cyclopropyl)piperidine-1-carboxylate

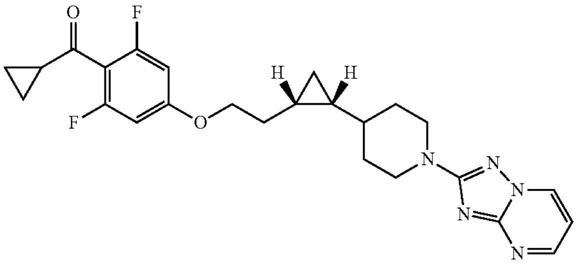 [SMILES: O=C(c1c(F)cc(OCC[C@@H]2C[C@@H]2C2CCN(c3nc4ncccn4n3)CC2)cc1F)C1CC1]

To a suspension of 2-[(1S,2R)-2-(1-[1,2,4]triazolo[1,5-a]pyrimidin-2-ylpiperidin-4-yl)cyclopropyl]ethanol (Step A, Example 133; 20 mg, 0.07 mmol), cyclopropyl(2,6-difluoro-4-hydroxyphenyl)methanone and polymer supported triphenylphosphine (69 mg, 0.21 mmol) in anhydrous THF (1 mL) was added DIAD (32 mg, 0.14 mol) at 0° C. and the resulting mixture stirred for 3 hours allowing to slowly warm to RT. The mixture was concentrated under reduced pressure and the residue purified via preparative TLC plate (1000 mM silica gel) eluting with 5% methanol in DCM. The product was extracted from the silica gel using 10% methanol in DCM and the solvents removed under reduced pressure to afford the title compound. GPR119 Human EC50: 6 nM The Examples in Table 17 were synthesized according to the methods described in the prior example (251) employing the appropriate fused heteroaryl halides and solvents.

TABLE 17

| Example # | Chemical Structure | Observed Mass $[M + H]^+$ | GPR119 Human $EC_{50}$ (nM) |
|---|---|---|---|
| 252 | 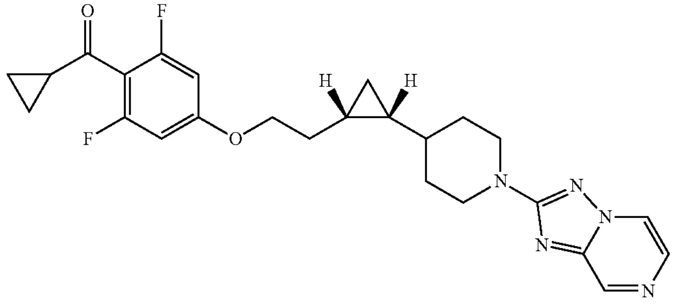 | 468 | 4.1 |
| 253 | 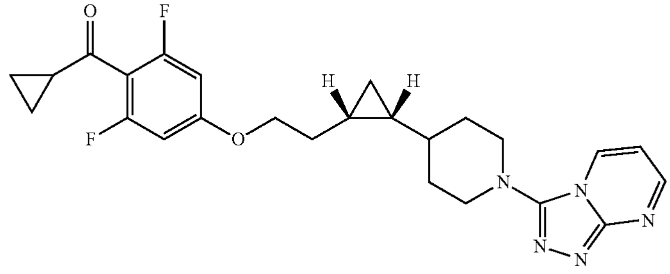 [SMILES: O=C(c1c(F)cc(OCC[C@@H]2C[C@@H]2C2CCN(c3nnc4ncccn34)CC2)cc1F)C1CC1] | 468 | 3.0 |
| 254 | 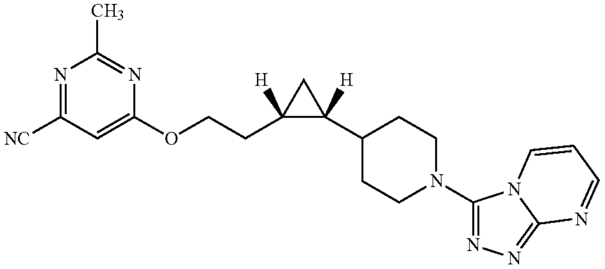 [SMILES: Cc1nc(C#N)cc(OCC[C@@H]2C[C@@H]2C2CCN(c3nnc4ncccn34)CC2)n1] | 406 | 25 |

Example 255

Preparation of 1-[(2-fluoro-4-{2-[(1S,2R)-2-{1-(5-isopropyl-1,2,4-oxadiazol-3-yl)piperidin-4-yl}cyclopropyl]ethoxy}phenyl)acetyl]azetidin-3-ol

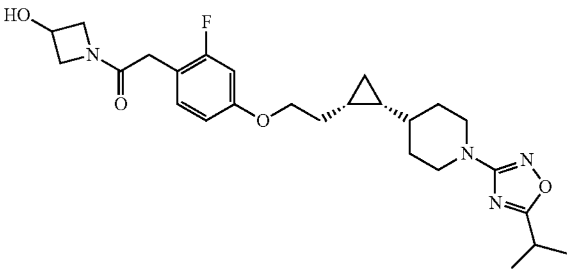 [SMILES: CC(C)c1nc(N2CCC([C@H]3C[C@H]3CCOc3ccc(CC(=O)N4CC(O)C4)c(F)c3)CC2)no1]

Step A: 2-((1S,2R)-2-(piperidin-4-yl)cyclopropyl) ethanol

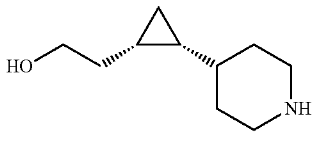 [SMILES: OCC[C@@H]1C[C@@H]1C1CCNCC1]

Benzyl 4-((1R,2S)-2-(2-hydroxyethyl)cyclopropyl)piperidine-1-carboxylate (10 g, 33 mmol) was dissolved in 100 mL of EtOAc/MeOH (1:1 v/v), to which was added 1 g of 5% Pd/C and apply hydrogen balloon. After stirring at rt for 1 h, the reaction mixture was filtered through Celite to give the product that was used in the next step without further purification. Rf was 0 @ 50% EtOAc in hexanes (blue spot on CAM stain).

Step B: 4-((1R,2S)-2-(2-hydroxyethyl)cyclopropyl) piperidine-1-carbonitrile

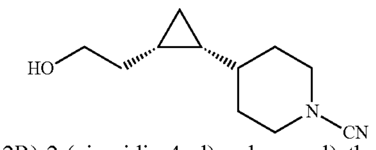

2-((1S,2R)-2-(piperidin-4-yl)cyclopropyl)ethanol (3.6 g, 21.27 mmol) was dissolved in DCM (100 ml) and NaHCO3 (7.15 g, 85 mmol) in 30 mL of water was added. The mixture was stirred at 0° C. for 5 min and cyanogen bromide (7.80 ml, 23.40 mmol, 3 M solution in DCM) was added dropwise. The mixture was stirred at 0° C. for 30 min and 1 h at RT. The two phases were separated and the water phase was extracted with DCM (50 mL). The combined DCM was washed with sat. NaHCO3, dried over MgSO4, evaporated to afford of the crude material which was used for the next step.

Rf was 0.5 @ 70% EtOAc in hexanes (blue spot on CAM stain).

Step C: N-hydroxy-4-((1R,2S)-2-(2-hydroxyethyl) cyclopropyl)piperidine-1-carboximidamide

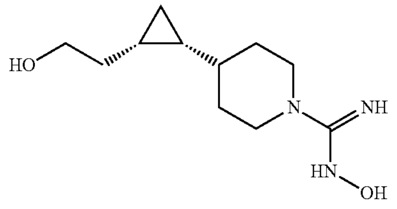 [SMILES: N=C(NO)N1CCC([C@H]2C[C@H]2CCO)CC1]

4-((1R,2S)-2-(2-hydroxyethyl)cyclopropyl)piperidine-1-carbonitrile (4.1 g, 21.10 mmol) was dissolved in Ethanol (60 ml) and hydroxylamine (5.17 ml, 84 mmol) (50% water solution) was added dropwise. The mixture was heated at 65° C. for 1 h. The mixture was evaporated to afford the desired product which was used for the next step without further purification. Rf was 0 @ 70% EtOAc in hexanes (blue spot on CAM stain)

Step D: 2-((1S,2R)-2-(1-(5-isopropyl-1,2,4-oxadiazol-3-yl)piperidin-4-yl)cyclopropyl)ethanol

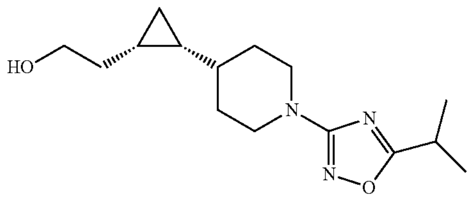 [SMILES: CC(C)c1nc(N2CCC([C@H]3C[C@H]3CCO)CC2)no1]

N-hydroxy-4-((1R,2S)-2-(2-hydroxyethyl)cyclopropyl) piperidine-1-carboximidamide (4.8 g, 21.10 mmol) was dissolved in Pyridine (60 ml) and isobutyryl chloride (18.44 ml, 176 mmol) was added. The mixture was stirred at 80° C. for 3 h and the solvent was evaporated to dryness. The residue was dissolved in MeOH (100 ml) and potassium carbonate (24.32 g, 176 mmol) was added. The mixture was stirred at 50° C. for 2 h. Another potassium carbonate (24.32 g, 176 mmol) was added and the mixture was stirred at 50° C. for another 2 h. The mixture was cooled down and diluted with EtOAc (100 mL), washed with water, sat. NH4Cl, dried over MgSO4, evaporated. The crude material was purified by silica gel column eluting with 20-70% EtOAc in hexane to afford the desired product. LC/MS (m/z): 280 $(M+H)^+$.

Step E: Methyl 2-(2-fluoro-4-(241S,2R)-2-(1-(5-isopropyl-1,2,4-oxadiazol-3-yl)piperidin-4-yl)cyclopropyl)ethoxy)phenyl)acetate

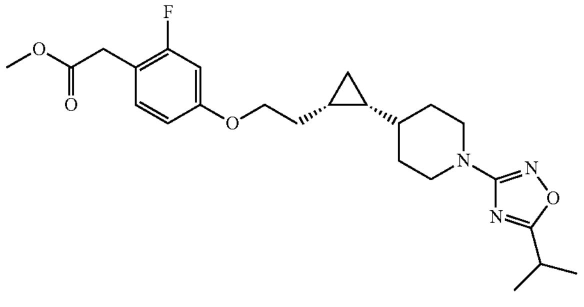 [SMILES: COC(=O)Cc1ccc(OCC[C@@H]2C[C@@H]2C2CCN(c3noc(C(C)C)n3)CC2)cc1F]

2-((1S,2R)-2-(1-(5-isopropyl-1,2,4-oxadiazol-3-yl)piperidin-4-yl)cyclopropyl)ethanol (1.4 g, 5.01 mmol), Methyl 2-(2-fluoro-4-hydroxyphenyl)acetate (1.015 g, 5.51 mmol) and triphenylphosphine (1.972 g, 7.52 mmol) were dissolved in Dichloromethane (20 ml). The mixture was stirred at RT under N2 for 5 min and disisopropyl azodicarboxylate (1.476 ml, 7.52 mmol) was added. The mixture was stirred at RT overnight. The mixture was diluted with DCM (50 ml), washed with water, dried and evaporated. The crude material was purified by silica gel column (100 g SNAP, 2~6% EtOAc in DCM) to afford 1.9 g of the desired product which contains the impurities. This material was re-purified by silica gel column (25 g SNAP, 2~6% EtOAc in DCM) to afford the pure desired product. LC/MS (m/z): 446 $(M+H)^+$.

Step F: 2-(2-fluoro-4-(241S,2R)-2-(1-(5-isopropyl-1,2,4-oxadiazol-3-yl)piperidin-4-yl)cyclopropyl) ethoxy)phenyl) acetic acid

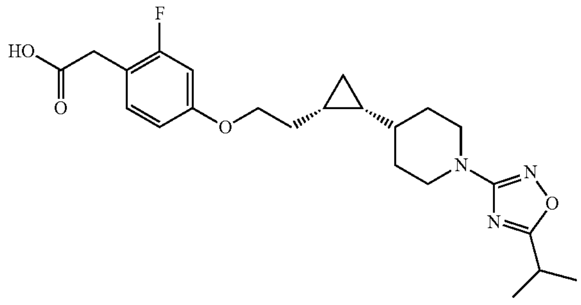 [SMILES: CC(C)c1nc(N2CCC([C@H]3C[C@H]3CCOc3ccc(CC(=O)O)c(F)c3)CC2)no1]

Methyl 2-(2-fluoro-4-(2-((1S,2R)-2-(1-(5-isopropyl-1,2,4-oxadiazol-3-yl)piperidin-4-yl)cyclopropyl)ethoxy)phenyl)acetate (1.27 g, 2.85 mmol) was dissolved in MeOH (15 ml) and sodium hydroxide (5 M, 4.56 ml, 22.80 mmol) was added. The mixture was stirred at RT for 1 h and neutralized to pH 5 with 5 M HCl (5 ml), extracted with EtOAc (50 ml). The EtOAc phase was dried over MgSO4, and evaporated to afford the desired product. LC/MS (m/z): 432 $(M+H)^+$.

Step G: 1-[(2-fluoro-4-{2-[(1S,2R)-2-[1-(5-isopropyl-1,2,4-oxadiazol-3-yl)piperidin-4-yl] cyclopropyl}ethoxy]phenyl)acetyl]azetidin-3-ol

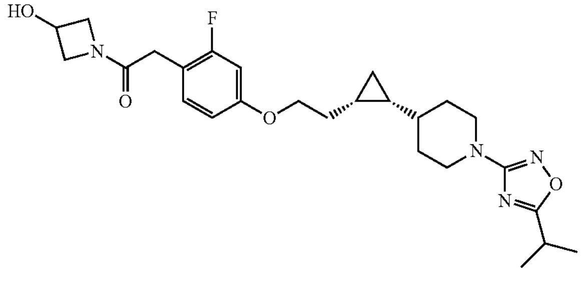 [SMILES: CC(C)c1nc(N2CCC([C@H]3C[C@H]3CCOc3ccc(CC(=O)N4CC(O)C4)c(F)c3)CC2)no1]

2-(2-fluoro-4-(24(1S,2R)-2-(1-(5-isopropyl-1,2,4-oxadiazol-3-yl)piperidin-4-yl)cyclopropyl)ethoxy)phenyl)acetic acid (80 mg, 0.185 mmol), 1-hydroxybenzotriazole hydrate (42.6 mg, 0.278 mmol), 3-hydroxyazetidine hydrochloride (30.5 mg, 0.278 mmol) and (E)-3-(ethyldiazenyl)-N,N-dimethylpropan-1-amine hydrochloride (50.0 mg, 0.278 mmol) were dissolved in $CH_2Cl_2$ (4 ml). The mixture was stirred at RT for 5 min. and triethylamine (0.078 ml, 0.556 mmol) was added. The mixture was stirred at RT overnight and loaded directly on Preparative TLC that was developed with 5% MeOH in EtOAc. The desired product (Rf=0.35 @ 5% MeOH in EtOAc) was collected to give the title compound. $^1$H NMR (500 MHz, $CDCl_3$) 7.22 (t, 1H), 6.61 (m, 2H), 4.62 (broad s, 1H), 4.38 (m, 1H), 4.25 (m, 1H), 4.03 (m, 5H), 3.90 (m, 1H), 3.40 (s, 2H), 3.25 (broad, s, 1H), 3.10 (m, 1H), 2.92 (m, 2H), 2.15 (m, 1H), 1.84 (m, 3H), 1.51 (m, 2H), 1.40 (d, 6H), 0.95 (m, 2H), 0.68 (m, 2H), −0.40 (m, 1H). LC/MS (m/z): 487 $(M+H)^+$, GPR119 Human $EC_{50}$: 1.6 nM Example 256

Preparation of 4-((1R,2S)-2-{2-[3-fluoro-4-(1,3,4-oxadiazol-2-ylmethyl)phenoxy]ethyl}cyclopropyl)-1-(3-isopropyl-1,2,4-oxadiazol-5-yl)piperidine

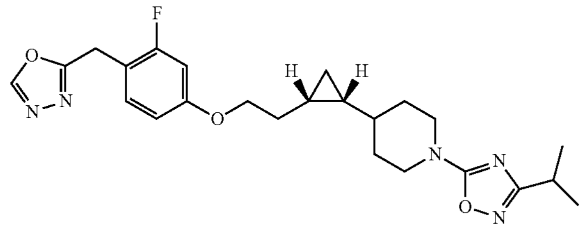 [SMILES: CC(C)c1noc(N2CCC([C@H]3C[C@H]3CCOc3ccc(Cc4nnco4)c(F)c3)CC2)n1]

Step A: 2-[2-fluoro-4-(2-{(1S,2R)-2-[1-(3-isopropyl-1,2,4-oxadiazol-5-yl)piperidin-4-yl]cyclopropyl}ethoxy)phenyl]acetohydrazide

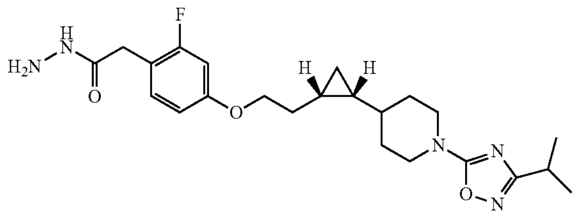 [SMILES: CC(C)c1noc(N2CCC([C@H]3C[C@H]3CCOc3ccc(CC(=O)NN)c(F)c3)CC2)n1]

To a solution [2-fluoro-4-(2-{(1S,2R)-2-[1-(3-isopropyl-1,2,4-oxadiazol-5-yl)piperidin-4-yl]cyclopropyl}ethoxy)phenyl]acetic acid (500 mg, 1.152 mmol) in 5 mL of THF cooled to −10° C. via dry ice/methanol bath was added TEA (0.177 mL, 1.268 mmol) followed by methyl chloroformate (0.098 mL, 1.268 mmol) and the resulting mixture stirred for 30 minutes at −10° C. (Precipitate formed after 1 minute of stirring). Filter off the precipitate and wash the solids with 10 mL THF. The filtrate was concentrated under reduced pressure and the residue was used as is for the next reaction sequence. To a solution of this mixed anhydride (265 mg, 0.539 mmol) in 1 mL DMF was added hydrazine monohydrate (0.052 mL, 1.077 mmol) and the resulting mixture stirred overnight at room temperature. The mixture was diluted with ethyl acetate (3 mL) and washed with water (2 mL) followed by brine (2 mL). The organics were dried over sodium sulfate, filtered, and concentrated under reduced pressure. The residue was purified via preparative TLC plate (1000 μM, silica gel) developing with 5% methanol in DCM. The band containing the product was washed with 10% methanol in DCM to elute off the product. The solution was concentrated under reduced pressure to afford the product as a white solid. HPLC/MS; 1.35 min (2 minute run), 446 $(M+H)^+$.

Step B: 2-[2-fluoro-4-(2-{(1S,2R)-2-[1-(3-isopropyl-1,2,4-oxadiazol-5-yl)piperidin-4-yl]cyclopropyl}ethoxy)phenyl]acetohydrazide

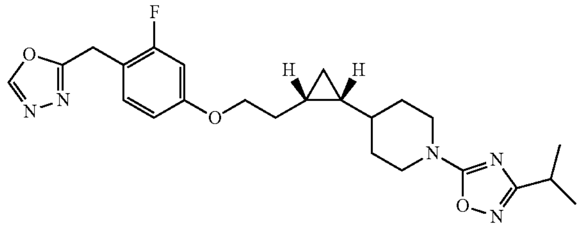 [SMILES: CC(C)c1noc(N2CCC([C@H]3C[C@H]3CCOc3ccc(Cc4nnco4)c(F)c3)CC2)n1]

2-[2-fluoro-4-(2-{(1S,2R)-2-[1-(3-isopropyl-1,2,4-oxadiazol-5-yl)piperidin-4-yl]cyclopropyl}ethoxy)phenyl]acetohydrazide (25 mg, 0.056 mmol) was taken up in 1 mL of trimethyl orthoformate and the resulting solution set under nitrogen atmosphere and heated to 120° C. overnight. The mixture was cooled to room temperature and then concentrated under reduced pressure. The residue was taken up into 0.5 mL of DMSO and sent to the Singleton Purification lab to be purified by Mass directed HPLC. HPLC/MS; 1.39 min (2 minute run), 456 $(M+H)^+$.

GPR119 Human EC50: 2.5 nM

The Examples in Table 11 were synthesized according to the methods described in the prior examples employing the appropriate reagents and solvents.

TABLE 11

| Example # | Chemical Structure | Observed Mass $[M + H]^+$ | GPR119 Human $EC_{50}$ (nM) |
|---|---|---|---|
| 257 | 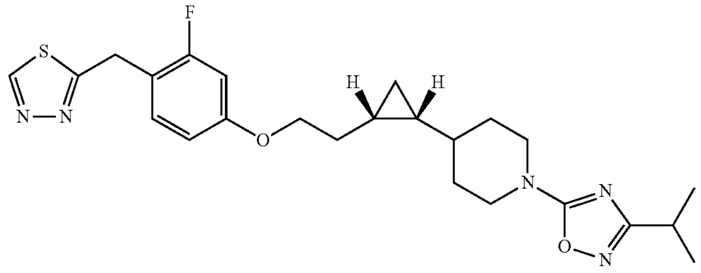 [SMILES: CC(C)c1noc(N2CCC([C@H]3C[C@H]3CCOc3ccc(Cc4nncs4)c(F)c3)CC2)n1] | 472 | 1.4 |

Example 258

Preparation of 5-[2-(3-fluoroazetidin-1-yl)-2-oxoethyl]-2-(2-{(1S,2R)-2-[1-(3-isopropyl-1,2,4-oxadiazol-5-yl)piperidin-4-yl]cyclopropyl}ethoxy)-3-methylpyridine

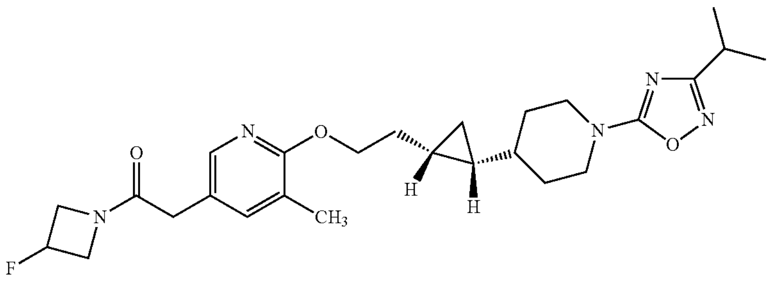 [SMILES: Cc1cc(CC(=O)N2CC(F)C2)cnc1OCC[C@@H]1C[C@@H]1C1CCN(c2nc(C(C)C)no2)CC1]

Step A: benzyl 4-((1R,2S)-2-{2-[(5-bromo)-3-methylpyridin-2-yl]oxy}ethyl)cyclopropyl)piperidine-1-carboxylate

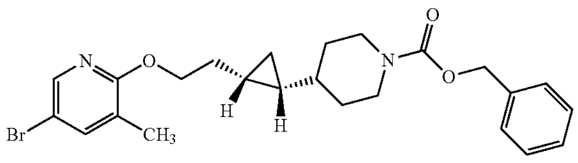 [SMILES: Cc1cc(Br)cnc1OCC[C@@H]1C[C@@H]1C1CCN(C(=O)OCc2ccccc2)CC1]

To the solution of benzyl 4-((1R,2S)-2-(2-hydroxyethyl)cyclopropyl)piperidine-1-carboxylate (5 g, 16.5 mmol) in 25 mL of DMF was added NaH (1.2 eq. 791 mg) at 0° C., stirred for 15 min. Then, 2,5 dibromo-3-methyl-pyridine, (1.05 eq. 4.34 g) was added in portions and the resulting mixture was then stirred for 4 hrs at room temperature and 1 hr at 40° C. The reaction mixture was quenched by $NH_4Cl$ sat'd aq. soln and extracted with ethyl acetate (2×), washed by brine, dried on $Na_2SO_4$, filtered and concentrated in vacuo. The residue was purified by ISCO column (330 g) using ethyl acetate in hexane (0-40% EA, 2500 ml) to give the product. LCMS (ESI) m/z 472 and 474 $[M+]^+$ and $[M+2]^+$.

Step B: benzyl 4-[(1R,2S)-2-(2-{[5-(2-tert-butoxy-2-oxoethyl)-3-methylpyridin-2-yl]oxy}ethyl)cyclopropyl]piperidine-1-carboxylate

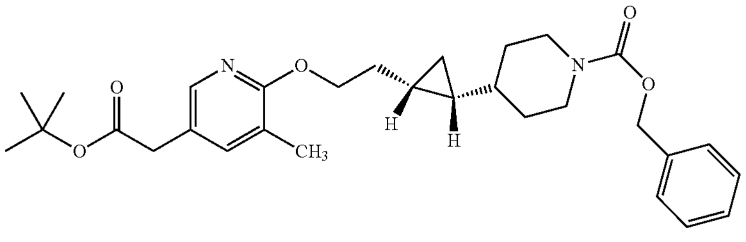 [SMILES: Cc1cc(CC(=O)OC(C)(C)C)cnc1OCC[C@@H]1C[C@@H]1C1CCN(C(=O)OCc2ccccc2)CC1]

To the solution of benzyl 4-((1R,2S)-2-{2-[(5-bromo)-3-methylpyridin-2-yl]oxy}ethyl)cyclopropyl)piperidine-1-carboxylate (1.6 g, 38 mmol), xphos (0.07 eq., 113 mg) and $Pd_2(dba)_3$ (0.07 eq., 217 mg) in 10 ml of anhydrous THF (which was degassed by nitrogen gas for 40 mins before the reactants were added) in a 20 mL microwave reaction vial was added zinc bromide (1.1 eq. 7.4 ml of 0.5M soln in THF) and the resulting solution degassed for 5 minutes. The vial was then sealed and the reaction mixture stirred at 60° C. for 18 hrs. The mixture was diluted with ethyl acetate and filtered through a celite pad. The filtrate was concentrated in vacuo and the residue was purified by ISCO column using ethyl acetate in hexane (0-30%, 1500 ml) to give the product. LCMS (ESI) m/z 509 $[M+H]^+$.

Step C: tert-butyl (5-methyl-6-{2-[(1S,2R)-2-piperidin-4-ylcyclopropyl]ethoxy}pyridin-3-yl)acetate

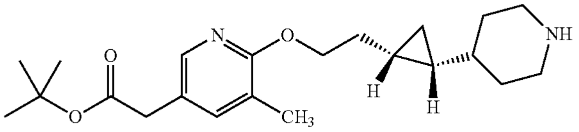 [SMILES: Cc1cc(CC(=O)OC(C)(C)C)cnc1OCC[C@@H]1C[C@@H]1C1CCNCC1]

Benzyl 4-[(1R,2S)-2-(2-{[5-(2-tert-butoxy-2-oxoethyl)-3-methylpyridin-2-yl]oxy}ethyl)cyclopropyl]piperidine-1-carboxylate (2.6 g, 5.1 mmol) in 30 mL of EtOH was treated with 10% palladium on carbon (300 mg) for 2.5 hrs under 1 atm. of hydrogen gas. The suspension was filtered through a celite pad and concentrated in vacuo to give product used for the next reaction without further purification. LCMS (ESI) m/z 375 $[M+H]^+$.

Step D: tert-butyl (6-{2-[(1S,2R)-2-(cyanopiperidin-4-yl)cyclopropyl]ethoxy}-5-methylpyridin-3-yl)acetate

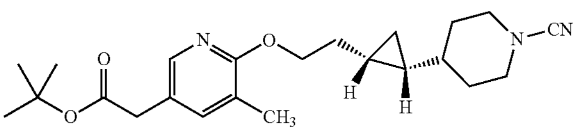 [SMILES: Cc1cc(CC(=O)OC(C)(C)C)cnc1OCC[C@@H]1C[C@@H]1C1CCN(C#N)CC1]

To the solution of tert-butyl (5-methyl-6-{2-[(1S,2R)-2-piperidin-4-ylcyclopropyl]ethoxy}pyridin-3-yl)acetate (770 mg, 2.1 mmol) in 15 mL of DCM was added $K_2CO_3$ (3 eq., 852 mg, in 5 mL of water) at room temperature followed by addition of cyanogen bromide (1.2 eq., 0.85 mL of 3M soln in DCM) at room temperature. The mixture was then stirred for 30 min at room temperature and then diluted with 20 mL DCM. The solution was washed with sat'd $NaHCO_3$ aq. soln, separated, dried over $Na_2SO_4$, filtered and the filtrate concentrated in vacuo. The residue was purified by ISCO column (40 g silica gel) using ethyl acetate in hexane (0-60%, 700 ml) to give the title compound. LCMS (ESI) m/z 400 $[M+H]^+$.

Step E: tert-butyl [6-(2-{(1S,2R)-2-[1-(3-isopropyl-1,2,4-oxadiazol-5-yl)piperidin-4-yl]cyclopropyl}ethoxy)-5-methylpyridin-3-yl]acetate

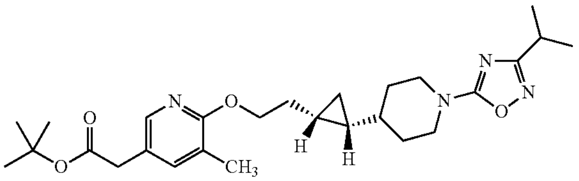 [SMILES: Cc1cc(CC(=O)OC(C)(C)C)cnc1OCC[C@@H]1C[C@@H]1C1CCN(c2nc(C(C)C)no2)CC1]

The mixture of tert-butyl (6-{2-[(1S,2R)-2-(cyanopiperidin-4-yl)cyclopropyl]ethoxy}-5-methylpyridin-3-yl)acetate (650 mg, 1.63 mmol), N-hydroxy-2-methylpropanimidamide (1.38 eq., 230 mg) and zinc chloride (1.58 eq., 350 mg) in 5 mL of DMF was stirred 2 hrs at 80° C., then PTSA (1.0 eq, 280 mg) was added and stirred for additional 2 hrs at 85° C. The mixture was cooled to room temperature and then quenched by said aq soln of $NaHCO_3$. The mixture was extracted with EtOAc (2×75 mL), and the combined organics were then washed with brine, dried over sodium sulfate, filtered and the filtrate concentrated in vacuo. The residue was purified by ISCO column (40 g silica gel) using ethyl acetate in hexane (0-40% EA, 400 ml, and 40-100% EA 200 ml) to give the product. LCMS (ESI) m/z 485 $[M+H]^+$.

Step F: [6-(2-{(1S,2R)-2-[1-(3-isopropyl-1,2,4-oxadiazol-5-yl)piperidin-4-yl]cyclopropyl}ethoxy)-5-methylpyridin-3-yl]acetic acid

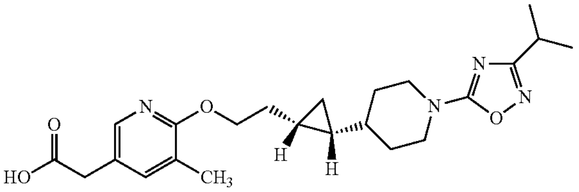 [SMILES: Cc1cc(CC(=O)O)cnc1OCC[C@@H]1C[C@@H]1C1CCN(c2nc(C(C)C)no2)CC1]

tert-Butyl [6-(2-{(1S,2R)-2-[1-(3-isopropyl-1,2,4-oxadiazol-5-yl)piperidin-4-yl]cyclopropyl}ethoxy)-5-methylpyridin-3-yl]acetate (380 mg, 0.89 mmol) was treated with 3 mL of HCl (4M in dioxane) and 2 mL of water for 2 hrs at 40° C., then overnight at room temperature. The removal of the volatiles in vacuo gave the crude product which was then used for next step. LCMS (ESI) m/z 429 $[M+H]^+$.

Step G: 5-[2-(3-fluoroazetidin-1-yl)-2-oxoethyl]-2-(2-{(1S,2R)-2-[1-(3-isopropyl-1,2,4-oxadiazol-5-yl)piperidin-4-yl]cyclopropyl}ethoxy)-3-methylpyridine

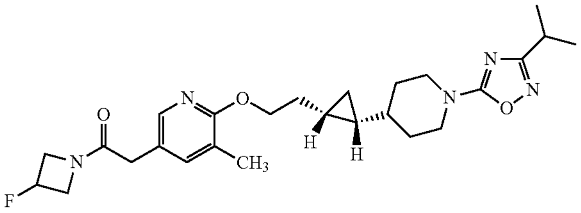 [SMILES: Cc1cc(CC(=O)N2CC(F)C2)cnc1OCC[C@@H]1C[C@@H]1C1CCN(c2nc(C(C)C)no2)CC1]

The mixture of [6-(2-{(1S,2R)-2-[1-(3-isopropyl-1,2,4-oxadiazol-5-yl)piperidin-4-yl]cyclopropyl}ethoxy)-5-methylpyridin-3-yl]acetic acid (25 mg, 0.058 mM), 3-floroazetidine (8.7 mg, 0.116 mmol), EDC (17 mg, 0.087 mmol), HOBt (13 mg. 0.087 mmol) and triethyl amine (33 μL, 0.232 mmol) in 2 mL of DCM was stirred for 16 hrs at room temperature. The volatiles were then removed in vacuo and the residue was dissolved in $CH_3CN$ and water (1/1, 1.5 ml) and submitted to the Rahway High Throughput Purification Group to be purified. The HTP group used an HP mass-directed LC eluting with a gradient of 20-80% acetonitrile in water with 0.05% formic acid buffer to purify the compound. The desired product was obtained with 97.5% purity measured via Gilson HPLC analytical analysis. LCMS (ESI) m/z 486 $[M+H]^+$. GPR119 Human EC50: 8 nM The Examples in Table 13 were synthesized according to the methods described in the prior example (258) employing the appropriate reagents and solvents.

TABLE 13

| Example # | Chemical Structure | Observed Mass $[M + H]^+$ | GPR119 Human $EC_{50}$ (nM) |
|---|---|---|---|
| 259 | 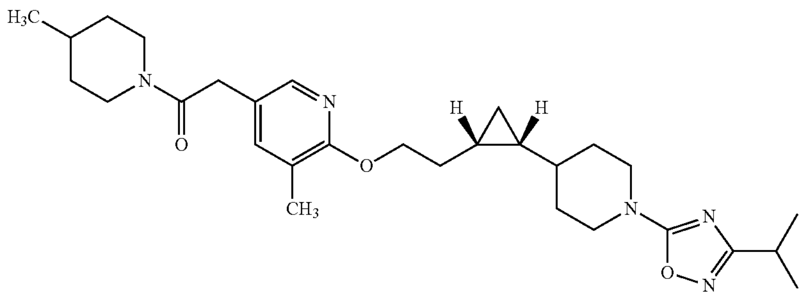 [SMILES: Cc1cc(CC(=O)N2CCC(C)CC2)cnc1OCC[C@@H]1C[C@@H]1C1CCN(c2nc(C(C)C)no2)CC1] | 510 | 18 |
| 260 | 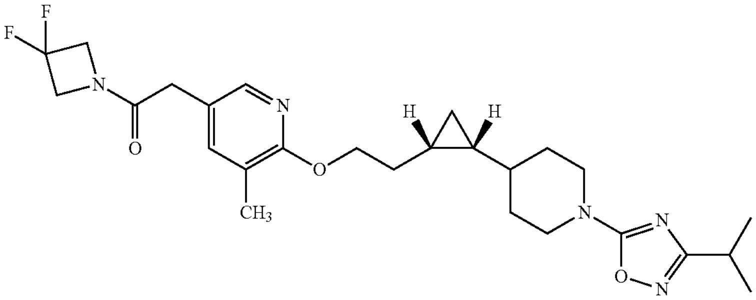 [SMILES: Cc1cc(CC(=O)N2CC(F)(F)C2)cnc1OCC[C@@H]1C[C@@H]1C1CCN(c2nc(C(C)C)no2)CC1] | 504 | 3.8 |
| 261 | 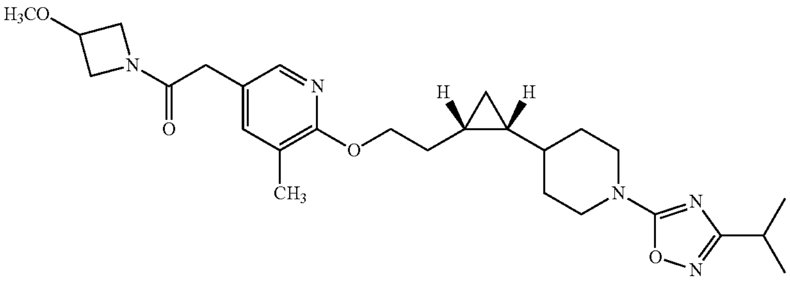 [SMILES: COC1CN(C(=O)Cc2cnc(OCC[C@@H]3C[C@@H]3C3CCN(c4nc(C(C)C)no4)CC3)c(C)c2)C1] | 498 | 19 |
| 262 | 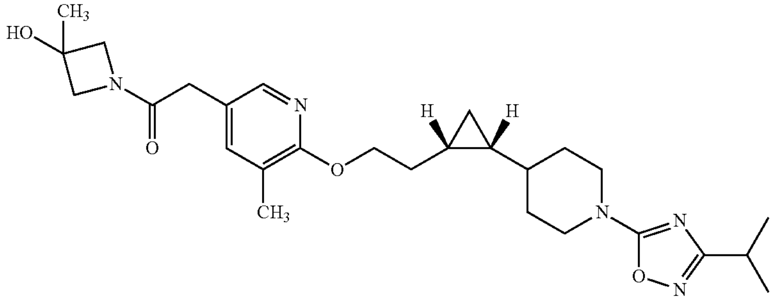 [SMILES: Cc1cc(CC(=O)N2CC(C)(O)C2)cnc1OCC[C@@H]1C[C@@H]1C1CCN(c2nc(C(C)C)no2)CC1] | 498 | 12 |

TABLE 13-continued

| Example # | Chemical Structure | Observed Mass [M + H]$^+$ | GPR119 Human $EC_{50}$ (nM) |
|---|---|---|---|
| 263 | 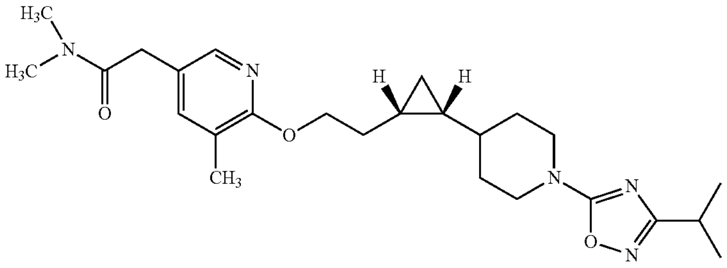 [SMILES: Cc1cc(CC(=O)N(C)C)cnc1OCC[C@@H]1C[C@@H]1C1CCN(c2nc(C(C)C)no2)CC1] | 456 | 14 |
| 264 | 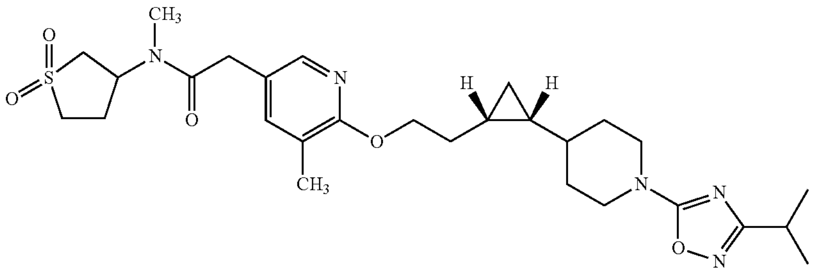 [SMILES: Cc1cc(CC(=O)N(C)C2CCS(=O)(=O)C2)cnc1OCC[C@@H]1C[C@@H]1C1CCN(c2nc(C(C)C)no2)CC1] | 560 | 11 |

Example of a Pharmaceutical Formulation

As a specific embodiment of an oral composition of a compound of the present invention, 50 mg of any of the examples is formulated with sufficient finely divided lactose to provide a total amount of 580 to 590 mg to fill a size 0 hard gelatin capsule.

While the invention has been described and illustrated in reference to specific embodiments thereof, various changes, modifications, and substitutions can be made therein without departing from the invention. For example, alternative effective dosages may be applicable, based upon the responsiveness of the patient being treated. Likewise, the pharmacologic response may vary depending upon the particular active compound selected, formulation and mode of administration. All such variations are included within the present invention.

What is claimed is:

1. A compound represented by the formula:

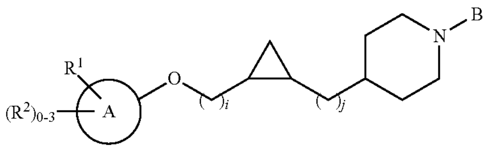

or a pharmaceutically acceptable salt thereof, wherein:

ring A is phenyl or a 6-membered heteroaryl, containing 1-2 N atoms;

B is a member selected from the group consisting of (1) $C(O)R^3$, (2) $C(O)OR^3$, (3) $C(O)NHR^3$, and (4) 5-membered heteroaryl containing 1-4 heteroatoms selected from O, S and N, wherein the 5-membered heteroaryl ring can be optionally fused with a 5- or 6-membered ring system; which can be optionally substituted with 1-3 $R^4$;

$R^1$ represents a member selected from the group consisting of (1) 3- to 6-membered heterocyclyl, containing 1-3 O, S, or N, (2) 5-membered heteroaryl, containing 1-4 O, S, or N, (3) aryl, (4) $C(O)C_{1-6}$alkyl, (5) $C(O)C_{3-8}$cycloalkyl, (6) $S(O)C_{1-6}$alkyl, (7) $SO_2C_{1-6}$alkyl, (8) $SO_2NH_2$, (9) $SO_2C_{3-8}$cycloalkyl,

(10) $SO_2NHC_{1-6}$alkyl,

(11) $SO_2N(C_{1-6}alkyl)_2$,

(12) CN,

(13) $C(O)NR^8R^9$, and

(14) $CH_2C(O)NR^5R^6$, wherein the heterocyclyl and heteroaryl moieties are optionally substituted by oxo, hydroxy, $C_{1-3}$alkyl, $C_{1-3}$alkoxy, or halo$C_{1-3}$alkyl, and the heterocyclyl moiety is further optionally substituted by oxo;

each $R^2$ is independently selected from the group consisting of (1) halogen, (2) $C_{1-6}$alkyl, (3) —$OC_{1-6}$alkyl, (4) CN, and (5) halo$C_{1-6}$alkyl;

$R^3$ represents a member selected from the group consisting of:

(1) $C_{1-6}$ alkyl, (2) halo$C_{1-6}$alkyl, (3) $C_{3-8}$cycloalkyl and (4) aryl, wherein alkyl is optionally substituted with 1-2 of $C_{3-8}$cycloalkyl, phenyl, or 5-membered heteroaryl containing 1-3 O, S, or N; and wherein the cycloalkyl is optionally fused with a $C_{3-6}$cycloalkyl or $C_{3-6}$cycloalkenyl;

$R^4$ is selected from the group consisting of:

(1) hydroxy,
(2) $C_{1-6}$alkyl,
(3) $C_{1-6}$alkoxy,
(4) $C_{1-6}$alkyl-O—$C_{1-3}$alkyl,
(5) $C_{1-6}$alkyl-O-halo$C_{1-3}$alkyl,
(6) $C_{3-6}$cycloalkyl, optionally substituted by $C_{1-3}$alkyl or halo$C_{1-3}$alkyl,
(7) $C_{3-6}$cycloalkoxy, and
(8) aryl, wherein the alkyl moiety is optionally substituted by 1-3 halo, or hydroxy;

$R^5$ and $R^6$ are independently selected from the group consisting of (1) hydrogen,
(2) $C_{1-6}$alkyl,
(3) $C_{3-6}$cycloalkyl, optionally substituted by halo, haloalkyl, or alkyl
(4) $C_{1-6}$alkyl-OH,
(5) $C_{1-3}$alkyl-$C_{3-6}$cycloalkyl,
(6) $C_{1-3}$alkyl-$C_{3-5}$heterocyclyl containing 1-3 N, O, or S,
(7) $C_{3-5}$heterocyclyl containing 1-3 N, O or S, optionally substituted by 1-2 oxo, or alkyl,
(8) $C_{1-3}$alkyl-5-membered heteroaryl containing 1-3 N, O or S, optionally substituted by $C_{1-3}$alkyl,
(9) halo$C_{1-6}$alkyl, or $R^5$ and $R^6$ are linked together with the nitrogen to which they are both attached to form a 4-9 membered monocyclic or bicyclic heterocyclic ring, comprising C, O, N, and S ring atoms, wherein the heterocyclic ring is optionally substituted with 1-3 $R^7$;

each $R^7$ is selected from the group consisting of:

(1) halo,
(2) hydroxy,
(3) $C_{1-3}$alkoxy,
(4) $C_{1-3}$alkyl,
(5) halo$C_{1-3}$alkyl,
(6) $C_{1-3}$ alkyl-OH,
(7) $C_{3-6}$cycloalkyl,
(8) 5- or 6-membered heteroaryl, containing 1-3 N, O, or S, and
(9) oxo;

$R^8$ and $R^9$ are independently selected from the group consisting of (1) hydrogen,
(2) $C_{1-6}$alkyl,
(3) $C_{1-6}$alkyl-OH, and
(4) $C_{3-8}$cycloalkyl; and i and j independently represent integers selected from 0, 1 and 2, such that i plus j is 0, 1 or 2.

2. The compound of claim 1, wherein ring A is phenyl, pyridinyl, pyrimidinyl, pyridazinyl, or pyrazinyl.

3. The compound of claim 1, wherein ring A is phenyl or pyrimidine.

4. The compound of claim 1, wherein ring A is a pyridine ring.

5. The compound of claim 1, wherein B is selected from the group consisting of:

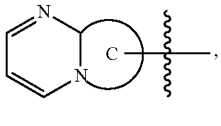, 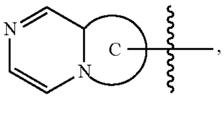,

-continued

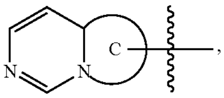, 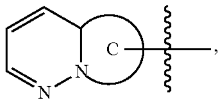,
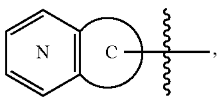, 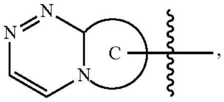,
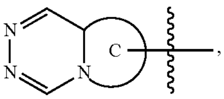, 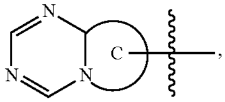,
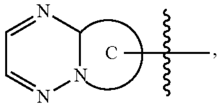, 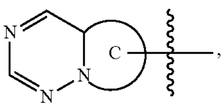,
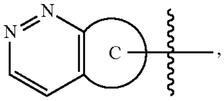, 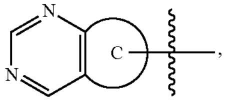,
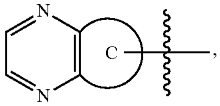, 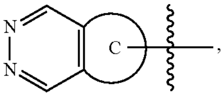,
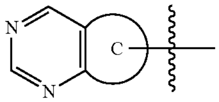 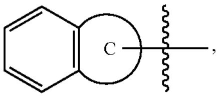,
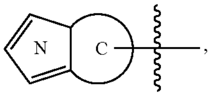, 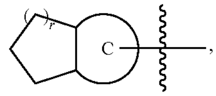, and
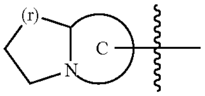

wherein C is any 5-membered heteroaryl moiety and r is an integer selected from 1 or 2.

6. The compound of claim 1, wherein B is selected from the group consisting of

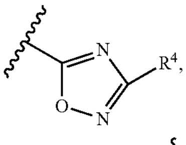, 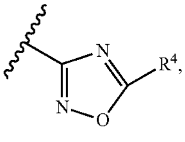, and
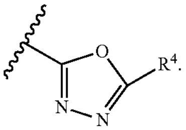.

7. The compound of claim 6, wherein $R^4$ is selected from the group consisting of

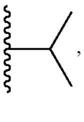, 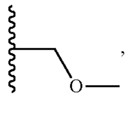, 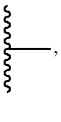, 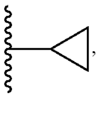, 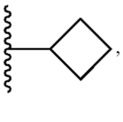,

-continued

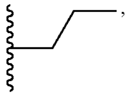, 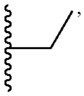, 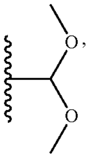, 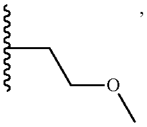,

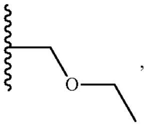, 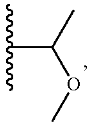, 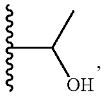, 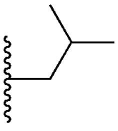,

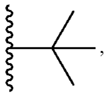, 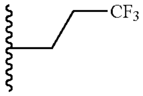, 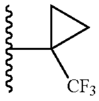,

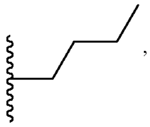, and 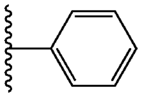.

8. The compound of claim 1, wherein B is $C(O)R^3$, or $C(O)OR^3$.

9. The compound of claim 8, wherein B is selected from the group consisting of

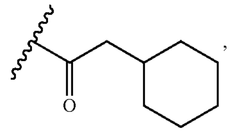, 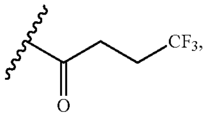

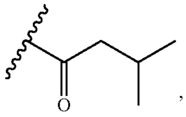, 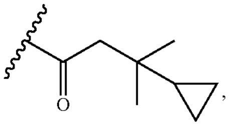,

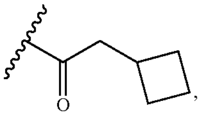, 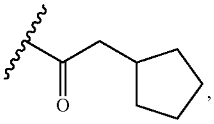,

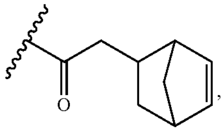, 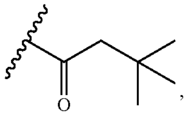,

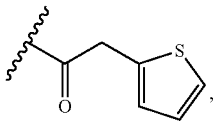, 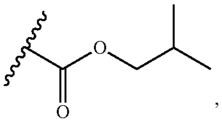,

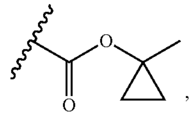, 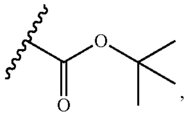,

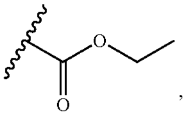, 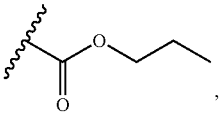,

-continued

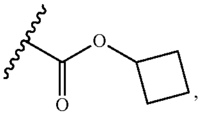, 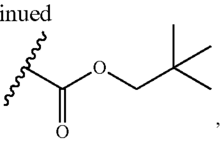,

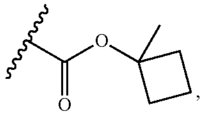, 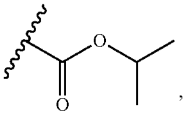,

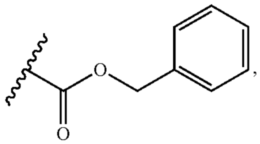, 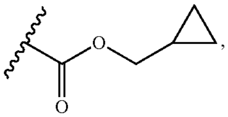,

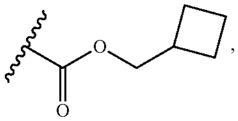, 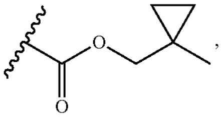,

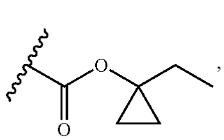, 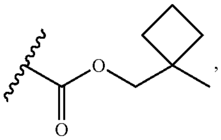, and

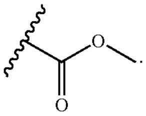.

10. The compound of claim 1, wherein $R^1$ represents a member selected from the group consisting of 3- to 6-membered heterocyclyl, containing 1-3 O, S, or N, optionally substituted by oxo; 5-membered heteroaryl, containing 1-4 O, S, or N, optionally substituted by $C_{1-3}$alkyl; aryl; $C(O)C_{1-6}$alkyl; $C(O)C_{3-8}$cycloalkyl; $SO_2C_{1-6}$alkyl; $SO_2C_{3-8}$cycloalkyl; CN; $C(O)NR^8R^9$; and $CH_2C(O)NR^5R^6$.

11. The compound of claim 10, wherein $R^1$ is 5-membered heteroaryl, containing 1-4 O, S, or N, optionally substituted by $C_{1-3}$alkyl.

12. The compound of claim 11, wherein $R^1$ is $SO_2C_{1-6}$ alkyl, or $SO_2C_{3-8}$cycloalkyl.

13. The compound of claim 12, wherein $R^1$ is $C(O)NR^8R^9$ or $CH_2C(O)NR^5R^6$.

14. The compound of claim 1, wherein each $R^2$ is methyl, chloro, fluoro, CN, or methoxy.

15. A compound represented by the formula I-G:

I-G

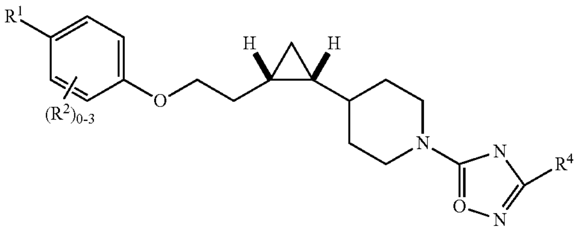

or a pharmaceutically acceptable salt thereof, wherein:

$R^1$ represents a member selected from the group consisting of (1) 3- to 6-membered heterocyclyl, containing 1-3 O, S, or N, (2) 5-membered heteroaryl, containing 1-4 O, S, or N, (3) $C(O)C_{1-6}$alkyl, (4) $C(O)C_{3-8}$cycloalkyl, (5) $SO_2C_{1-6}$alkyl, (6) CN, (7) $C(O)NR^8R^9$, and (8) $CH_2C(O)NR^5R^6$, wherein the heterocyclyl and heteroaryl moieties are optionally substituted by oxo, hydroxy, $C_{1-3}$alkyl, $C_{1-3}$alkoxy, or halo$C_{1-3}$alkyl, and the heterocyclyl moiety is further optionally substituted by oxo;

each $R^2$ is independently selected from the group consisting of (1) halogen, (2) $C_{1-6}$alkyl, (3) —$OC_{1-6}$alkyl, and (4) CN;

$R^4$ is selected from the group consisting of:

(1) hydroxy, (2) $C_{1-6}$alkyl, (3) $C_{1-6}$alkoxy, (4) $C_{1-6}$alkyl-O—$C_{1-3}$alkyl, (5) $C_{1-6}$alkyl-O-halo$C_{1-3}$alkyl, (6) $C_{3-6}$cycloalkyl, optionally substituted by $C_{1-3}$alkyl or halo$C_{1-3}$alkyl, (7) $C_{3-6}$cycloalkoxy, and (8) aryl, wherein the alkyl moiety is optionally substituted by 1-3 halo, or hydroxy;

$R^5$ and $R^6$ are independently selected from the group consisting of (1) hydrogen, (2) $C_{1-6}$alkyl, (3) $C_{3-6}$cycloalkyl, optionally substituted by halo, haloalkyl, or alkyl (4) $C_{1-6}$alkyl-OH, (5) $C_{1-3}$alkyl-$C_{3-6}$cycloalkyl, (6) $C_{1-3}$alkyl-$C_{3-5}$heterocyclyl containing 1-3 N, O, or S, (7) $C_{3-5}$heterocyclyl containing 1-3 N, O or S, optionally substituted by 1-2 oxo, or alkyl, (8) $C_{1-3}$alkyl-5-membered heteroaryl containing 1-3 N, O or S, optionally substituted by $C_{1-3}$alkyl, (9) halo$C_{1-6}$alkyl, or $R^5$ and $R^6$ are linked together with the nitrogen to which they are both attached to form a 4-9 membered monocyclic or bicyclic heterocyclic ring, comprising C, O, N, and S ring atoms, wherein the heterocyclic ring is optionally substituted with 1-3 $R^7$;

each $R^7$ is selected from the group consisting of:

(1) halo, (2) hydroxy, (3) $C_{1-3}$alkoxy, (4) $C_{1-3}$alkyl, (5) halo$C_{1-3}$alkyl, (6) $C_{1-3}$alkyl-OH, (7) $C_{3-6}$cycloalkyl, (8) 5- or 6-membered heteroaryl, containing 1-3 N, O, or S, and (9) oxo; and $R^8$ and $R^9$ are independently selected from the group consisting of (1) hydrogen, (2) $C_{1-6}$alkyl, (3) $C_{1-6}$alkyl-OH, and (4) $C_{3-8}$cycloalkyl.

16. A compound of claim 1 or a pharmaceutically acceptable salt thereof, selected from the group consisting of:

1

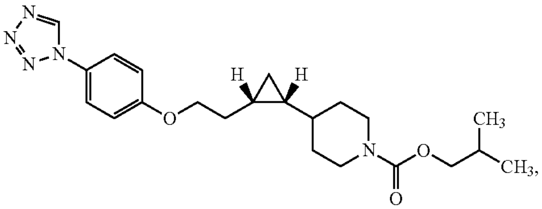

,

2

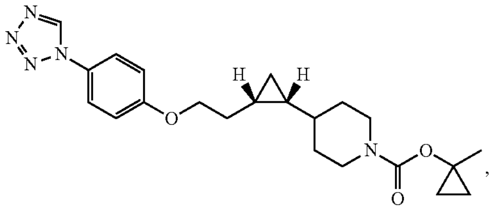

,

3

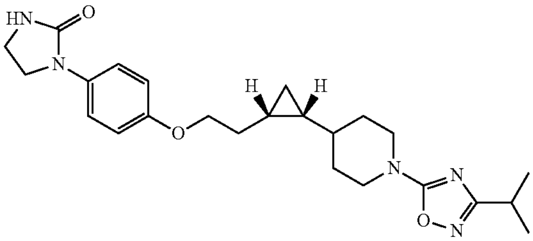

,

4

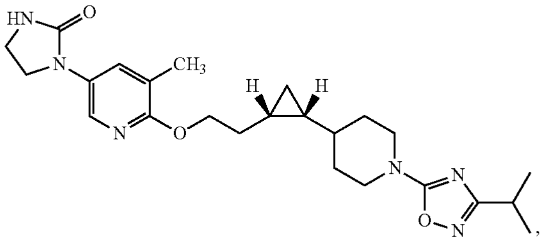

,

5

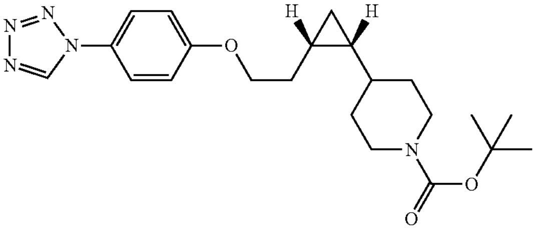

,

6

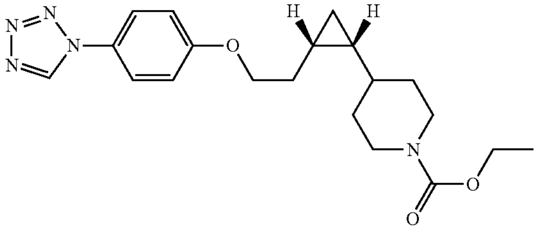

,

-continued
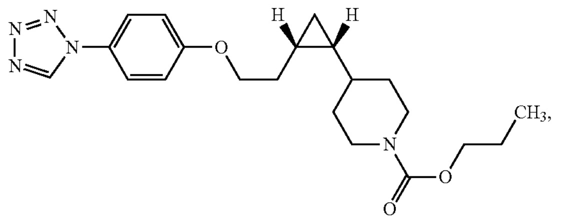
7
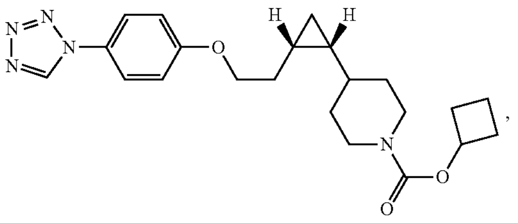
8
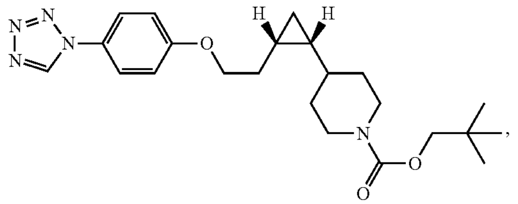
9
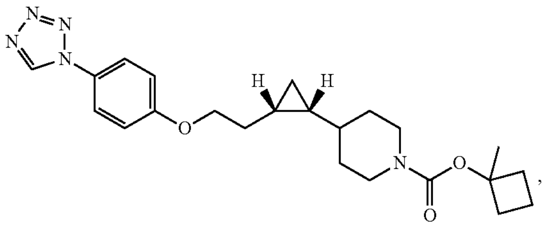
10
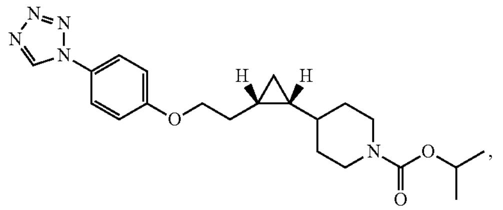
11
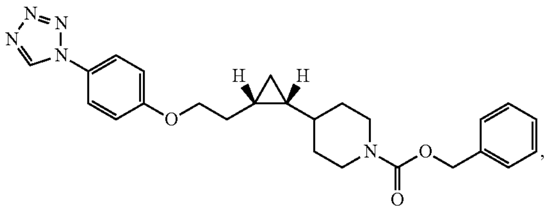
12
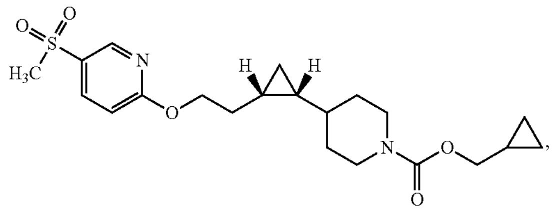
13
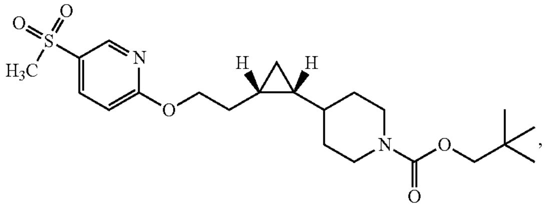
14
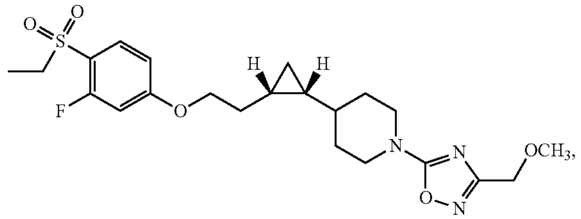
15
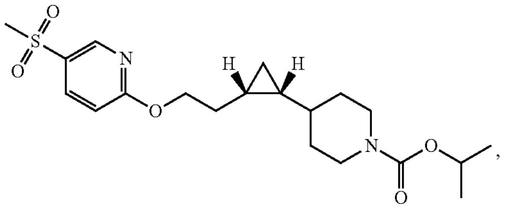
16
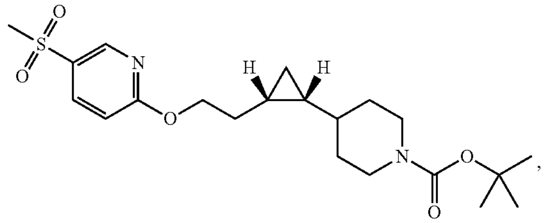
17
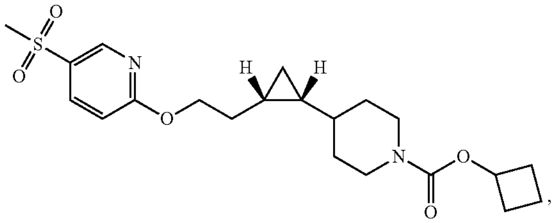
18

-continued
19
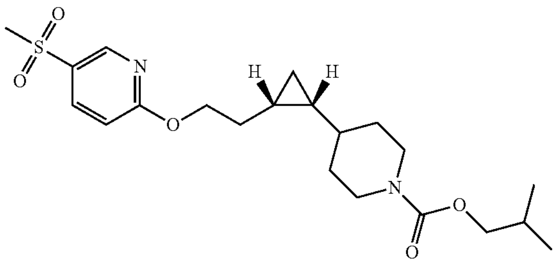
,
20
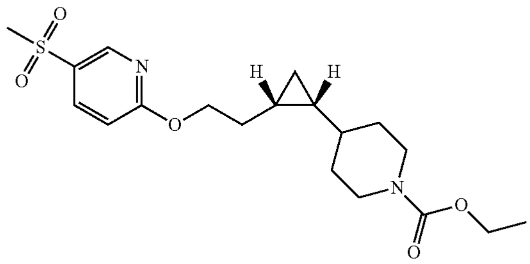
,
21
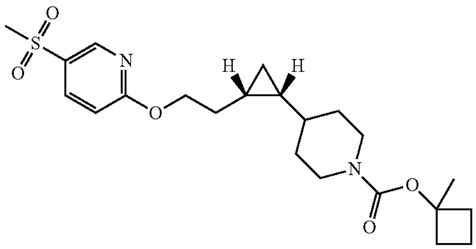
,
22
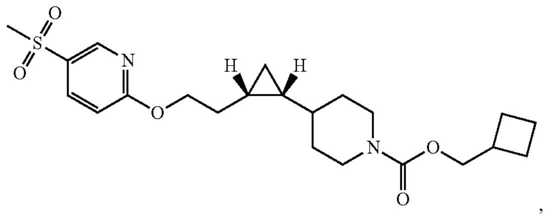
,
23
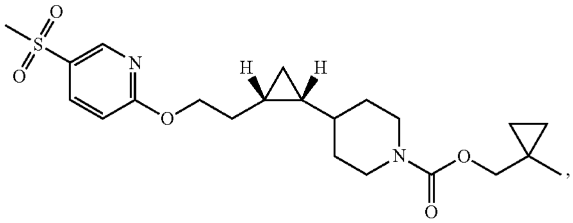
,
24
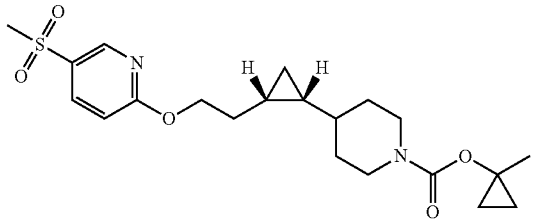
,
25
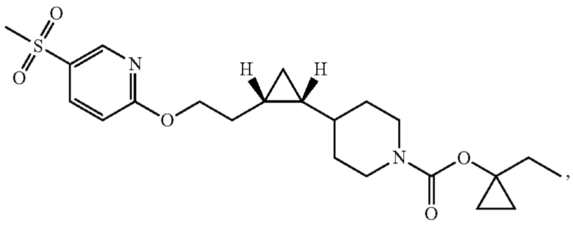
,
26
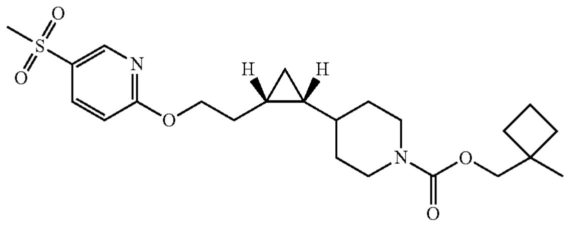
,
27
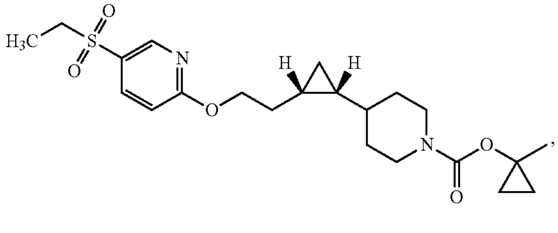
,
28
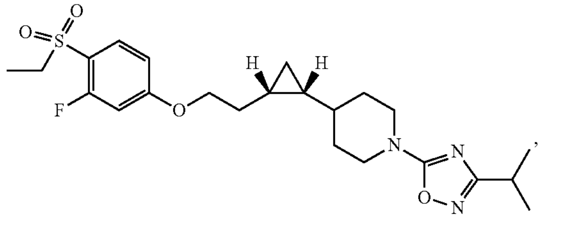
,
29
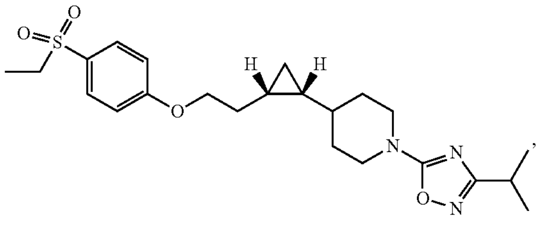
,
30
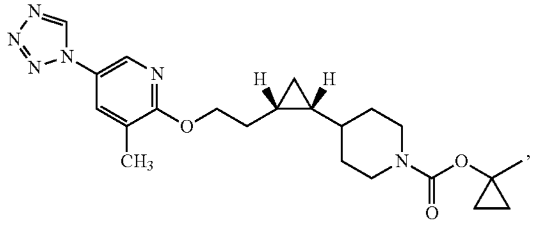
, -continued
31
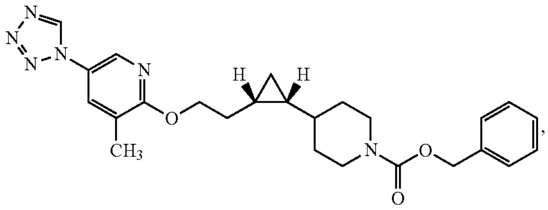,
32
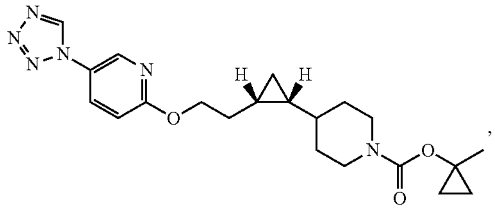,
33
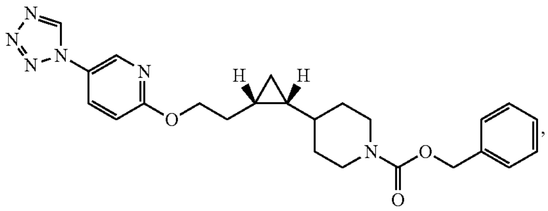,
34
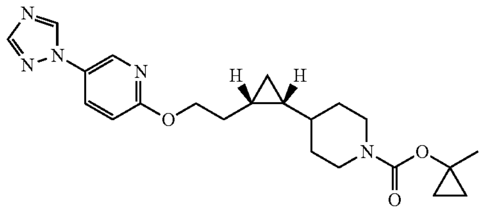,
35
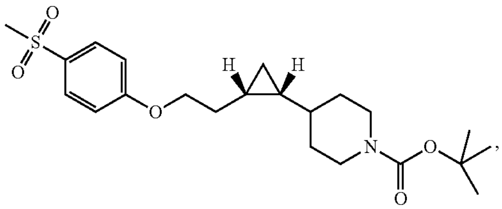,
36
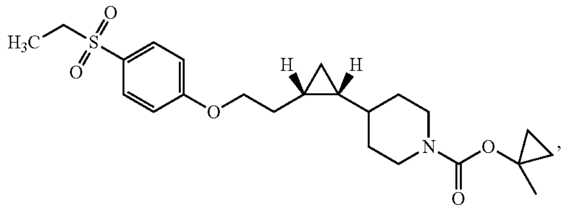,
37
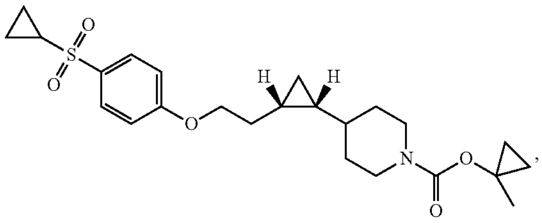,
38
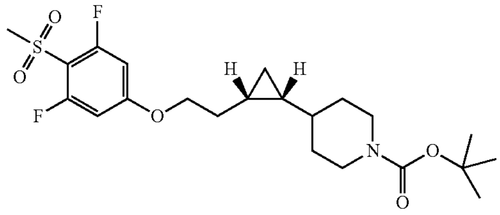,
39
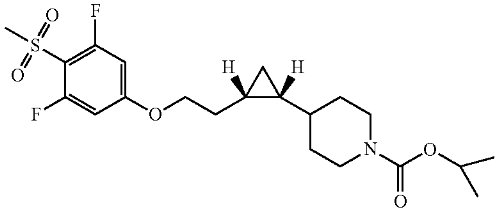,
40
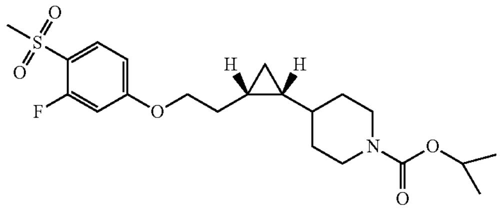,
41
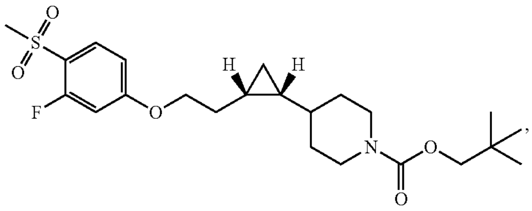,
42
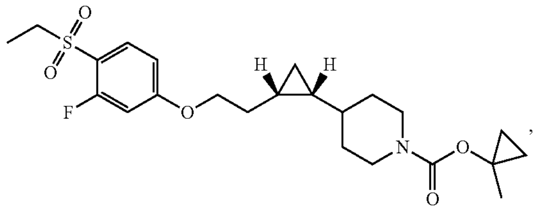,
43
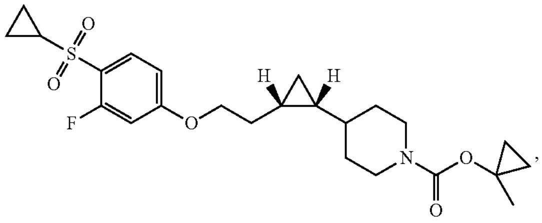,
44
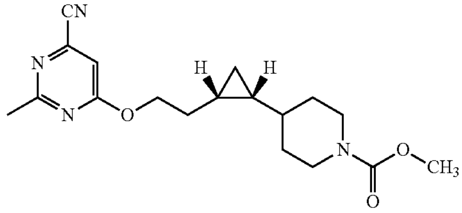, -continued
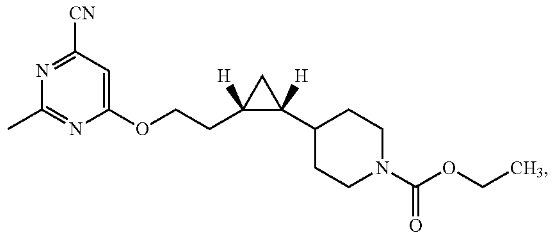
45
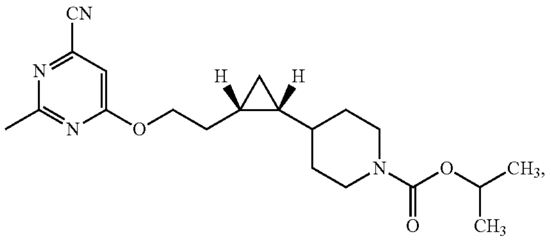
46
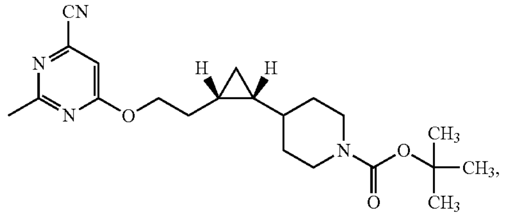
47
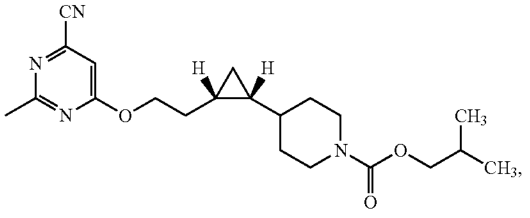
48
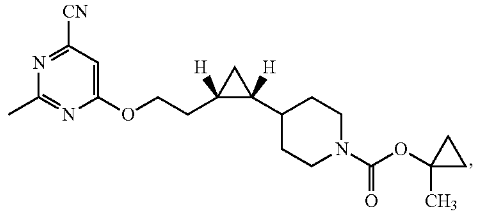
49
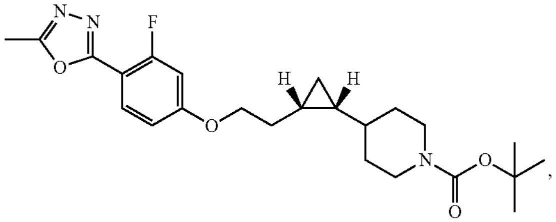
50
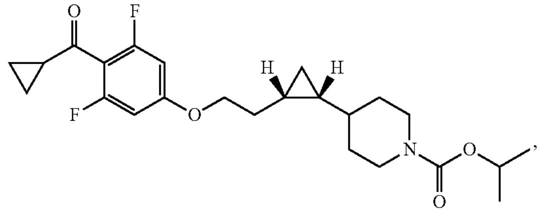
51
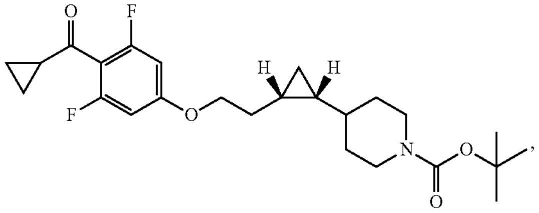
52
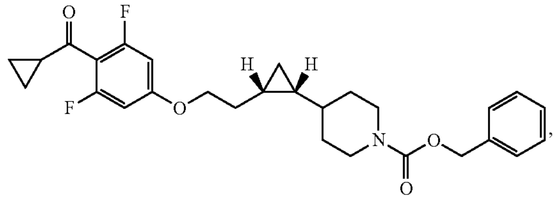
53
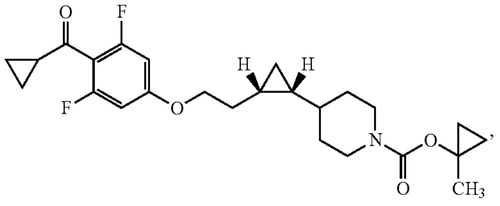
54
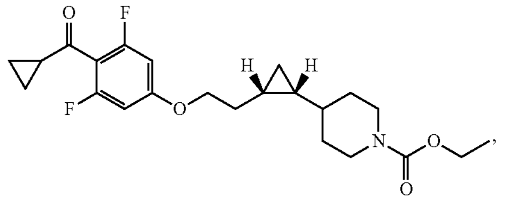
55
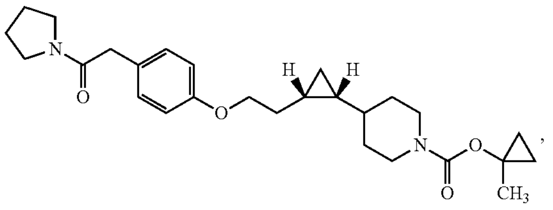
56
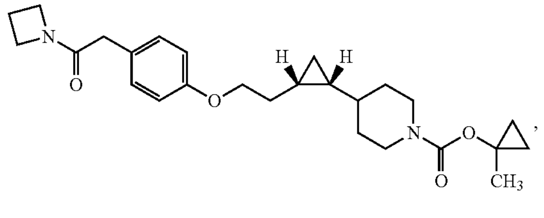
57
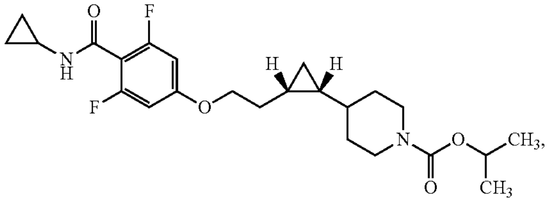
58

-continued
59
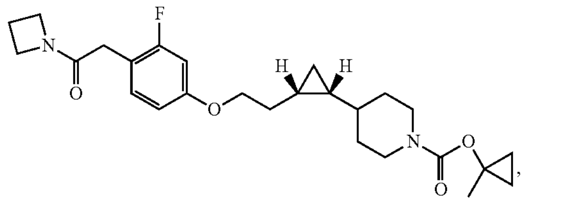
60
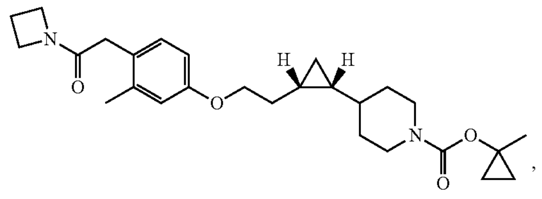
61
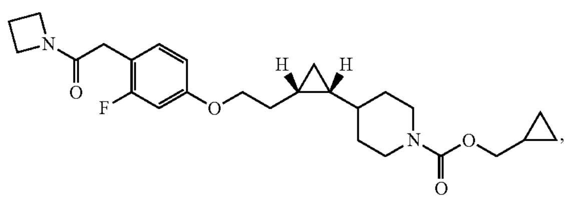
62
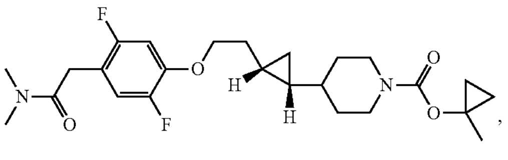
63
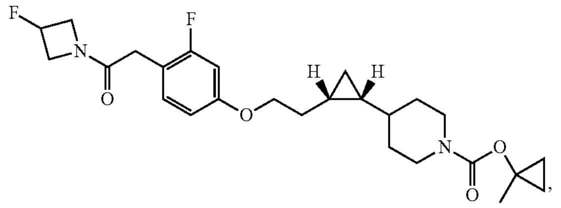
64
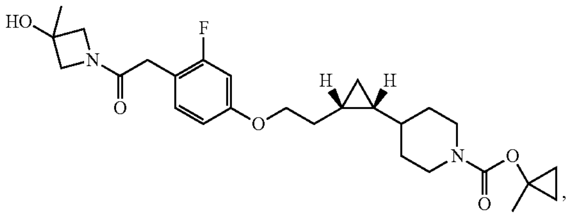
65
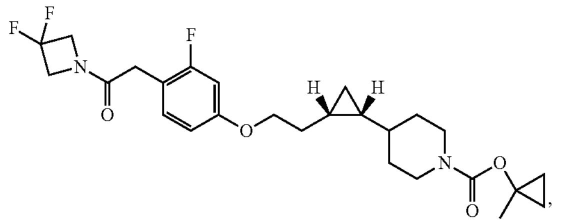
66
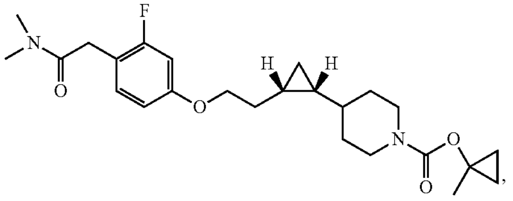
67
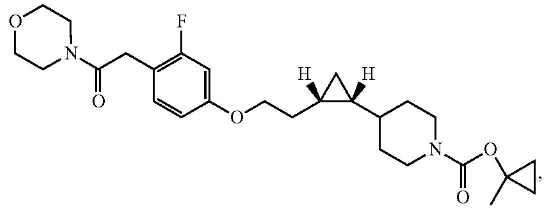
68
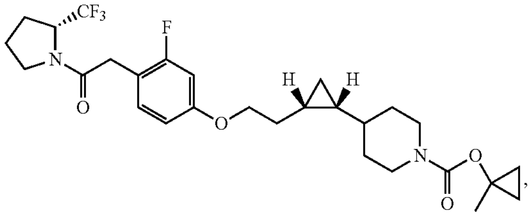
69
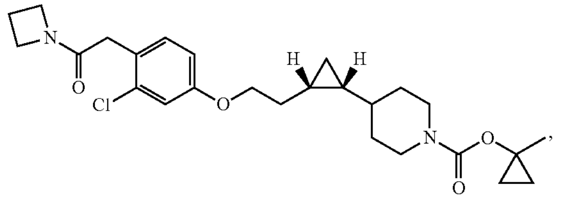
70
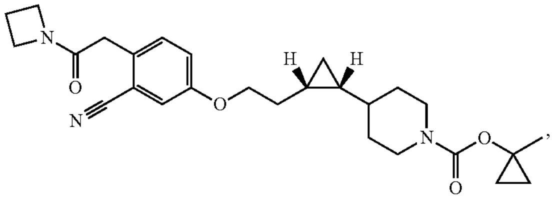
71
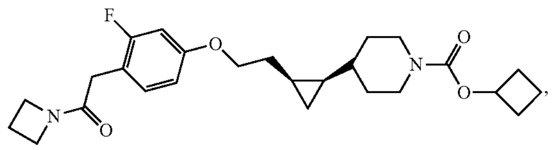
72
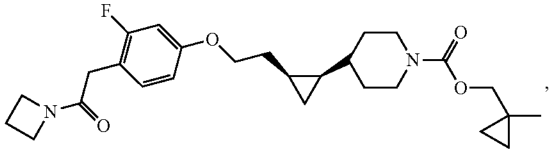

-continued
73
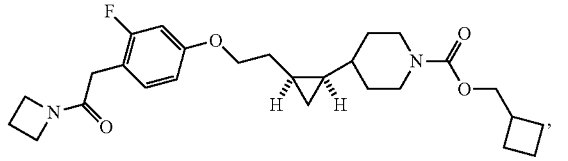
74
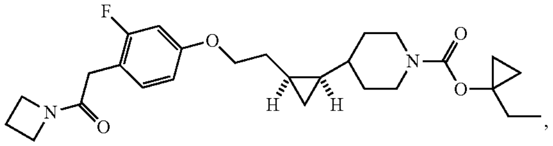
75
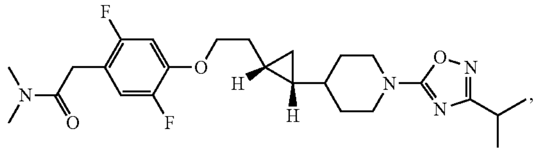
76
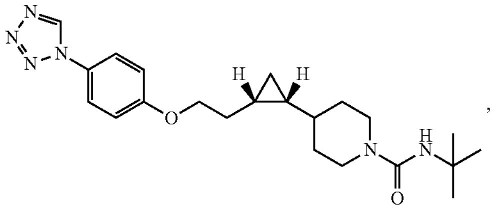
77
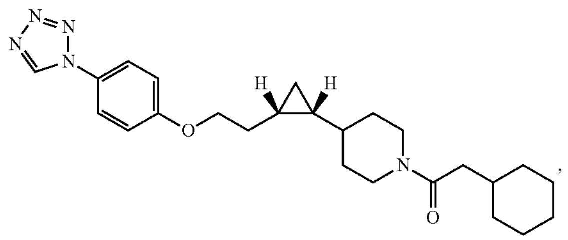
78
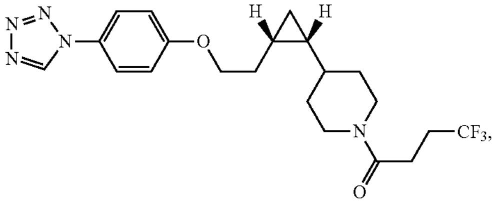
79
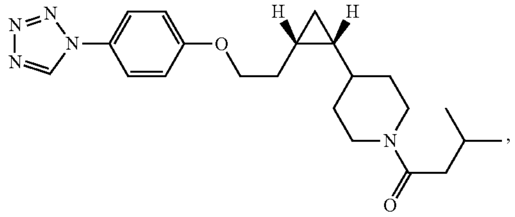
80
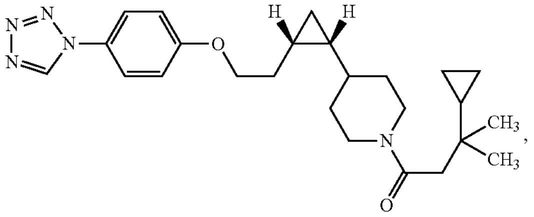
81
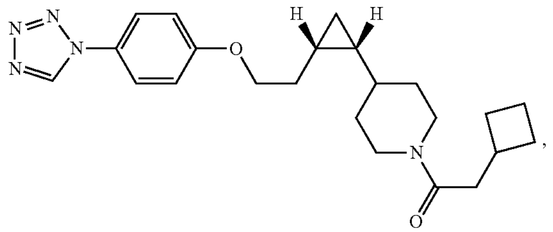
82
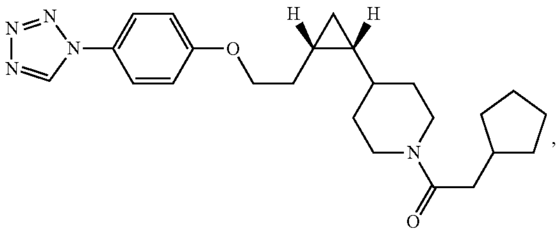
83
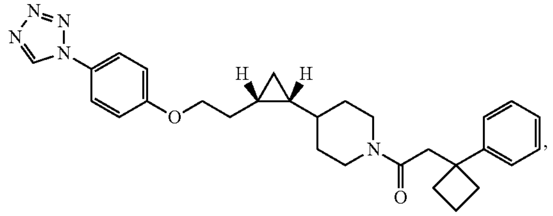
84
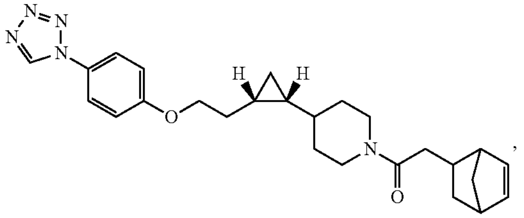
85
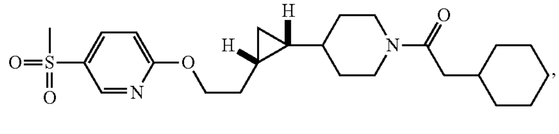
86
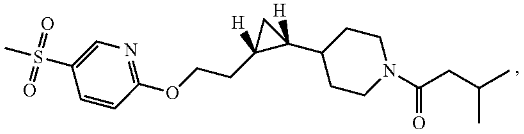

-continued
87
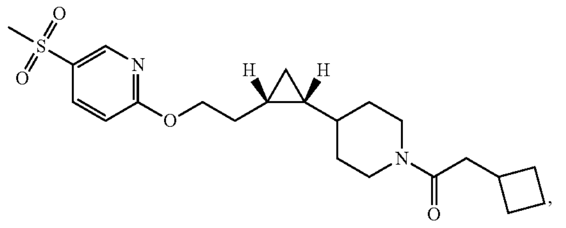
88
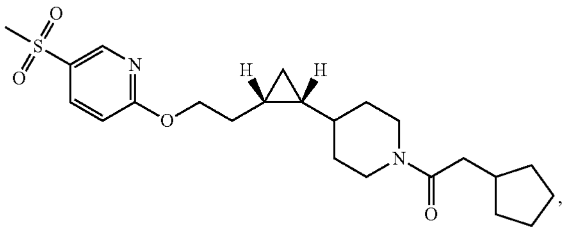
89
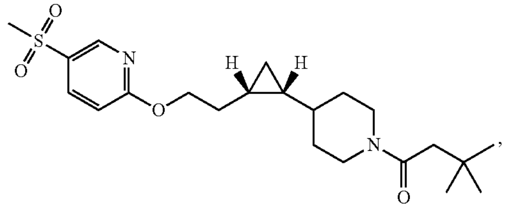
90
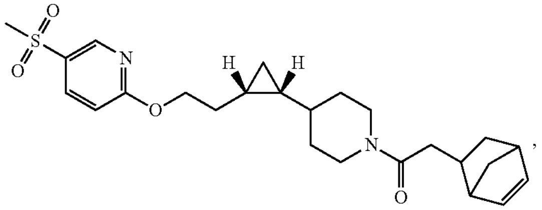
91
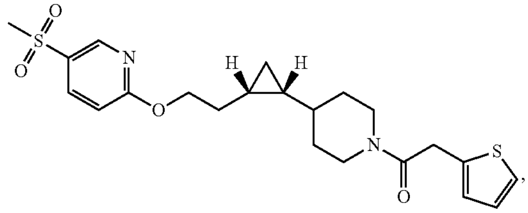
92
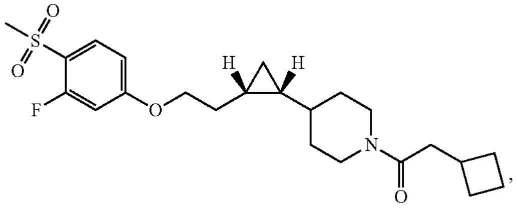
93
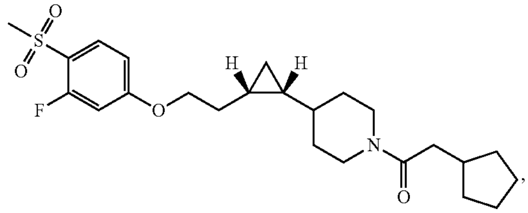
94
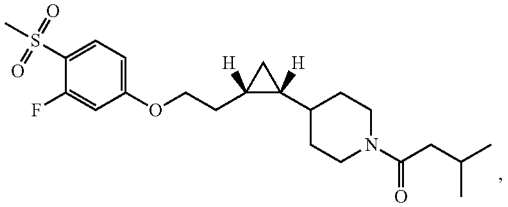
95
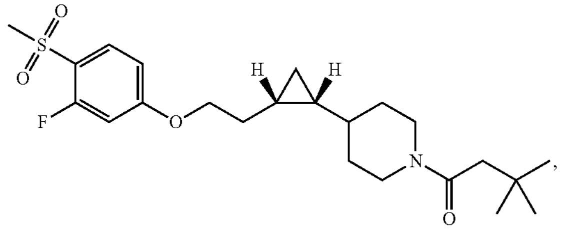
96
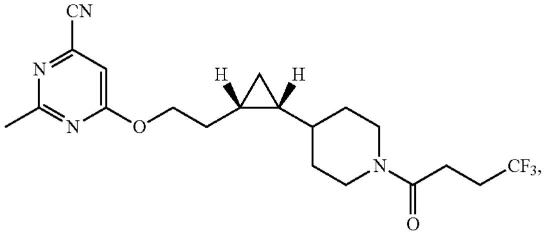
97
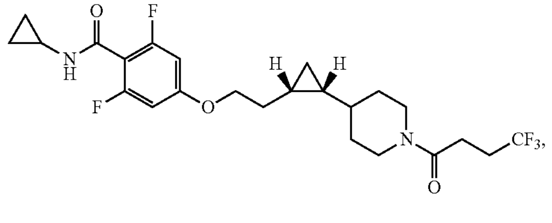
98
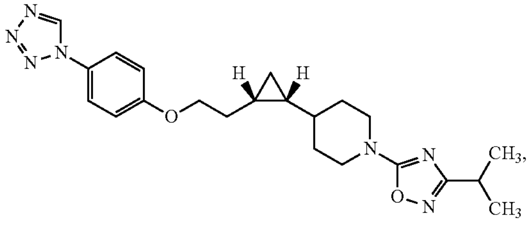
99
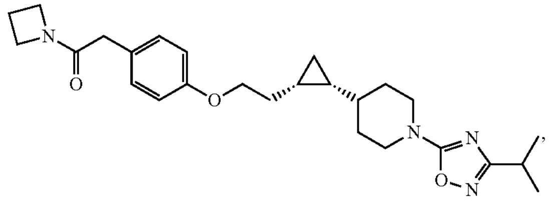
100
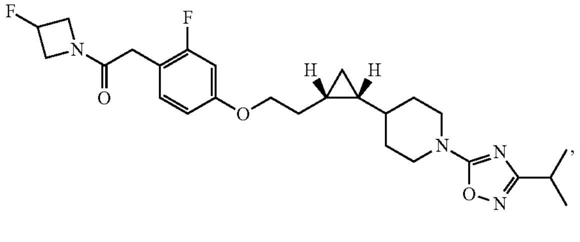

-continued
101
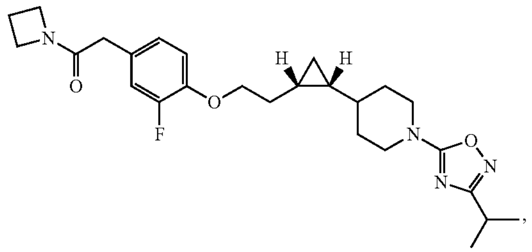
,
102
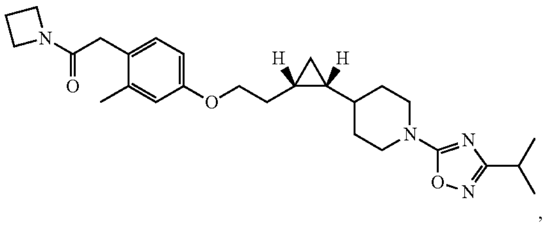
,
103
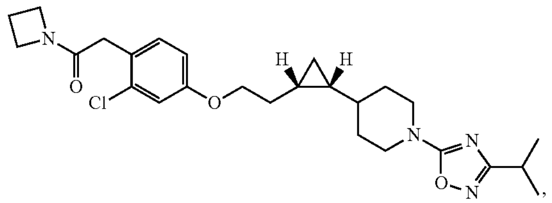
,
104
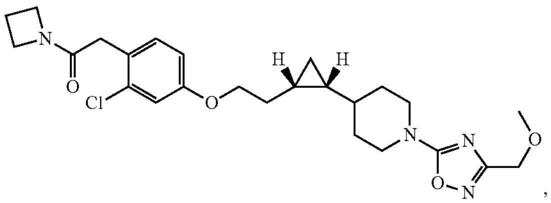
,
105
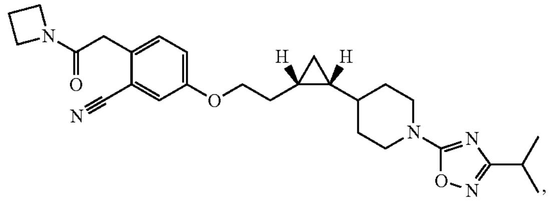
,
106
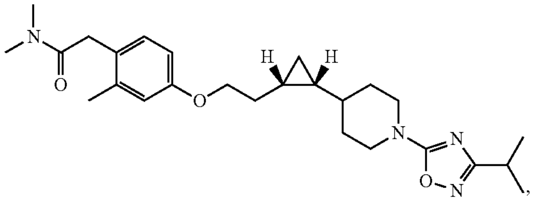
,
107
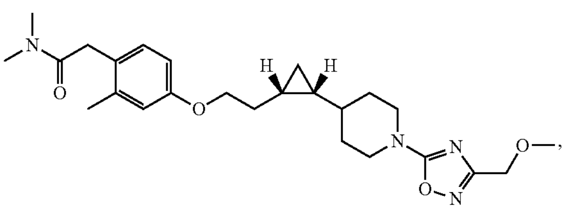
,
108
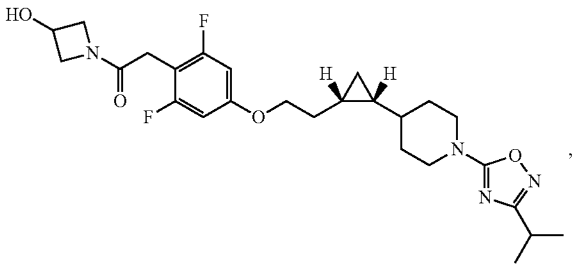
,
109
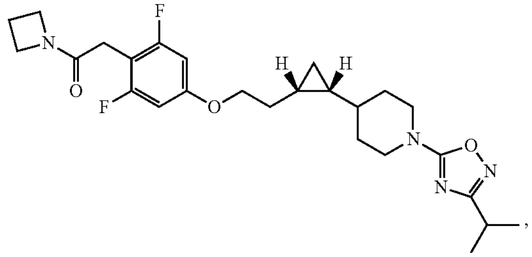
,
110
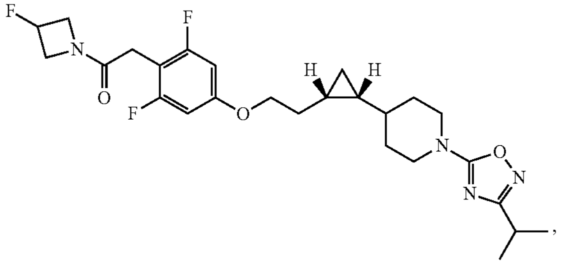
,
111
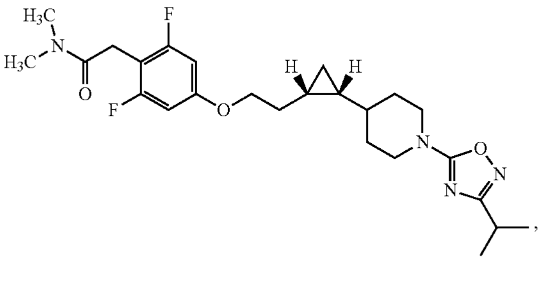
,
112
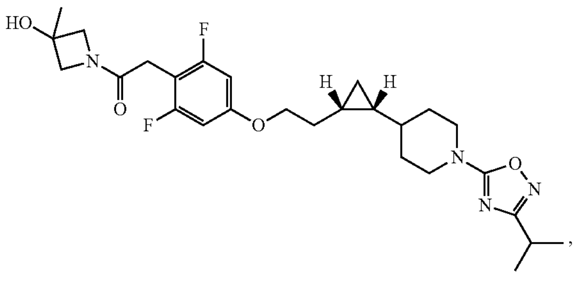
, -continued
113
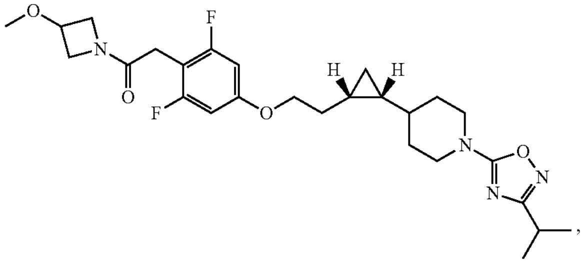
114
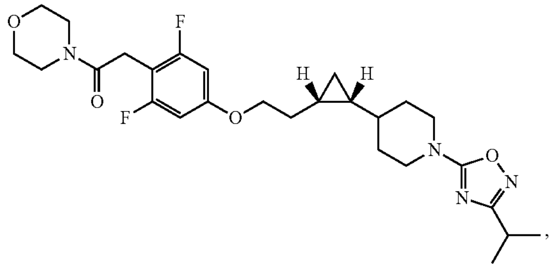
115
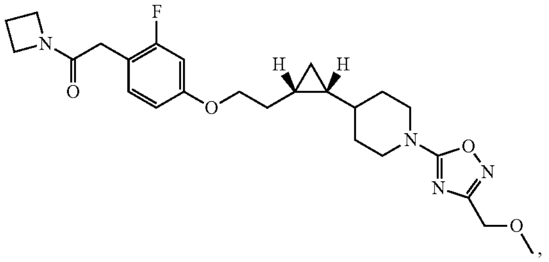
116
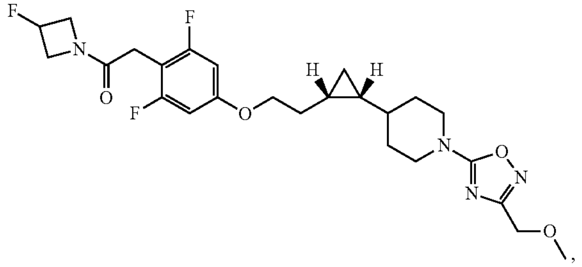
117
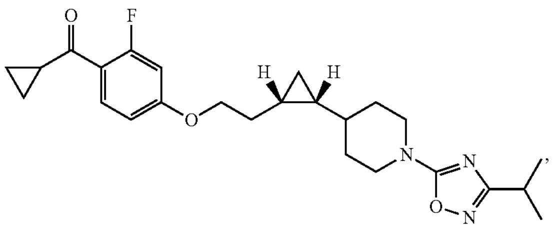
118
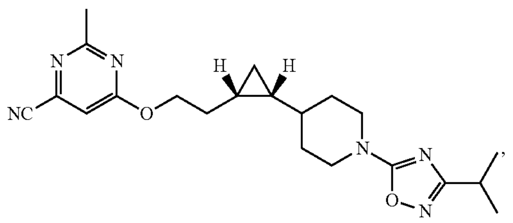
119
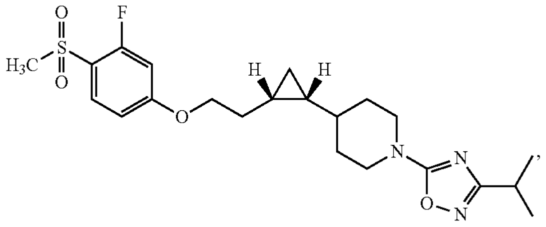
120
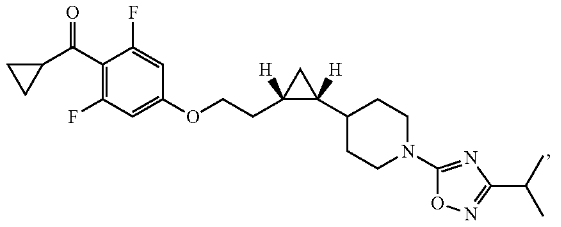
121
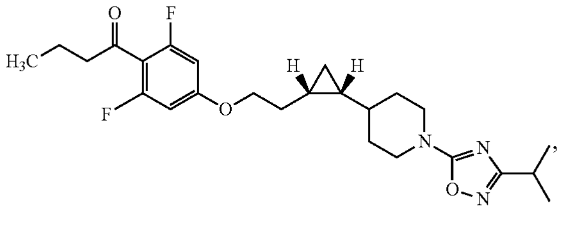
122
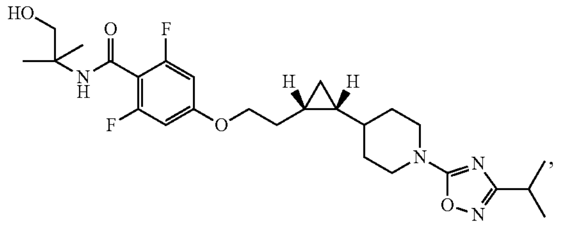
123
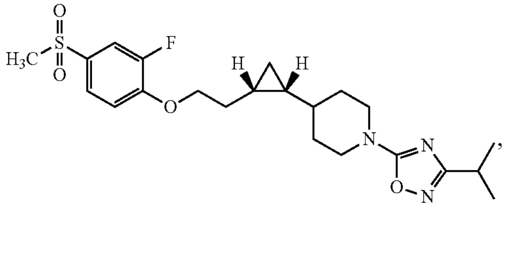
124
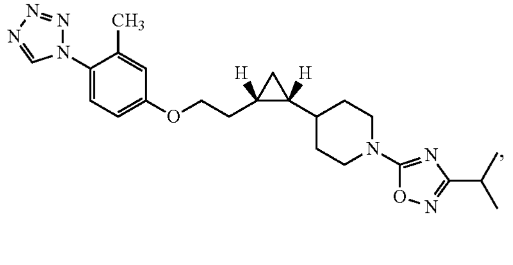

-continued
125
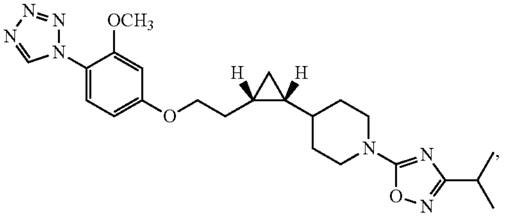
126
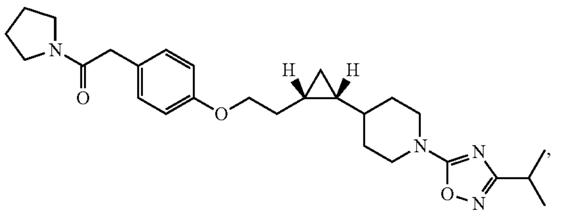
127
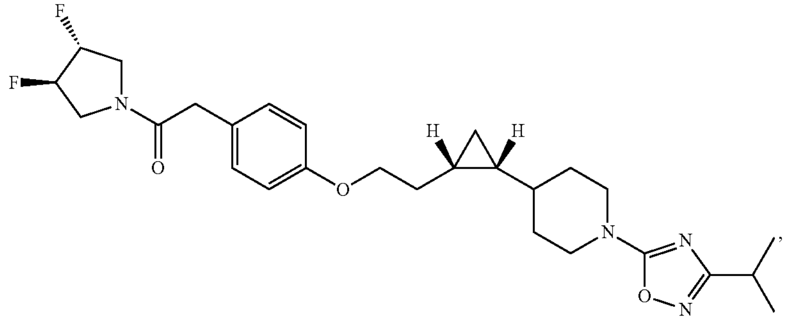
128
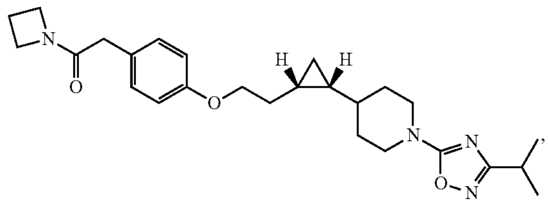
129
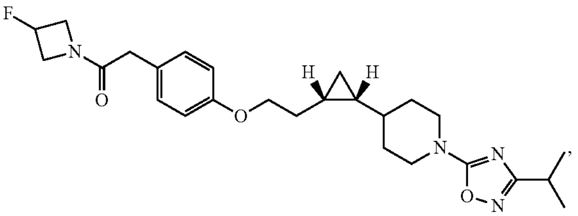
130
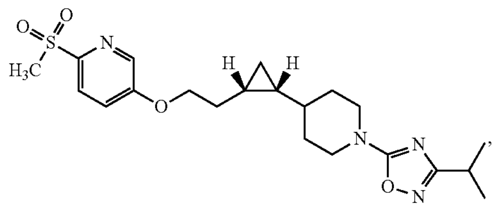
131
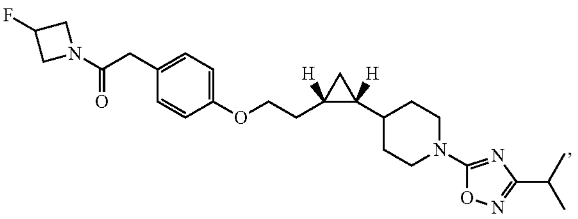
132
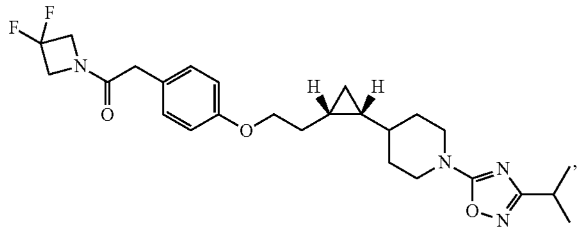
133
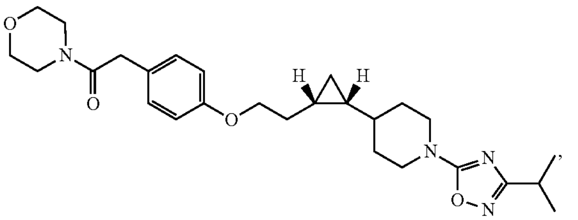
134
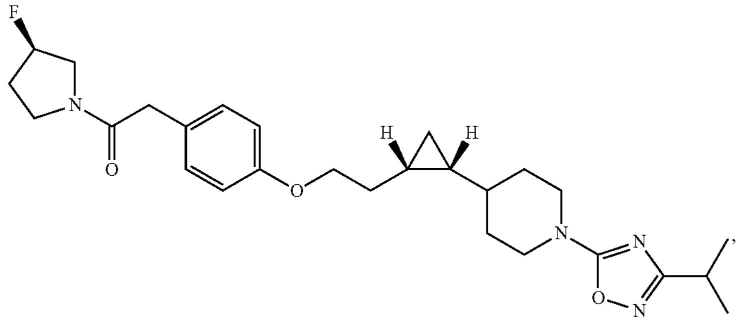

-continued
135
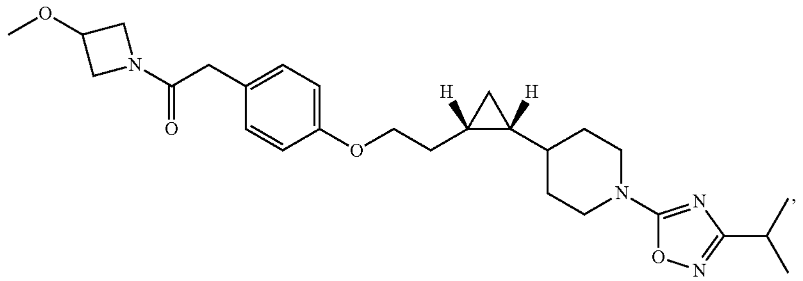
136
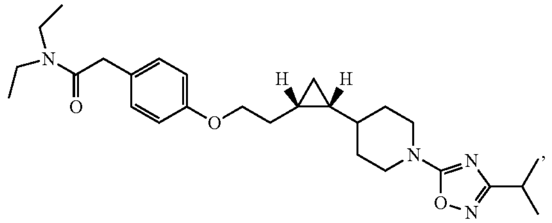
137
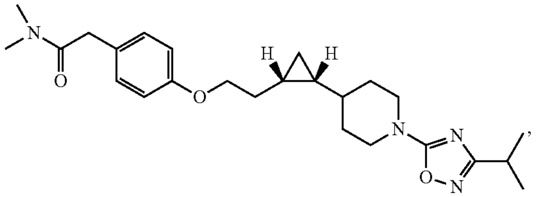
138
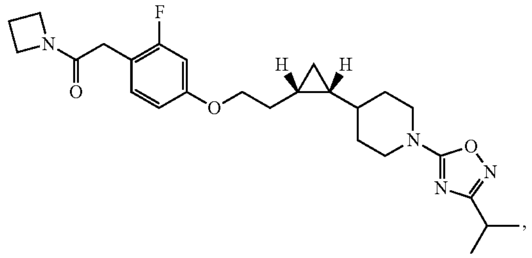
139
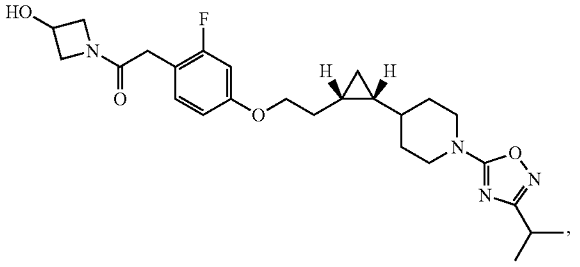
140
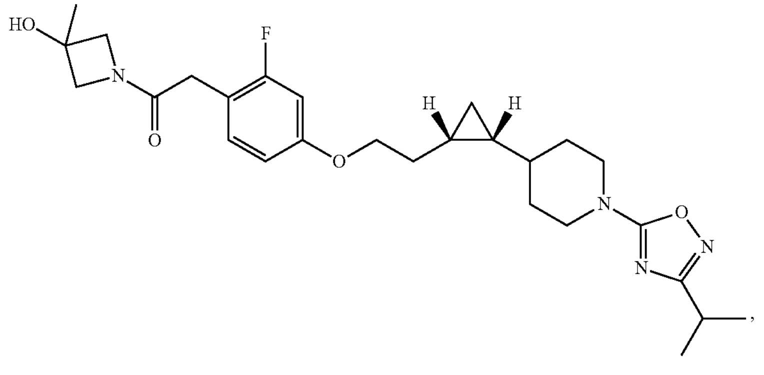
141
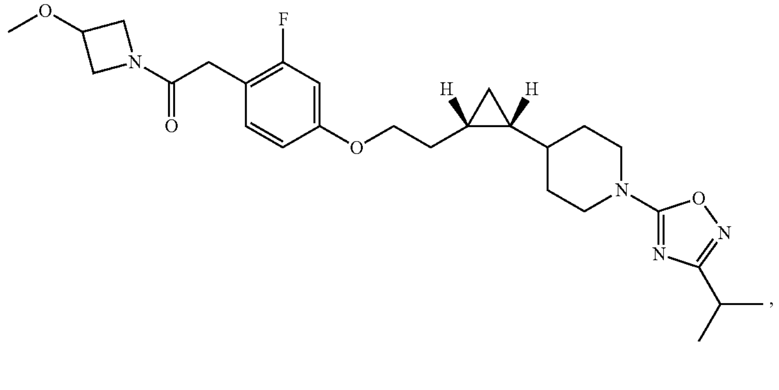

-continued
142
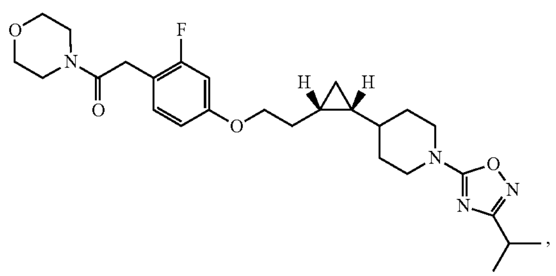
143
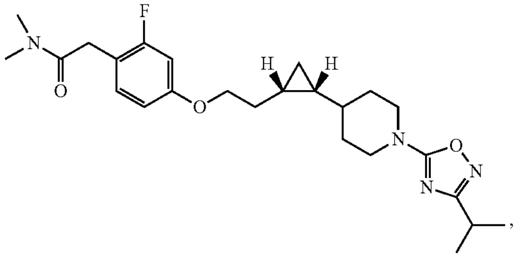
144
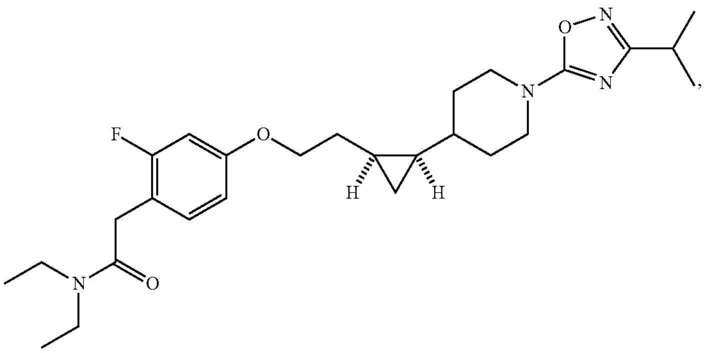
145
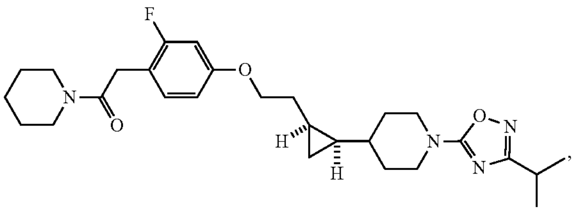
146
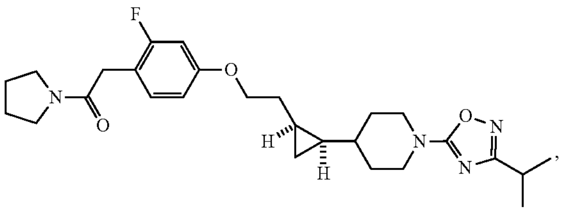
147
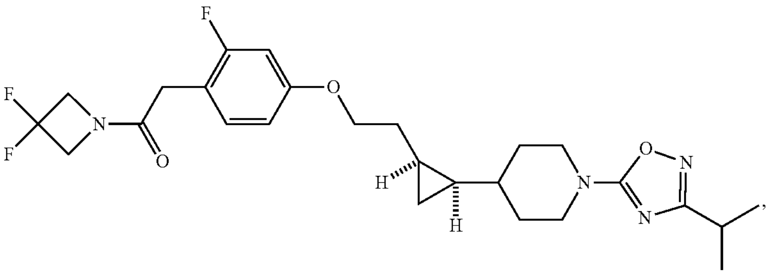
148
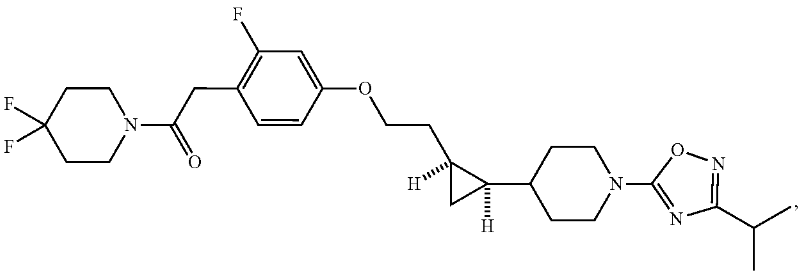

-continued
149
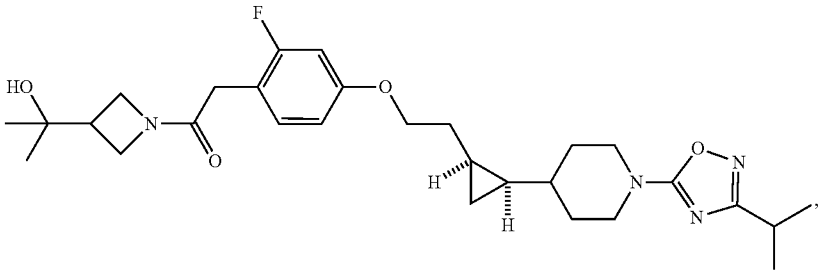
150
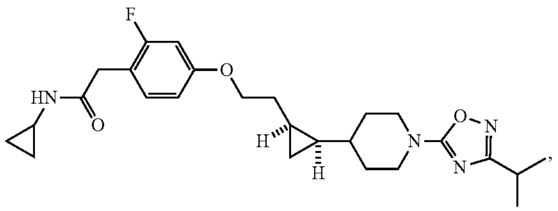
151
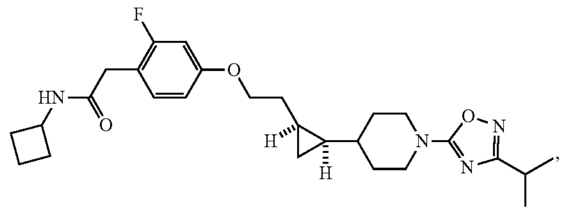
152
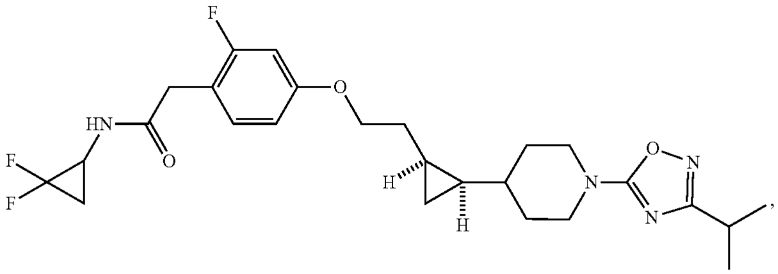
153
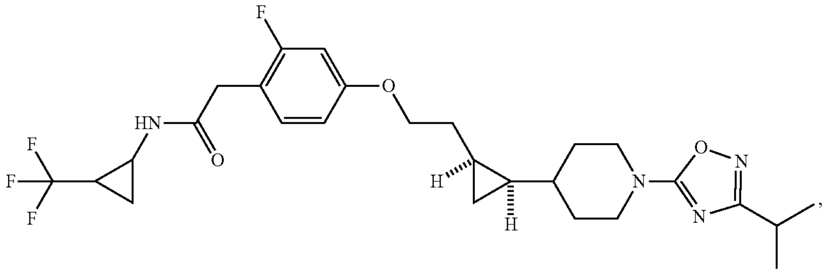
154
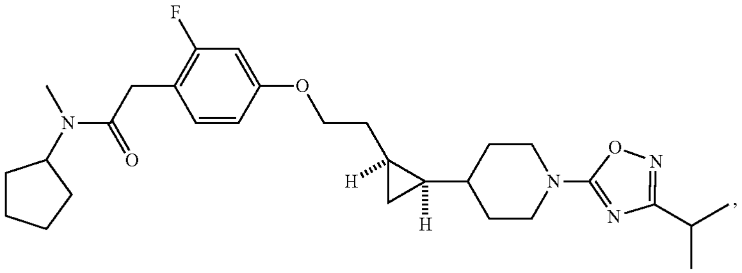
155
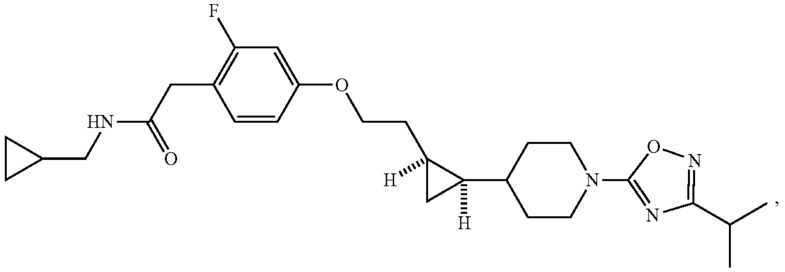

-continued
156
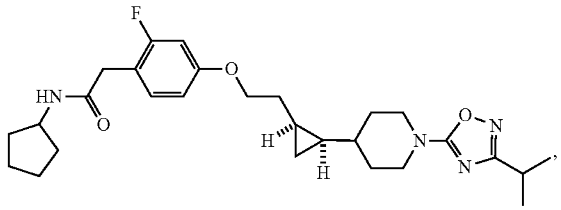
157
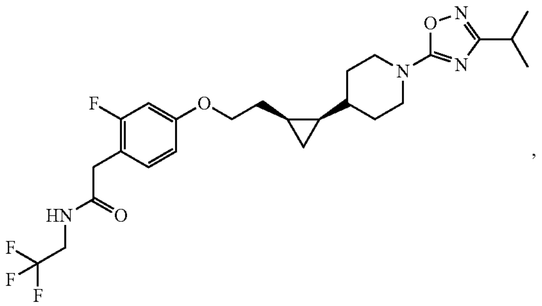
158
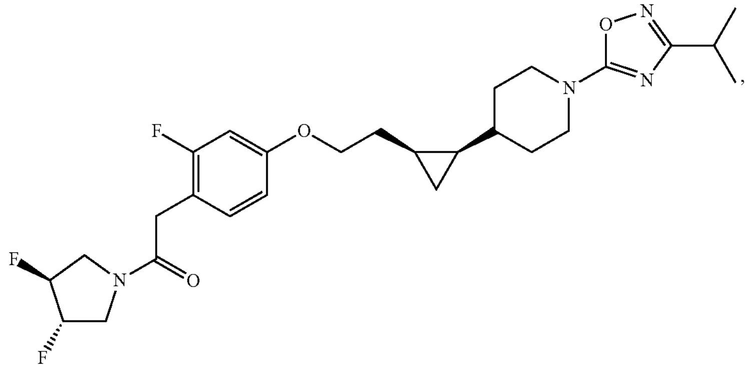
159
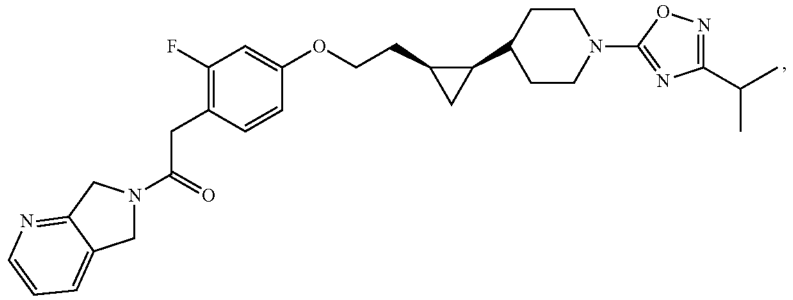
160
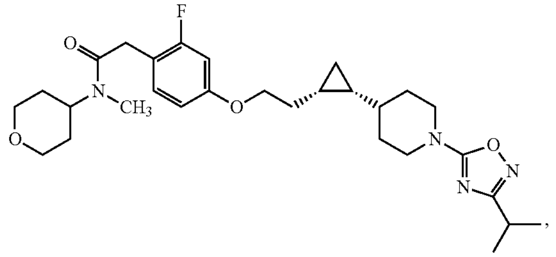
161
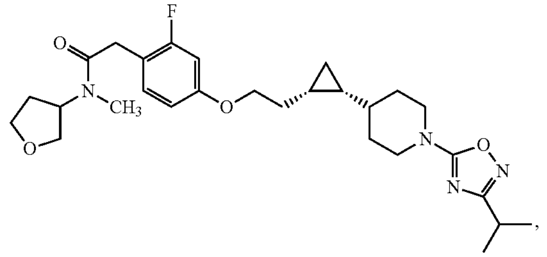
162
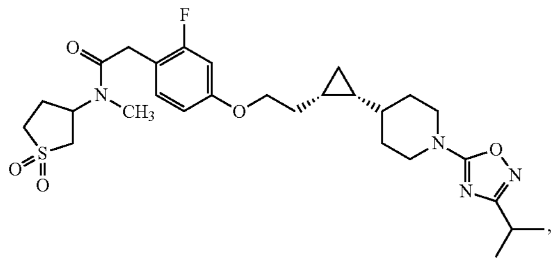
163
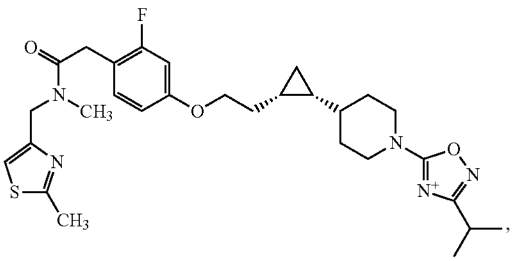

-continued
164
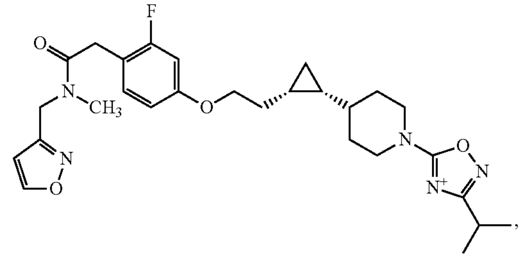
165
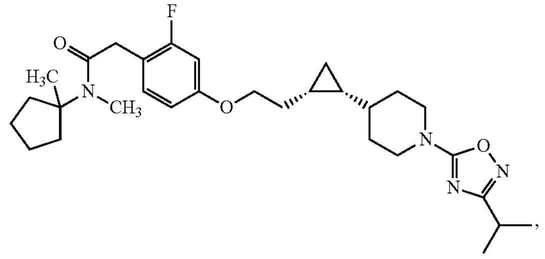
166
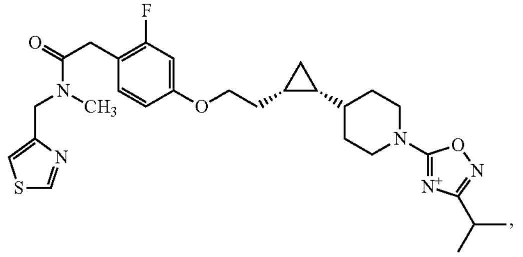
167
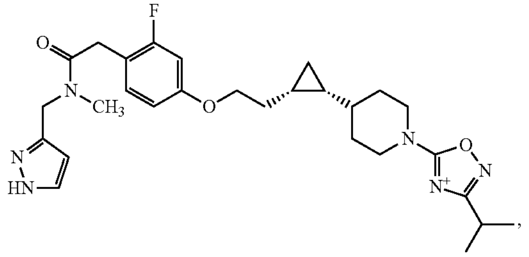
168
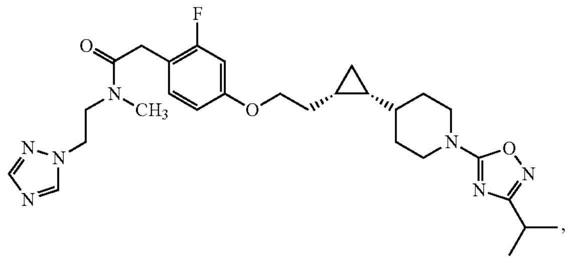
169
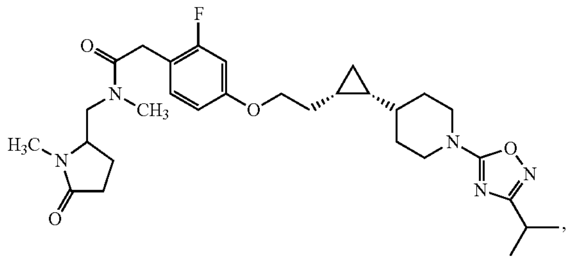
170
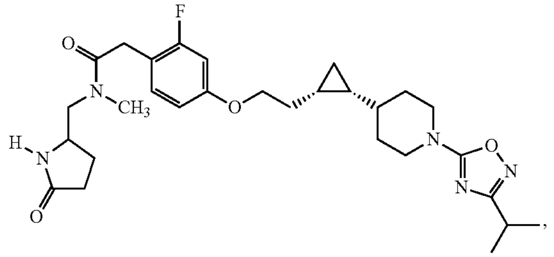
171
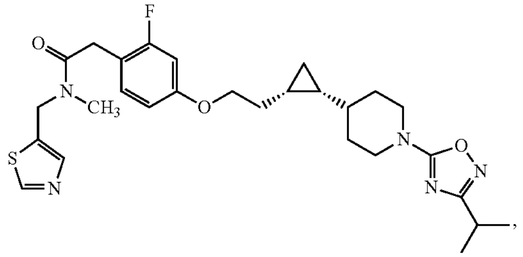
172
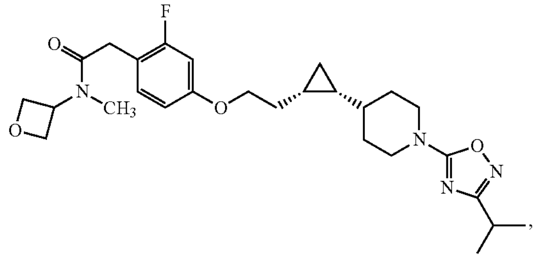
173
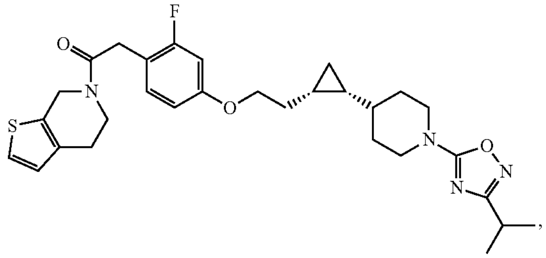
174
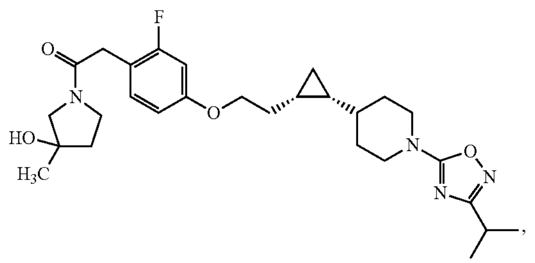
175
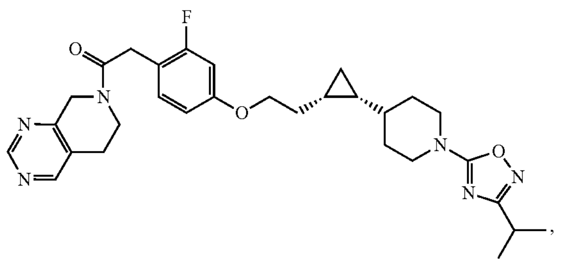

-continued
176
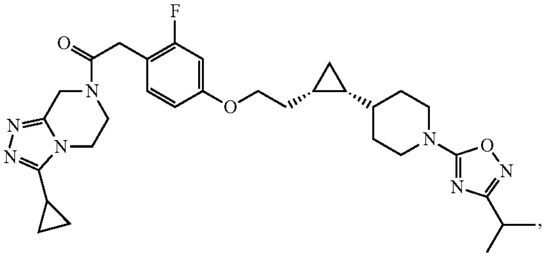
177
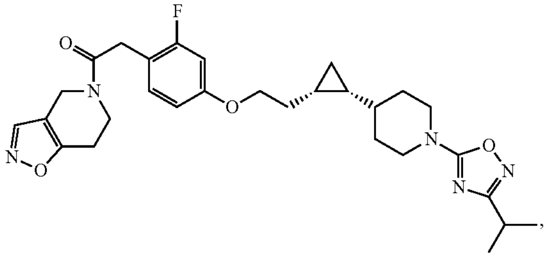
178
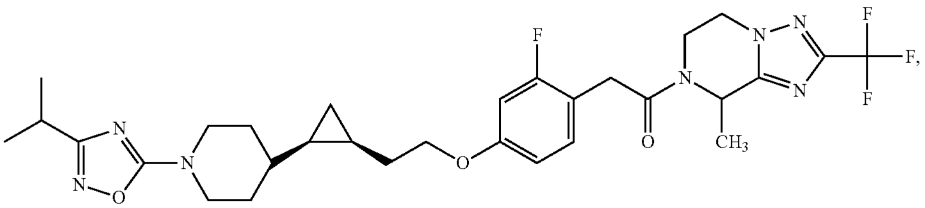
179
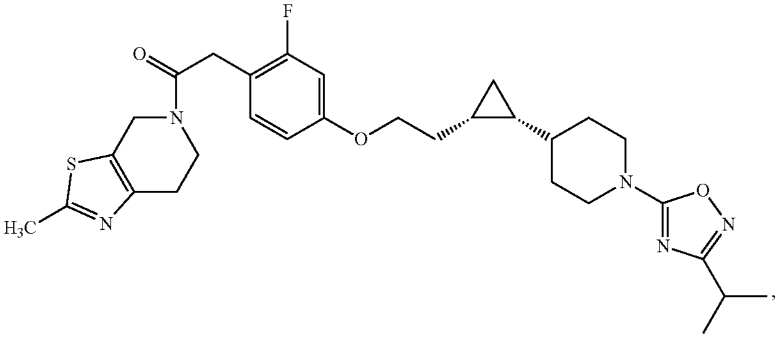
180
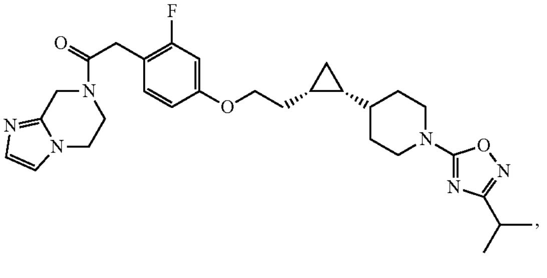
181
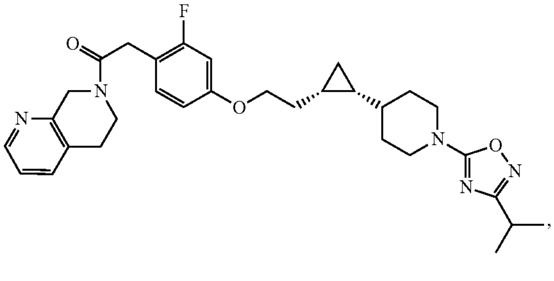
182
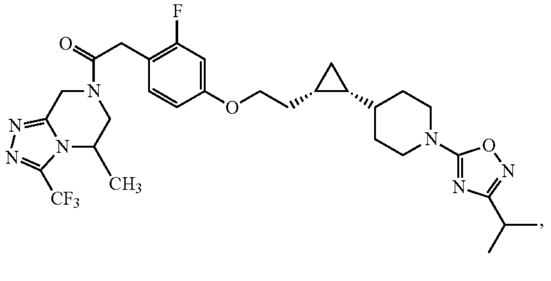

-continued
183
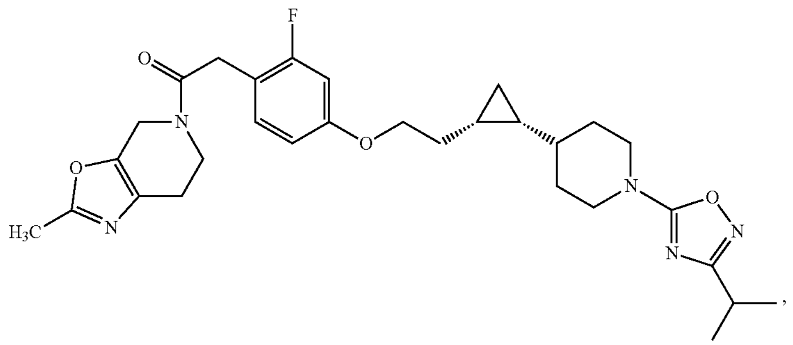
184
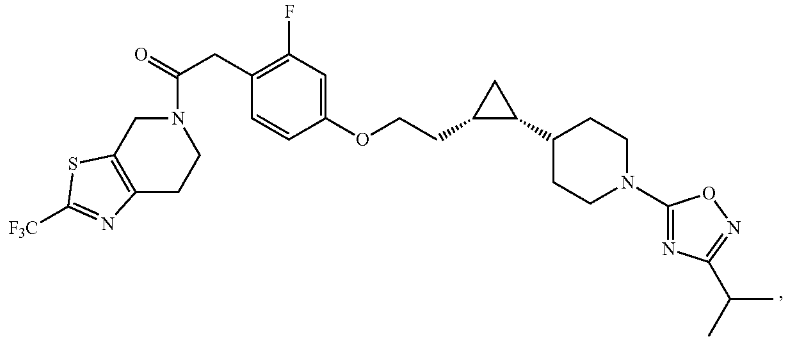
185
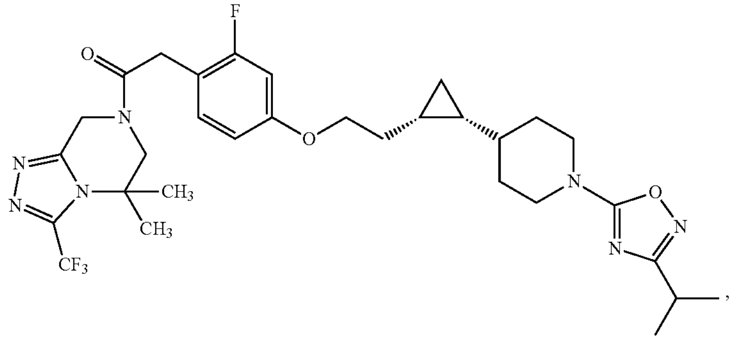
186
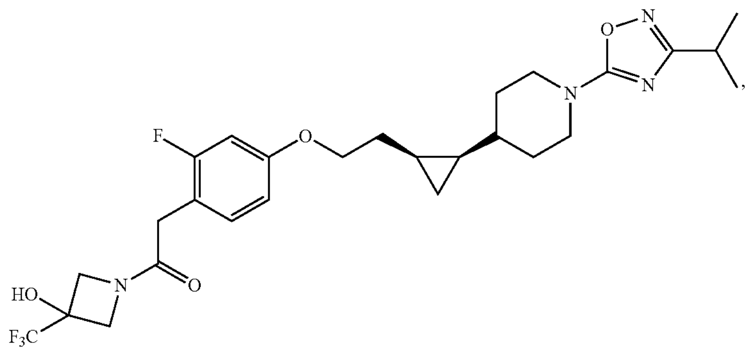

-continued
187
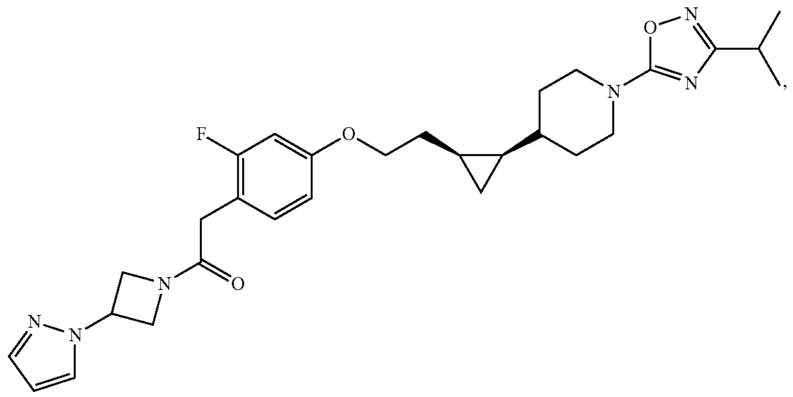
188
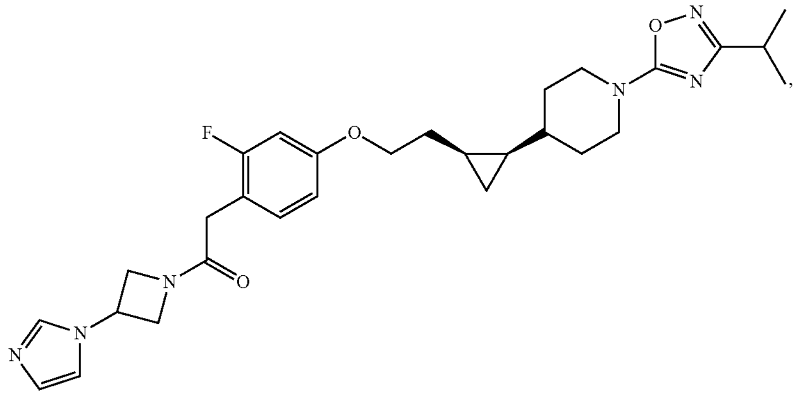
189
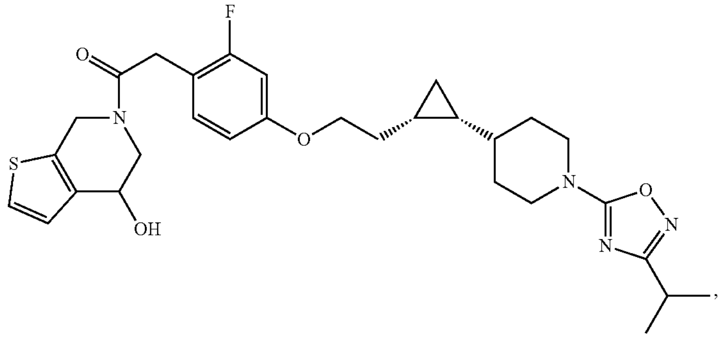
190
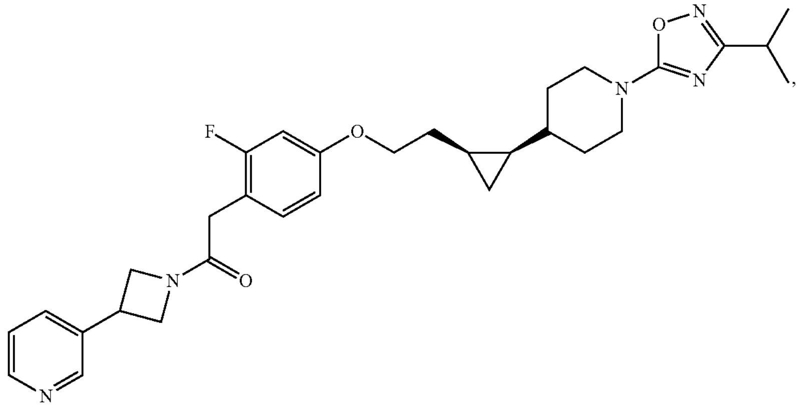

-continued
191
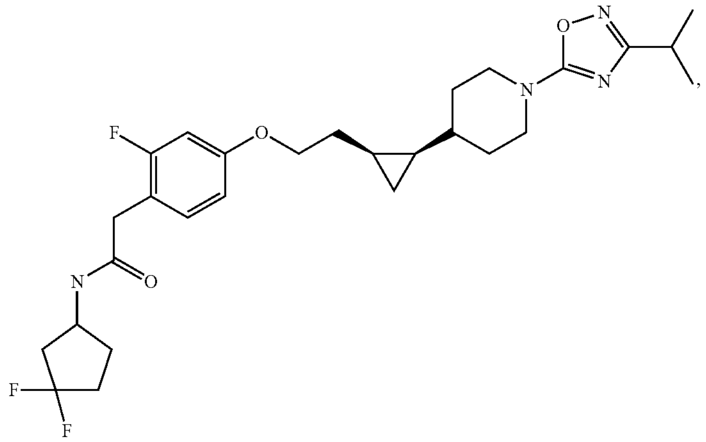
192
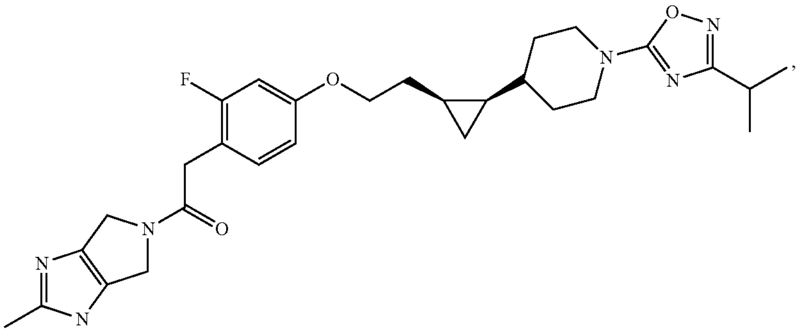
193
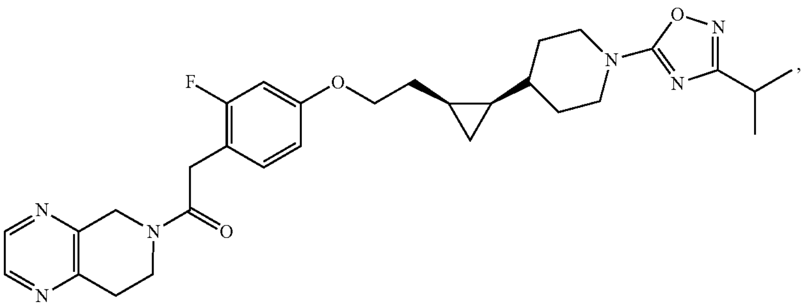
194
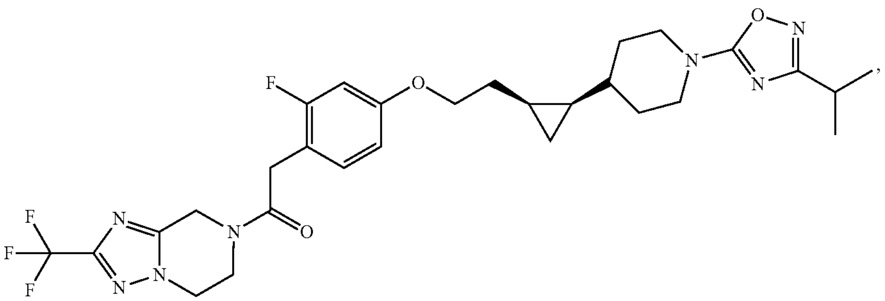

-continued
195
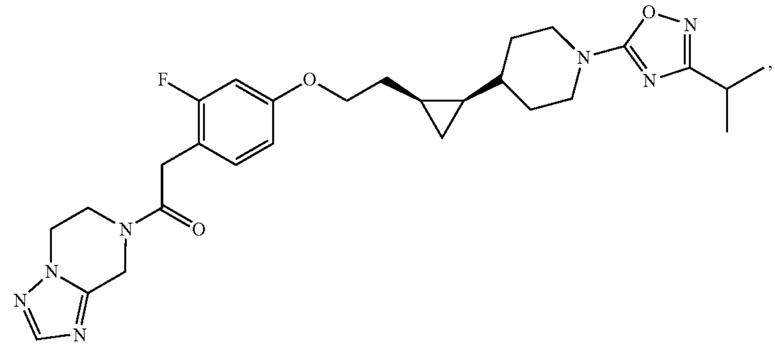
196
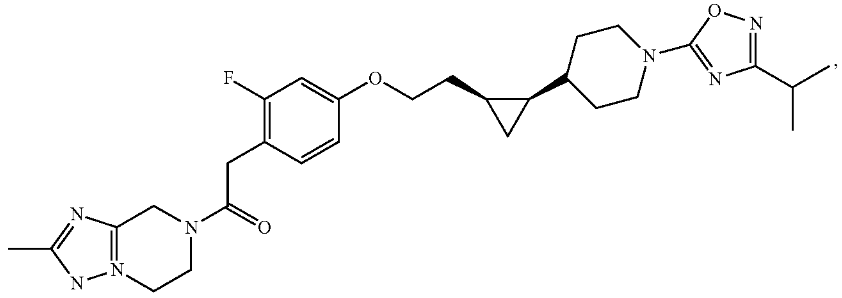
197
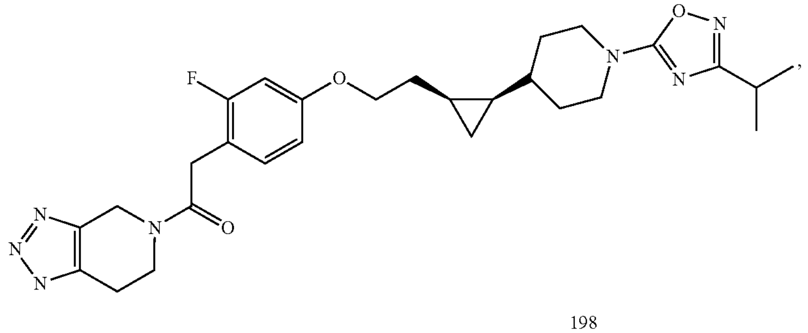
198
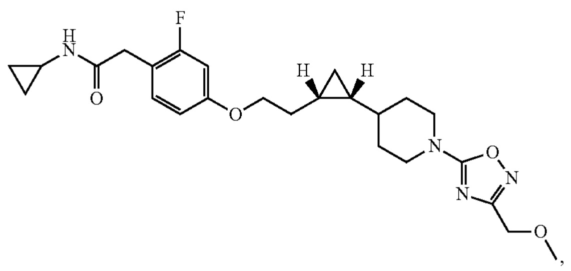
199
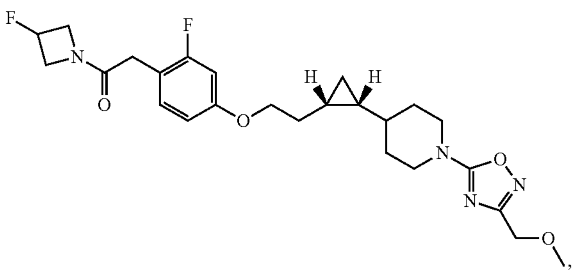
200
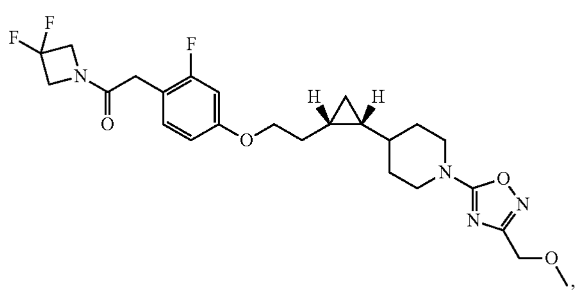
201
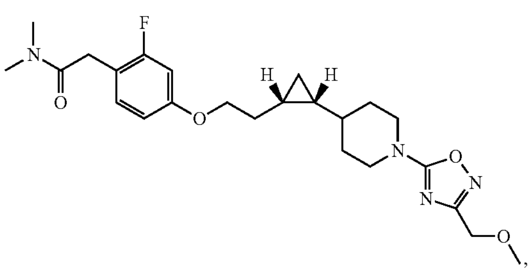

-continued
202
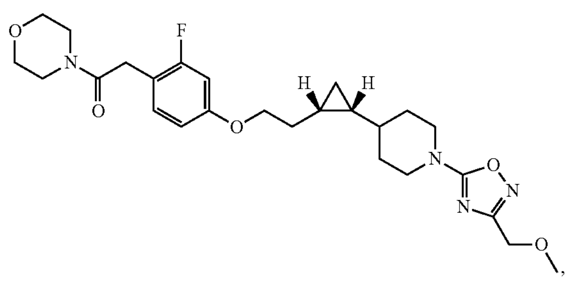,
203
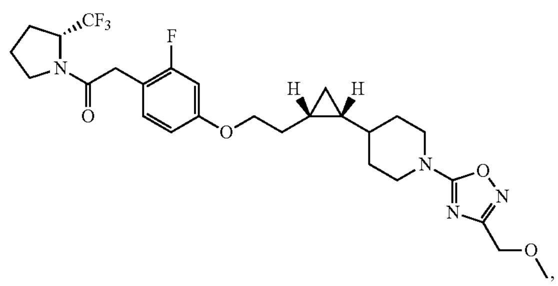,
204
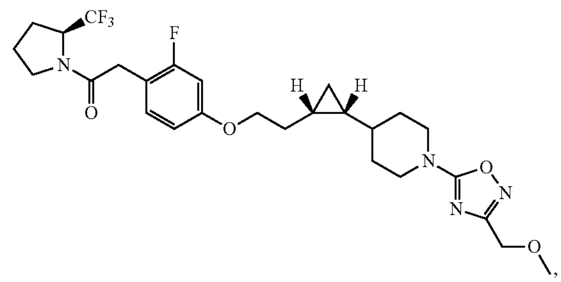,
205
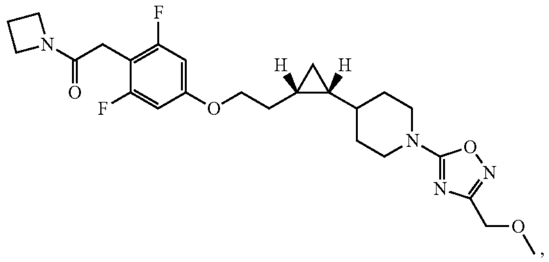,
206
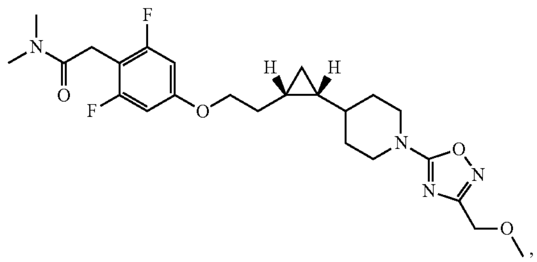,
207
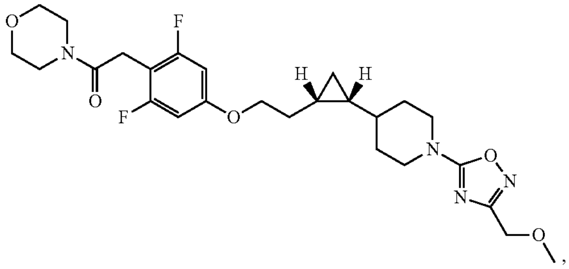,
208
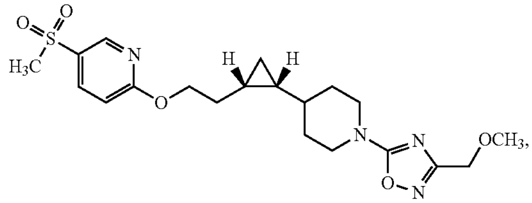,
209
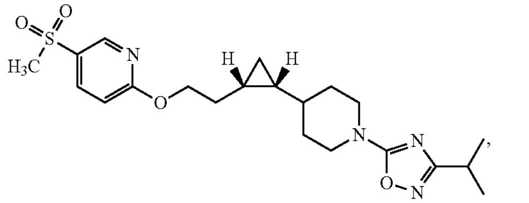,
210
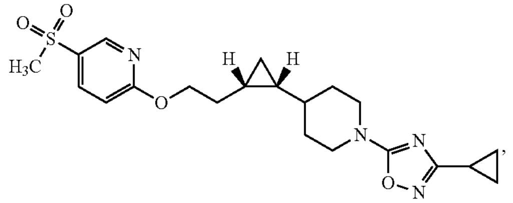,
211
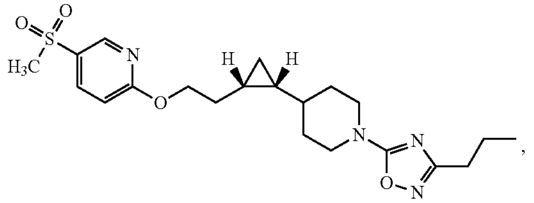,
212
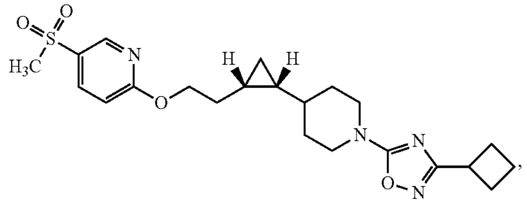,
213
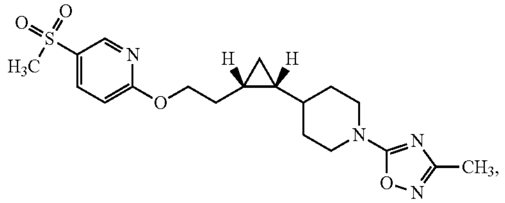, -continued
214
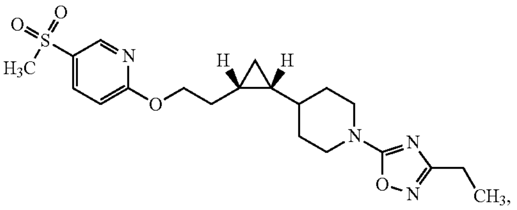
,
215
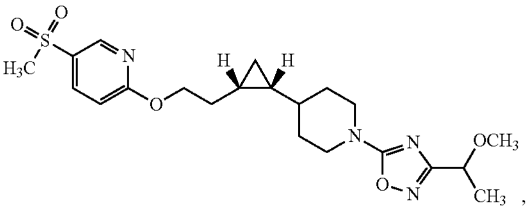
,
216
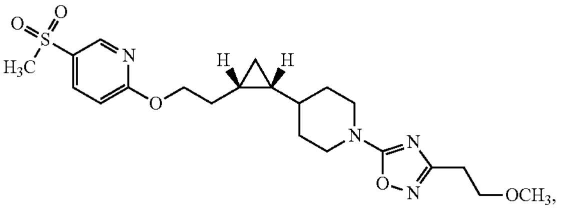
,
217
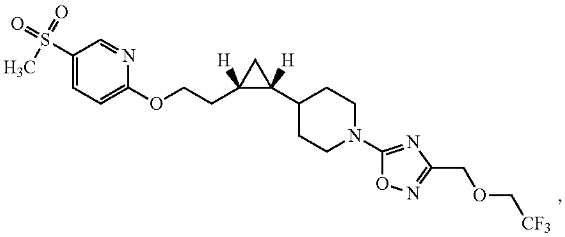
,
218
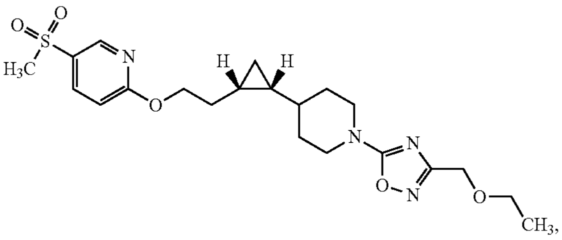
,
219
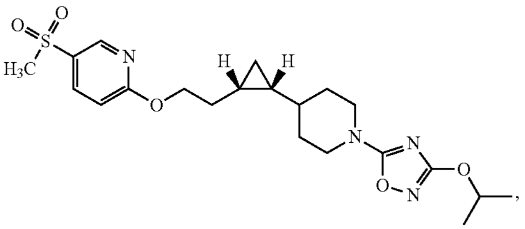
,
220
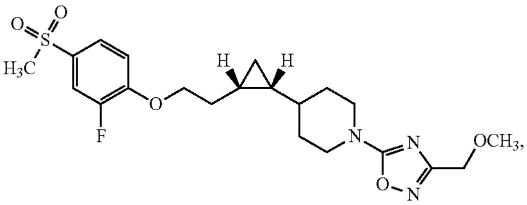
,
221
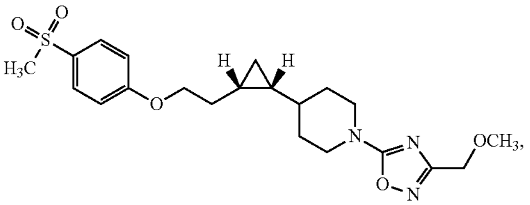
,
222
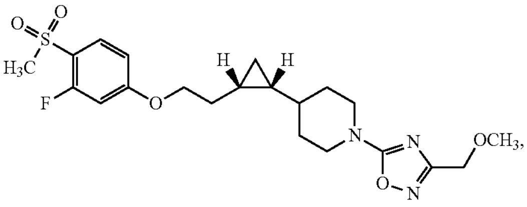
,
223
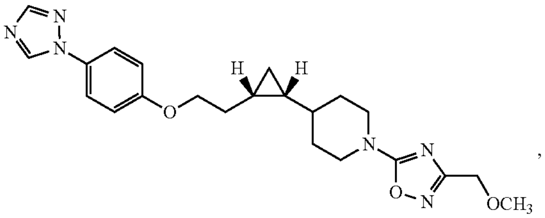
,
224
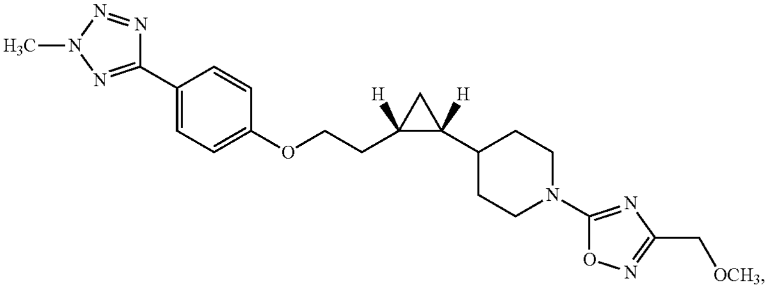
, -continued
225
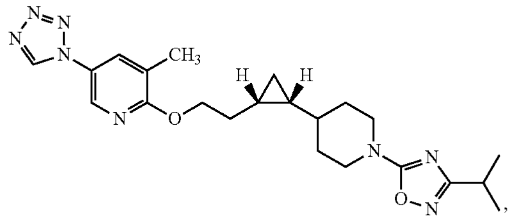
,
226
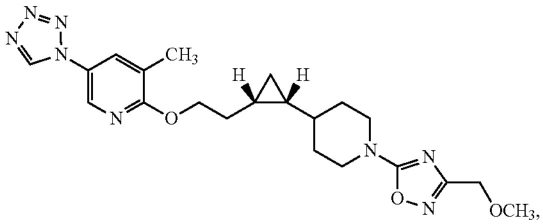
,
227
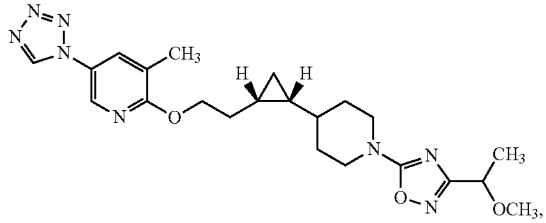
,
228
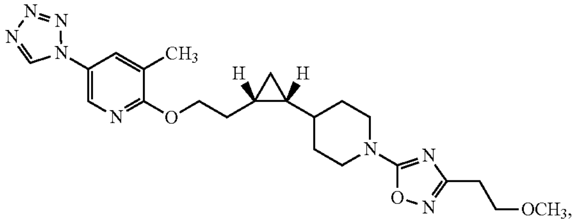
,
229
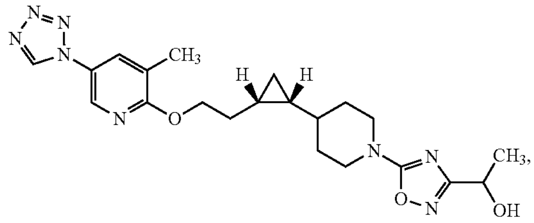
,
230
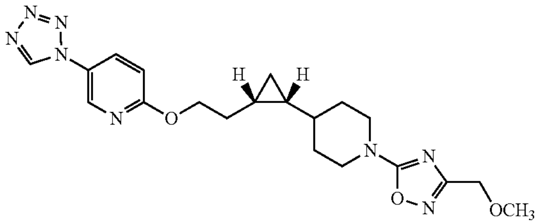
,
231
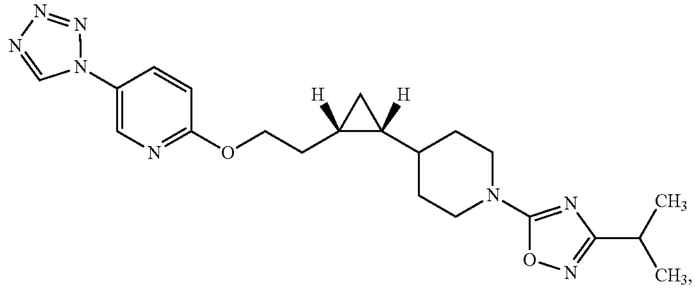
,
232
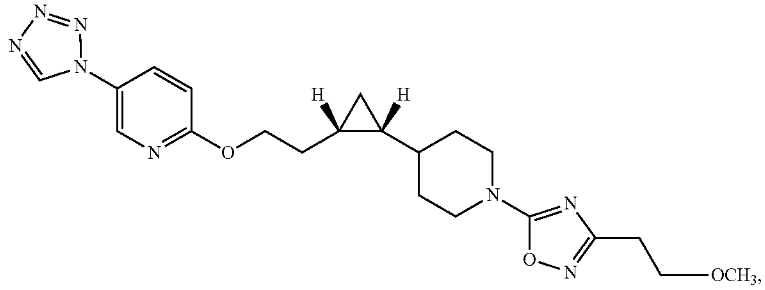
,
233
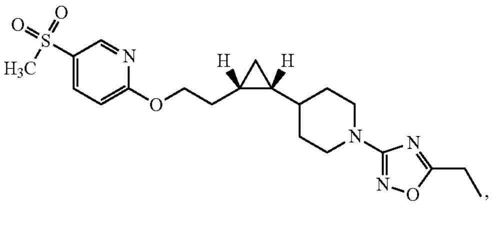
,
234
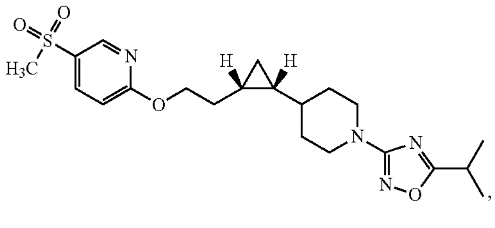
, -continued
235
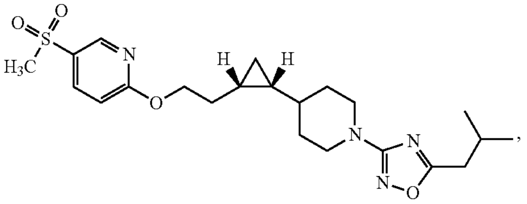
,
236
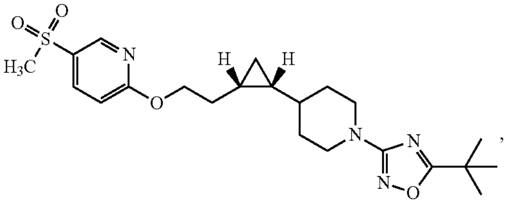
,
237
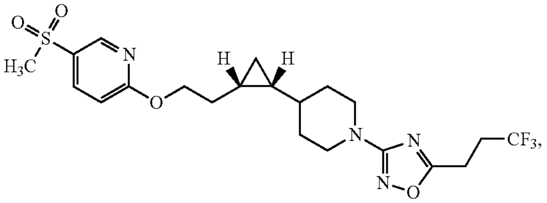
,
238
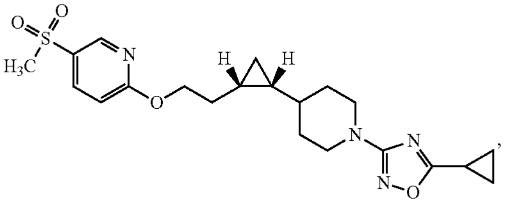
,
239
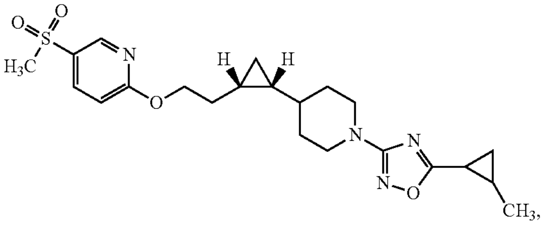
,
240
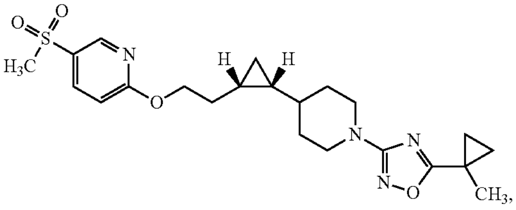
,
241
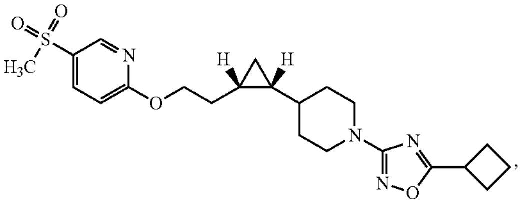
,
242
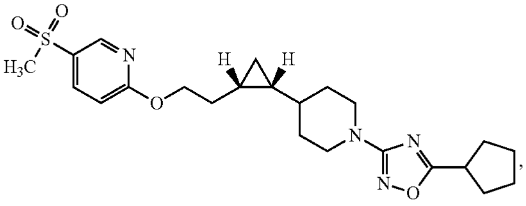
,
243
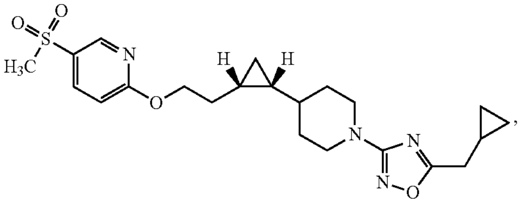
,
244
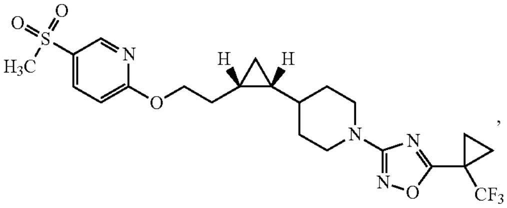
,
245
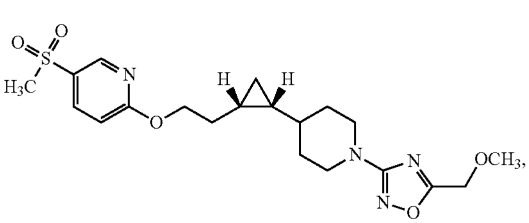
,
246
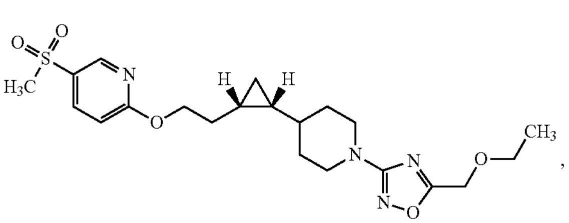
,
247
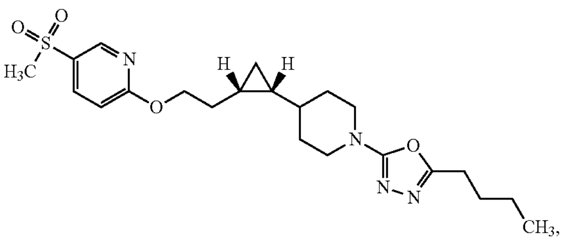
,
248
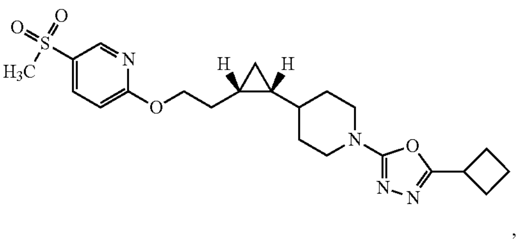
, -continued
249
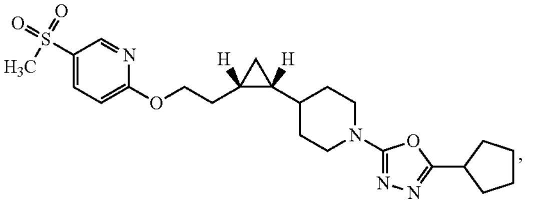
250
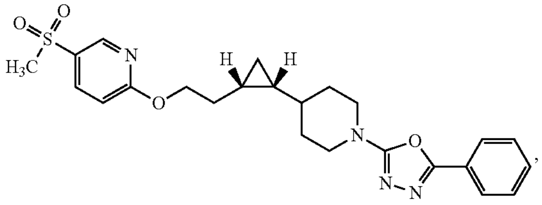
251
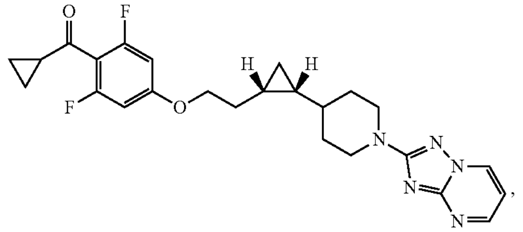
252
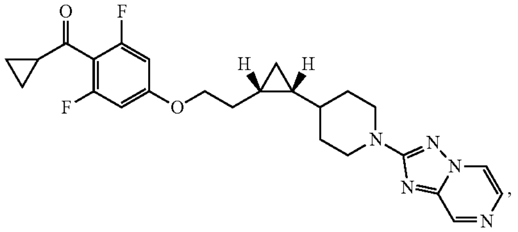
253
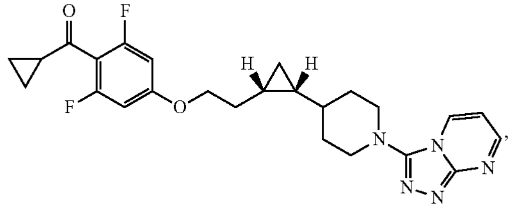
254
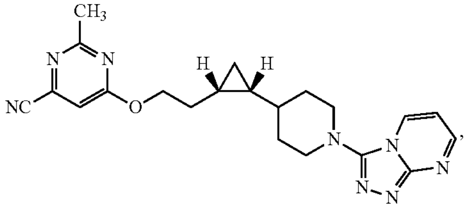
255
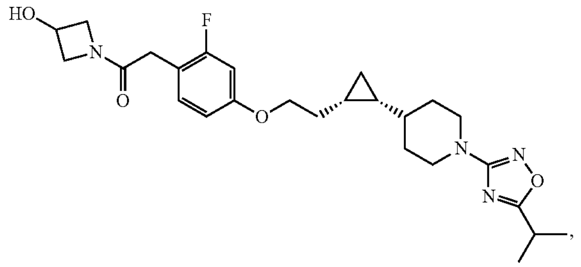
256
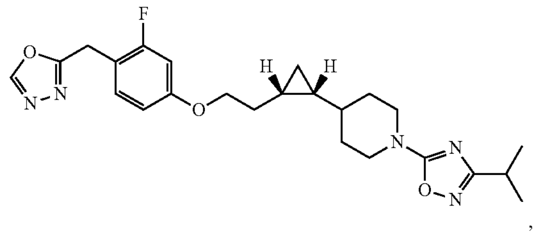
257
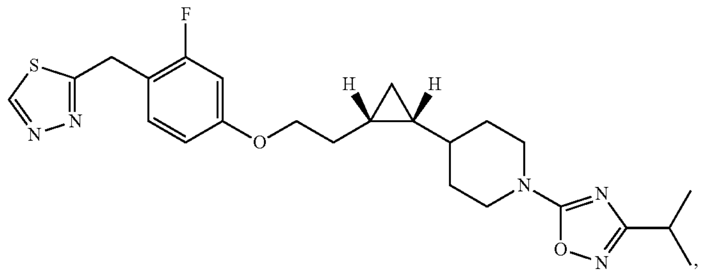
258
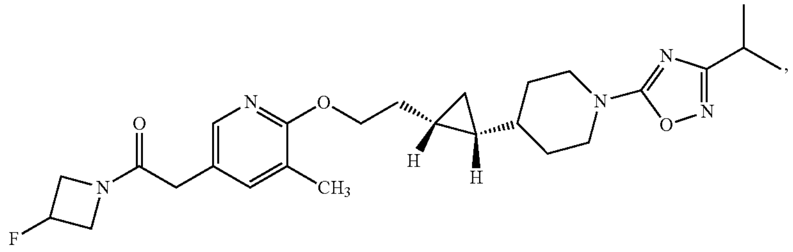

-continued
259
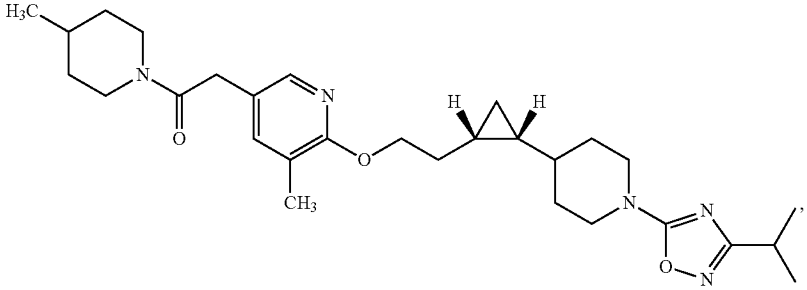
,
260
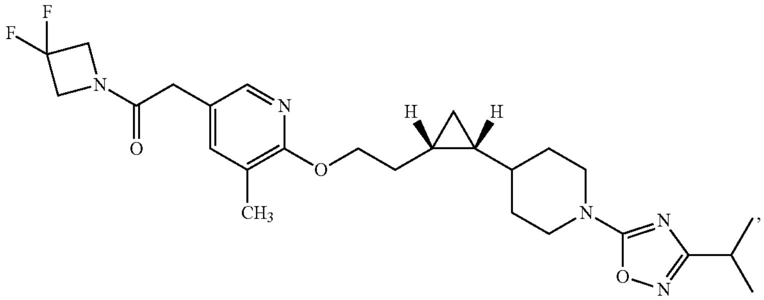
,
261
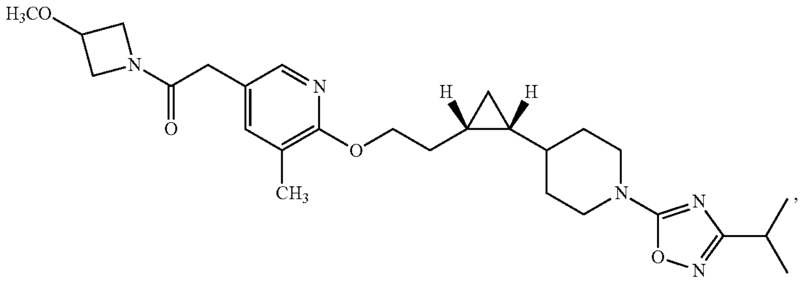
,
262
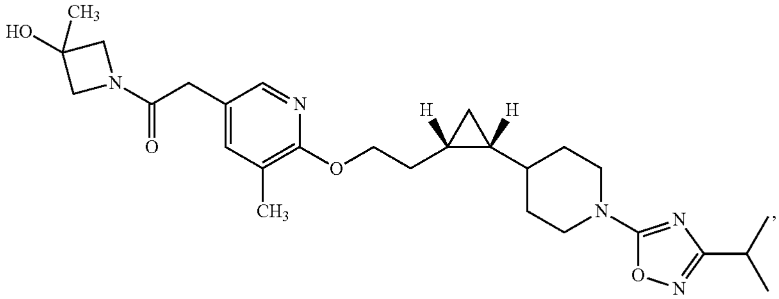
,
263
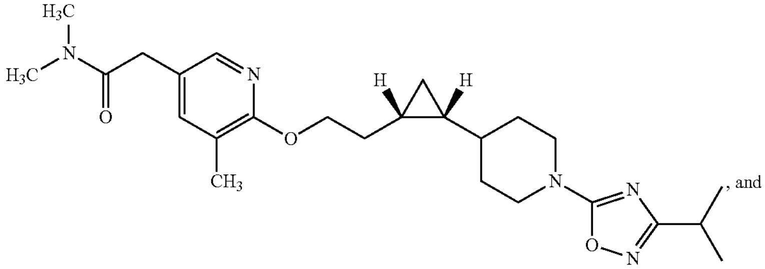
, and -continued

264

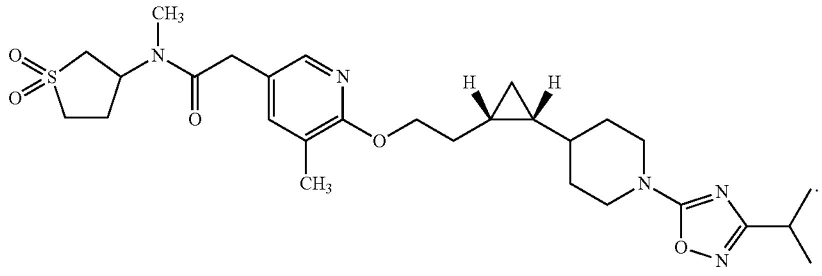

17. A pharmaceutical composition comprising a compound of claim 1, or a pharmaceutically acceptable salt thereof, and a pharmaceutically acceptable carrier.

18. A method for the treatment of a condition selected from the group consisting of obesity and diabetes comprising administering to an individual a pharmaceutical composition comprising the compound of claim 1.

* * * * *